US008227212B2

(12) United States Patent
von Figura et al.

(10) Patent No.: US 8,227,212 B2
(45) Date of Patent: Jul. 24, 2012

(54) CELL THAT EXPRESSES A SULFATASE AND A FORMYLGLYCINE GENERATING ENZYME

(75) Inventors: Kurt von Figura, Gottingen (DE); Bernhard Schmidt, Gottingen (DE); Thomas Dierks, Gottingen (DE); Michael W. Heartlein, Boxborough, MA (US); Maria Pia Cosma, Naples (IT); Andrea Ballabio, Naples (IT)

(73) Assignee: Shire Human Genetic Therapies, Inc., Lexington, MA (US)

( * ) Notice: Subject to any disclaimer, the term of this patent is extended or adjusted under 35 U.S.C. 154(b) by 692 days.

(21) Appl. No.: 10/775,678

(22) Filed: Feb. 10, 2004

(65) Prior Publication Data

US 2004/0229250 A1 Nov. 18, 2004

Related U.S. Application Data

(60) Provisional application No. 60/447,747, filed on Feb. 11, 2003.

(51) Int. Cl.
C12P 21/04 (2006.01)
C12N 5/10 (2006.01)
C12N 1/20 (2006.01)

(52) U.S. Cl. ... 435/70.1; 435/41.2; 435/325; 435/252.3; 435/252.33

(58) Field of Classification Search .......................... None
See application file for complete search history.

(56) References Cited

U.S. PATENT DOCUMENTS

| 7,083,793 | B2 * | 8/2006 | Fraser .................. 424/192.1 |
| 7,282,209 | B2 | 10/2007 | Fraser |
| 7,285,398 | B2 | 10/2007 | Fraser |
| 7,368,531 | B2 * | 5/2008 | Rosen et al. .................. 530/350 |

FOREIGN PATENT DOCUMENTS

| WO | WO 01/60991 A | 8/2001 |
| WO | WO0155411 A2 | 8/2001 |

OTHER PUBLICATIONS

Szameit et al., J. Biol. Chem. 274:15375-15381, 1999.*
Rommerskirch et al., PNAS 89:2561-2565, 1992.*
Fang et al., J. Biol. Chem. 279:14570-14578, 2004.*
GenBank Accession No. AJ131525, Apr. 1999, 3 pages.*
Wraith, Hum. Genet. 87:205-206, 1991.*
Juengst, E.T., "What next for human gene therapy?", BMJ 326:1410-1411, 2003.*
Merriam-Webster online dictionary definition of "exogenous", obtained from www.merriam-webster.com/dictionary/exogenous, last viewed on Dec. 18, 2009, 2 pages.*
Merriam-Webster online dictionary definition of "endogenous", obtained from www.merriam-webster.com/dictonary/endogenous, last viewed on Aug. 4, 2010, 1 page.*
Sang, Mechanisms of Development 121:1179-1186, 2004.*
Eto et al., Eur. J. Pediatr. 135:85-89, 1980.*
Landgrebe et al., Gene 316:47-56, 2003.*
"Plasmid Vectors", obtained from www.mfa.od.ua/page275.htm, last viewed on May 9, 2011, 2 pages.*
Ferrante et al., Eur. J. Human Genet. 10:813-818, 2002.*
Schirmer et al., "Computational Analysis of Bacterial Sulfatases and their Modifying Enzymes", *Chemistry and Biology* (London), 5(8), pp. R181-R186 (Aug. 1998).
Fay, et al., "Characterization of Posttranslational Formylglycine Formation by Luminal Components of the Endoplasmic Reticulum", *Journal of Biological Chemistry*, 276(50), pp. 47021-47028, (Dec. 14, 2001).
Database EMBL, Database Accession No. BD551115, (Sep. 18, 2002).
Database EMBL, Database Accession No. ABB62912, (Mar. 26, 2002).
Database EMBL, Database Accession No. Q98BQ8, (Oct. 1, 2001).
Database EMBL, Database Accession No. AK076022 (Dec. 13, 2002).
Database EMBL, Database Accession No. AAB88402, (May 23, 2001).
Database EMBL, Database Accession No. AAY95971, (Dec. 5, 2000).
Database EMBL, Database Accession No. AAAB01008987, (Jul. 24, 2002).
Database EMBL, Database Accession No. Q9F3C7, (Mar. 1, 2001).
Database EMBL, Database Accession No. P95060, (May 1, 1997).
Database EMBL, Database Accession No. Q92WL9, (Dec. 1, 2001).
Database EMBL, Database Accession No. Q93PA2, (Dec. 1, 2001).
Database EMBL, Database Accession No. Q9A921, (Jun. 1, 2001).
Schmidt et al., A Novel Amino Acid Modification in Sulfatases that is Defective in Multiple Sulfatase Deficiency, *Cell*, 82(2), pp. 271-278, (1995).
Database EMBL, Database Accession No. Q7V5N5, (Oct. 1, 2003).
Database EMBL, Database Accession No. Q8FTJ8, (Mar. 1, 2003).
Database EMBL, Database Accession No. Q88HK3, (Jun. 1, 2003).
Dierks et al., "Multiple Sulfatase Deficiency is Caused by Mutations in the Gene Encoding the Human $C_\alpha$-Formylglycine Generating Enyme", *Cell*, 113(4), pp. 435-444, (May 16, 2003).
Abdella et al.; Bio Chem. Biophy. research Comm., vol. 87, No. 3, pp. 734-742 (1979).
Benjdia et al.,"First Evidences for a Third Sulfate Maturation System in Prokaryotes from *E. coli* asIB and ydeM Deletion Mutant", Federation of European Biochemical Societies, 581 pp. 1009-1014, (2007).
Cosma, et al., "The Multiple Sulfatase Deficiency Gene Encodes an Essential and Limiting Factor for the Activity of Sulfatases", Cell, vol. 113, pp. 445-456 (2003).
Dierks et al., "Sequence determinants directing conversation of cysteine to formylglycine in eukaryotic sulfatases", The EMBO Journal, vol. 18, No. 8, pp. 2084-7091 (1999).

* cited by examiner

*Primary Examiner* — David J Steadman
(74) *Attorney, Agent, or Firm* — Choate Hall & Stewart LLP; Fangli Chen

(57) ABSTRACT

This invention relates to methods and compositions for the diagnosis and treatment of Multiple Sulfatase Deficiency (MSD) as well as other sulfatase deficiencies. More specifically, the invention relates to isolated molecules that modulate post-translational modifications on sulfatases. Such modifications are essential for proper sulfatase function.

22 Claims, 9 Drawing Sheets

CELL THAT EXPRESSES A SULFATASE AND A FORMYLGLYCINE GENERATING ENZYME

RELATED APPLICATIONS

This application claims priority under 35 U.S.C. §119(e) from Provisional U.S. Patent Application Ser. No. 60/447,747, filed Feb. 11, 2003, and entitled DIAGNOSIS AND TREATMENT OF MULTIPLE SULFATASE DEFICIENCY AND OTHER SULFATASE DEFICIENCIES. The contents of the provisional application are hereby expressly incorporated by reference.

FIELD OF THE INVENTION

This invention relates to methods and compositions for the diagnosis and treatment of Multiple Sulfatase Deficiency (MSD) as well as other sulfatase deficiencies. More specifically, the invention relates to isolated molecules that modulate post-translational modifications on sulfatases. Such modifications are essential for proper sulfatase function.

BACKGROUND OF THE INVENTION

Sulfatases are members of a highly conserved gene family, sharing extensive sequence homology (Franco, B., et al., *Cell*, 1995, 81:15-25; Parenti, G., et al., *Curr. Opin. Gen. Dev.*, 1997, 7:386-391), a high degree of structural similarity (Bond, C. S., et al., *Structure*, 1997, 5:277-289; Lukatela, G., et al., *Biochemistry*, 1998, 37:3654-64), and a unique post-translational modification that is essential for sulfate ester cleavage (Schmidt, B., et al., *Cell*, 1995, 82:271-278; Selmer, T., et al., *Eur. J. Biochem.*, 1996, 238:341-345). The post-translational modification involves the oxidation of a conserved cysteine (in eukaryotes) or serine (in certain prokaryotes) residue, at $C_\beta$, yielding L-$C_\alpha$-formylglycine (a.k.a. FGly; 2-amino-3-oxopropanoic acid) in which an aldehyde group replaces the thiomethyl group of the side chain. The aldehyde is an essential part of the catalytic site of the sulfatase and likely acts as an aldehyde hydrate. One of the geminal hydroxyl groups accepts the sulfate during sulfate ester cleavage leading to the formation of a covalently sulfated enzyme intermediate. The other hydroxyl is required for the subsequent elimination of the sulfate and regeneration of the aldehyde group. This modification occurs in the endoplasmic reticulum during, or shortly after, import of the nascent sulfatase polypeptide and is directed by a short linear sequence surrounding the cysteine (or serine) residue to be modified. This highly conserved sequence is hexapeptide L/V-C(S)-X-P-S-R (SEQ ID NO:32), present in the N-terminal region of all eukaryotic sulfatases and most frequently carries a hydroxyl or thiol group on residue X (Dierks, T., et al., *Proc. Natl. Acad. Sci. U. S. A.*, 1997, 94:11963-11968).

To date thirteen sulfatase genes have been identified in humans. They encode enzymes with different substrate specificity and subcellular localization such as lysosomes, Golgi and ER. Four of these genes, ARSC, ARSD, ARSE, and ARSF, encoding arylsulfatase C, D, E and F, respectively, are located within the same chromosomal region (Xp22.3). They share significant sequence similarity and a nearly identical genomic organization, indicating that they arose from duplication events that occurred recently during evolution (Franco B, et al., *Cell*, 1995, 81:15-25; Meroni G, et al., *Hum Mol Genet*, 1996, 5:423-31).

The importance of sulfatases in human metabolism is underscored by the identification of at least eight human monogenic diseases caused by the deficiency of individual sulfatase activities. Most of these conditions are lysosomal storage disorders in which phenotypic consequences derive from the type and tissue distribution of the stored material. Among them are five different types of mucopolysaccharidoses (MPS types II, IIIA, IIID, IVA, and VI) due to deficiencies of sulfatases acting on the catabolism of glycosaminoglycans (Neufeld and Muenzer, 2001, The mucopolysaccharidoses, *In The Metabolic and Molecular Bases of Inherited Disease*, C. R. Scriver, A. L. Beaudet, W. S. Sly, D. Valle, B. Childs, K. W. Kinzler and B. Vogelstein, eds. New York: Mc Graw-Hill, pp. 3421-3452), and metachromatic leukodystrophy (MLD), which is characterized by the storage of sulfolipids in the central and peripheral nervous systems leading to severe and progressive neurologic deterioration. Two additional human diseases are caused by deficiencies of non-lysosomal sulfatases. These include X-linked ichthyosis, a skin disorder due to steroid sulfatase (STS/ARSC) deficiency, and chondrodysplasia punctata, a disorder affecting bone and cartilage due to arylsulfatase E (ARSE) deficiency. Sulfatases are also implicated in drug-induced human malformation syndromes, such as Warfarin embryopathy, caused by inhibition of ARSE activity due to in utero exposure to warfarin during pregnancy.

In an intriguing human monogenic disorder, multiple sulfatase deficiency (MSD), all sulfatase activities are simultaneously defective. Consequently, the phenotype of this severe multisystemic disease combines the features observed in individual sulfatase deficiencies. Cells from patients with MSD are deficient in sulfatase activities even after transfection with cDNAs encoding human sulfatases, suggesting the presence of a common mechanism required for the activity of all sulfatases (Rommerskirch and von Figura, *Proc. Natl. Acad. Sci., USA*, 1992, 89:2561-2565). The post-translational modification of sulfatases was found to be defective in one patient with MSD, suggesting that this disorder is caused by a mutation in a gene, or genes, implicated in the cysteine-to-formylglycine conversion machinery (Schmidt, B., et al., *Cell*, 1995, 82:271-278). In spite of intense biological and medical interest, efforts aimed at the identification of this gene(s) have been hampered by the rarity of MSD patients and consequent lack of suitable familial cases to perform genetic mapping.

SUMMARY OF THE INVENTION

This invention provides methods and compositions for the diagnosis and treatment of Multiple Sulfatase Deficiency (MIM 272200), and the treatment of other sulfatase deficiencies. More specifically, we have identified a gene that encodes Formylglycine Generating Enzyme (FGE), an enzyme responsible for the unique post-translational modification occurring on sulfatases that is essential for sulfatase function (formation of L-$C_\alpha$-formylglycine; a.k.a. FGly and/or 2-amino-3-oxopropanoic acid). It has been discovered, unexpectedly, that mutations in the FGE gene lead to the development of Multiple Sulfatase Deficiency (MSD) in subjects. It has also been discovered, unexpectedly, that FGE enhances the activity of sulfatases, including, but not limited to, Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6. In view of these discoveries, the molecules of the present invention can be used in the diagnosis and treatment of Multiple Sulfatase Deficiency as well as other sulfatase deficiencies.

Methods for using the molecules of the invention in the diagnosis of Multiple Sulfatase Deficiency, are provided.

Additionally, methods for using these molecules in vivo or in vitro for the purpose of modulating FGly formation on sulfatases, methods for treating conditions associated with such modification, and compositions useful in the preparation of therapeutic preparations for the treatment of Multiple Sulfatase Deficiency, as well as other sulfatase deficiencies, are also provided.

The present invention thus involves, in several aspects, polypeptides modulating FGly formation on sulfatases, isolated nucleic acids encoding those polypeptides, functional modifications and variants of the foregoing, useful fragments of the foregoing, as well as therapeutics and diagnostics, research methods, compositions and tools relating thereto.

According to one aspect of the invention, an isolated nucleic acid molecule selected from the group consisting of: (a) nucleic acid molecules which hybridize under stringent conditions to a molecule consisting of a nucleotide sequence set forth as SEQ ID NO:1 and which code for a Formylglycine Generating Enzyme (FGE) polypeptide having $C_\alpha$-formylglycine generating activity, (b) nucleic acid molecules that differ from the nucleic acid molecules of (a) in codon sequence due to the degeneracy of the genetic code, and (c) complements of (a) or (b), is provided. In certain embodiments, the isolated nucleic acid molecule comprises the nucleotide sequence set forth as SEQ ID NO:1. In some embodiments, the isolated nucleic acid molecule consists of the nucleotide sequence set forth as SEQ ID NO:3 or a fragment thereof.

The invention in another aspect provides an isolated nucleic acid molecule selected from the group consisting of (a) unique fragments of a nucleotide sequence set forth as SEQ ID NO:1, and (b) complements of (a), provided that a unique fragment of (a) includes a sequence of contiguous nucleotides which is not identical to any sequence selected from the sequence group consisting of: (1) sequences identical to SEQ ID NO. 4 and/or nucleotides 20-1141 of SEQ ID NO. 4, and (2) complements of (1). In any of the foregoing embodiments, complements refer to full-length complements.

In one embodiment, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, and (6) at least seven contiguous nucleotides nonidentical to the sequence group.

In another embodiment, the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

According to another aspect, the invention provides expression vectors, and host cells transformed or transfected with such expression vectors, comprising the nucleic acid molecules described above.

According to still another aspect, the invention provides cells expressing activated forms of the endogenous FGE gene. In one embodiment, activation of the endogenous FGE gene occurs via homologous recombination.

According to another aspect of the invention, an isolated polypeptide is provided. The isolated polypeptide is encoded by the foregoing nucleic acid molecules of the invention. In some embodiments, the isolated polypeptide is encoded by the nucleic acid of SEQ ID NO:1, giving rise to a polypeptide having the sequence of SEQ ID NO:2 that has $C_\alpha$-formylglycine generating activity. In other embodiments, the isolated polypeptide may be a fragment or variant of the foregoing of sufficient length to represent a sequence unique within the human genome, and identifying with a polypeptide that has $C_\alpha$-formylglycine generating activity, provided that the fragment includes a sequence of contiguous amino acids which is not identical to any sequence encoded for by a nucleic acid sequence having SEQ ID NO. 4. In another embodiment, immunogenic fragments of the polypeptide molecules described above are provided. The immunogenic fragments may or may not have $C_\alpha$-formylglycine generating activity.

According to another aspect of the invention, isolated binding polypeptides are provided which selectively bind a polypeptide encoded by the foregoing nucleic acid molecules of the invention. Preferably the isolated binding polypeptides selectively bind a polypeptide which comprises the sequence of SEQ ID NO:2, fragments thereof, or a polypeptide belonging to the family of isolated polypeptides having $C_\alpha$-formylglycine generating activity described elsewhere herein. In preferred embodiments, the isolated binding polypeptides include antibodies and fragments of antibodies (e.g., Fab, $F(ab)_2$, Fd and antibody fragments which include a CDR3 region which binds selectively to the FGE polypeptide). In certain embodiments, the antibodies are human. In some embodiments, the antibodies are monoclonal antibodies. In one embodiment, the antibodies are polyclonal antisera. In further embodiments, the antibodies are humanized. In yet further embodiments, the antibodies are chimeric.

According to another aspect of the invention, a family of isolated polypeptides having $C_\alpha$-formylglycine generating activity, are provided. Each of said polypeptides comprises from amino terminus to carboxyl terminus: (a) an amino-terminal subdomain 1; a subdomain 2; a carboxy-terminal subdomain 3 containing from 35 to 45 amino acids; and wherein subdomain 3 has at least about 75% homology and a length approximately equal to subdomain 3 of a polypeptide selected from the group consisting of SEQ ID NO. 2, 5, 46, 48, 50, 52, 54, 56, 58, 60, 62, 64, 66, 68, 70, 72, 74, 76, and 78. In important embodiments, subdomain 2 contains from 120 to 140 amino acids. In further important embodiments, at least 5% of the amino acids of subdomain 2 are Tryptophans. In some embodiments, subdomain 2 has at least about 50% homology to subdomain 2 of a polypeptide selected from the group consisting of SEQ ID NO. 2, 5, 46, 48, 50, 52, 54, 56, 58, 60, 62, 64, 66, 68, 70, 72, 74, 76, and 78. In certain embodiments, subdomain 3 of each of the polypeptides has at least between about 80% and about 100% homology to subdomain 3 of a polypeptide selected from the group consisting of SEQ ID NO. 2, 5, 46, 48, 50, 52, 54, 56, 58, 60, 62, 64, 66, 68, 70, 72, 74, 76, and 78.

According to a further aspect of the invention, a method for determining the level of FGE expression in a subject, is provided. The method involves measuring expression of FGE in a test sample from a subject to determine the level of FGE expression in the subject. In certain embodiments, the measured FGE expression in the test sample is compared to FGE expression in a control containing a known level of FGE expression. Expression is defined as FGE mRNA expression, FGE polypeptide expression, or FGE $C_\alpha$-formylglycine generating activity as defined elsewhere herein. Various methods can be used to measure expression. Preferred embodiments of the invention include PCR and Northern blotting for measuring mRNA expression, FGE monoclonal antibodies or FGE polyclonal antisera as reagents to measure FGE polypeptide expression, as well as methods for measuring FGE $C_\alpha$-formylglycine generating activity.

In certain embodiments, test samples such as biopsy samples, and biological fluids such as blood, are used as test samples. FGE expression in a test sample of a subject is compared to FGE expression in control.

According to another aspect of the invention, a method for identifying an agent useful in modulating $C_\alpha$-formylglycine generating activity of a molecule, is provided. The method involves (a) contacting a molecule having $C_\alpha$-formylglycine generating activity with a candidate agent, (b) measuring $C_\alpha$-formylglycine generating activity of the molecule, and (c) comparing the measured $C_\alpha$-formylglycine generating activity of the molecule to a control to determine whether the candidate agent modulates $C_\alpha$-formylglycine generating activity of the molecule, wherein the molecule is a nucleic acid molecule having the nucleotide sequence selected from the group consisting of SEQ ID NO: 1, 3, 4, 45, 47, 49, 51, 53, 55, 57, 59, 61, 63, 65, 67, 69, 71, 73, 75, 77, and 80-87, or an expression product thereof (e.g., a peptide having a sequence selected from the group consisting of SEQ ID NO. 2, 5, 46, 48, 50, 52, 54, 56, 58, 60, 62, 64, 66, 68, 70, 72, 74, 76, and 78). In certain embodiments, the control is $C_\alpha$-formylglycine generating activity of the molecule measured in the absence of the candidate agent.

According to still another aspect of the invention, a method of diagnosing Multiple Sulfatase Deficiency in a subject, is provided. The method involves contacting a biological sample from a subject suspected of having Multiple Sulfatase Deficiency with an agent, said agent specifically binding to a molecule selected from the group consisting of: (i) a FGE nucleic acid molecule having the nucleotide sequence of SEQ ID NO:1, 3, or 4, (ii) an expression product of the nucleic acid molecule of (i), or (iii) a fragment of the expression product of (ii); and measuring the amount of bound agent and determining therefrom if the expression of said nucleic acid molecule or of an expression product thereof is aberrant, aberrant expression being diagnostic of the Multiple Sulfatase Deficiency in the subject.

According to still another aspect of the invention, a method for diagnosing a condition characterized by aberrant expression of a nucleic acid molecule or an expression product thereof, is provided. The method involves contacting a biological sample from a subject with an agent, wherein said agent specifically binds to said nucleic acid molecule, an expression product thereof, or a fragment of an expression product thereof; and measuring the amount of bound agent and determining therefrom if the expression of said nucleic acid molecule or of an expression product thereof is aberrant, aberrant expression being diagnostic of the condition, wherein the nucleic acid molecule has the nucleotide sequence of SEQ ID NO:1 and the condition is Multiple Sulfatase Deficiency.

According to another aspect of the invention, a method for determining Multiple Sulfatase Deficiency in a subject characterized by aberrant expression of a nucleic acid molecule or an expression product thereof, is provided. The method involves monitoring a sample from a patient for a parameter selected from the group consisting of (i) a nucleic acid molecule having the nucleotide sequence of SEQ ID NO:1, 3, 4, or a nucleic acid molecule having a sequence derived from the FEG genomic locus, (ii) a polypeptide encoded by the nucleic acid molecule, (iii) a peptide derived from the polypeptide, and (iv) an antibody which selectively binds the polypeptide or peptide, as a determination of Multiple Sulfatase Deficiency in the subject. In some embodiments, the sample is a biological fluid or a tissue as described in any of the foregoing embodiments. In certain embodiments the step of monitoring comprises contacting the sample with a detectable agent selected from the group consisting of (a) an isolated nucleic acid molecule which selectively hybridizes under stringent conditions to the nucleic acid molecule of (i), (b) an antibody which selectively binds the polypeptide of (ii), or the peptide of (iii), and (c) a polypeptide or peptide which binds the antibody of (iv). The antibody, polypeptide, peptide, or nucleic acid can be labeled with a radioactive label or an enzyme. In further embodiments, the method further comprises assaying the sample for the peptide.

According to another aspect of the invention, a kit is provided. The kit comprises a package containing an agent that selectively binds to any of the foregoing FGE isolated nucleic acids, or expression products thereof, and a control for comparing to a measured value of binding of said agent any of the foregoing FGE isolated nucleic acids or expression products thereof. In some embodiments, the control is a predetermined value for comparing to the measured value. In certain embodiments, the control comprises an epitope of the expression product of any of the foregoing FGE isolated nucleic acids. In one embodiment, the kit further comprises a second agent that selectively binds to a polypeptide selected from the group consisting of Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6, or a peptide thereof, and a control for comparing to a measured value of binding of said second agent to said polypeptide or peptide thereof.

According to a further aspect of the invention, a method of treating Multiple Sulfatase Deficiency, is provided. The method involves administering to a subject in need of such treatment an agent that modulates $C_\alpha$-formylglycine generating activity, in an amount effective to treat Multiple Sulfatase Deficiency in the subject. In some embodiments, the method further comprises co-administering an agent selected from the group consisting of a nucleic acid molecule encoding Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, or HSulf-6, an expression product of the nucleic acid molecule, and a fragment of the expression product of the nucleic acid molecule. In certain embodiments, the agent that modulates $C_\alpha$-formylglycine generating activity is an isolated nucleic acid molecule of the invention (e.g., a nucleic acid molecule as claimed in claims 1-8, or a nucleic acid having a sequence selected from the group consisting of SEQ ID NO:1, 3, 4, 45, 47, 49, 51, 53, 55, 57, 59, 61, 63, 65, 67, 69, 71, 73, 75, 77, and 80-87). In important embodiments, the agent that modulates $C_\alpha$-formylglycine generating activity is a peptide of the invention (e.g., a peptide as claimed in claims 11-15, 19, 20, or a peptide having a sequence selected from the group consisting of SEQ ID NO. 2, 5, 46, 48, 50, 52, 54, 56, 58, 60, 62, 64, 66, 68, 70, 72, 74, 76, and 78). The agent that modulates $C_\alpha$-formylglycine generating activity may be produced by a cell expressing an endogenous and/or exogenous FGE nucleic acid molecule. In important embodiments, the endogenous FGE nucleic acid molecule may be activated.

According to one aspect of the invention, a method for for increasing $C_\alpha$-formylglycine generating activity in a subject, is provided. The method involves administering an isolated FGE nucleic acid molecule of the invention (e.g., a nucleic acid molecule as claimed in claims 1-8, or a nucleic acid having a sequence selected from the group consisting of SEQ ID NO: 1, 3, 4, 45, 47, 49, 51, 53, 55, 57, 59, 61, 63, 65, 67, 69, 71, 73, 75, 77, and 80-87), and/or an expression product thereof, to a subject, in an amount effective to increase $C_\alpha$-formylglycine generating activity in the subject.

According to one aspect of the invention, a method for treating a subject with Multiple Sulfatase Deficiency, is provided. The method involves administering to a subject in need of such treatment an agent that modulates $C_\alpha$-formylglycine generating activity, in an amount effective to increase $C_\alpha$-formylglycine generating activity in the subject. In some embodiments, the agent that modulates $C_\alpha$-formylglycine generating activity is a sense nucleic acid of the invention (e.g., a nucleic acid molecule as claimed in claims 1-8, or a nucleic acid having a sequence selected from the group consisting of SEQ ID NO: 1, 3, 4, 45, 47, 49, 51, 53, 55, 57, 59, 61, 63, 65, 67, 69, 71, 73, 75, 77, and 80-87). In certain embodiments, the agent that modulates $C_\alpha$-formylglycine generating activity is an isolated polypeptide of the invention (e.g., a polypeptide as claimed in claims 11-15, 19, 20, or a peptide having a sequence selected from the group consisting of SEQ ID NO. 2, 5, 46, 48, 50, 52, 54, 56, 58, 60, 62, 64, 66, 68, 70, 72, 74, 76, and 78).

According to still another aspect of the invention, a method for increasing $C_\alpha$-formylglycine generating activity in a cell, is provided. The method involves contacting the cell with an isolated nucleic acid molecule of the invention (e.g., a nucleic acid molecule as claimed in claims 1-8, or a nucleic acid having a sequence selected from the group consisting of SEQ ID NO: 1, 3, 4, 45, 47, 49, 51, 53, 55, 57, 59, 61, 63, 65, 67, 69, 71, 73, 75, 77, and 80-87), or an expression product thereof, in an amount effective to increase $C_\alpha$-formylglycine generating activity in the cell. In important embodiments, the method involves activating the endogenous FGE gene to increase $C_\alpha$-formylglycine generating activity in the cell.

According to a further aspect of the invention, a pharmaceutical composition is provided. The composition comprises an agent comprising an isolated nucleic acid molecule of the invention (e.g., an isolated nucleic acid molecule as claimed in any one of claims 1-8, an FGE nucleic acid molecule having a sequence selected from the group consisting of SEQ ID NO: 1, 3, 4, 45, 47, 49, 51, 53, 55, 57, 59, 61, 63, 65, 67, 69, 71, 73, 75, 77, and 80-87), or an expression product thereof, in a pharmaceutically effective amount to treat Multiple Sulfatase Deficiency, or an expression product thereof, in a pharmaceutically effective amount to treat Multiple Sulfatase Deficiency, and a pharmaceutically acceptable carrier.

According to one aspect of the invention, a method for identifying a candidate agent useful in the treatment of Multiple Sulfatase Deficiency, is provided. The method involves determining expression of a set of nucleic acid molecules in a cell or tissue under conditions which, in the absence of a candidate agent, permit a first amount of expression of the set of nucleic acid molecules, wherein the set of nucleic acid molecules comprises at least one nucleic acid molecule selected from the group consisting of: (a) nucleic acid molecules which hybridize under stringent conditions to a molecule consisting of a nucleotide sequence set forth as SEQ ID NO:1 and which code for a polypeptide having $C_\alpha$-formylglycine generating activity (FGE), (b) nucleic acid molecules that differ from the nucleic acid molecules of (a) or (b) in codon sequence due to the degeneracy of the genetic code, (c) a nucleic acid molecule having a sequence selected from the group consisting of SEQ ID NO: 1, 3, 4, 45, 47, 49, 51, 53, 55, 57, 59, 61, 63, 65, 67, 69, 71, 73, 75, 77, and 80-87), and (d) complements of (a) or (b) or (c), contacting the cell or tissue with the candidate agent, and detecting a test amount of expression of the set of nucleic acid molecules, wherein an increase in the test amount of expression in the presence of the candidate agent relative to the first amount of expression indicates that the candidate agent is useful in the treatment of the Multiple Sulfatase Deficiency.

According to a further aspect of the invention, methods for preparing medicaments useful in the treatment of Multiple Sulfatase Deficiency and/or other sulfatase deficiencies, are provided.

According to still another aspect of the invention, a solid-phase nucleic acid molecule array, is provided. The array consists essentially of a set of nucleic acid molecules, expression products thereof, or fragments (of either the nucleic acid or the polypeptide molecule) thereof, each nucleic acid molecule encoding for a polypeptide selected from the group consisting of SEQ ID NO. 2, 5, 46, 48, 50, 52, 54, 56, 58, 60, 62, 64, 66, 68, 70, 72, 74, 76, and 78, Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6, fixed to a solid substrate. In some embodiments, the solid-phase array further comprises at least one control nucleic acid molecule. In certain embodiments, the set of nucleic acid molecules comprises at least one, at least two, at least three, at least four, or even at least five nucleic acid molecules, each selected from the group consisting of SEQ ID NO. 2, 5, 46, 48, 50, 52, 54, 56, 58, 60, 62, 64, 66, 68, 70, 72, 74, 76, and 78, Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6.

According to a further aspect of the invention, a method for treating a sulfatase deficiency in a subject, is provided. The method involves administering to a subject in need of such treatment a sulfatase that has been produced according to the invention, in an amount effective to treat the sulfatase deficiency in the subject and the sulfatase deficiency is not Multiple Sulfatase Deficiency. In important embodiments, the sulfatase is produced by a cell that has been contacted with an an agent that modulates $C_\alpha$-formylglycine generating activity. In certain embodiments, the sulfatase deficiency includes, but is not limited to, Mucopolysaccharidosis II (MPS II; Hunter Syndrome), Mucopolysaccharidosis IIIA (MPS IIIA; Sanfilippo Syndrome A), Mucopolysaccharidosis VIII (MPS VIII), Mucopolysaccharidosis IVA (MPS IVA; Morquio Syndrome A), Mucopolysaccharidosis VI (MPS VI; Maroteaux-Lamy Syndrome), Metachromatic Leukodystrophy (MLD), X-linked Recessive Chondrodysplasia Punctata 1, or X-linked Ichthyosis (Steroid Sulfatase Deficiency). In certain embodiments, the agent that modulates $C_\alpha$-formylglycine generating activity can be a nucleic acid molecule or peptide of the invention. In one embodiment, the sulfatase and the agent that modulates $C_\alpha$-formylglycine generating activity are co-expressed in the same cell. The sulfatase and/or the agent that modulates $C_\alpha$-formylglycine generating activity can be endogenous or exogenous in origin. If endogenous in origin it can be activated (e.g., by insertion of strong promoter and/or other elements at the appropriates places known in the art). If exogenous, its expression can be driven by elements on the expression vector, or it can be targeted to appropriated places within the cell genome that will allow for its enhanced expression (e.g., downstream of a strong promoter).

According to another aspect of the invention, a pharmaceutical composition, is provided. The composition comprises an agent comprising an isolated nucleic acid molecule of the invention, or an expression product thereof, in a pharmaceutically effective amount to treat a sulfatase deficiency, and a pharmaceutically acceptable carrier.

According to a still further aspect of the invention, a method for increasing sulfatase activity in a cell, is provided. The method involves contacting a cell expressing a sulfatase with an isolated nucleic acid molecule of of the invention (e.g., an isolated nucleic acid molecule as claimed in any one of claims 1-8, an FGE nucleic acid molecule having a sequence selected from the group consisting of SEQ ID NO: 1, 3, 4, 45, 47, 49, 51, 53, 55, 57, 59, 61, 63, 65, 67, 69, 71, 73, 75, 77, and 80-87), or an expression product thereof (e.g., a polypeptide as claimed in claims 11-15, 19, 20, or a peptide having a sequence selected from the group consisting of SEQ ID NO. 2, 5, 46, 48, 50, 52, 54, 56, 58, 60, 62, 64, 66, 68, 70, 72, 74, 76, and 78), in an amount effective to increase sulfatase activity in the cell. The cell may express an endogenous and/or an exogenous sulfatase. In important embodiments, the endogenous sulfatase is activated. In certain embodiments, the sulfatase is Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and/or HSulf-6. In certain embodiments the cell is a mammalian cell.

According to another aspect of the invention, a pharmaceutical composition, is provided. The composition comprises a sulfatase that is produced by cell, in a pharmaceutically effective amount to treat a sulfatase deficiency, and a pharmaceutically acceptable carrier, wherein said cell has been contacted with an agent comprising an isolated nucleic acid molecule of the invention (e.g., as claimed in claims 1-8, or a nucleic acid molecule having a sequence selected from the group consisting of SEQ ID NO: 1, 3, 4, 45, 47, 49, 51, 53, 55, 57, 59, 61, 63, 65, 67, 69, 71, 73, 75, 77, and 80-87), or an expression product thereof (e.g., a peptide selected from the group consisting of SEQ ID NO. 2, 5, 46, 48, 50, 52, 54, 56, 58, 60, 62, 64, 66, 68, 70, 72, 74, 76, and 78).

According to still another aspect of the invention, an isolated variant allele of a human FGE gene which encodes a variant FGE polypeptide, is provided. The isolated variant allele comprises an amino acid sequence comprising at least one variation in SEQ ID NO:2, wherein the at least one variation comprises: Met1Arg; Met1Val; Leu20Phe; Ser155Pro; Ala177Pro; Cys218Tyr; Arg224Trp; Asn259Ile; Pro266Leu; Ala279Val; Arg327Stop; Cys336Arg; Arg345Cys; Ala348Pro; Arg349Gln; Arg349Trp; Arg349Trp; Ser359Stop; or a combination thereof.

According to yet another aspect of the invention, an isolated variant human FGE polypeptide, is provided. The isolated variant human FGE polypeptide comprises an amino acid sequence comprising at least one variation in SEQ ID NO:2, wherein the at least one variation comprises: Met1Arg; Met1Val; Leu20Phe; Ser155Pro; Ala177Pro; Cys218Tyr; Arg224Trp; Asn259Ile; Pro266Leu; Ala279Val; Arg327Stop; Cys336Arg; Arg345Cys; Ala348Pro; Arg349Gln; Arg349Trp; Arg349Trp; Ser359Stop; or a combination thereof.

Antibodies having any of the foregoing variant human FGE polypeptides as an immunogen are also provided. Such antibodies include polyclonal antisera, monoclonal, chimeric, and can also be detectably labeled. A detectable label may comprise a radioactive element, a chemical which fluoresces, or an enzyme.

According to another aspect of the invention, a sulfatase-producing cell wherein the ratio of active sulfatase to total sulfatase produced by the cell is increased, is provided. The cell comprises: (i) a sulfatase with an increased expression, and (ii) a Formylglycine Generating Enzyme with an increased expression, wherein the ratio of active sulfatase to total sulfatase (i.e., the specific activity of the sulfatase) produced by the cell is increased by at least 5% over the ratio of active sulfatase to total sulfatase produced by the cell in the absence of the Formylglycine Generating Enzyme. In certain embodiments, the ratio of active sulfatase to total sulfatase produced by the cell is increased by at least 10%, 15%, 20%, 50%, 100%, 200%, 500%, 1000%, over the ratio of active sulfatase to total sulfatase produced by the cell in the absence of the Formylglycine Generating Enzyme.

According to a further aspect of the invention, an improved method for treating a sulfatase deficiency in a subject is provided. The method involves administering to a subject in need of such treatment a sulfatase in an effective amount to treat the sulfatase deficiency in the subject, wherein the sulfatase is contacted with a Formylglycine Generating Enzyme in an amount effective to increase the specific activity of the sulfatase. In an important embodiment, the sulfatase is selected from the group consisting of Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6. In certain embodiments, the Formylglycine Generating Enzyme is encoded by a nucleic acid molecule as claimed in claims 1-8, or a nucleic acid having a sequence selected from the group consisting of SEQ ID NO:1, 3, 4, 45, 47, 49, 51, 53, 55, 57, 59, 61, 63, 65, 67, 69, 71, 73, 75, 77, and 80-87. In some embodiments, the Formylglycine Generating Enzyme is a peptide as claimed in claims 11-15, 19, 20, or a peptide having a sequence selected from the group consisting of SEQ ID NO. 2, 5, 46, 48, 50, 52, 54, 56, 58, 60, 62, 64, 66, 68, 70, 72, 74, 76, and 78.

These and other objects of the invention will be described in further detail in connection with the detailed description of the invention.

BRIEF DESCRIPTION OF THE SEQUENCES

SEQ ID NO:1 is the nucleotide sequence of the human FGE cDNA.

SEQ ID NO:2 is the predicted amino acid sequence of the translation product of human FGE cDNA (SEQ ID NO:1).

SEQ ID NO:3 is the nucleotide sequence of the human FGE cDNA encoding the polypeptide of SEQ ID NO:2 (i.e., nucleotides 20-1141 of SEQ ID NO:1).

SEQ ID NO:4 is the nucleotide sequence of GenBank Acc. No. AK075459.

SEQ ID NO:5 is the predicted amino acid sequence of the translation product of SEQ ID NO:4, an unnamed protein product having GenBank Acc. No. BAC11634.

SEQ ID NO:6 is the nucleotide sequence of the human Iduronate 2-Sulfatase cDNA (GenBank Acc. No. M58342).

SEQ ID NO:7 is the predicted amino acid sequence of the translation product of human Iduronate 2-Sulfatase cDNA (SEQ ID NO:6).

SEQ ID NO:8 is the nucleotide sequence of the human Sulfamidase cDNA (GenBank Acc. No. U30894).

SEQ ID NO:9 is the predicted amino acid sequence of the translation product of human Sulfamidase cDNA (SEQ ID NO:8).

SEQ ID NO:10 is the nucleotide sequence of the human N-Acetylgalactosamine 6-Sulfatase cDNA (GenBank Acc. No. U06088).

SEQ ID NO:11 is the predicted amino acid sequence of the translation product of human N-Acetylgalactosamine 6-Sulfatase cDNA (SEQ ID NO:10).

SEQ ID NO:12 is the nucleotide sequence of the human N-Acetylglucosamine 6-Sulfatase cDNA (GenBank Acc. No. Z12173).

SEQ ID NO:13 is the predicted amino acid sequence of the translation product of human N-Acetylglucosamine 6-Sulfatase cDNA (SEQ ID NO:12).

SEQ ID NO:14 is the nucleotide sequence of the human Arylsulfatase A cDNA (GenBank Acc. No. X52151).

SEQ ID NO:15 is the predicted amino acid sequence of the translation product of human Arylsulfatase A cDNA (SEQ ID NO:14).

SEQ ID NO:16 is the nucleotide sequence of the human Arylsulfatase B cDNA (GenBank Acc. No. J05225).

SEQ ID NO:17 is the predicted amino acid sequence of the translation product of human Arylsulfatase B cDNA (SEQ ID NO:16).

SEQ ID NO:18 is the nucleotide sequence of the human Arylsulfatase C cDNA (GenBank Acc. No. J04964).

SEQ ID NO:19 is the predicted amino acid sequence of the translation product of human Arylsulfatase C cDNA (SEQ ID NO:18).

SEQ ID NO:20 is the nucleotide sequence of the human Arylsulfatase D cDNA (GenBank Acc. No. X83572).

SEQ ID NO:21 is the predicted amino acid sequence of the translation product of human Arylsulfatase D cDNA (SEQ ID NO:20).

SEQ ID NO:22 is the nucleotide sequence of the human Arylsulfatase E cDNA (GenBank Acc. No. X83573).

SEQ ID NO:23 is the predicted amino acid sequence of the translation product of human Arylsulfatase E cDNA (SEQ ID NO:22).

SEQ ID NO:24 is the nucleotide sequence of the human Arylsulfatase F cDNA (GenBank Acc. No. X97868).

SEQ ID NO:25 is the predicted amino acid sequence of the translation product of human Arylsulfatase F cDNA (SEQ ID NO:24).

SEQ ID NO:26 is the nucleotide sequence of the human Arylsulfatase G cDNA (GenBank Acc. No. BC012375).

SEQ ID NO:27 is the predicted amino acid sequence of the translation product of the human Arylsulfatase G (SEQ ID NO:26).

SEQ ID NO:28 is the nucleotide sequence of the HSulf-1 cDNA (GenBank Acc. No. AY101175).

SEQ ID NO:29 is the predicted amino acid sequence of the translation product of HSulf-1 cDNA (SEQ ID NO:28).

SEQ ID NO:30 is the nucleotide sequence of the HSulf-2 cDNA (GenBank Acc. No. AY101176).

SEQ ID NO:31 is the predicted amino acid sequence of the translation product of HSulf-2 cDNA (SEQ ID NO:30).

SEQ ID NO:32 is the highly conserved hexapeptide L/V-FGly-X-P-S-R present on sulfatases.

SEQ ID NO:33 is a synthetic FGly formation substrate; its primary sequence is derived from human Arylsulfatase A.

SEQ ID NO:34 is scrambled oligopeptide PVSLPTRSCAALLTGR.

SEQ ID NO:35 is Ser69 oligopeptide PVSLSTPSRAALLTGR.

SEQ ID NO:36 is human FGE-specific primer 1199nc.

SEQ ID NO:37 is human FGE-specific forward primer 1c.

SEQ ID NO:38 is human FGE-specific reverse primer 1182c.

SEQ ID NO:39 is human 5'-FGE-specific primer containing EcoRI site.

SEQ ID NO:40 is a HA-specific primer.

SEQ ID NO:41 is a c-myc-specific primer.

SEQ ID NO:42 is a RGS-$His_6$-specific primer.

SEQ ID NO:43 is tryptic oligopeptide SQNTPDSSASNLGFR from a human FGE preparation.

SEQ ID NO:44 is tryptic oligopeptide MVPIPAGVFTMGTDDPQIK from a human FGE preparation.

SEQ ID NO:45 is the nucleotide sequence of the human FGE2 paralog (GenBank GI: 24308053).

SEQ ID NO:46 is the predicted amino acid sequence of the translation product of the human FGE2 paralog (SEQ ID NO:45).

SEQ ID NO:47 is the nucleotide sequence of the mouse FGE paralog (GenBank GI: 26344956).

SEQ ID NO:48 is the predicted amino acid sequence of the translation product of the mouse FGE paralog (SEQ ID NO:47).

SEQ ID NO:49 is the nucleotide sequence of the mouse FGE ortholog (GenBank GI: 22122361).

SEQ ID NO:50 is the predicted amino acid sequence of the translation product of the mouse FGE ortholog (SEQ ID NO:49).

SEQ ID NO:51 is the nucleotide sequence of the fruitfly FGE ortholog (GenBank GI: 20130397).

SEQ ID NO:52 is the predicted amino acid sequence of the translation product of the fruitfly FGE ortholog (SEQ ID NO:51).

SEQ ID NO:53 is the nucleotide sequence of the mosquito FGE ortholog (GenBank GI: 21289310).

SEQ ID NO:54 is the predicted amino acid sequence of the translation product of the mosquito FGE ortholog (SEQ ID NO:53).

SEQ ID NO:55 is the nucleotide sequence of the closely related *S. coelicolor* FGE ortholog (GenBank GI: 21225812).

SEQ ID NO:56 is the predicted amino acid sequence of the translation product of the *S. coelicolor* FGE ortholog (SEQ ID NO:55).

SEQ ID NO:57 is the nucleotide sequence of the closely related *C. efficiens* FGE ortholog (GenBank GI: 25028125).

SEQ ID NO:58 is the predicted amino acid sequence of the translation product of the *C. efficiens* FGE ortholog (SEQ ID NO:57).

SEQ ID NO:59 is the nucleotide sequence of the *N. aromaticivorans* FGE ortholog (GenBank GI: 23108562).

SEQ ID NO:60 is the predicted amino acid sequence of the translation product of the *N. aromaticivorans* FGE ortholog (SEQ ID NO:59).

SEQ ID NO:61 is the nucleotide sequence of the *M. loti* FGE ortholog (GenBank GI: 13474559).

SEQ ID NO:62 is the predicted amino acid sequence of the translation product of the *M. loti* FGE ortholog (SEQ ID NO:61).

SEQ ID NO:63 is the nucleotide sequence of the *B. fungorum* FGE ortholog (GenBank GI: 22988809).

SEQ ID NO:64 is the predicted amino acid sequence of the translation product of the *B. fungorum* FGE ortholog (SEQ ID NO:63).

SEQ ID NO:65 is the nucleotide sequence of the *S. meliloti* FGE ortholog (GenBank GI:16264068).

SEQ ID NO:66 is the predicted amino acid sequence of the translation product of the *S. meliloti* FGE ortholog (SEQ ID NO:65).

SEQ ID NO:67 is the nucleotide sequence of the *Microscilla* sp. FGE ortholog (GenBank GI: 14518334).

SEQ ID NO:68 is the predicted amino acid sequence of the translation product of the *Microscilla* sp. FGE ortholog (SEQ ID NO:67).

SEQ ID NO:69 is the nucleotide sequence of the *P. putida* KT2440 FGE ortholog (GenBank GI: 26990068).

SEQ ID NO:70 is the predicted amino acid sequence of the translation product of the *P. putida* KT2440 FGE ortholog (SEQ ID NO:69).

SEQ ID NO:71 is the nucleotide sequence of the *R. metallidurans* FGE ortholog (GenBank GI: 22975289).

SEQ ID NO:72 is the predicted amino acid sequence of the translation product of the *R. metallidurans* FGE ortholog (SEQ ID NO:71).

SEQ ID NO:73 is the nucleotide sequence of the *P. marinus* FGE ortholog (GenBank GI: 23132010).

SEQ ID NO:74 is the predicted amino acid sequence of the translation product of the *P. marinus* FGE ortholog (SEQ ID NO:73).

SEQ ID NO:75 is the nucleotide sequence of the *C. crescentus* CB15 FGE ortholog (GenBank GI: 16125425).

SEQ ID NO:76 is the predicted amino acid sequence of the translation product of the *C. crescentus* CB15 FGE ortholog (SEQ ID NO:75).

SEQ ID NO:77 is the nucleotide sequence of the *M. tuberculosis* Ht37Rv FGE ortholog (GenBank GI: 15607852).

SEQ ID NO:78 is the predicted amino acid sequence of the translation product of the *M. tuberculosis* Ht37Rv FGE ortholog (SEQ ID NO:77).

SEQ ID NO:79 is the highly conserved heptapeptide present on subdomain 3 of FGE orthologs and paralogs.

SEQ ID NO:80 is the nucleotide sequence of FGE ortholog EST fragment having GenBank Acc. No.: CA379852.

SEQ ID NO:81 is the nucleotide sequence of FGE ortholog EST fragment having GenBank Acc. No.: AI721440.

SEQ ID NO:82 is the nucleotide sequence of FGE ortholog EST fragment having GenBank Acc. No.: BJ505402.

SEQ ID NO:83 is the nucleotide sequence of FGE ortholog EST fragment having GenBank Acc. No.: BJ054666.

SEQ ID NO:84 is the nucleotide sequence of FGE ortholog EST fragment having GenBank Acc. No.: AL892419.

SEQ ID NO:85 is the nucleotide sequence of FGE ortholog EST fragment having GenBank Acc. No.: CA064079.

SEQ ID NO:86 is the nucleotide sequence of FGE ortholog EST fragment having GenBank Acc. No.: BF189614.

SEQ ID NO:87 is the nucleotide sequence of FGE ortholog EST fragment having GenBank Acc. No.: AV609121.

SEQ ID NO:88 is the nucleotide sequence of the HSulf-3 cDNA.

SEQ ID NO:89 is the predicted amino acid sequence of the translation product of HSulf-3 cDNA (SEQ ID NO:88).

SEQ ID NO:90 is the nucleotide sequence of the HSulf-4 cDNA.

SEQ ID NO:91 is the predicted amino acid sequence of the translation product of HSulf-4 cDNA (SEQ ID NO:90).

SEQ ID NO:92 is the nucleotide sequence of the HSulf-5 cDNA.

SEQ ID NO:93 is the predicted amino acid sequence of the translation product of HSulf-5 cDNA (SEQ ID NO:92).

SEQ ID NO:94 is the nucleotide sequence of the HSulf-6 cDNA.

SEQ ID NO:95 is the predicted amino acid sequence of the translation product of HSulf-6 cDNA (SEQ ID NO:94).

DETAILED DESCRIPTION OF THE INVENTION

Figure 1:
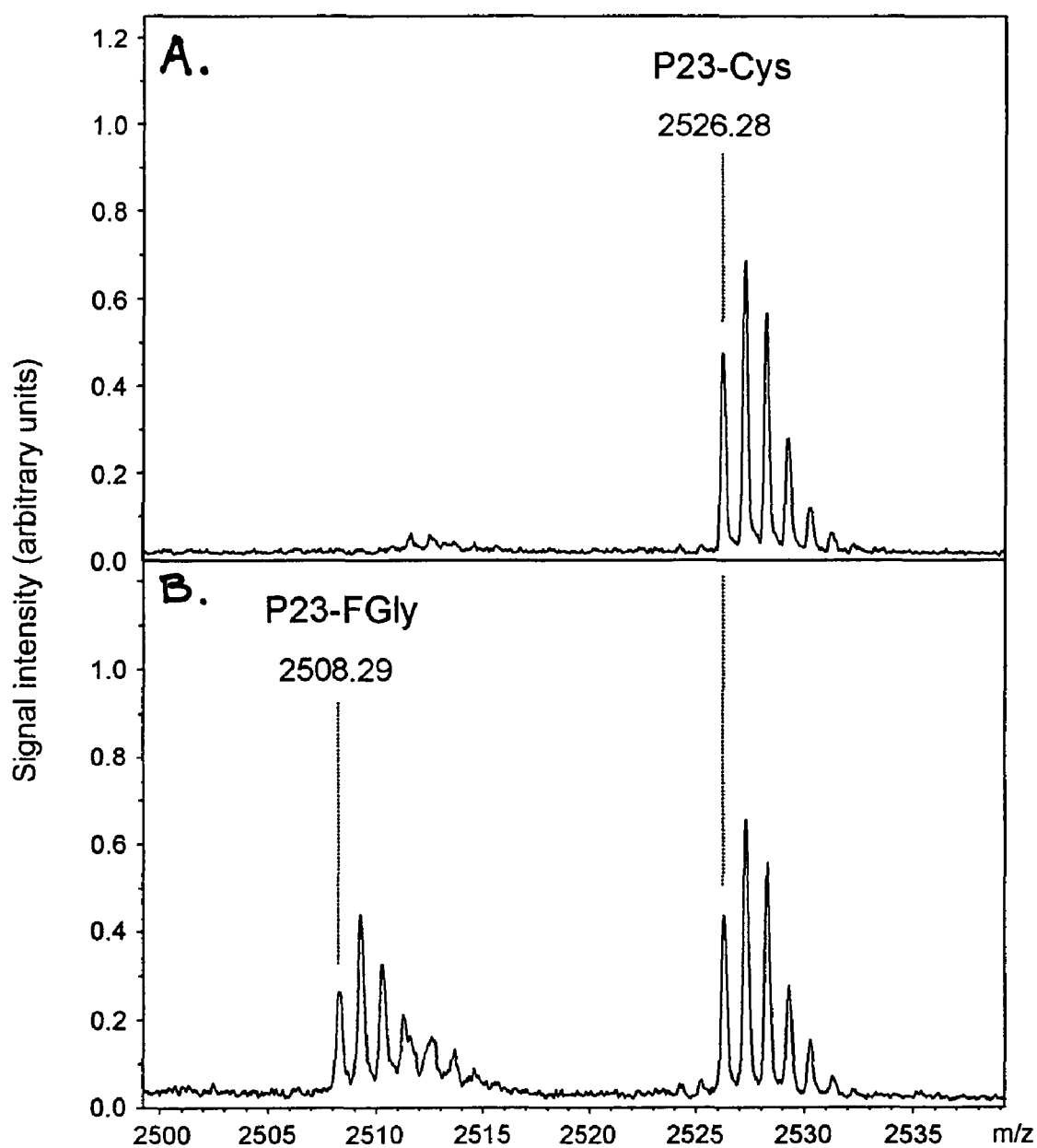
FIG. 1: A MALDI-TOF mass spectra schematic of P23 after incubation in the absence (A) or presence (B) of a soluble extract from bovine testis microsomes.

The invention involves the discovery of the gene that encodes Formylglycine Generating Enzyme (FGE), an enzyme responsible for the unique post-translational modification occurring on sulfatases that is essential for sulfatase function: the formation of L-$C_\alpha$-formylglycine (a.k.a. FGly and/or 2-amino-3-oxopropanoic acid). It has been discovered, unexpectedly, that mutations in the FGE gene lead to the development of Multiple Sulfatase Deficiency (MSD) in subjects. It has also been discovered, unexpectedly, that FGE enhances the activity of sulfatases, including, but not limited to, Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6, and sulfatases described in U.S. Provisional applications with publication numbers 20030073118, 20030147875, 20030148920, 20030162279, and 20030166283 (the contents of which are expressly incorporated herein). In view of these discoveries, the molecules of the present invention can be used in the diagnosis and/or treatment of Multiple Sulfatase Deficiency, as well as the treatment of other sulfatase deficiencies.

Methods for using the molecules of the invention in the diagnosis of Multiple Sulfatase Deficiency are provided.

Additionally, methods for using these molecules in vivo or in vitro for the purpose of modulating FGly formation on sulfatases, methods for treating conditions associated with such modification, and compositions useful in the preparation of therapeutic preparations for the treatment of Multiple Sulfatase Deficiency as well as other sulfatase deficiencies, are also provided.

The present invention thus involves, in several aspects, polypeptides modulating FGly formation on sulfatases, isolated nucleic acids encoding those polypeptides, functional modifications and variants of the foregoing, useful fragments of the foregoing, as well as therapeutics and diagnostics, research methods, compositions and tools relating thereto.

"$C_\alpha$-formylglycine generating activity" refers to the ability of a molecule to form, or enhance the formation of, FGly on a substrate. The substrate may be a sulfatase as described elsewhere herein, or a synthetic oligopeptide (see, e.g., SEQ ID NO:33, and the Examples). The substrate preferably contains the conserved hexapeptide of SEQ ID NO:32 [L/V-C(S)-X-P-S-R]. Methods for assaying FGly formation are as described in the art (see, e.g., Dierks, T., et al., *Proc. Natl. Acad. Sci. U. S. A.*, 1997, 94:11963-11968), and elsewhere herein (see, e.g., the Examples). A "molecule," as used herein, embraces both "nucleic acids" and "polypeptides." FGE molecules are capable of forming, or enhancing/increasing formation of, FGly both in vivo and in vitro.

"Enhancing (or "increasing")" $C_\alpha$-formylglycine generating activity, as used herein, typically refers to increased expression of FGE and/or its encoded polypeptide. Increased expression refers to increasing (i.e., to a detectable extent) replication, transcription, and/or translation of any of the nucleic acids of the invention (FGE nucleic acids as described elsewhere herein), since upregulation of any of these processes results in concentration/amount increase of the polypeptide encoded by the gene (nucleic acid). Enhancing (or increasing) $C_\alpha$-formylglycine generating activity also refers to preventing or inhibiting FGE degradation (e.g., via increased ubiquitinization), downregulation, etc., resulting, for example, in increased or stable FGE molecule $t_{1/2}$ (half-life) when compared to a control. Downregulation or decreased expression refers to decreased expression of a gene and/or its encoded polypeptide. The upregulation or downregulation of gene expression can be directly determined by detecting an increase or decrease, respectively, in the level of mRNA for the gene (e.g, FGE), or the level of protein expression of the gene-encoded polypeptide, using any suitable means known to the art, such as nucleic acid hybridization or antibody detection methods, respectively, and in comparison to controls. Upregulation or downregulation of FGE gene expression can also be determined indirectly by detecting a change in $C_\alpha$-formylglycine generating activity.

"Expression," as used herein, refers to nucleic acid and/or polypeptide expression, as well as to activity of the polypeptide molecule (e.g., $C_\alpha$-formylglycine generating activity of the molecule).

One aspect of the invention involves the cloning of a cDNA encoding FGE. FGE according to the invention is an isolated nucleic acid molecule that comprises a nucleic acid molecule of SEQ ID NO:1, and codes for a polypeptide with $C_\alpha$-formylglycine generating activity. The sequence of the human FGE cDNA is presented as SEQ ID NO:1, and the predicted amino acid sequence of this cDNA's encoded protein product is presented as SEQ ID NO:2.

As used herein, a subject is a mammal or a non-human mammal. In all embodiments human FGE and human subjects are preferred.

The invention thus involves in one aspect an isolated FGE polypeptide, the cDNA encoding this polypeptide, functional modifications and variants of the foregoing, useful fragments of the foregoing, as well as diagnostics and therapeutics relating thereto.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulated by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulated by standard techniques known to those of ordinary skill in the art.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, (iii) for sequencing, (iv) as a therapeutic, etc.

According to the invention, isolated nucleic acid molecules that code for a FGE polypeptide having $C_\alpha$-formylglycine generating activity include: (a) nucleic acid molecules which hybridize under stringent conditions to a molecule consisting of a nucleic acid of SEQ ID NO:1 and which code for a FGE polypeptide having $C_\alpha$-formylglycine generating activity, (b) deletions, additions and substitutions of (a) which code for a respective FGE polypeptide having $C_\alpha$-formylglycine generating activity, (c) nucleic acid molecules that differ from the nucleic acid molecules of (a) or (b) in codon sequence due to the degeneracy of the genetic code, and (d) complements of (a), (b) or (c). "Complements," as used herein, includes "full-length complementary strands or 100% complementary strands of (a), (b) or (c).

Homologs and alleles of the FGE nucleic acids of the invention also having $C_\alpha$-formylglycine generating activity are encompassed by the present invention. Homologs, as described herein, include the molecules identified elsewhere herein (see e.g., SEQ ID NOs:4, 5, 45-78, and 80-87) i.e. orthologs and paralogs. Further homologs can be identified following the teachings of the present invention as well as by conventional techniques. Since the FGE homologs described herein all share $C_\alpha$-formylglycine generating activity, they can be used interchangeably with the human FGE molecule in all aspects of the invention.

Thus, an aspect of the invention is those nucleic acid sequences which code for FGE polypeptides and which hybridize to a nucleic acid molecule consisting of the coding region of SEQ ID NO:1, under stringent conditions. In an important embodiment, the term "stringent conditions," as used herein, refers to parameters with which the art is familiar. With nucleic acids, hybridization conditions are said to be stringent typically under conditions of low ionic strength and a temperature just below the melting temperature ($T_m$) of the DNA hybrid complex (typically, about 3° C. below the $T_m$ of the hybrid). Higher stringency makes for a more specific correlation between the probe sequence and the target. Stringent conditions used in the hybridization of nucleic acids are well known in the art and may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. An example of "stringent conditions" is hybridization at 65° C. in 6×SSC. Another example of stringent conditions is hybridization at 65° C. in hybridization buffer that consists of 3.5× SSC, 0.02% Ficoll, 0.02% polyvinyl pyrolidone, 0.02% Bovine Serum Albumin, 2.5 mM $NaH_2PO_4$[pH7], 0.5% SDS, 2 mM EDTA. (SSC is 0.15M sodium chloride/0.15M sodium citrate, pH7; SDS is sodium dodecyl sulphate; and EDTA is ethylenediaminetetracetic acid). After hybridization, the membrane upon which the DNA is transferred is washed at 2×SSC at room temperature and then at 0.1×SSC/0.1×SDS at temperatures up to 68° C. In a further example, an alternative to the use of an aqueous hybridization solution is the use of a formamide hybridization solution. Stringent hybridization conditions can thus be achieved using, for example, a 50% formamide solution and 42° C. There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of FGE nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:1 and SEQ ID NO:2, respectively, in some instances will share at least 50% nucleotide identity and/or at least 65% amino acid identity and in still other instances will share at least 60% nucleotide identity and/or at least 75% amino acid identity. In further instances, homologs and alleles typically will share at least 90%, 95%, or even 99% nucleotide identity and/or at least 95%, 98%, or even 99% amino acid identity to SEQ ID NO:1 and SEQ ID NO:2, respectively. The homology can be calculated using various, publicly available software tools developed by NCBI (Bethesda, Md.). Exemplary tools include the heuristic algorithm of Altschul S F, et al., (*J Mol Biol*, 1990, 215:403-410), also known as BLAST. Pairwise and ClustalW alignments (BLOSUM30 matrix setting) as well as Kyte-Doolittle hydropathic analysis can be obtained using public (EMBL, Heidelberg, Germany) and commercial (e.g., the MacVector sequence analysis software from Oxford Molecular Group/enetics Computer Group, Madison, Wis.). Watson-Crick complements of the foregoing nucleic acids also are embraced by the invention.

In screening for FGE related genes, such as homologs and alleles of FGE, a Southern blot may be performed using the foregoing conditions, together with a radioactive probe. After washing the membrane to which the DNA is finally transferred, the membrane can be placed against X-ray film or a phosphoimager plate to detect the radioactive signal.

Given the teachings herein of a full-length human FGE cDNA clone, other mammalian sequences such as the mouse cDNA clone corresponding to the human FGE gene can be isolated from a cDNA library, using standard colony hybridization techniques.

The invention also includes degenerate nucleic acids which include alternative codons to those present in the native materials. For example, serine residues are encoded by the codons TCA, AGT, TCC, TCG, TCT and AGC. Thus, it will be apparent to one of ordinary skill in the art that any of the serine-encoding nucleotide triplets may be employed to direct the protein synthesis apparatus, in vitro or in vivo, to incorporate a serine residue into an elongating FGE polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1 or SEQ ID NO:3 or complements of thereof. A unique fragment is one that is a 'signature' for the larger nucleic acid. For example, the unique fragment is long enough to assure that its precise sequence is not found in molecules within the human genome outside of the FGE nucleic acids defined above (and human alleles). Those of ordinary skill in the art may apply no more than routine procedures to determine if a fragment is unique within the human genome. Unique fragments, however, exclude fragments completely composed of the nucleotide sequences selected from the group consisting of SEQ ID NO:4, and/or other previously published sequences as of the filing date of this application.

A fragment which is completely composed of the sequence described in the foregoing GenBank deposits is one which does not include any of the nucleotides unique to the sequences of the invention. Thus, a unique fragment according to the invention must contain a nucleotide sequence other than the exact sequence of those in the GenBank deposits or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the FGE polypeptides, useful, for example, in the preparation of antibodies, immunoassays or therapeutic applications. Unique fragments further can be used as antisense molecules to inhibit the expression of FGE nucleic acids and polypeptides respectively.

As will be recognized by those skilled in the art, the size of the unique fragment will depend upon its conservancy in the genetic code. Thus, some regions of SEQ ID NO:1 or SEQ ID NO:3 and complements will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). Virtually any segment of the region of SEQ ID NO:1 beginning at nucleotide 1 and ending at nucleotide 1180, or SEQ ID NO:3 beginning at nucleotide 1 and ending at nucleotide 1122, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As mentioned above, the invention embraces antisense oligonucleotides that selectively bind to a nucleic acid molecule encoding a FGE polypeptide, to decrease FGE activity.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med*, 1995, 1(11):1116-1118; *Nat. Biotech.*, 1996, 14:840-844). Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5): 439-457, 1994) and at which proteins are not expected to bind. Finally, although, SEQ ID No: 1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO:1. Similarly, antisense to allelic or homologous FGE cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding FGE polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves methods for increasing $C_\alpha$-formylglycine generating activity in a cell. In important embodiments, this is accomplished by the use of vectors ("expression vectors" and/or "targeting vectors").

"Vectors," as used herein, may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An "expression vector" is one into which a desired DNA sequence (e.g., the FGE cDNA of SEQ ID NO:3) may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein).

A "targeting vector" is one which typically contains targeting constructs/sequences that are used, for example, to insert a regulatory sequence within an endogenous gene (e.g., within the sequences of an exon and/or intron), within the endogenous gene promoter sequences, or upstream of the endogenous gene promoter sequences. In another example, a targeting vector may contain the gene of interest (e.g., encoded by the cDNA of SEQ ID NO:1) and other sequences necessary for the targeting of the gene to a preferred location in the genome (e.g., a trascriptionally active location, for example downstream of an enogenous promoter of an unrelated gene). Construction of targeting constructs and vectors are described in detail in U.S. Pat. Nos. 5,641,670 and 6,270,989, and which are expressly incorporated herein by reference.

Virtually any cells, prokaryotic or eukaryotic, which can be transformed with heterologous DNA or RNA and which can be grown or maintained in culture, may be used in the practice of the invention. Examples include bacterial cells such as *Escherichia coli*, insect cells, and mammalian cells such as human, mouse, hamster, pig, goat, primate, etc. They may be primary or secondary cell strains (which exhibit a finite number of mean population doublings in culture and are not immortalized) and immortalized cell lines (which exhibit an apparently unlimited lifespan in culture). Primary and secondary cells include, for example, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types including embryonic stem cells. Where the cells are to be used in gene therapy, primary cells are preferably obtained from the individual to whom the manipulated cells are administered. However, primary cells can be obtained from a donor (other than the recipient) of the same species. Examples of immortalized human cell lines which may be used with the DNA constructs and methods of the present invention include, but are not limited to, HT-1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (Van der Blick, A. M. et al., *Cancer Res*, 48:5927-5932 (1988), Raji cells (ATCC CCL 86), WiDr colon adenocarcinoma cells (ATCC CCL 218), SW620 colon adenocarcinoma cells (ATCC CCL 227), Jurkat cells (ATCC TIB 152), Namalwa cells (ATCC CRL1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), CHO cells, and COS cells, as well as heterohybridoma cells produced by fusion of human cells and cells of another species. Secondary human fibroblast strains, such as WI-38 (ATCC CCL 75) and MRC-5 (ATCC CCL 171) may also be used. Further discussion of the types of cells that may be used in practicing the methods of the present invention are described in U.S. Pat. Nos. 5,641,670 and 6,270,989. Cell-free transcription systems also may be used in lieu of cells.

The cells of the invention are maintained under conditions, as are known in the art, which result in expression of the FGE protein or functional fragments thereof. Proteins expressed using the methods described may be purified from cell lysates or cell supernatants. Proteins made according to this method can be prepared as a pharmaceutically-useful formulation and delivered to a human or non-human animal by conventional pharmaceutical routes as is known in the art (e.g., oral, intravenous, intramuscular, intranasal, intratracheal or subcutaneous). As described elsewhere herein, the recombinant cells can be immortalized, primary, or secondary cells, preferably human. The use of cells from other species may be desirable in cases where the non-human cells are advantageous for protein production purposes where the non-human FGE produced is useful therapeutically.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Clon-* ing: *A Laboratory Manual*, Second Edition, Cold Spring Harbor Laboratory Press, 1989. Cells are genetically engineered by the introduction into the cells of heterologous DNA (RNA) encoding FGE polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal injection in mice for immunization against P1A (*Int. J. Cancer*, 67:303-310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, FGE cDNA sequence containing expression vectors, to transfect host cells and cell lines, be these prokaryotic (e.g., *Escherichia coli*), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and immortalized cell lines as described elsewhere herein. Specific examples include HT-1080 cells, CHO cells, dendritic cells, U293 cells, peripheral blood leukocytes, bone marrow stem cells, embryonic stem cells, and insect cells. The invention also permits the construction of FGE gene "knock-outs" in cells and in animals, providing materials for studying certain aspects of FGE activity.

The invention also provides isolated polypeptides (including whole proteins and partial proteins), encoded by the foregoing FGE nucleic acids, and include the polypeptide of SEQ ID NO:2 and unique fragments thereof. Such polypeptides are useful, for example, alone or as part of fusion proteins to generate antibodies, as components of an immunoassay, etc. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of a FGE polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2 will require longer segments to be unique while others will require only short segments, typically between 5 and 12 amino acids (e.g. 5, 6, 7, 8, 9, 10, 11 and 12 amino acids long or more, including each integer up to the full length, 287 amino acids long).

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, interaction with other molecules, etc. One important activity is the ability to act as a signature for identifying the polypeptide. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the FGE polypeptides described above. As used herein, a "variant" of a FGE polypeptide is a polypeptide which contains one or more modifications to the primary amino acid sequence of a FGE polypeptide. Modifications which create a FGE polypeptide variant are typically made to the nucleic acid which encodes the FGE polypeptide, and can include deletions, point mutations, truncations, amino acid substitutions and addition of amino acids or non-amino acid moieties to: 1) reduce or eliminate an activity of a FGE polypeptide; 2) enhance a property of a FGE polypeptide, such as protein stability in an expression system or the stability of protein-ligand binding; 3) provide a novel activity or property to a FGE polypeptide, such as addition of an antigenic epitope or addition of a detectable moiety; or 4) to provide equivalent or better binding to a FGE polypeptide receptor or other molecule. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the FGE amino acid sequence. One of skill in the art will be familiar with methods for predicting the effect on protein conformation of a change in protein sequence, and can thus "design" a variant FGE polypeptide according to known methods. One example of such a method is described by Dahiyat and Mayo in *Science* 278:82-87, 1997, whereby proteins can be designed de novo. The method can be applied to a known protein to vary only a portion of the polypeptide sequence. By applying the computational methods of Dahiyat and Mayo, specific variants of the FGE polypeptide can be proposed and tested to determine whether the variant retains a desired conformation.

Variants can include FGE polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a FGE polypeptide by eliminating proteolysis by proteases in an expression system (e.g., dibasic amino acid residues in yeast expression systems in which KEX2 protease activity is present).

Mutations of a nucleic acid which encodes a FGE polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant FGE polypeptides) which are silent as to the amino acid sequence of the polypeptide, but which provide preferred codons for translation in a particular host, or alter the structure of the mRNA to, for example, enhance stability and/or expression. The preferred codons for translation of a nucleic acid in, e.g., *Escherichia coli*, mammalian cells, etc. are well known to those of ordinary skill in the art. Still other mutations can be made to the noncoding sequences of a FGE gene or cDNA clone to enhance expression of the polypeptide.

The skilled artisan will realize that conservative amino acid substitutions may be made in FGE polypeptides to provide functionally equivalent variants of the foregoing polypeptides, i.e, the variants retain the functional capabilities of the FGE polypeptides. As used herein, a "conservative amino acid substitution" refers to an amino acid substitution which does not significantly alter the the tertiary structure and/or activity of the polypeptide. Variants can be prepared according to methods for altering polypeptide sequence known to one of ordinary skill in the art, and include those that are found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Exemplary functionally equivalent variants of the FGE polypeptides include conservative amino acid substitutions of SEQ ID NO:2. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of FGE polypeptides, i.e., variants of FGE polypeptides which retain the function of the natural FGE polypeptides, are contemplated by the invention. Conservative amino-acid substitutions in the amino acid sequence of FGE polypeptides to produce functionally equivalent variants of FGE polypeptides typically are made by alteration of a nucleic acid encoding FGE polypeptides (SEQ ID NOs:1, 3). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a FGE polypeptide. The activity of functionally equivalent fragments of FGE polypeptides can be tested by cloning the gene encoding the altered FGE polypeptide into a bacterial or mammalian expression vector, introducing the vector into an appropriate host cell, expressing the altered FGE polypeptide, and testing for a functional capability of the FGE polypeptides as disclosed herein (e.g., $C_\alpha$-formylglycine generating activity, etc.).

The invention as described herein has a number of uses, some of which are described elsewhere herein. First, the invention permits isolation of FGE polypeptides. A variety of methodologies well-known to the skilled practitioner can be utilized to obtain isolated FGE molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of FGE mRNA in cell-free extracts such as the reticulocyte lysate system also may be used to produce FGE polypeptides. Those skilled in the art also can readily follow known methods for isolating FGE polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from FGE polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and use standard mutagenesis techniques to create one or more dominant negative variant polypeptides. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected activity and/or for retention of such an activity. Other similar methods for creating and testing dominant negative variants of a protein will be apparent to one of ordinary skill in the art.

The isolation of the FGE cDNA also makes it possible for the artisan to diagnose a disorder characterized by an aberrant expression of FGE. These methods involve determining expression of the FGE gene, and/or FGE polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the secreted FGE protein. A preferred disorder that can be diagnosed according to the invention is Multiple Sulfatase Deficiency.

The invention also embraces isolated peptide binding agents which, for example, can be antibodies or fragments of antibodies ("binding polypeptides"), having the ability to selectively bind to FGE polypeptides. Antibodies include polyclonal and monoclonal antibodies, prepared according to conventional methodology. In certain embodiments, the invention excludes binding agents (e.g., antibodies) that bind to the polypeptides encoded by the nucleic acids of SEQ ID NO:4.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to FGE polypeptides, and complexes of both FGE polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the FGE polypeptide or a complex of FGE and a binding partner. This process can be repeated through several cycles of reselection of phage that bind to the FGE polypeptide or complex. Repeated rounds lead to enrichment of phage bearing particular sequences. DNA sequence analysis can be conducted to identify the sequences of the expressed polypeptides. The minimal linear portion of the sequence that binds to the FGE polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the FGE polypeptides. Thus, the FGE polypeptides of the invention, or a fragment thereof, or complexes of FGE and a binding partner can be used to screen peptide libraries, including phage display libraries, to identify and select peptide binding partners of the FGE polypeptides of the invention. Such molecules can be used, as described, for screening assays, for purification protocols, for interfering directly with the functioning of FGE and for other purposes that will be apparent to those of ordinary skill in the art.

An FGE polypeptide, or a fragment thereof, also can be used to isolate their native binding partners. Isolation of binding partners may be performed according to well-known methods. For example, isolated FGE polypeptides can be attached to a substrate, and then a solution suspected of containing a FGE binding partner may be applied to the substrate. If the binding partner for FGE polypeptides is present in the solution, then it will bind to the substrate-bound FGE polypeptide. The binding partner then may be isolated. Other proteins which are binding partners for FGE, may be isolated by similar methods without undue experimentation. A preferred binding partner is a sulfatase.

The invention also provides methods to measure the level of FGE expression in a subject. This can be performed by first obtaining a test sample from the subject. The test sample can be tissue or biological fluid. Tissues include brain, heart, serum, breast, colon, bladder, uterus, prostate, stomach, testis, ovary, pancreas, pituitary gland, adrenal gland, thyroid gland, salivary gland, mammary gland, kidney, liver, intestine, spleen, thymus, blood vessels, bone marrow, trachea, and lung. In certain embodiments, test samples originate from heart and blood vessel tissues, and biological fluids include blood, saliva and urine. Both invasive and non-invasive techniques can be used to obtain such samples and are well documented in the art. At the molecular level both PCR and Northern blotting can be used to determine the level of FGE mRNA using products of this invention described herein, and protocols well known in the art that are found in references which compile such methods. At the protein level, FGE expression can be determined using either polyclonal or monoclonal anti-FGE sera in combination with standard immunological assays. The preferred methods will compare the measured level of FGE expression of the test sample to a control. A control can include a known amount of a nucleic acid probe, a FGE epitope (such as a FGE expression product), or a similar test sample of a subject with a control or 'normal' level of FGE expression.

FGE polypeptides preferably are produced recombinantly, although such polypeptides may be isolated from biological extracts. Recombinantly produced FGE polypeptides include chimeric proteins comprising a fusion of a FGE protein with another polypeptide, e.g., a polypeptide capable of providing or enhancing protein-protein binding, sequence specific nucleic acid binding (such as GAL4), enhancing stability of the FGE polypeptide under assay conditions, or providing a detectable moiety, such as green fluorescent protein. A polypeptide fused to a FGE polypeptide or fragment may also provide means of readily detecting the fusion protein, e.g., by immunological recognition or by fluorescent labeling.

The invention also is useful in the generation of transgenic non-human animals. As used herein, "transgenic non-human animals" includes non-human animals having one or more exogenous nucleic acid molecules incorporated in germ line cells and/or somatic cells. Thus the transgenic animals include "knockout" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination may be facilitated using, for example, the cre/lox system or other recombinase systems known to one of ordinary skill in the art. In certain embodiments, the recombinase system itself is expressed conditionally, for example, in certain tissues or cell types, at certain embryonic or post-embryonic developmental stages, is induced by the addition of a compound which increases or decreases expression, and the like. In general, the conditional expression vectors used in such systems use a variety of promoters which confer the desired gene expression pattern (e.g., temporal or spatial). Conditional promoters also can be operably linked to FGE nucleic acid molecules to increase expression of FGE in a regulated or conditional manner. Trans-acting negative regulators of FGE activity or expression also can be operably linked to a conditional promoter as described above. Such trans-acting regulators include antisense FGE nucleic acids molecules, nucleic acid molecules which encode dominant negative FGE molecules, ribozyme molecules specific for FGE nucleic acids, and the like. The transgenic non-human animals are useful in experiments directed toward testing biochemical or physiological effects of diagnostics or therapeutics for conditions characterized by increased or decreased FGE expression. Other uses will be apparent to one of ordinary skill in the art.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention further provides efficient methods of identifying agents or lead compounds for agents active at the level of a FGE or FGE fragment dependent cellular function. In particular, such functions include interaction with other polypeptides or fragments. Generally, the screening methods involve assaying for compounds which interfere with FGE activity (such as $C_\alpha$-formylglycine generating activity), although compounds which enhance FGE $C_\alpha$-formylglycine generating activity also can be assayed using the screening methods. Such methods are adaptable to automated, high throughput screening of compounds. Target indications include cellular processes modulated by FGE such as $C_\alpha$-formylglycine generating activity.

A wide variety of assays for candidate (pharmacological) agents are provided, including, labeled in vitro protein-ligand binding assays, electrophoretic mobility shift assays, immunoassays, cell-based assays such as two- or three-hybrid screens, expression assays, etc. The transfected nucleic acids can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding a FGE polypeptide fused to a GAL4 DNA binding domain and a nucleic acid encoding a reporter gene operably linked to a gene expression regulatory region, such as one or more GAL4 binding sites. Activation of reporter gene transcription occurs when the FGE and reporter fusion polypeptide binds such as to enable transcription of the reporter gene. Agents which modulate a FGE polypeptide mediated cell function are then detected through a change in the expression of reporter gene. Methods for determining changes in the expression of a reporter gene are known in the art.

FGE fragments used in the methods, when not produced by a transfected nucleic acid are added to an assay mixture as an isolated polypeptide. FGE polypeptides preferably are produced recombinantly, although such polypeptides may be isolated from biological extracts. Recombinantly produced FGE polypeptides include chimeric proteins comprising a fusion of a FGE protein with another polypeptide, e.g., a polypeptide capable of providing or enhancing protein-protein binding, sequence specific nucleic acid binding (such as GAL4), enhancing stability of the FGE polypeptide under assay conditions, or providing a detectable moiety, such as green fluorescent protein or Flag epitope.

The assay mixture is comprised of a natural intracellular FGE binding target capable of interacting with FGE. While natural FGE binding targets may be used, it is frequently preferred to use portions (e.g., peptides—see e.g., the peptide of SEQ ID NO:33—or nucleic acid fragments) or analogs (i.e., agents which mimic the FGE binding properties of the natural binding target for purposes of the assay) of the FGE binding target so long as the portion or analog provides binding affinity and avidity to the FGE fragment measurable in the assay.

The assay mixture also comprises a candidate agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be modified through conventional chemical, physical, and biochemical means. Further, known (pharmacological) agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate agent, the FGE polypeptide specifically binds a cellular binding target, a portion thereof or analog thereof. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the FGE polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of FGE polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc), or indirect detection (e.g., epitope tag such as the FLAG epitope, enzyme tag such as horseradish peroxidase, etc.). The label may be bound to a FGE binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The invention provides FGE-specific binding agents, methods of identifying and making such agents, and their use in diagnosis, therapy and pharmaceutical development. For example, FGE-specific pharmacological agents are useful in a variety of diagnostic and therapeutic applications, especially where disease or disease prognosis is associated with altered FGE binding characteristics such as in Multiple Sulfatase Deficiency. Novel FGE-specific binding agents include FGE-specific antibodies, cell surface receptors, and other natural intracellular and extracellular binding agents identified with assays such as two hybrid screens, and non-natural intracellular and extracellular binding agents identified in screens of chemical libraries and the like.

In general, the specificity of FGE binding to a specific molecule is determined by binding equilibrium constants. Targets which are capable of selectively binding a FGE polypeptide preferably have binding equilibrium constants of at least about $10^7 M^{-1}$, more preferably at least about $10^8 M^{-1}$, and most preferably at least about $10^9 M^{-1}$. A wide variety of cell based and cell free assays may be used to demonstrate FGE-specific binding. Cell based assays include one, two and three hybrid screens, assays in which FGE-mediated transcription is inhibited or increased, etc. Cell free assays include FGE-protein binding assays, immunoassays, etc. Other assays useful for screening agents which bind FGE polypeptides include fluorescence resonance energy transfer (FRET), and electrophoretic mobility shift analysis (EMSA).

According to another aspect of the invention, a method for identifying an agent useful in modulating $C_\alpha$-formylglycine generating activity of a molecule of the invention, is provided. The method involves (a) contacting a molecule having $C_\alpha$-formylglycine generating activity with a candidate agent, (b) measuring $C_\alpha$-formylglycine generating activity of the molecule, and (c) comparing the measured $C_\alpha$-formylglycine generating activity of the molecule to a control to determine whether the candidate agent modulates $C_\alpha$-formylglycine generating activity of the molecule, wherein the molecule is an FGE nucleic acid molecule of the invention, or an expression product thereof. "Contacting" refers to both direct and indirect contacting of a molecule having $C_\alpha$-formylglycine generating activity with the candidate agent. "Indirect" contacting means that the candidate agent exerts its effects on the $C_\alpha$-formylglycine generating activity of the molecule via a third agent (e.g., a messenger molecule, a receptor, etc.). In certain embodiments, the control is $C_\alpha$-formylglycine generating activity of the molecule measured in the absence of the candidate agent. Assaying methods and candidate agents are as described above in the foregoing embodiments with respect to FGE.

According to still another aspect of the invention, a method of diagnosing a disorder characterized by aberrant expression of a nucleic acid molecule, an expression product thereof, or a fragment of an expression product thereof, is provided. The method involves contacting a biological sample isolated from a subject with an agent that specifically binds to the nucleic acid molecule, an expression product thereof, or a fragment of an expression product thereof, and determining the interaction between the agent and the nucleic acid molecule or the expression product as a determination of the disorder, wherein the nucleic acid molecule is an FGE molecule according to the invention. The disorder is Multiple Sulfatase Deficiency. Mutations in the FGE gene that cause the aberrant expression of FGE molecules result in the following amino acid changes on SEQ ID NO:2: Met1Arg; Met1Val; Leu20Phe; Ser155Pro; Ala177Pro; Cys218Tyr; Arg224Trp; Asn259Ile; Pro266Leu; Ala279Val; Arg327Stop; Cys336Arg; Arg345Cys; Ala348Pro; Arg349Gln; Arg349Trp; Arg349Trp; Ser359Stop; or a combination thereof.

In the case where the molecule is a nucleic acid molecule, such determinations can be carried out via any standard nucleic acid determination assay, including the polymerase chain reaction, or assaying with labeled hybridization probes as exemplified herein. In the case where the molecule is an expression product of the nucleic acid molecule, or a fragment of an expression product of the nucleic acid molecule, such determination can be carried out via any standard immunological assay using, for example, antibodies which bind to any of the polypeptide expression products.

"Aberrant expression" refers to decreased expression (underexpression) or increased expression (overexpression) of FGE molecules (nucleic acids and/or polypeptides) in comparison with a control (i.e., expression of the same molecule in a healthy or "normal" subject). A "healthy subject", as used herein, refers to a subject who, according to standard medical standards, does not have or is at risk for developing Multiple Sulfatase Deficiency. Healthy subjects also do not otherwise exhibit symptoms of disease. In other words, such subjects, if examined by a medical professional, would be characterized as healthy and free of symptoms of a Multiple Sulfatase Deficiency. These include features of metachromatic leukodystrophy and of a mucopolysaccharidosis, such as increased amounts of acid mucopolysaccharides in several tissues, mild 'gargoylism', rapid neurologic deterioration, excessive presence of mucopolysaccharide and sulfatide in the urine, increased cerebrospinal fluid protein, and metachromatic degeneration of myelin in peripheral nerves.

The invention also provides novel kits which could be used to measure the levels of the nucleic acids of the invention, or expression products of the invention.

In one embodiment, a kit comprises a package containing an agent that selectively binds to any of the foregoing FGE isolated nucleic acids, or expression products thereof, and a control for comparing to a measured value of binding of said agent any of the foregoing FGE isolated nucleic acids or expression products thereof. In some embodiments, the control is a predetermined value for comparing to the measured value. In certain embodiments, the control comprises an epitope of the expression product of any of the foregoing FGE isolated nucleic acids. In one embodiment, the kit further comprises a second agent that selectively binds to a polypeptide selected from the group consisting of Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6, or a peptide thereof, and a control for comparing to a measured value of binding of said second agent to said polypeptide or peptide thereof.

In the case of nucleic acid detection, pairs of primers for amplifying a nucleic acid molecule of the invention can be included. The preferred kits would include controls such as known amounts of nucleic acid probes, epitopes (such as Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6, expression products) or anti-epitope antibodies, as well as instructions or other printed material. In certain embodiments the printed material can characterize risk of developing a sulfatase deficiency condition based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with FGE protein and a container containing labeled anti-human IgG antibodies. A well of the plate is contacted with, for example, a biological fluid, washed and then contacted with the anti-IgG antibody. The label is then detected. A kit embodying features of the present invention, generally designated by the numeral 11, is illustrated in FIG. 25. Kit 11 is comprised of the following major elements: packaging 15, an agent of the invention 17, a control agent 19 and instructions 21. Packaging 15 is a box-like structure for holding a vial (or number of vials) containing an agent of the invention 17, a vial (or number of vials) containing a control agent 19, and instructions 21. Individuals skilled in the art can readily modify packaging 15 to suit individual needs.

The invention also embraces methods for treating Multiple Sulfatase Deficiency in a subject. The method involves administering to a subject in need of such treatment an agent that modulates $C_\alpha$-formylglycine generating activity, in an amount effective to increase $C_\alpha$-formylglycine generating activity in the subject. In some embodiments, the method further comprises co-administering an agent selected from the group consisting of a nucleic acid molecule encoding Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6, an expression product of the nucleic acid molecule, and/or a fragment of the expression product of the nucleic acid molecule.

"Agents that modulate expression" of a nucleic acid or a polypeptide, as used herein, are known in the art, and refer to sense and antisense nucleic acids, dominant negative nucleic acids, antibodies to the polypeptides, and the like. Any agents that modulate expression of a molecule (and as described herein, modulate its activity), are useful according to the invention. In certain embodiments, the agent that modulates $C_\alpha$-formylglycine generating activity is an isolated nucleic acid molecule of the invention (e.g., a nucleic acid of SEQ ID NO.3). In important embodiments, the agent that modulates $C_\alpha$-formylglycine generating activity is a peptide of the invention (e.g., a peptide of SEQ ID NO.2). In some embodiments, the agent that modulates $C_\alpha$-formylglycine generating activity is a sense nucleic acid of the invention.

According to one aspect of the invention, a method for for increasing $C_\alpha$-formylglycine generating activity in a subject, is provided. The method involves administering an isolated FGE nucleic acid molecule of the invention, and/or an expression product thereof, to a subject, in an amount effective to increase $C_\alpha$-formylglycine generating activity in the subject.

According to still another aspect of the invention, a method for increasing $C_\alpha$-formylglycine generating activity in a cell, is provided. The method involves contacting the cell with an isolated nucleic acid molecule of the invention (e.g., a nucleic acid of SEQ ID NO.1), or an expression product thereof (e.g., a peptide of SEQ ID NO.2), in an amount effective to increase $C_\alpha$-formylglycine generating activity in the cell. In important embodiments, the method involves activating the endogenous FGE gene to increase $C_\alpha$-formylglycine generating activity in the cell.

In any of the foregoing embodiments the nucleic acid may be operatively coupled to a gene expression sequence which directs the expression of the nucleic acid molecule within a eukaryotic cell such as an HT-1080 cell. The "gene expression sequence" is any regulatory nucleotide sequence, such as a promoter sequence or promoter-enhancer combination, which facilitates the efficient transcription and translation of the nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, α-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are activated in the presence of an inducing agent. For example, the metallothionein promoter is activated to increase transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined nucleic acid. The gene expression sequences optionally includes enhancer sequences or upstream activator sequences as desired.

Preferably, any of the FGE nucleic acid molecules of the invention is linked to a gene expression sequence which permits expression of the nucleic acid molecule in a cell of a specific cell lineage, e.g., a neuron. A sequence which permits expression of the nucleic acid molecule in a cell such as a neuron, is one which is selectively active in such a cell type, thereby causing expression of the nucleic acid molecule in these cells. The synapsin-1 promoter, for example, can be used to express any of the foregoing nucleic acid molecules of the invention in a neuron; and the von Willebrand factor gene promoter, for example, can be used to express a nucleic acid molecule in a vascular endothelial cell. Those of ordinary skill in the art will be able to easily identify alternative promoters that are capable of expressing a nucleic acid molecule in any of the preferred cells of the invention.

The nucleic acid sequence and the gene expression sequence are said to be "operably linked" when they are covalently linked in such a way as to place the transcription and/or translation of the nucleic acid coding sequence (e.g, in the case of FGE, SEQ ID NO. 3) under the influence or control of the gene expression sequence. If it is desired that the nucleic acid sequence be translated into a functional protein, two DNA sequences are said to be operably linked if induction of a promoter in the 5' gene expression sequence results in the transcription of the nucleic acid sequence and if the nature of the linkage between the two DNA sequences does not (1) result in the introduction of a frame-shift mutation, (2) interfere with the ability of the promoter region to direct the transcription of the nucleic acid sequence, and/or (3) interfere with the ability of the corresponding RNA transcript to be translated into a protein. Thus, a gene expression sequence would be operably linked to a nucleic acid sequence if the gene expression sequence were capable of effecting transcription of that nucleic acid sequence such that the resulting transcript might be translated into the desired protein or polypeptide.

The molecules of the invention can be delivered to the preferred cell types of the invention alone or in association with a vector (see also earlier discussion on vectors). In its broadest sense (and consistent with the description of expression and targeting vectors elsewhere herein), a "vector" is any vehicle capable of facilitating: (1) delivery of a molecule to a target cell and/or (2) uptake of the molecule by a target cell. Preferably, the delivery vectors transport the molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing a nucleic acid or a protein) can be selectively delivered to a neuron. Methodologies for targeting include conjugates, such as those described in U.S. Pat. No. 5,391,723 to Priest. Another example of a well-known targeting vehicle is a liposome. Liposomes are commercially available from Gibco BRL. Numerous methods are published for making targeted liposomes.

In general, the vectors useful in the invention include, but are not limited to, plasmids, phagemids, viruses, other vehicles derived from viral or bacterial sources that have been manipulated by the insertion or incorporation of the nucleic acid sequences of the invention, and additional nucleic acid fragments (e.g., enhancers, promoters) which can be attached to the nucleic acid sequences of the invention. Viral vectors are a preferred type of vector and include, but are not limited to, nucleic acid sequences from the following viruses: adenovirus; adeno-associated virus; retrovirus, such as moloney murine leukemia virus; harvey murine sarcoma virus; murine mammary tumor virus; rouse sarcoma virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

A particularly preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Cliffton, N.J. (1991).

Another preferred retroviral vector is the vector derived from the moloney murine leukemia virus, as described in Nabel, E. G., et al., Science,1990, 249:1285-1288. These vectors reportedly were effective for the delivery of genes to all three layers of the arterial wall, including the media. Other preferred vectors are disclosed in Flugelman, et al., Circulation, 1992, 85:1110-1117. Additional vectors that are useful for delivering molecules of the invention are described in U.S. Pat. No. 5,674,722 by Mulligan, et. al.

In addition to the foregoing vectors, other delivery methods may be used to deliver a molecule of the invention to a cell such as a neuron, liver, fibroblast, and/or a vascular endothelial cell, and facilitate uptake thereby.

A preferred such delivery method of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 μm can encapsulate large macromolecules. RNA, DNA, and intact virions can be encapsulated within the aqueous interior and be delivered to cells in a biologically active form (Fraley, et al., Trends Biochem. Sci., 1981, 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, such as the myocardium or the vascular cell wall, by coupling the liposome to a specific ligand such as a monoclonal antibody, sugar, glycolipid, or protein. Ligands which may be useful for targeting a liposome to the vascular wall include, but are not limited to the viral coat protein of the Hemagglutinating virus of Japan. Additionally, the vector may be coupled to a nuclear targeting peptide, which will direct the nucleic acid to the nucleus of the host cell.

Liposomes are commercially available from Gibco BRL, for example, as LIPOFECTIN™ and LIPOFECTACE™, which are formed of cationic lipids such as N-[1-(2, 3 dioley-loxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in Trends in Biotechnology, V. 3, p. 235-241 (1985). Novel liposomes for the intracellular delivery of macromolecules, including nucleic acids, are also described in PCT International application no. PCT/US96/07572 (Publication No. WO 96/40060, entitled "Intracellular Delivery of Macromolecules").

In one particular embodiment, the preferred vehicle is a biocompatible micro particle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the nucleic acids described herein are encapsulated or dispersed within the biocompatible, preferably biodegradable polymeric matrix disclosed in PCT/US/03307. The polymeric matrix preferably is in the form of a micro particle such as a micro sphere (wherein a nucleic acid is dispersed throughout a solid polymeric matrix) or a microcapsule (wherein a nucleic acid is stored in the core of a polymeric shell). Other forms of the polymeric matrix for containing the nucleic acids of the invention include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver the nucleic acids of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is crosslinked with multi-valent ions or other polymers.

In general, the nucleic acids of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described molecules of the invention for use as a medicament, methods for preparing the medicament and methods for the sustained release of the medicament in vivo.

Compaction agents also can be used in combination with a vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver an isolated nucleic acid of the invention in a form that is more efficiently taken up by the cell or, more preferably, in combination with one or more of the above-described vectors.

Other exemplary compositions that can be used to facilitate uptake by a target cell of the nucleic acids of the invention include calcium phosphate and other chemical mediators of intracellular transport, microinjection compositions, and electroporation.

The invention embraces methods for increasing sulfatase activity in a cell. Such methods involve contacting a cell expressing a sulfatase with an isolated nucleic acid molecule of of the invention (e.g., an isolated nucleic acid molecule as claimed in any one of claims 1-8, an FGE nucleic acid molecule having a sequence selected from the group consisting of SEQ ID NO:1, 3, 4, 45, 47, 49, 51, 53, 55, 57, 59, 61, 63, 65, 67, 69, 71, 73, 75, 77, and 80-87), or an expression product thereof (e.g., a polypeptide as claimed in claims 11-15, 19, 20, or a peptide having a sequence selected from the group consisting of SEQ ID NO. 2, 5, 46, 48, 50, 52, 54, 56, 58, 60, 62, 64, 66, 68, 70, 72, 74, 76, and 78), in an amount effective to increase sulfatase activity in the cell. "Increasing" sulfatase activity, as used herein, refers to increased affinity for, and/or conversion of, the specific substrate for the sulfatase, typically the result of an increase in FGly formation on the sulfatase molecule. In one embodiment, the cell expresses a sulfatase at levels higher than those of wild type cells. By "increasing sulfatase activity in a cell" also refers to increasing activity of a sulfatase that is secreted by the cell. The cell may express an endogenous and/or an exogenous sulfatase. Said contacting of the FGE molecule also refers to activating the cells's endogenous FGE gene. In important embodiments, the endogenous sulfatase is activated. In certain embodiments, the sulfatase is Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and/ or HSulf-6. In certain embodiments the cell is a mammalian cell.

According to another aspect of the invention, a pharmaceutical composition, is provided. The composition comprises a sulfatase that is produced by cell, in a pharmaceutically effective amount to treat a sulfatase deficiency, and a pharmaceutically acceptable carrier, wherein said cell has been contacted with an agent comprising an isolated nucleic acid molecule of the invention (e.g., as claimed in claims 1-8, or a nucleic acid molecule having a sequence selected from the group consisting of SEQ ID NO:1, 3, 4, 45, 47, 49, 51, 53, 55, 57, 59, 61, 63, 65, 67, 69, 71, 73, 75, 77, and 80-87), or an expression product thereof (e.g., a peptide selected from the group consisting of SEQ ID NO. 2, 5, 46, 48, 50, 52, 54, 56, 58, 60, 62, 64, 66, 68, 70, 72, 74, 76, and 78). In important embodiments, the sulfatase is expressed at higher levels than normal/control cells.

The invention also embraces a sulfatase producing cell wherein the ratio of active sulfatase to total sulfatase produced by the cell is increased. The cell comprises: (i) a sulfatase with an increased activity compared to a control, and (ii) a Formylglycine Generating Enzyme with an increased activity compared to a control, wherein the ratio of active sulfatase to total sulfatase produced by the cell is increased by at least 5% over the ratio of active sulfatase to total sulfatase produced by the cell in the absence of the Formylglycine Generating Enzyme. It is known in the art that overexpression of sulfatases can decrease the activity of endogenous sulfatases (Anson et al., *Biochem. J.*, 1993, 294:657-662). Furthermore, only a fraction of the recombinant sulfatases is active. We have discovered, unexpectedly, that increased expression/ activity of FGE in a cell with increased expression/activity of a sulfatase results in the production of a sulfatase that is more active. Since the presence of FGly on a sulfatase molecule is associated with sulfatase activity, "active sulfatase" can be quantitated by determining the presence of FGly on the sulfatase cell product using MALDI-TOF mass spectrometry, as described elsewhere herein. The ratio with total sulfatase can then be easily determined.

The invention also provides methods for the diagnosis and therapy of sulfatase deficiencies. Such disorders include, but are not limited to, Multiple Sulfatase Deficiency, Mucopolysaccharidosis II (MPS II; Hunter Syndrome), Mucopolysaccharidosis IIIA (MPS IIIA; Sanfilippo Syndrome A), Mucopolysaccharidosis VIII (MPS VIII), Mucopolysaccharidosis IVA (MPS IVA; Morquio Syndrome A), Mucopolysaccharidosis VI (MPS VI; Maroteaux-Lamy Syndrome), Metachromatic Leukodystrophy (MLD), X-linked Recessive Chondrodysplasia Punctata 1, and X-linked Ichthyosis (Steroid Sulfatase Deficiency).

The methods of the invention are useful in both the acute and the prophylactic treatment of any of the foregoing conditions. As used herein, an acute treatment refers to the treatment of subjects having a particular condition. Prophylactic treatment refers to the treatment of subjects at risk of having the condition, but not presently having or experiencing the symptoms of the condition.

In its broadest sense, the terms "treatment" or "to treat" refer to both acute and prophylactic treatments. If the subject in need of treatment is experiencing a condition (or has or is having a particular condition), then treating the condition refers to ameliorating, reducing or eliminating the condition or one or more symptoms arising from the condition. In some preferred embodiments, treating the condition refers to ameliorating, reducing or eliminating a specific symptom or a specific subset of symptoms associated with the condition. If the subject in need of treatment is one who is at risk of having a condition, then treating the subject refers to reducing the risk of the subject having the condition.

The mode of administration and dosage of a therapeutic agent of the invention will vary with the particular stage of the condition being treated, the age and physical condition of the subject being treated, the duration of the treatment, the nature of the concurrent therapy (if any), the specific route of administration, and the like factors within the knowledge and expertise of the health practitioner.

As described herein, the agents of the invention are administered in effective amounts to treat any of the foregoing sulfatase deficiencies. In general, an effective amount is any amount that can cause a beneficial change in a desired tissue of a subject. Preferably, an effective amount is that amount sufficient to cause a favorable phenotypic change in a particular condition such as a lessening, alleviation or elimination of a symptom or of a condition as a whole.

In general, an effective amount is that amount of a pharmaceutical preparation that alone, or together with further doses, produces the desired response. This may involve only slowing the progression of the condition temporarily, although more preferably, it involves halting the progression of the condition permanently or delaying the onset of or preventing the condition from occurring. This can be monitored by routine methods. Generally, doses of active compounds would be from about 0.01 mg/kg per day to 1000 mg/kg per day. It is expected that doses ranging from 50 µg-500 mg/kg will be suitable, preferably orally and in one or several administrations per day.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agents of the invention may be combined, optionally, with a pharmaceutically-acceptable carrier to form a pharmaceutical preparation. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. In some aspects, the pharmaceutical preparations comprise an agent of the invention in an amount effective to treat a disorder.

The pharmaceutical preparations may contain suitable buffering agents, including: acetic acid in a salt; citric acid in a salt; boric acid in a salt; or phosphoric acid in a salt. The pharmaceutical compositions also may contain, optionally, suitable preservatives, such as: benzalkonium chloride; chlorobutanol; parabens or thimerosal.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, transdermal, or parenteral routes. The term "parenteral" includes subcutaneous, intravenous, intraomental, intramuscular, or infusion. Intravenous or intramuscular routes are not particularly suitable for long-term therapy and prophylaxis. As an example, pharmaceutical compositions for the acute treatment of subjects having a migraine headache may be formulated in a variety of different ways and for a variety of administration modes including tablets, capsules, powders, suppositories, injections and nasal sprays.

The pharmaceutical preparations may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of an agent of the invention, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Formulations suitable for oral, subcutaneous, intravenous, intramuscular, etc. administrations can be found in *Remington's Pharmaceutical Sciences*, Mack Publishing Co., Easton, Pa.

According to one aspect of the invention, a method for increasing $C_\alpha$-formylglycine generating activity in a cell, is provided. The method involves contacting the cell with an isolated nucleic acid molecule of the invention (e.g., a nucleic acid of SEQ ID NO.1), or an expression product thereof (e.g., a peptide of SEQ ID NO.2), in an amount effective to increase $C_\alpha$-formylglycine generating activity in the cell. In important embodiments, the method involves activating the endogenous FGE gene to increase $C_\alpha$-formylglycine generating activity in the cell. In some embodiments, the contacting is performed under conditions that permit entry of a molecule of the invention into the cell.

The term "permit entry" of a molecule into a cell according to the invention has the following meanings depending upon the nature of the molecule. For an isolated nucleic acid it is meant to describe entry of the nucleic acid through the cell membrane and into the cell nucleus, where upon the "nucleic acid transgene" can utilize the cell machinery to produce functional polypeptides encoded by the nucleic acid. By "nucleic acid transgene" it is meant to describe all of the nucleic acids of the invention with or without the associated vectors. For a polypeptide, it is meant to describe entry of the polypeptide through the cell membrane and into the cell cytoplasm, and if necessary, utilization of the cell cytoplasmic machinery to functionally modify the polypeptide (e.g., to an active form).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of an agent of the present invention, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S.

Pat. Nos. 3,854,480, 5,133,974 and 5,407,686. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active ingredient for at least 30 days, and preferably 60 days. Long-term sustained release implants are well-known to those of ordinary skill in the art and include some of the release systems described above. Specific examples include, but are not limited to, long-term sustained release implants described in U.S. Pat. No. 4,748,024, and Canadian Patent No. 1330939.

The invention also involves the administration, and in some embodiments co-administration, of agents other than the FGE molecules of the invention that when administered in effective amounts can act cooperatively, additively or synergistically with a molecule of the invention to: (i) modulate $C_\alpha$-formylglycine generating activity, and (ii) treat any of the conditions in which $C_\alpha$-formylglycine generating activity of a molecule of the invention is involved (e.g., a sulfatase deficiency including MSD). Agents other than the molecules of the invention include Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, or HSulf-6, (nucleic acids and polypeptides, and/or fragments thereof), and/or combinations thereof.

"Co-administering," as used herein, refers to administering simultaneously two or more compounds of the invention (e.g., an FGE nucleic acid and/or polypeptide, and an agent known to be beneficial in the treatment of, for example, a sulfatase deficiency e.g., Iduronate 2-Sulfatase in the treatment of MPSII-), as an admixture in a single composition, or sequentially, close enough in time so that the compounds may exert an additive or even synergistic effect.

The invention also embraces solid-phase nucleic acid molecule arrays. The array consists essentially of a set of nucleic acid molecules, expression products thereof, or fragments (of either the nucleic acid or the polypeptide molecule) thereof, each nucleic acid molecule selected from the group consisting of FGE, Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6, fixed to a solid substrate. In some embodiments, the solid-phase array further comprises at least one control nucleic acid molecule. In certain embodiments, the set of nucleic acid molecules comprises at least one, at least two, at least three, at least four, or even at least five nucleic acid molecules, each selected from the group consisting of FGE, Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and HSulf-6. In preferred embodiments, the set of nucleic acid molecules comprises a maximum number of 100 different nucleic acid molecules. In important embodiments, the set of nucleic acid molecules comprises a maximum number of 10 different nucleic acid molecules.

According to the invention, standard hybridization techniques of microarray technology are utilized to assess patterns of nucleic acid expression and identify nucleic acid expression. Microarray technology, which is also known by other names including: DNA chip technology, gene chip technology, and solid-phase nucleic acid array technology, is well known to those of ordinary skill in the art and is based on, but not limited to, obtaining an array of identified nucleic acid probes (e.g., molecules described elsewhere herein such as of FGE, Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, HSulf-2, HSulf-3, HSulf-4, HSulf-5, and/or HSulf-6) on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

According to the present invention, microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more of the nucleic acid molecules set forth as SEQ ID NOs: 1, 3, 4, 6, 8, 10, and/or 12. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, but are not limited to: amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium (Gwynne and Page, 2000). In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezo-electric delivery. Probes may be covalently linked to the substrate with methods that include, but are not limited to, UV-irradiation. In another embodiment probes are linked to the substrate with heat.

Targets are nucleic acids selected from the group, including but not limited to: DNA, genomic DNA, cDNA, RNA, mRNA and may be natural or synthetic. In all embodiments, nucleic acid molecules from subjects suspected of developing or having a sulfatase deficiency, are preferred. In certain embodiments of the invention, one or more control nucleic acid molecules are attached to the substrate. Preferably, control nucleic acid molecules allow determination of factors including but not limited to: nucleic acid quality and binding characteristics; reagent quality and effectiveness; hybridization success; and analysis thresholds and success. Control nucleic acids may include, but are not limited to, expression products of genes such as housekeeping genes or fragments thereof.

To select a set of sulfatase deficiency disease markers, the expression data generated by, for example, microarray analysis of gene expression, is preferably analyzed to determine which genes in different categories of patients (each category of patients being a different sulfatase deficiency disorder), are significantly differentially expressed. The significance of gene expression can be determined using Permax computer software, although any standard statistical package that can discriminate significant differences is expression may be used. Permax performs permutation 2-sample t-tests on large arrays of data. For high dimensional vectors of observations, the Permax software computes t-statistics for each attribute, and assesses significance using the permutation distribution of the maximum and minimum overall attributes. The main use is to determine the attributes (genes) that are the most different between two groups (e.g., control healthy subject and a subject with a particular sulfatase deficiency), measuring "most different" using the value of the t-statistics, and their significance levels.

Expression of sulfatase deficiency disease related nucleic acid molecules can also be determined using protein measurement methods to determine expression of SEQ ID NOs: 2, e.g., by determining the expression of polypeptides encoded by SEQ ID NOs: 1, and/or 3. Preferred methods of specifically and quantitatively measuring proteins include, but are not limited to: mass spectroscopy-based methods such as surface enhanced laser desorption ionization (SELDI; e.g., Ciphergen ProteinChip System), non-mass spectroscopy-based methods, and immunohistochemistry-based methods such as 2-dimensional gel electrophoresis.

SELDI methodology may, through procedures known to those of ordinary skill in the art, be used to vaporize microscopic amounts of protein and to create a "fingerprint" of individual proteins, thereby allowing simultaneous measurement of the abundance of many proteins in a single sample. Preferably SELDI-based assays may be utilized to characterize multiple sulfatase deficiency as well as stages of such conditions. Such assays preferably include, but are not limited to the following examples. Gene products discovered by RNA microarrays may be selectively measured by specific (antibody mediated) capture to the SELDI protein disc (e.g., selective SELDI). Gene products discovered by protein screening (e.g., with 2-D gels), may be resolved by "total protein SELDI" optimized to visualize those particular markers of interest from among SEQ ID NOs: 1, 6, 8, 10, 12, 14, 16, 18, 20, 22, 24, 26, and/or 28. Predictive models of a specific sulfatase deficiency from SELDI measurement of multiple markers from among SEQ ID NOs: 1, 6, 8, 10, 12, 14, 16, 18, 20, 22, 24, 26, and/or 28, may be utilized for the SELDI strategies.

The use of any of the foregoing microarray methods to determine expression of a sulfatase deficiency disease related nucleic acids can be done with routine methods known to those of ordinary skill in the art and the expression determined by protein measurement methods may be correlated to predetermined levels of a marker used as a prognostic method for selecting treatment strategies for sulfatase deficiency disease patients.

The invention also embraces a sulfatase-producing cell wherein the ratio of active sulfatase to total sulfatase produced (i.e., the specific activity) by the cell is increased. The cell comprises: (i) a sulfatase with an increased expression, and (ii) a Formylglycine Generating Enzyme with an increased expression, wherein the ratio of active sulfatase to total sulfatase produced by the cell is increased by at least 5% over the ratio of active sulfatase to total sulfatase produced by the cell in the absence of the Formylglycine Generating Enzyme.

A "sulfatase with an increased expression," as used herein, typically refers to increased expression of a sulfatase and/or its encoded polypeptide compared to a control. Increased expression refers to increasing (i.e., to a detectable extent) replication, transcription, and/or translation of any of the sulfatase nucleic acids (sulfatase nucleic acids of the invention as described elsewhere herein), since upregulation of any of these processes results in concentration/amount increase of the polypeptide encoded by the gene (nucleic acid). This can be accomplished using a number of methods known in the art, also described elsewhere herein, such as transfection of a cell with the sulfatase cDNA, and/or genomic DNA encompassing the sulfatase locus, activating the endogenous sulfatase gene by placing, for example, a strong promoter element upstream of the endogenous sulfatase gene genomic locus using homologous recombination (see, e.g., the gene activation technology described in detail in U.S. Pat. Nos. 5,733,761, 6,270,989, and 6,565,844, all of which are expressly incorporated herein by reference), etc. A typical control would be an identical cell transfected with a vector plasmid(s). Enhancing (or increasing) sulfatase activity also refers to preventing or inhibiting sulfatase degradation (e.g., via increased ubiquitinization), downregulation, etc., resulting, for example, in increased or stable sulfatase molecule $t_{1/2}$ (half-life) when compared to a control. Downregulation or decreased expression refers to decreased expression of a gene and/or its encoded polypeptide. The upregulation or downregulation of gene expression can be directly determined by detecting an increase or decrease, respectively, in the level of mRNA for the gene (e.g, a sulfatase), or the level of protein expression of the gene-encoded polypeptide, using any suitable means known to the art, such as nucleic acid hybridization or antibody detection methods, respectively, and in comparison to controls. Upregulation or downregulation of sulfatase gene expression can also be determined indirectly by detecting a change in sulfatase activity.

Similarly, a "Formylglycine Generating Enzyme with an increased expression," as used herein, typically refers to increased expression of an FGE nucleic acid of the invention and/or its encoded polypeptide compared to a control. Increased expression refers to increasing (i.e., to a detectable extent) replication, transcription, and/or translation of any of the FGE nucleic acids of the invention (as described elsewhere herein), since upregulation of any of these processes results in concentration/amount increase of the polypeptide encoded by the gene (nucleic acid). This can be accomplished using the methods described above (for the sulfatases), and elsewhere herein.

In certain embodiments, the ratio of active sulfatase to total sulfatase produced by the cell is increased by at least 10%, 15%, 20%, 50%, 100%, 200%, 500%, 1000%, over the ratio of active sulfatase to total sulfatase produced by the cell in the absence of the Formylglycine Generating Enzyme.

The invention further embraces an improved method for treating a sulfatase deficiency in a subject. The method involves administering to a subject in need of such treatment a sulfatase in an effective amount to treat the sulfatase deficiency in the subject, wherein the sulfatase is contacted with a Formylglycine Generating Enzyme in an amount effective to increase the specific activity of the sulfatase. As described elsewhere herein, "specific activity" refers to the ratio of active sulfatase to total sulfatase produced. "Contacted," as used herein, refers to FGE post-translationally modifying the sulfatase as described elsewhere herein. It would be apparent to one of ordinary skill in the art that an FGE can contact a sulfatase and modify it if nucleic acids encoding FGE and a sulfatase are co-expressed in a cell, or even if an isolated FGE polypeptide contacts an isolated sulfatase polypeptide in vivo or in vitro. Even though an isolated FGE polypeptide can be co-administered with an isolated sulfatase polypeptide to a subject to treat a sulfatase deficiency in the subject, it is preferred that the contact between FGE and the sulfatase takes place in vitro prior to administration of the sulfatase to the subject. This improved method of treatment is beneficial to a subject since lower amounts of the sulfatase need to be administered, and/or with less frequency, since the sulfatase is of higher specific activity.

The invention will be more fully understood by reference to the following examples. These examples, however, are merely intended to illustrate the embodiments of the invention and are not to be construed to limit the scope of the invention.

EXAMPLES

Example 1

Multiple Sulfatase Deficiency is Caused by Mutations in the Gene Encoding the Human $C_\alpha$-formylglycine Generating Enzyme (FGE)

Experimental Procedures

Materials and Methods

In Vitro Assay for FGE

For monitoring the activity of FGE, the N-acetylated and C-amidated 23mer peptide P23 (MTDFYVPVS-LCTPSRAALLTGRS) (SEQ ID NO:33) was used as substrate. The conversion of the Cysteine residue in position 11 to FGly was monitored by MALDI-TOF mass spectrometry. A 6 µM stock solution of P23 in 30% acetonitrile and 0.1% trifluoroacetic acid (TFA) was prepared. Under standard conditions 6 pmol of P23 were incubated at 37° C. with up to 10 µl enzyme in a final volume of 30 µl 50 mM Tris/HCl, pH 9.0, containing 67 mM NaCl, 15 µM $CaCl_2$, 2 mM DTT, and 0.33 mg/ml bovine serum albumin. To stop the enzyme reaction 1.5 µl 10% TFA were added. P23 then was bound to ZipTip C18 (Millipore), washed with 0.1% TFA and eluted in 3 µl 50% acetonitrile, 0.1% TFA. 0.5 µl of the eluate was mixed with 0.5 µl of matrix solution (5 mg/ml a-cyano-4-hydroxy-cinnamic acid (Bruker Daltonics, Billerica, Mass.) in 50% acetonitrile, 0.1% TFA) on a stainless steel target. MALDI-TOF mass spectrometry was performed with a Reflex III (Bruker Daltonics) using reflectron mode and laser energy just above the desorption/ionization threshold. All spectra were averages of 200-300 shots from several spots on the target. The mass axis was calibrated using peptides of molecular masses ranging from 1000 to 3000 Da as external standards. Monoisotopic $MH^+$ of P23 is 2526.28 and of the FGly containing product 2508.29. Activity (pmol product/h) was calculated on the basis of the peak height of the product divided by the sum of the peak heights of P23 and the product.

Purification of FGE from Bovine Testis

Bovine testes were obtained from the local slaughter house and stored for up to 20 h on ice. The parenchyme was freed from connective tissue and homogenized in a waring blendor and by three rounds of motor pottering. Preparation of rough microsomes (RM) by cell fractionation of the obtained homogenate was performed as described (Meyer et al., *J. Biol. Chem.*, 2000, 275:14550-14557) with the following modifications. Three differential centrifugation steps, 20 minutes each at 4° C., were performed at 500 g (JA10 rotor), 3000 g (JA10) and 10000 g (JA20). From the last supernatant the RM membranes were sedimented (125000 g, Ti45 rotor, 45 min, 4° C.), homogenized by motor pottering and layered on a sucrose cushion (50 mM Hepes, pH 7.6, 50 mM KAc, 6 mM $MgAc_2$, 1 mM EDTA, 1.3 M sucrose, 5 mM β-mercaptoethanol). RMs were recovered from the pellet after spinning for 210 minutes at 45000 rpm in a Ti45 rotor at 4° C. Usually 100000-150000 equivalents RM, as defined by Walter and Blobel (*Methods Enzymol.*,1983, 96:84-93), were obtained from 1 kg of testis tissue. The reticuloplasm, i.e. the luminal content of the RM, was obtained by differential extraction at low concentrations of deoxy Big Chap, as described (Fey et al., *J. Biol. Chem.*, 2001, 276:47021-47028). For FGE purification, 95 ml of reticuloplasm were dialyzed for 20 h at 4° C. against 20 mM Tris/HCl, pH 8.0, 2.5 mM DTT, and cleared by centrifugation at 125000 g for 1 h. 32 ml-aliquots of the cleared reticuloplasm were loaded on a MonoQ HR10/10 column (Amersham Biosciences, Piscataway, N.J.) at room temperature, washed and eluted at 2 ml/min with a linear gradient of 0 to 0.75 M NaCl in 80 ml of the Tris buffer. The fractions containing FGE activity, eluting at 50-165 mM NaCl, of three runs were pooled (42 ml) and mixed with 2 ml of Concanavalin A-Sepharose (Amersham Biosciences) that had been washed with 50 mM Hepes buffer, pH 7.4, containing 0.5 M KCl, 1 mM $MgCl_2$, 1 mM $MnCl_2$, 1 mM $CaCl_2$, and 2.5 mM DTT. After incubation for 16 h at 4° C., the Concanavalin A-Sepharose was collected in a column and washed with 6 ml of the same Hepes buffer. The bound material was eluted by incubating the column for 1 h at room temperature with 6 ml 0.5 M a-methylmannoside in 50 mM Hepes, pH 7.4, 2.5 mM DTT. The elution was repeated with 4 ml of the same eluent. The combined eluates (10 ml) from Concanavalin A-Sepharose were adjusted to pH 8.0 with 0.5 M Tris/HCl, pH 9.0, and mixed with 2 ml of Affigel 10 (Bio-Rad Laboratories, Hercules, Calif.) that had been derivatized with 10 mg of the scrambled peptide (PVSLPTRSCAALLTGR) (SEQ ID NO:34) and washed with buffer A (50 mM Hepes, pH 8.0, containing 0.15 M potassium acetate, 0.125 M sucrose, 1 mM $MgCl_2$, and 2.5 mM DTT). After incubation for 3 h at 4° C. the affinity matrix was collected in a column. The flow through and a wash fraction with 4 ml of buffer A were collected, combined and mixed with 2 ml of Affigel 10 that had been substituted with 10 mg of the Ser69 peptide (PVSL-STPSRAALLTGR) (SEQ ID NO:35) and washed with buffer A. After incubation overnight at 4° C., the affinity matrix was collected in a column, washed 3 times with 6 ml of buffer B (buffer A containing 2 M NaCl and a mixture of the 20 proteinogenic amino acids, each at 50 mg/ml). The bound material was eluted from the affinity matrix by incubating the Affigel twice for 90 min each with 6 ml buffer B containing 25 mM Ser69 peptide. An aliqout of the eluate was substituted with 1 mg/ml bovine serum albumin, dialyzed against buffer A and analyzed for activity. The remaining part of the activity (11.8 ml) was concentrated in a Vivaspin 500 concentrator (Vivascience AG, Hannover, Germany), and solubilized at 95° C. in Laemmli SDS sample buffer. The polypeptide composition of the starting material and preparations obtained after the chromatographic steps were monitored by SDSPAGE (15% acrylamide, 0.16% bisacrylamide) and staining with SYPRO Ruby (Bio-Rad Laboratories).

Identification of FGE by Mass Spectrometry

For peptide mass fingerprint analysis the purified polypeptides were in-gel digested with trypsin (Shevchenko et al., *Anal. Chem.*, 1996, 68:850-855), desalted on C18 ZipTip and analyzed by MALDI-TOF mass spectrometry using dihydrobenzoic acid as matrix and two autolytic peptides from trypsin (m/z 842.51 and 2211.10) as internal standards. For tandem mass spectrometry analysis selected peptides were analyzed by MALDI-TOF post-source decay mass spectrometry. Their corresponding doubly charged ions were isolated and fragmented by offline nano-ESI ion trap mass spectrometry (EsquireLC, Bruker Daltonics). The mass spectrometric data were used by Mascot search algorithm for protein identification in the NCBInr protein database and the NCBI EST nucleotide database.

Bioinformatics

Signal peptides and clevage sites were described with the method of von Heijne (von Heijne, *Nucleic Acids Res.*, 1986, 14:4683-90) implemented in EMBOSS (Rice et al., *Trends in Genetics*, 2000, 16:276-277). N-glycosylation sites were predicted using the algorithm of Brunak (Gupta and Brunak, *Pac. Symp. Biocomput.*, 2002, 310-22). Functional domains were detected by searching PFAM-Hidden-Markov-Models (version 7.8) (Sonnhammer et al., *Nucleic Acids Res.*, 1998, 26:320-322). To search for FGE homologs, the databases of the National Center for Biotechnology Information (Wheeler et al., *Nucleic Acids Res.*, 2002, 20:13-16) were queried with BLAST (Altschul et al., *Nucleic Acids Res.*, 1997, 25:3389-3402). Sequence similarities were computed using standard tools from EMBOSS. Genomic loci organisation and synteny were determined using the NCBI's human and mouse genome resources and the Human-Mouse Homology Map also form NCBI, Bethesda, Md.).

Cloning of Human FGE cDNA

Total RNA, prepared from human fibroblasts using the RNEASY™ Mini kit (Qiagen, Inc., Valencia, Calif.) was reverse transcribed using the OMNISCRIPT RT™ kit (Qiagen, Inc., Valencia, Calif.) and either an oligo(dT) primer or the FGE-specific primer 1199nc (CCAATGTAGGTCAGACACG) (SEQ ID NO:36). The first strand cDNA was amplified by PCR using the forward primer 1c (ACATGGCCCGCGGGAC) (SEQ ID NO:37) and, as reverse primer, either 1199nc or 1182nc (CGACTGCTCCTTGGACTGG) (SEQ ID NO:38). The PCR products were cloned directly into the pCR4-TOPO™ vector (Invitrogen Corporation, Carlsbad, Calif.). By sequencing multiple of the cloned PCR products, which had been obtained from various individuals and from independent RT and PCR reactions, the coding sequence of the FGE cDNA was determined (SEQ ID NOs:1 and 3).

Mutation Detection, Genomic Sequencing, Site-directed Mutagenesis and Northern Blot Analysis Standard protocols utilized in this study were essentially as described in Lübke et al. (*Nat. Gen.*, 2001, 28:73-76) and Hansske et al. (*J. Clin. Invest.*, 2002, 109:725-733). Northern blots were hybridized with a cDNA probe covering the entire coding region and a β-actin cDNA probe as a control for RNA loading.

Cell Lines and Cell Culture

The fibroblasts from MSD patients 1-6 were obtained from E. Christenson (Rigshospitalet Copenhagen), M. Beck (Universitätskinderklinik Mainz), A. Kohlschütter (Universitätskrankenhaus Eppendorf, Hamburg), E. Zammarchi (Meyer Hospital, University of Florence), K. Harzer (Institut für Hirnforschung, Universität Tübingen), and A. Fensom (Guy's Hospital, London), respectively. Human skin fibroblasts, HT-1080, BHK21 and CHO cells were maintained at 37° C. under 5% $CO_2$ in Dulbecco's modified Eagle's medium containing 10% fetal calf serum.

Transfection, Indirect Immunofluorescence, Western Blot Analysis and Detection of FGE Activity The FGE cDNA was equipped with a 5' EcoRI-site and either a 3' HA-, c-Myc or RGS-$His_6$-tag sequence, followed by a stop-codon and a HindIII site, by add-on PCR using Pfu polymerase (Stratagene, La Jolla, Calif.) and the following primers: GGAATTCGGGACAACATGGCTGCG (EcoRI) (SEQ ID NO:39), CCCAAGCTTATGC GTAGTCAGGCA-CATCATACGGATAGTCCATGGTGGGCAGGC(HA) (SEQ ID NO:40), CCCAAGCTTACAGGTCTTCTTCA-GAAATCAGCTTTTGTTCGTCCATGGTGGGCAG GC (c-Myc) (SEQ ID NO:41), CCCAAGCTTAGTGATGGT-GATGGTGATGCGATC CTCTGTCCATG-GTGGGCAGGC (RGS-$His_6$) (SEQ ID NO:42). The resulting PCR products were cloned as EcoRI/HindIII fragments into pMPSVEH (Artelt et al., *Gene*, 1988, 68:213-219). The plasmids obtained were transiently transfected into HT-1080, BHK21 and CHO cells, grown on cover slips, using EFFECT-ENE™ (Qiagen) as transfection reagent. 48 h after transfection the cells were analyzed by indirect immunofluorescence as described previously (Lübke et al., *Nat. Gen.*, 2001, 28:73-76; Hansske et al., *J. Clin. Invest.*, 2002, 109:725-733), using monoclonal IgG1 antibodies against HA (Berkeley Antibody Company, Richmond, Calif.), c-Myc (Santa Cruz Biotechnology, Inc., Santa Cruz, Calif.) or RGS-His (Qiagen) as primary antibodies. The endoplasmic reticulum marker protein proteindisulfide isomerase (PDI) was detected with a monoclonal antibody of different subtype (IgG2A, Stressgen Biotech., Victoria BC, Canada). The primary antibodies were detected with isotype-specific goat secondary antibodies coupled to CY2 or CY3, respectively (Molecular Probes, Inc., Eugene, Oreg.). Immunofluorescence images were obtained on a Leica TCS Sp2 AOBS laser scan microscope. For Western blot analysis the same monoclonal antibodies and a HRP-conjugated anti-mouse IgG as secondary antibody were used. For determination of FGE activity, the trypsinised cells were washed with phosphate buffered saline containing a mixture of proteinase inhibitors (208 µM 4-(2-aminoethyl)benzene sulfonyl fluoride hydrochloride, 0.16 µM aprotinin, 4.2 µM leupeptin, 7.2 µM bestatin, 3 µM pepstatin A, 2.8 µM E-64), solubilized in 10 mM Tris, pH 8.0, containing 2.5 mM DTT, the proteinase inhibitors and 1% Triton X-100, and cleared by centrifugation at 125,000 g for 1 h. The supernatant was subjected to chromatography on a MonoQ PC 1.6/5 column using the conditions described above. Fractions eluting at 50-200 mM NaCl were pooled, lyophilised and reconstituted in one tenth of the original pool volume prior determination of FGE activity with peptide P23.

Retroviral Transduction cDNAs of interest were cloned into the Moloney murine leukemia virus based vector pLPCX and pLNCX2 (BD Biosciences Clontech, Palo Alto, Calif.). The transfection of ecotropic FNX-Eco cells (ATCC, Manassas, Va.) and the transduction of amphotropic RETROPACK™ PT67 cells (BD Biosciences Clontech) and human fibroblasts was performed as described (Lübke et al., *Nat. Gen.*, 2001, 28:73-76; Thiel et al., *Biochem. J.*, 2002, 376, 195-201). For some experiments pLPCX-transduced PT67 cells were selected with puromycin prior determination of sulfatase activities.

Sulfatase Assays

Activity of ASA, STS and GalNAc6S were determined as described in Rommerskirch and von Figura, *Proc. Natl. Acad. Sci., USA*, 1992, 89:2561-2565; Glössl and Kresse, *Clin. Chim. Acta*, 1978, 88:111-119.

Results

A Rapid Peptide Based Assay for FGE Activity

We had developed an assay for determining FGE activity in microsome extracts using in vitro synthesized [$^{35}$S] ASA fragments as substrate. The fragments were added to the assay mixture as ribosome-associated nascent chain complexes. The quantitation of the product included tryptic digestion, separation of the peptides by RP-HPLC and identification and quantitation of the [$^{35}$S]-labeled FGly containing tryptic peptide by a combination of chemical derivatization to hydrazones, RP-HPLC separation and liquid scintillation counting (Fey et al., *J. Biol. Chem.*, 2001, 276:47021-47028). For monitoring the enzyme activity during purification, this cumbersome procedure needed to be modified. A synthetic 16mer peptide corresponding to ASA residues 65-80 and containing the sequence motif required for FGly formation inhibited the FGE activity in the in vitro assay. This suggested that peptides such as ASA65-80 may serve as substrates for FGE. We synthesized the 23mer peptide P23 (SEQ ID NO:33), which corresponds to ASA residues 60-80 with an additional N-acetylated methionine and a C-amidated serine residue to protect the N- and C-terminus, respectively. The cysteine and the FGly containing forms of P23 could be identified and quantified by matrix-assisted laser desorption/ionisation time of flight (MALDI-TOF) mass spectrometry. The presence of the FGly residue in position 11 of P23 was verified by MALDI-TOF post source decay mass spectrometry (see Peng et al., *J. Mass Spec.*, 2003, 38:80-86). Incubation of P23 with extracts from microsomes of bovine pancreas or bovine testis converted up to 95% of the peptide into a FGly containing derivative (FIG. 1). Under standard conditions the reaction was proportional to the amount of enzyme and time of incubation as long as less than 50% of the substrate was consumed and the incubation period did not exceed 24 h. The $k_m$ for P23 was 13 nM. The effects of reduced and oxidized glutathione, $Ca^{2+}$ and pH were comparable to those seen in the assay using ribosome-associated nascent chain complexes as substrate (Fey et al., *J. Biol. Chem.*, 2001, 276: 47021-47028).

Purification of FGE

Figure 2:
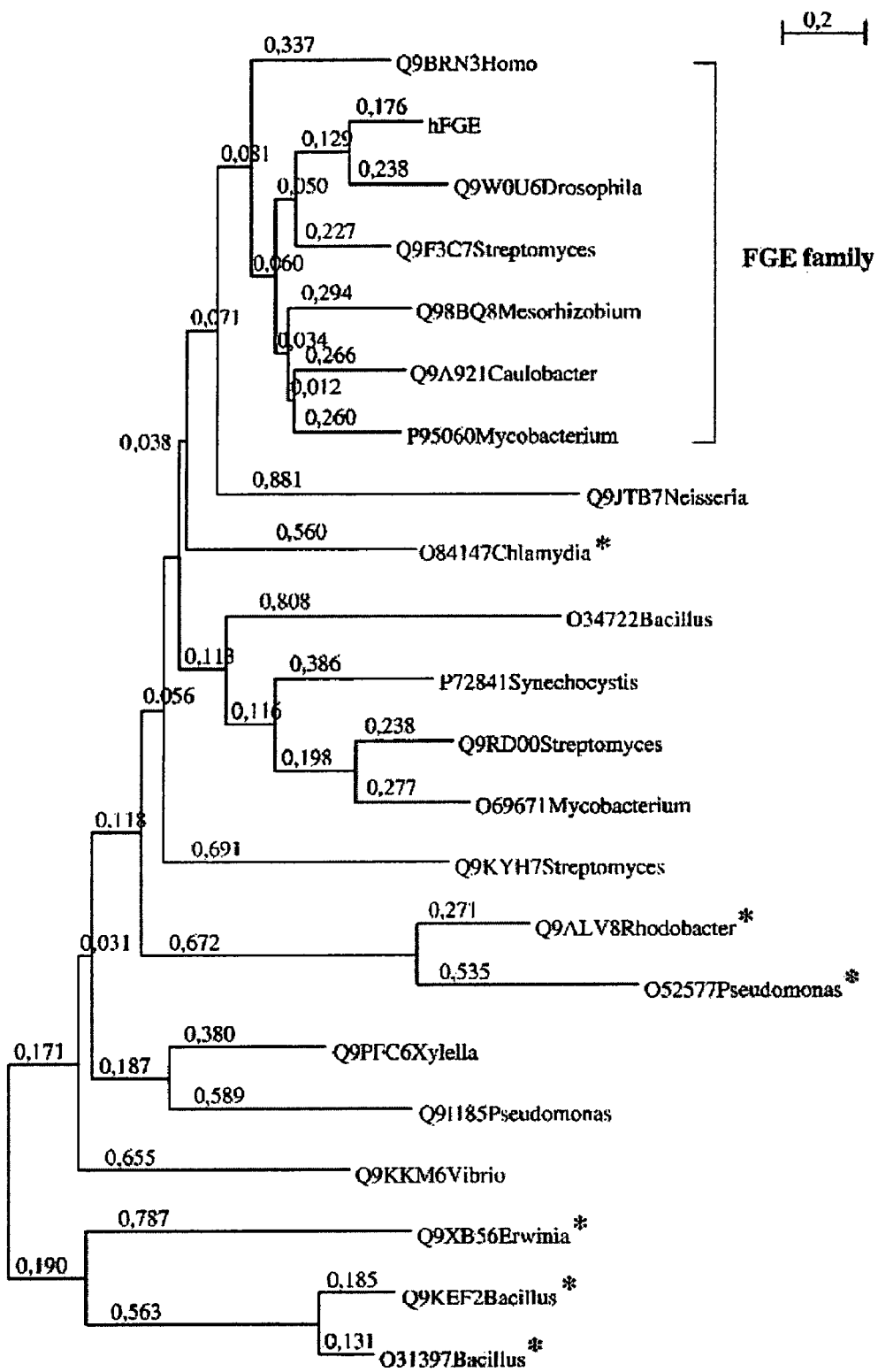
FIG. 2: A phylogenetic tree derived from an alignment of human FGE and 21 proteins of the PFAM-DUF323 seed.

For purification of FGE the soluble fraction (reticuloplasm) of bovine testis microsomes served as the starting material. The specific activity of FGE was 10-20 times higher than that in reticuloplasm from bovine pancreas microsomes (Fey et al., *J. Biol. Chem.*, 2001, 276:47021-47028). Purification of FGE was achieved by a combination of four chromatographic steps. The first two steps were chromatography on a MonoQ anion exchanger and on Concanavalin A-Sepharose. At pH 8 the FGE activity bound to MonoQ and was eluted at 50-165 mM NaCl with 60-90% recovery. When this fraction was mixed with Concanavalin A-Sepharose, FGE was bound. 30-40% of the starting activity could be eluted with 0.5 M a-methyl mannoside. The two final purification steps were chromatography on affinity matrices derivatized with 16mer peptides. The first affinity matrix was Affigel 10 substituted with a variant of the ASA65-80 peptide, in which residues Cys69, Pro71 and Arg73, critical for FGly formation, were scrambled (scrambled peptide PVSLPTR-SCAALLTGR—SEQ ID NO:34). This peptide did not inhibit FGE activity when added at 10 mM concentration to the in vitro assay and, when immobilized to Affigel 10, did not retain FGE activity. Chromatography on the scrambled peptide affinity matrix removed peptide binding proteins including chaperones of the endoplasmic reticulum. The second affinity matrix was Affigel 10 substituted with a variant of the ASA65-80 peptide, in which the Cys69 was replaced by a serine (Ser69 peptide PVSLSTPSRAALLTGR-SEQ ID NO:35). The Ser69 peptide affinity matrix efficiently bound FGE. The FGE activity could be eluted with either 2 M KSCN or 25 mM Ser69 peptide with 20-40% recovery. Prior to activity determination the KSCN or Ser69 peptide had to be removed by dialysis. The substitution of Cys69 by serine was crucial for the elution of active FGE. Affigel 10 substituted with the wildtype ASA65-80 peptide bound FGE efficiently. However, nearly no activity could be recovered in eluates with chaotropic salts (KSCN, $MgCl_2$), peptides (ASA65-80 or Ser69 peptide) or buffers with low or high pH. In FIG. 2 the polypeptide pattern of the starting material and of the active fractions obtained after the four chromatographic steps of a typical purification is shown. In the final fraction 5% of the starting FGE activity and 0.0006% of the starting protein were recovered (8333-fold purification).

The Purified 39.5 and 41.5 kDa Polypeptides are Encoded by a Single Gene

The 39.5 and 41.5 kDa polypeptides in the purified FGE preparation were subjected to peptide mass fingerprint analysis. The mass spectra of the tryptic peptides of the two polypeptides obtained by MALDI-TOF mass spectrometry were largely overlapping, suggesting that the two proteins originate from the same gene. Among the tryptic peptides of both polypeptides two abundant peptides MH$^+$1580.73, SQNTPDSSASNLGFR (SEQ ID NO:43), and MH$^+$2049.91, MVPIPAGVFTMGTDDPQIK-SEQ ID NO:44 plus two methionine oxidations) were found, which matched to the protein encoded by a cDNA with GenBank Acc. No. AK075459 (SEQ ID NO:4). The amino acid sequence of the two peptides was confirmed by MALDI-TOF post source decay spectra and by MS/MS analysis using offline nano-electrospray ionisation (ESI) iontrap mass spectrometry. An EST sequence of the bovine ortholog of the human cDNA covering the C-terminal part of the FGE and matching the sequences of both peptides provided additional sequence information for bovine FGE.

Evolutionary Conservation and Domain Structure of FGE

Figure 3:
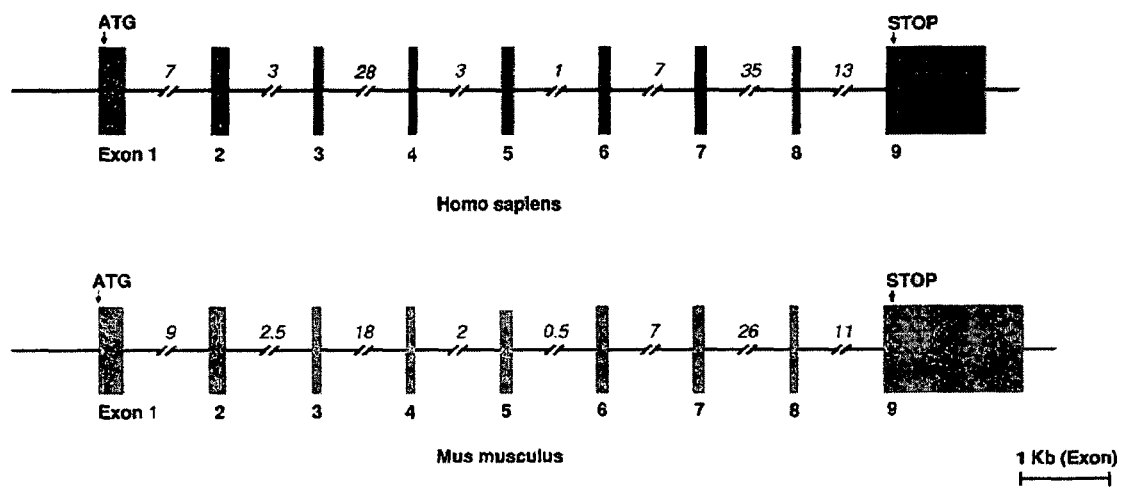
FIG. 3: Organisation of the human and murine FGE gene locus. Exons are shown to scale as boxes and bright boxes (murine locus). The numbers above the intron lines indicate the size of the introns in kilobases.

The gene for human FGE is encoded by the cDNA of (SEQ ID NOs:1 and/or 3) and located on chromosome 3p26. It spans ~105 kb and the coding sequence is distributed over 9 exons. Three orthologs of the human FGE gene are found in mouse (87% identity), *Drosophila melanogaster* (48% identity), and *Anopheles gambiae* (47% identity). Orthologous EST sequences are found for 8 further species including cow, pig, *Xenopus laevis, Silurana tropicalis*, zebra fish, salmon and other fish species (for details see Example 2). The exon-intron structure between the human and the mouse gene is conserved and the mouse gene on chromosome 6E2 is located within a region syntenic to the human chromosome 3p26. The genomes of *S. cerevisiae* and *C. elegans* lack FGE homologs. In prokaryotes 12 homologs of human FGE were found. The cDNA for human FGE is predicted to encode a protein of 374 residues (FIG. 3 and SEQ ID NO:2). The protein contains a cleavable signal sequence of 33 residues, which indicates translocation of FGE into the endoplasmic reticulum, and contains a single N-glycosylation site at Asn141. The binding of FGE to concanavalin A suggests that this N-glycosylation site is utilized. Residues 87-367 of FGE are listed in the PFAM protein motif database as a domain of unknown function (PFAM: DUF323). Sequence comparison analysis of human FGE and its eukaryotic orthologs identified in data bases indicates that this domain is composed of three distinct subdomains.

The N-terminal subdomain (residues 91-154 in human FGE) has a sequence identity of 46% and a similarity of 79% within the four known eukaryotic FGE orthologs. In human FGE, this domain carries the N-glycosylation site at Asn 141, which is conserved in the other orthologs. The middle part of FGE (residues 179-308 in human FGE) is represented by a tryptophan-rich subdomain (12 tryptophans per 129 residues). The identity of the eukaryotic orthologs within this subdomain is 57%, the similarity is 82%. The C-terminal subdomain (residues 327-366 in human FGE) is the most highly conserved sequence within the FGE family. The sequence identity of the human C-terminal subdomain with the eukaryotic orthologs (3 full length sequences and 8 ESTs) is 85%, the similarity 97%. Within the 40 residues of the subdomain 3 four cysteine residues are fully conserved. Three of cysteins are also conserved in the prokaryotic FGE orthologs. The 12 prokaryotic members of the FGE-family (for details see Example 2) share the subdomain structure with eukaryotic FGEs. The boundaries between the three subdomains are more evident in the prokaryotic FGE family due to non-conserved sequences of variable length separating the subdomains from each other. The human and the mouse genome encode two closely related homologs of FGE (SEQ ID NOs:43 and 44, GenBank Acc. No. NM_015411, in man, and SEQ ID NOs:45 and 46, GenBank Acc. No. AK076022, in mouse). The two paralogs are 86% identical. Their genes are located on syntenic chromosome regions (7q11 in human, 5G1 in mouse). Both paralogs share with the FGE orthologs the subdomain structure and are 35% identical and 47% similar to human FGE. In the third subdomain, which is 100% identical in both homologs, the cysteine containing undecamer sequence of the subdomain 3 is missing.

Expression, Subcellular Localization and Molecular Forms

A single transcript of 2.1 kb is detectable by Northern blot analysis of total RNA from skin fibroblasts and poly A+ RNA from heart, brain, placenta, lung, liver, skeletal muscle, kidney and pancreas. Relative to β-actin RNA the abundance varies by one order of magnitude and is highest in pancreas and kidney and lowest in brain. Various eukaryotic cell lines stably or transiently expressing the cDNA of human FGE or FGE derivatives C-terminally extended by a HA-, Myc- or His$_6$-tag were assayed for FGE activity and subcellular localization of FGE. Transient expression of tagged and non-tagged FGE increased the FGE activity 1.6-3.9-fold. Stable expression of FGE in PT67 cells increased the activity of FGE about 100-fold. Detection of the tagged FGE form by indirect immunofluorescence in BHK 21, CHO, and HT1080 cells showed a colocalization of the variously tagged FGE forms with proteindisulfide isomerase, a lumenal protein of the endoplasmic reticulum. Western blot analysis of extracts from BHK 21 cells transiently transfected with cDNA encoding tagged forms of FGE showed a single immunoreactive band with an apparent size between 42 to 44 kDa.

The FGE Gene Carries Mutations in MSD

MSD is caused by a deficiency to generate FGly residues in sulfatases (Schmidt, B., et al., *Cell*, 1995, 82:271-278). The FGE gene is therefore a candidate gene for MSD. We amplified and sequenced the FGE encoding cDNA of seven MSD patients and found ten different mutations that were confirmed by sequencing the genomic DNA (Table 1).

TABLE 1

Mutations in MSD patients

| Mutation | Effect on Protein | Remarks | Patient |
|---|---|---|---|
| 1076C > A | S359X | Truncation of the C-terminal 16 residues | 1* |
| IVS3 + 5-8 del | Deletion of residues 149-173 | In-frame deletion of exon 3 | 1, 2 |
| 979C > T | R327X | Loss of subdomain 3 | 2 |
| 1045C > T | R349W | Substitution of a conserved residue in subdomain 3 | 3, 7 |
| 1046G > A | R349Q | Substitution of a conserved residue in subdomain 3 | 4 |
| 1006T > C | C336R | Substitution of a conserved residue in subdomain 3 | 4 |
| 836C > T | A279V | Substitution of a conserved residue in subdomain 2 | 5 |
| 243delC | frameshift and truncation | Loss of all three subdomains | 5 |
| 661delG | frameshift and truncation | Loss of the C-terminal third of FGE including subdomain 3 | 6** |
| IVS6-1G > A | Deletion of residues 281-318 | In-frame deletion of exon 7 | 5 |

*Patient 1 is the MSD patient Mo. in Schmidt, B., et al., Cell, 1995, 82: 271-278 and Rommerskirch and von Figura, Proc. Natl. Acad. Sci., USA, 1992, 89: 2561-2565.
**Patient 6 is the MSD patient reported by Burk et al., J. Pediatr., 1984, 104: 574-578.
The other patients represent unpublished cases.

The first patient was heterozygous for a 1076C>A substitution converting the codon for serine 359 into a stop codon (S359X) and a mutation causing the deletion of the 25 residues 149-173 that are encoded by exon 3 and space the first and the second domain of the protein. Genomic sequencing revealed a deletion of nucleotides +5-8 of the third intron (IVS3+5-8 del) thereby destroying the splice donor site of intron 3. The second patient was heterozygous for the mutation causing the loss of exon 3 (IVS3+5-8 del) and a 979C>T substitution converting the codon for arginine 327 into a stop codon (R327X). The truncated FGE encoded by the 979C>T allele lacks most of subdomain 3. The third patient was homozygous for a 1045C>T substitution replacing the conserved arginine 349 in subdomain 3 by tryptophan (R349W). The fourth patient was heterozygous for two missense mutations replacing conserved residues in the FGE domain: a 1046>T substitution replacing arginine 349 by glutamine (R349Q) and a 1006T>C substitution replacing cysteine 336 by arginine (C336R). The fifth patient was heterozygous for a 836 C>T substitution replacing the conserved alanine 279 by valine (A279V). The second mutation is a single nucleotide deletion (243delC) changing the sequence after proline 81 and causing a translation stop after residue 139. The sixth patient was heterozygous for the deletion of a single nucleotide (661delG) changing the amino acid sequence after residue 220 and introducing a stop codon after residue 266. The second mutation is a splice acceptor site mutation of intron 6 (IVS6-1G>A) causing an in-frame deletion of exon 7 encoding residues 281-318. In the seventh patient the same 1045C>T substitution was found as in the third patient. In addition we detected two polymorphisms in the coding region of 18 FGE alleles from controls and MSD patients. 22% carried a 188G>A substitution, replacing serine 63 by asparagine (S63N) and 28% a silent 1116C>T substitution.

Transduction of MSD Fibroblasts with Wild Type and Mutant FGE cDNA

In order to confirm the deficiency of FGE as the cause of the inactivity of sulfatases synthesized in MSD, we expressed the FGE cDNA in MSD fibroblasts utilizing retroviral gene transfer. As a control we transduced the retroviral vector without cDNA insert. To monitor the complementation of the metabolic defect the activity of ASA, steroid sulfatase (STS) and N-acetylgalactosamine 6-sulfatase (GalNAc6S) were measured in the transduced fibroblasts prior or after selection. Transduction of the wild type FGE partially restored the catalytic activity of the three sulfatases in two MSD-cell lines (Table 2) and for STS in a third MSD cell line. It should be noted that for ASA and GalNAc6S the restoration was only partial after selection of the fibroblasts reaching 20 to 50% of normal activity. For STS the activity was found to be restored to that in control fibroblasts after selection. Selection increased the activity of ASA and STS by 50 to 80%, which is compatible with the earlier observation that 15 to 50% of the fibroblasts become transduced (Lübke et al., *Nat. Gen.*, 2001, 28:73-76). The sulfatase activities in the MSD fibroblasts transduced with the retroviral vector alone (Table 2) were comparable to those in non-transduced MSD fibroblasts (not shown). Transduction of FGE cDNA carrying the IVS3+5-8del mutation failed to restore the sulfatase activities (Table 2).

TABLE 2

Complementation of MSD fibroblasts by transduction of wild type or mutant FGE cDNA

| Fibroblasts | FGE-insert | Sulfatase | | |
|---|---|---|---|---|
| | | ASA[1] | STS[1] | GalNAc6S[1] |
| MSD 3° | — | 1.9 ± 0.2 | <3 | 56.7 ± 32 |
| | FGE[+] | 7.9 | 13.5 | n.d. |
| | FGE[++] | 12.2 ± 0.2 | 75.2 | 283 ± 42 |
| | FGE-IVS3 + 5-8del[+] | 1.8 | <3 | n.d. |
| | FGE-IVS3 + 5-8del[++] | 2.1 | <3 | 98.5 |
| MSD 4° | — | 1.1 ± 0.3 | <3 | n.d. |
| | FGE[+] | 4.7 | 17.0 | n.d. |
| Control fibroblasts | | 58 ± 11 | 66 ± 31 | 828 ± 426 |

[1]The values give the ratio between ASA (mU/mg cell protein), STS (µU/mg cell protein), GalNAc6S (µU/mg cell protein) and that of β-hexosaminidase (U/mg cell protein). For control fibroblasts the mean and the variation of 6-11 cell lines is given. Where indicated the range of two cultures transduced in parallel is given for MSD fibroblasts.
°The number of MSD fibroblasts refers to that of the patient in Table 1.
[+]Activity determination prior to selection.
[++]Activity determination after selection.
n.d.: not determined Discussion FGE is a Highly Conserved Glycoprotein of the Endoplasmic Reticulum.

Purification of FGE from bovine testis yielded two polypeptides of 39.5 and 41.5 kDa which originate from the same gene. The expression of three differently tagged versions of FGE in three different eukaryotic cell lines as a single form suggests that one of the two forms observed in the FGE preparation purified from bovine testis may have been generated by limited proteolysis during purification. The substitution of Cys69 in ASA65-80 peptide by serine was critical for the purification of FGE by affinity chromatography. FGE has a cleavable signal sequence that mediates translocation across the membrane of the endoplasmic reticulum. The greater part of the mature protein (275 residues out of 340) defines a unique domain, which is likely to be composed of three subdomains (see Example 2), for none of the three subdomains homologs exist in proteins with known function. The recognition of the linear FGly modification motif in newly synthesized sulfatase polypeptides (Dierks et al., *EMBO J.*, 1999, 18:2084-2091) could be the function of a FGE subdomain. The catalytic domain could catalyse the FGly formation in several ways. It has been proposed that FGE abstracts electrons from the thiol group of the cysteine and transfers them to an acceptor. The resulting thioaldehyde would spontaneously hydrolyse to FGly and $H_2S$ (Schmidt, B., et al., *Cell*, 1995, 82:271-278). Alternatively FGE could act as a mixed-function oxygenase (monooxygenase) introducing one atom of $O_2$ into the cysteine and the other in $H_2O$ with the help of an electron donor such as $FADH_2$. The resulting thioaldehyde hydrate derivative of cysteine would spontaneously react to FGly and $H_2S$. Preliminary experiments with a partially purified FGE preparation showed a critical dependence of the FGly formation on molecular oxygen. This would suggest that FGE acts as a mixed-function oxygenase. The particular high conservation of subdomain 3 and the presence of three fully conserved cysteine residues therein make this subdomain a likely candidate for the catalytic site. It will be interesting to see whether the structural elements mediating the recognition of the FGly motif and the binding of an electron acceptor or electron donor correlate with the domain structure of FGE.

Recombinant FGE is localized in the endoplasmic reticulum, which is compatible with the proposed site of its action. FGly residues are generated in newly synthesized sulfatases during or shortly after their translocation into the endoplasmic reticulum (Dierks et al., *Proc. Natl. Acad. Sci. U.S.A.*, 1997, 94:11963-11968; Dierks et al., *FEBS Lett.*, 1998, 423:61-65). FGE itself does not contain an ER-retention signal of the KDEL (SEQ ID NO:96) type. Its retention in the endoplasmic reticulum may therefore be mediated by the interaction with other ER proteins. Components of the translocation/N-glycosylation machinery are attractive candidates for such interacting partners.

Mutations in FGE Cause MSD

We have shown that mutations in the gene encoding FGE cause MSD. FGE also may interact with other components, and defects in genes encoding the latter could equally well cause MSD. In seven MSD patients we indeed found ten different mutations in the FGE gene. All mutations have severe effects on the FGE protein by replacing highly conserved residues in subdomain 3 (three mutations) or subdomain 2 (one mutation) or C-terminal truncations of various lengths (four mutations) or large inframe deletions (two mutations). For two MSD-cell lines and one of the MSD mutations it was shown that transduction of the wild type, but not of the mutant FGE cDNA, partially restores the sulfatase activities. This clearly identifies the FGE gene as the site of mutation and the disease causing nature of the mutation. MSD is both clinically and biochemically heterogenous. A rare neonatal form presenting at birth and developing a hydrocephalus, a common form resembling initially to an infantile metachromatic leukodystrophy and subsequently developing ichthyosis- and mucopolysaccharidosis-like features, and a less frequent mild form in which the clinical features of a mucopolysaccharidosis prevail, have been differentiated. Biochemically it is characteristic that a residual activity of sulfatases can be detected, which for most cases in cultured skin fibroblasts is below 10% of controls (Burch et al., *Clin. Genet.*, 1986, 30:409-15; Basner et al., *Pediatr. Res.*, 1979, 13:1316-1318). However, in some MSD cell lines the activity of selected sulfatases can reach the normal range (Yutaka et al., *Clin. Genet.*, 1981, 20:296-303). Furthermore, the residual activity has been reported to be subject to variations depending on the cell culture conditions and unknown factors. Biochemically, MSD has been classified into two groups. In group I the residual activity of sulfatases is below 15% including that of ASB. In group II the residual activity of sulfatases is higher and particularly that of ASB may reach values of up to 50-100% of control. All patients reported here fall into group I except patient 5, which falls into group II (ASB activity in the control range) of the biochemical phenotype. Based on clinical criteria patients 1 and 6 are neonatal cases, while patients 2-4 and 7 have the common and patient 5 the mucopolysaccharidosis-like form of MSD.

The phenotypic heterogeneity suggests that the different mutations in MSD patients are associated with different residual activities of FGE. Preliminary data on PT67 cells stably expressing FGE IVS3+5-8del indicate that the in-frame deletion of exon 3 abolishes FGE activity completely. The characterization of the mutations in MSD, of the biochemical properties of the mutant FGE and of the residual content of FGly in sulfatases using a recently developed highly sensitive mass spectrometric method (Peng et al., *J. Mass Spec.*, 2003, 38:80-86) will provide a better understanding of the genotype-phenotype correlation in MSD.

Example 2

The Human FGE Gene Defines a New Gene Family Modifying Sulfatases Which is Conserved from Prokaryotes to Eukaryotes
Bioinformatics Signal peptides and cleavage sites were described with the method of von Heijne (*Nucleic Acids Res.*, 1986, 14:4683) implemented in EMBOSS (Rice et al., *Trends in Genetics*, 2000, 16:276-277), and the method of Nielsen et al. (*Protein Engineering*, 1997, 10:1-6). N-glycosylation sites were predicted using the algorithm of Brunak (Gupta and Brunak, *Pac. Symp. Biocomput.*, 2002, 310-22).

Functional domains were detected by searching PFAM-Hidden-Markov-Models (version 7.8) (Sonnhammer et al., *Nucleic Acids Res.*, 1998, 26:320-322). Sequences from the PFAM DUF323 seed were obtained from TrEMBL (Bairoch, A. and Apweiler, R., *Nucleic Acids Res.*, 2000, 28:45-48). Multiple alignments and phylogenetic tree constructions were performed with Clustal W (Thompson, J., et al., *Nucleic Acids Res.*, 1994, 22:4673-4680). For phylogenetic tree computation, gap positions were excluded and multiple substitutions were corrected for. Tree bootstraping was performed to obtain significant results. Trees were visualised using Njplot (Perriere, G. and Gouy, M., *Biochimie*, 1996, 78:364-369). Alignments were plotted using the pret-typlot command from EMBOSS.

To search for FGE homologs, the databases NR, NT and EST of the National Center for Biotechnology Information (NCBI) (Wheeler et al., *Nucleic Acids Res.*, 2002, 20:13-16), were queried with BLAST (Altschul et al., *Nucleic Acids Res.*, 1997, 25:3389-3402). For protein sequences, the search was performed using iterative converging Psi-Blast against the current version of the NR database using an expectation value cutoff of $10^{-40}$, and default parameters. Convergence was reached after 5 iterations. For nucleotide sequences, the search was performed with Psi-TBlastn: using NR and the protein sequence of human FGE as input, a score matrix for hFGE was built with iterative converging Psi-Blast. This matrix was used as input for blastall to query the nucleotide databses NT and EST. For both steps, an expectation value cutoff of $10^{-20}$ was used.

Protein secondary structure prediction was done using Psipred (Jones, D., *J Mol Biol.*, 1999, 292:1950-202; McGuffin, L., et al., *Bioinfonnatics*, 2000, 16:404-405).

Similarity scores of the subdomains were computed from alignments using the cons algorithm form EMBOSS with default parameters. The metaalignments were generated by aligning consensus sequences of the FGE-family subgroups. Genomic loci organisation and synteny were determined using the NCBI's human and mouse genome resources at NCBI (Bethesda, Md.) and Softberry's (Mount Kisco, N.Y.) Human-Mouse-Rat Synteny. Bacterial genome sequences were downloaded from the NCBI-FTP-server. The NCBI microbial genome annotation was used to obtain an overview of the genomic loci of bacterial FGE genes.

Results and Discussion

Basic Features and Motifs of Human FGE and Related Proteins

The human FGE gene (SEQ ID NOs:1, 3) encodes the FGE protein (SEQ ID NO:2) which is predicted to have 374 residues. A cleavage signal between residues 22-33 (Heijne-Score of 15.29) and a hydropathy-score (Kyte, J. and Doolittle, R., *J Mol Biol.*, 1982, 157:105-132) of residues 17-29 between 1.7 and 3.3 indicate that the 33 N-terminal residues are cleaved off after ER-translocation. However with the algorithm of Nielsen et al. (*Protein Engineering*, 1997, 10:1-6), cleavage of the signal sequence is predicted after residue 34. The protein has a single potential N-glycosylation site at Asn 141.

A search with the FGE protein sequence against the protein motif database PFAM (Sonnhammer et al., *Nucleic Acids Res.*, 1998, 26:320-322) revealed that residues 87-367 of human FGE can be classified as the protein domain DUF323 ("domain of unknown function", PF03781) with a highly significant expectation value of $7:9*10^{-114}$. The PFAM-seed defining DUF323 consists of 25 protein sequences, of which the majority are hypothetical proteins derived from sequencing data. To analyse the relationship between human FGE and DUF323, a multiple alignment of FGE with the sequences of the DUF323 seed were performed. Based on this, a phylogenetic tree was constructed and bootstraped. Four of the hypothetical sequences (TrEMBL-IDs Q9CK12, Q9I761, O94632 and Q9Y405) had such a strong divergence from the other members of the seed that they prevented successful bootstraping and had to be removed from the set. FIG. 2 shows the bootstraped tree displaying the relationship between human FGE and the remaining 21 DUF323 seed proteins. The tree can be used to subdivide the seed members into two categories: homologs closely related to human FGE and the remaining, less related genes.

The topmost 7 proteins have a phylogenetic distance between 0.41 and 0.73 to human FGE. They only contain a single domain, DUF323. The homology within this group extends over the whole amino acid sequence, the greater part of which consists of the DUF323 domain. The DUF323 domain is strongly conserved within this group of homologs, while the other 15 proteins of the seed are less related to human FGE (phylogenetic distance between 1.14 and 1.93). Their DUF323 domain diverges considerably from the highly conserved DUF323-domain of the first group (cf. section "Subdomains of FGE and mutations in the FGE gene"). Most of these 15 proteins are hypothetical, six of them have been further investigated. One of them, a serine/threonine kinase (TrEMBL:O84147) from *C. trachomatis* contains other domains in addition to DUF323: an ATP-binding domain and a kinase domain. The sequences from *R. sphaeroides* (TrEMBL: Q9ALV8) and *Pseudomonas* sp. (TrEMBL: O52577) encode the protein NirV, a gene cotranscribed with the copper-containing nitrite reductase nirK (Jain, R. and Shapleigh, J., *Microbiology*, 2001, 147:2505-2515). CarC (TrEMBL: Q9XB56) is an oxygenase involved in the synthesis of a β-lactam antibiotic from *E. carotovora* (McGowan, S., et al., *Mol Microbiol.*, 1996, 22:415-426; Khaleeli N, T. C., and Busby R W, *Biochemistry*, 2000, 39:8666-8673). XylR (TrEMBL: O31397) and BH0900 (TrEMBL: Q9KEF2) are enhancer binding proteins involved in the regulation of pentose utilisation (Rodionov, D., et al., *FEMS Microbiol Lett.*, 2001, 205:305-314) in bacillaceae and clostridiaceae. The comparison of FGE and DUF323 led to the establishment of a homology threshold differentiating the FGE family from distant DUF323-containing homologs with different functions. The latter include a serine/threonine kinase and XylR, a transcription enhancer as well as FGE, a FGly generating enzyme and CarC, an oxygenase. As discussed in elsewhere herein, FGE might also exert its cysteine modifying function as an oxygenase, suggesting that FGE and non-FGE members of the DUF323 seed may share an oxygenase function.

Homologs of FGE

The presence of closely related homologs of human FGE in the DUF323 seed directed us to search for homologs of human FGE in NCBI's NR database (Wheeler et al., *Nucleic Acids Res.*, 2002, 20:13-16). The threshold of the search was chosen in such a way that all 6 homologs present in the DUF323 seed and other closely related homologs were obtained without finding the other seed members. This search led to the identification of three FGE orthologs in eukaryotes, 12 orthologs in prokaryotes and two paralogs in man and mouse

TABLE 3

The FGE gene family in eukaryotes and prokaryotes

| SEQ ID NOs: NA, AA [GI] | SPECIES | LENGTH [AA] | SUB-GROUP |
|---|---|---|---|
| 1/3, 2 | *Homo sapiens* | 374 | E1 |
| 49, 50 [22122361] | *Mus musculus* | 372f | E1 |
| 51, 52 [20130397] | *Drosophila melanogaster* | 336 | E1 |
| 53, 54 [21289310] | *Anopheles gambiae* | 290 | E1 |
| 47, 48 [26344956] | *Mus musculus* | 308 | E2 |
| 45, 46 [24308053] | *Homo sapiens* | 301 | E2 |
| 55, 56 [21225812] | *Streptomyces coelicolor* A3(2) | 314 | P1 |
| 57, 58 [25028125] | *Corynebacterium efficiens* YS-314 | 334 | P1 |
| 59, 60 [23108562] | *Novosphingobium aromaticivorans* | 338 | P2 |
| 61, 62 [13474559] | *Mesorhizobium loti* | 372 | P2 |
| 63, 64 [22988809] | *Burkholderia fungorum* | 416 | P2 |
| 65, 66 [16264068] | *Sinorhizobium meliloti* | 303 | P2 |
| 67, 68 [14518334] | *Microscilla* sp. | 354 | P2 |
| 69, 70 [26990068] | *Pseudomonas putida* KT2440 | 291 | P2 |
| 71, 72 [22975289] | *Ralstonia metallidurans* | 259 | P2 |
| 73, 74 [23132010] | *Prochlorococcus marinus* | 291 | P2 |
| 75, 76 [16125425] | *Caulobacter crescentus* CB15 | 338 | P2 |
| 77, 78 [15607852] | *Mycobacterium tuberculosis* Ht37Rv | 299 | P2 |

GI - GenBank protein identifier
NA - nucleic acid
AA - amino acids,
E1 - eukaryotic orthologs
E2 - eukaryotic paralogs
P1 - closely related prokaryotic orthologs
P2 - other prokaryotic orthologs
f - protein sequence mispredicted in GenBank Note that the mouse sequence GI 22122361 is predicted in GenBank to encode a protein of 284 aa, although the cDNA sequence NM 145937 encodes for a protein of 372 residues. This misprediction is based on the omission of the first exon of the murine FGE gene. All sequences found in the NR database are from higher eukaryotes or prokaryotes. FGE-homologs were not detected in archaebacteriae or plants. Searches with even lowered thresholds in the fully sequenced genomes of *C. elegans* and *S. cerevisiae* and the related ORF databases did not reveal any homologs. A search in the eukaryotic sequences of the NT and EST nucleotide databases led to the identification of 8 additional FGE orthologous ESTs with 3'-terminal cDNA sequence fragments showing a high degree of conservation on the protein level which are not listed in the NR database. These sequences do not encompass the full coding part of the mRNAs and are all from higher eukaryotes (Table 4).

TABLE 4

FGE ortholog EST fragments in eukaryotes

| SEQ ID NOs: NA [GB] | SPECIES |
|---|---|
| 80 [CA379852] | *Oncorhynchus mykiss* |
| 81 [AI721440] | *Danio rerio* |
| 82 [BJ505402] | *Oryzias latipes* |
| 83 [BJ054666] | *Xenopus laevis* |
| 84 [AL892419] | *Silurana tropicalis* |
| 85 [CA064079] | *Salmo salar* |
| 86 [BF189614] | *Sus scrofa* |
| 87 [AV609121] | *Bos taurus* |

GB - GenBank Accession No.
NA - nucleic acid

Multiple alignment and construction of a phylogenetic tree (using ClustalW) of the coding sequences from the NR database allowed the definition of four subgroups of homologs: eukaryotic orthologs (human, mouse, mosquito and fruitfly FGE, eukaryotic paralogs (human and mouse FGE paralog), prokaryotic orthologs closely related to FGE (*Streptomyces* and *Corynebacterium* and other prokaryotic orthologs (*Caulobacter, Pseudomanas, Mycobacterium, Prochlorococcus, Mesorhizobium, Sinorhizobium, Novosphingobium, Ralstonia, Burkholderia,* and *Microscilla*). The eukaryotic orthologs show an overall identity to human FGE of 87% (mouse), 48% (fruitfly) and 47% (anopheles). While FGE orthologs are found in prokaryotes and higher eukaryotes, they are missing in the completely sequenced genomes of lower eukaryotes phylogenetically situated between *S. cerevisiae* and *D. melanogaster*. In addition, FGE homologs are absent in the fully sequenced genomes of *E. coli* and the pufferfish.

As discussed elsewhere herein, the FGE paralogs found in human and mouse may have a minor FGly-generating activity and contribute to the residual activities of sulfatases found in MSD patients.

Subdomains of FGE

The members of the FGE gene family have three highly conserved parts/domains (as described elsewhere herein). In addition to the two non-conserved sequences separating the former, they have non-conserved extensions at the N- and C-terminus. The three conserved parts are considered to represent subdomains of the DUF323 domain because they are spaced by non-conserved parts of varying length. The length of the part spacing subdomains 1 and 2 varies between 22 and 29 residues and that spacing subdomains 2 and 3 between 7 to 38 amino acids. The N- and C-terminal non-conserved parts show an even stronger variation in length (N-terminal: 0-90 AA, Cterminal: 0-28 AA). The sequence for the FGE gene from Ralstonia metallidurans is probably incomplete as it lacks the first subdomain.

To verify the plausibility of defining subdomains of DUF323, we performed a secondary structure prediction of the human FGE protein using Psipred. The hydrophobic ER-signal (residues 1-33) is predicted to contain helix-structures confirming the signal prediction of the von-Heijne algorithm. The N-terminal non-conserved region (aa 34-89) and the spacing region between subdomains 2 and 3 (aa 308-327) contain coiled sections. The region spacing subdomains 1 and 2 contains a coil. The α-helix at aa 65/66 has a low prediction confidence and is probably a prediction artefact. The subdomain boundaries are situated within coils and do not interrupt α-helices or β-strands. The first subdomain is made up of several β-strands and an α-helix, the second subdomain contains two β-strands and four α-helices. The third subdomain has a α-helix region flanked by a sheet a the beginning and the end of the subdomain. In summary, the secondary structure is in agreement with the proposed subdomain structure as the subdomain boundaries are situated within coils and the subdomains contain structural elements α-helices and β-strands).

It should be noted that none of the subdomains exists as an isolated module in sequences listed in databases. Within each of the four subgroups of the FGE family, the subdomains are highly conserved, with the third subdomain showing the highest homology (Table 5). This subdomain shows also the strongest homology across the subgroups.

TABLE 5

Homology (% similarity) of the FGE family subdomains

| Subfamily | Members | Subdomain 1 | Subdomain 2 | Subdomain 3 |
|---|---|---|---|---|
| E1 | 4 | 79 | 82 | 100 |
| E2 | 2 | 90 | 94 | 100 |
| P1 | 2 | 70 | 79 | 95 |
| P2 | 10 | 59 | 79 | 80 |

E1 - eukaryotic orthologs
E2 - eukaryotic paralogs
P1 - closely related prokaryotic orthologs
P2 - other prokaryotic orthologs The first subdomain of the FGE-family shows the weakest homology across the subgroups. In the eukaryotic orthologs it carries the N-glycosylation site: at residue Asn 141 in human, at Asn 139 in the mouse and Asn 120 in the fruit fly. In anopheles, no asparagine is found at the residue 130 homologous to *D. melanogaster* Asn 120. However, a change of two nucleotides would create an N-glycosylation site Asn 130 in anopheles. Therefore, the sequence encompassing residue 130 needs to be resequenced. The second subdomain is rich in tryptophans with 12 Trp in 129 residues of human FGE. Ten of these tryptophans are conserved in the FGE family.

High conservation of subdomain 3: subdomain 3 between eukaryotic orthologs are 100% similar and 90% identical. The importance of the third subdomain for the function of the protein is underlined by the observation that this subdomain is a hot spot for disease causing mutations in MSD patients. Seven of nine mutations identified in six MSD patients described in Example 1 are located in sequences that encode the 40 residues of subdomain 3. The residues contain four cysteines, three of which are conserved among the pro- and eukaryotic orthologs. The two eukaryotic paralogs show the lowest homology to the other members of the FGE-family, e.g. they lack two of the three conserved cysteines of subdomain 3. Features conserved between subdomain 3 sequences of orthologs and paralogs are the initial RVXXGG(A)S motif (SEQ ID NO:79), a heptamer containing three arginines (residues 19-25 of the subdomain consensus sequence) and the terminal GFR motif. A comparison with the DUF323 domain of the 15 seed sequences that are no close homologs of FGE shows marked sequence differences: the 15 seed sequences have a less conserved first and second subdomain, although the overall subdomain structure is also visible. Subdomain 3, which is strongly conserved in the FGE family, is shorter and has a significantly weaker homology to the eukaryotic subdomain 3 (similarity of about 20%) as compared to the prokaryotic FGE family members (similarity of about 60%). Thus they lack all of the conserved cysteine residues of subdomain 3. The only conserved features are the initial RVXXGG(A)S motif (SEQ ID NO:79) and the terminal GFR motif.

Genomic Organisation of the Human and Murine FGE Gene

The human FGE gene is located on chromosome 3p26. It encompasses 105 kb and 9 exons for the translated sequence. The murine FGE gene has a length of 80 Kb and is located on chromosome 6E2. The 9 exons of the murine FGE gene have nearly the same size as the human exons (FIG. 3). Major differences between the human and the mouse gene are the lower conservation of the 3'-UTR in exon 9 and the length of exon 9, which is 461 bp longer in the murine gene. Segment 6E2 of mouse chromosome 6 is highly syntenic to the human chromosome segment 3p26. Towards the telomere, both the human and the murine FGE loci are flanked by the genes coding for LMCD1, KIAA0212, ITPR1, AXCAM, and IL5RA. In the centromeric direction, both FGE loci are flanked by the loci of CAV3 and OXTR.

Genomic Organisation of the Prokaryotic FGE Genes

In prokaryotes the sulfatases are classified either as cysteine- or serine-type sulfatases depending on the residue that is converted to FGly in their active center (Miech, C., et al., *J Biol Chem.*, 1998, 273:4835-4837; Dierks, T., et al., *J Biol Chem.*, 1998, 273:25560-25564). In *Klebsiella pneumoniae, E. coli* and *Yersinia pestis*, the serine-type sulfatases are part of an operon with AtsB, which encodes a cytosolic protein containing iron-sulfur cluster motifs and is critical for the generation of FGly from serine residues (Marquordt, C., et al., *J Biol Chem.*, 2003, 278:2212-2218; Szameit, C., et al., *J Biol Chem.*, 1999, 274:15375-15381).

It was therefore of interest to examine whether prokaryotic FGE genes are localized in proximity to cysteine-type sulfatases that are the substrates of FGE. Among the prokaryotic FGE genes shown in Table 3, seven have fully sequenced genomes allowing a neighbourhood analysis of the FGE loci. Indeed, in four of the 7 genomes (*C. efficiens*: PID 25028125, *P. putida*: PID 26990068, *C. crescentus*: PID 16125425 and *M. tuberculosis*: PID 15607852) a cysteine-type sulfatase is found in direct vicinity of FGE compatible with a cotranscription of FGE and the sulfatase. In two of them (*C. efficiens* and *P. putida*), FGE and the sulfatase have even overlapping ORFs, strongly pointing to their coexpression. Furthermore, the genomic neighbourhood of FGE and sulfatase genes in four prokaryotes provides additional evidence for the assumption that the bacterial FGEs are functional orthologs.

The remaining three organisms do contain cysteine-type sulfatases (*S. coelicolor*: PID 24413927, *M. loti*: PID 13476324, *S. meliloti*: PIDs 16262963, 16263377, 15964702), however, the genes neighbouring FGE in these organisms neither contain a canonical sulfatase signature (Dierks, T., et al., *J Biol Chem.*, 1998, 273:25560-25564) nor a domain that would indicate their function. In these organisms the expression of FGE and cysteine-type sulfatases is therefore likely to be regulated in trans.

Conclusions

The identification of human FGE whose deficiency causes the autosomal-recessively transmitted lysosomal storage disease Multiple Sulfatase Deficiency, allows the definition of a new gene family which comprises FGE orthologs from prokaryotes and eukaryotes as well as an FGE paralog in mouse and man. FGE is not found in the fully sequenced genomes of *E. coli, S. cerevisiae, C. elegans* and *Fugu rubripes*. In addition, there is a phylogenetic gap between prokaryotes and higher eukaryotes with FGE lacking in any species phylogenetically situated between prokaryotes and *D. melanogaster*. However, some of these lower eukaryotes, e.g. *C. elegans*, have cysteine-type sulfatase genes. This points to the existence of a second FGly generating system acting on cysteine-type sulfatases. This assumption is supported by the observation that *E. coli*, which lacks FGE, can generate FGly in cysteine-type sulfatases (Dierks, T., et al., *J Biol Chem.*, 1998, 273:25560-25564).

Example 3

FGE Expression Causes Significant Increases in Sulfatase Activity in Cell Lines that Overexpress a Sulfatase We wanted to examine the effects of FGE on cells expressing/overexpressing a sulfatase. To this end, HT-1080 cells expressing human sulfatases Iduronate 2-Sulfatase (I2S) or N-Acetylgalactosamine 6-Sulfatase (GALNS) were transfected in duplicate with either a FGE expression construct, pXMG.1.3 (Table 7 and FIG. 4) or a control plasmid, pXMG.1.2 (FGE in antisense orientation incapable of producing functional FGE, Table 7). Media samples were harvested 24, 48, and 72 hours following a 24 hour post-electroporation medium change. The samples of medium were tested for respective sulfatase activity by activity assay and total sulfatase protein level estimated by ELISA specific for either Iduronate 2-Sulfatase or N-Acetylgalactosamine 6-Sulfatase.

TABLE 6

Transfected Cell Lines Expressing Sulfatases Used as Substrates for Transfection

| Cell Strain | Plasmid | Sulfatase Expressed |
|---|---|---|
| 36F | pXFM4A.1 | N-Acetylgalactosamine 6-Sulfatase |
| 30C6 | pXI2S6 | Iduronate 2-Sulfatase |

TABLE 7

FGE and Control Plasmids Used to Transfect Iduronate 2-Sulfatase and N-Acetylgalactosamine 6-Sulfatase Expressing HT-1080 Cells

| Plasmid | Configuration of Major DNA Sequence Elements* |
|---|---|
| pXMG.1.3 (FGE expression) | >1.6 kb CMV enhancer/promoter>1.1 kb FGE cDNA> hGH3' untranslated sequence<amp<DHFR cassette<Cdneo cassette (neomycin phosphotransferase) |
| pXMG.1.2 (control, FGE reverse orientation) | >1.6 kb CMV enhancer/promoter<1.1 kb FGE cDNA< hGH3' untranslated sequence<amp<DHFR cassette<Cdneo cassette (neomycin phosphotransferase) |

*>denotes orientation 5' to 3'

Experimental Procedures

Materials and Methods

Transfection of HT-1080 Cells Producing Iduronate 2-Sulfatase and N-Acetylgalactosamine 6-Sulfatase HT-1080 cells were harvested to obtain $9-12\times10^6$ cells for each electroporation. Two plasmids were transfected in duplicate: one to be tested (FGE) and a control; in this case the control plasmid contained the FGE cDNA cloned in the reverse orientation with respect to the CMV promoter. Cells were centrifuged at approximately 1000 RPM for 5 minutes. Cells were suspended in 1×PBS at $16\times10^6$ cells/mL. To the bottom of electroporation cuvette, 100 µg of plasmid DNA was added, 750 µL of cell suspension ($12\times10^6$ cells) was added to the DNA solution in the cuvette. The cells and DNA were mixed gently with a plastic transfer pipette, being careful not to create bubbles. The cells were electroporated at 450 V, 250 µF (BioRad Gene Pulser). The time constant was recorded.

The electroporated cells were allowed to sit undisturbed for 10-30 minutes. 1.25 mL of DMEM/10% calf serum was then added to each cuvette, mixed, and all the cells transferred to a fresh T75 flask containing 20 mL DMEM/10. After 24 hours, the flask was re-fed with 20 mL DMEM/10 to remove dead cells. 48-72 hours after transfection, media samples were collected and the cells harvested from duplicate T75 flasks.

Medium Preparation

1 L DMEM/10 (contains: 23 ml of 2 mM L Glutamine, 115 mL calf serum)

Cells were transfected in media without methotrexate (MTX). 24 hours later cells were re-fed with media containing the appropriate amounts of MTX (36F=1.0 µM MTX, 30C6=0.1M MTX). Medium was harvested and cells collected 24, 48, and 72 hours after re-feed.

Activity Assays

Iduronate 2-Sulfatase (I2S). NAP5 Desalting columns (Amersham Pharmacia Biotech AB, Uppsala, Sweden) were equilibrated with Dialysis Buffer (5 mM sodium acetate, 5 mM tris, pH 7.0). I2S-containing sample was applied to the column and allowed to enter the bed. The sample was eluted in 1 mL of Dialysis Buffer. Desalted samples were further diluted to approximately 100 ng/mL I2S in Reaction Buffer (5 mM sodium acetate, 0.5 mg/L BSA, 0.1% Triton X-100, pH 4.5). 10 µL of each I2S sample was added to the top row of a 96-well Fluormetric Plate (Perkin Elmer, Norwalk, Conn.) and pre-incubated for 15 minutes at 37° C. Substrate was prepared by dissolving 4-methyl-umbelliferyl sulfate (Fluka, Buchs, Switzerland) in Substrate Buffer (5 mM sodium acetate, 0.5 mg/mL BSA, pH 4.5) at a final concentration of 1.5 mg/mL. 100 µL of Substrate was added to each well containing I2S sample and the plate was incubated for 1 hour at 37° C. in the dark. After the incubation 190 µL of Stop Buffer (332.5 mM glycine, 207.5 mM sodium carbonate, pH 10.7) was added to each well containing sample. Stock 4-methylumbelliferone (4-MUF, Sigma, St. Louis, Mo.) was prepared as the product standard in reagent grade water to a final concentration of 1 µM. 150 µL of 1 µM 4-MUF Stock and 150 µL Stop Buffer were added to one top row well in the plate. 150 µL of Stop Buffer was added to every remaining well in the 96-well plate. Two fold serial dilutions were made from the top row of each column down to the last row of the plate. The plate was read on a Fusion Universal Microplate Analyzer (Packard, Meriden, Conn.) with an excitation filter wavelength of 330 nm and an emission filter wavelength of 440 nm. A standard curve of µmoles of 4-MUF stock versus fluorescence was generated, and unknown samples have their fluorescence extrapolated from this curve. Results are reported as Units/mL where one Unit of activity was equal to 1 µmole of 4-MUF produced per minute at 37° C.

N-Acetylalactosamine 6-Sulfatase (GALNS). The GALNS activity assay makes use of the fluorescent substrate, 4-methylumbelliferyl-β-D-galactopyranoside-6-sulfate (Toronto Research Chemicals Inc., Catalogue No. M33448). The assay was comprised of two-steps. At the first step, 75 µL of the 1.3 mM substrate prepared in reaction buffer (0.1M sodium acetate, 0.1M sodium chloride, pH 4.3) was incubated for 4 hours at 37° C. with 10 µL of media/protein sample or its corresponding dilutions. The reaction was stopped by the addition of 5 µL of 2M monobasic sodium phosphate to inhibit the GALNS activity. Following the addition of approximately 500 U of β-galactosidase from *Aspergillus oryzae* (Sigma, Catalogue No. G5160), the reaction mixture was incubated at 37° C. for an additional hour to release the fluorescent moiety of the substrate. The second reaction was stopped by the addition of 910 µL of stop solution (1% glycine, 1% sodium carbonate, pH 10.7). The fluorescence of the resultant mixture was measured by using a measurement wavelength of 359 nm and a reference wavelength of 445 nm with 4-methylumbelliferone (sodium salt from Sigma, Catalogue No. M1508) serving as a reference standard. One unit of the activity corresponds to nmoles of released 4-methylumbelliferone per hour.

Immunoassays (ELISA)

Iduronate 2-Sulfatase (I2S). A 96-well flat bottom plate was coated with a mouse monoclonal anti-I2S antibody diluted to 10 µg/mL in 50 nM sodium bicarbonate pH 9.6 for 1 hour at 37° C. The mouse monoclonal anti-I2S antibody was developed under contract by Maine Biotechnology Services, Inc. (Portland, Me.) to a purified, recombinantly-produced, full-length, human I2S polypeptide using standard hybridoma-producing technology. The plate was washed 3 times with 1× PBS containing 0.1% Tween-20 and blocked for 1 hour with 2% BSA in wash buffer at 37° C. Wash buffer with 2% BSA was used to dilute samples and standards. I2S standard was diluted and used from 100 ng/mL to 1.56 ng/mL. After removal of the blocking buffer, samples and standards were applied to the plate and incubated for 1 hour at 37° C. Detecting antibody, horseradish peroxidase-conjugated mouse anti-I2S antibody, was diluted to 0.15 µg/mL in wash buffer with 2% BSA. The plate was washed 3 times, detecting antibody added to the plate, and it was incubated for 30 minutes at 37° C. To develop the plate, TMB substrate (Bio-Rad, Hercules, Calif.) was prepared. The plate was washed 3 times, 100 µL of substrate was added to each well and it was incubated for 15 minutes at 37° C. The reaction was stopped with 2 N sulfuric acid (100 µL/well) and the plate was read on a microtiter plate reader at 450 nm, using 655 nm as the reference wavelength.

N-Acetylgalactosamine 6-Sulfatase (GALNS). Two mouse monoclonal anti-GALNS antibodies provided the basis of the GALNS ELISA. The mouse monoclonal anti-GALNS antibodies were also developed under contract by Maine Biotechnology Services, Inc. (Portland, Me.) to a purified, recombinantly-produced, full-length, human GALNS polypeptide using standard hybridoma-producing technology. The first antibody, for capture of GALNS was used to coat a F96 MaxiSorp Nunc-Immuno Plate (Nalge Nunc, Catalogue No. 442404) in a coating buffer (50 mM sodium bicarbonate, pH 9.6). After incubation for one hour at 37° C. and washing with a wash buffer, the plate was blocked with blocking buffer (PBS, 0.05% Tween-20, 2% BSA) for one hour at 37° C. Experimental and control samples along with GALNS standards were then loaded onto the plate and further incubated for one hour at 37° C. After washing with a wash buffer, the second, detection antibody conjugated to HRP was applied in blocking buffer followed by 30 minute incubation at 37° C. After washing the plate again, the Bio-Rad TMB substrate reagent was added and incubated for 15 minutes. 2N sulfuric acid was then added to stop the reaction and results were scored spectrophotometrically by using a Molecular Device plate reader at 450 nm wavelength.

Discussion

Effect of FGE on Sulfatase Activity

Figure 5:
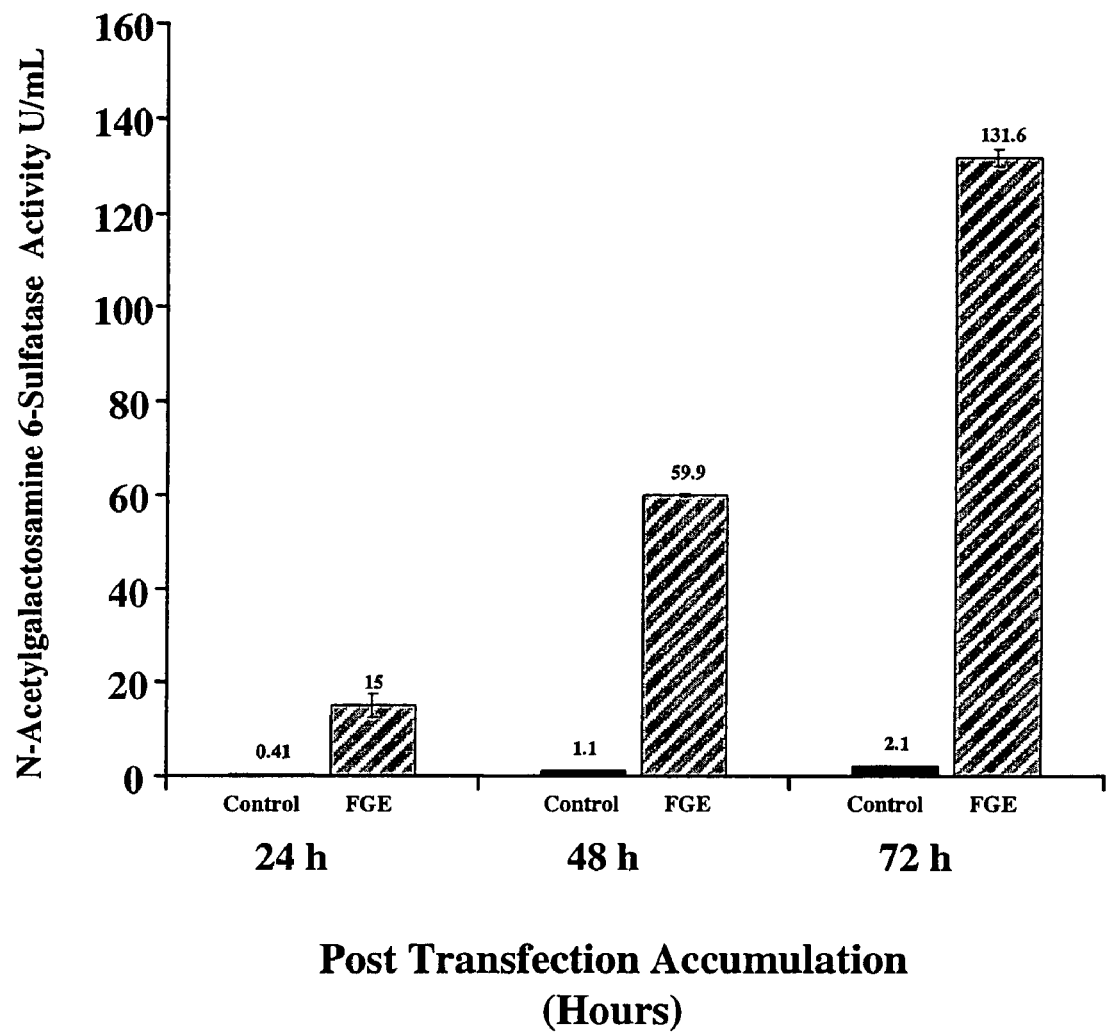
FIG. 5: Bar graph depicting N-Acetylgalactosamine 6-Sulfatase Activity in 36F Cells Transiently Transfected with FGE Expression Plasmid.

GALNS. An approximately 50-fold increase in total GALNS activity was observed over the control levels (FIG. 5). This level of increased activity was observed with all three medium sampling time points. Moreover, the GALNS activity was accumulated linearly over time with a four-fold increase between 24 and 48 hours and a two-fold increase between the 48 hour and 72 hour timepoints.

I2S. Although of smaller absolute magnitude, a similar effect was observed for total I2S activity where an approximately 5-fold increase in total I2S activity was observed over the control levels. This level of increased activity was sustained for the duration of the experiment. I2S activity accumulated in the medium linearly over time, similar to the results seen with GALNS (2.3-fold between 24 and 48 hours, and 1.8-fold between 48 and 72 hours).

Effect of FGE on Sulfatase Specific Activity

Figure 6:
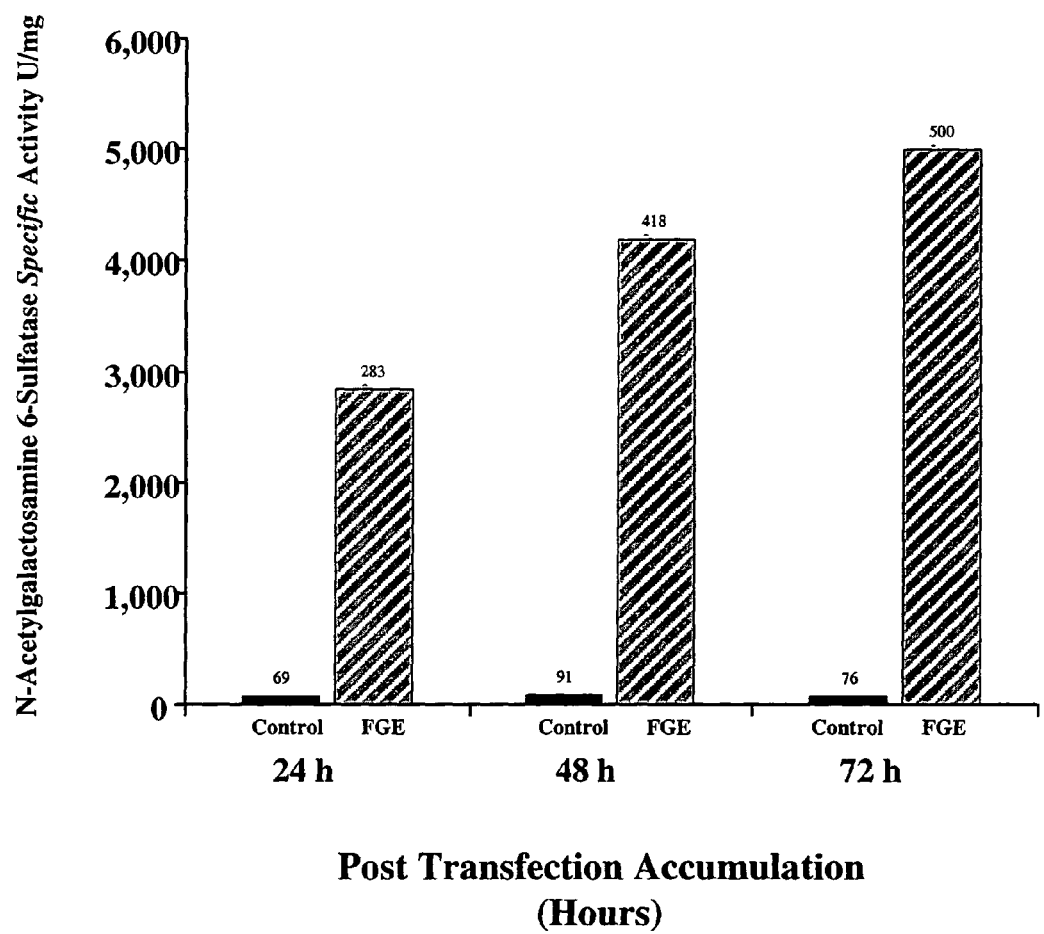
FIG. 6: Bar graph depicting N-Acetylgalactosamine 6-Sulfatase Specific Activity in 36F Cells Transiently Transfected with FGE Expression Plasmid.

GALNS. Expression of FGE in 36F cells enhanced apparent specific activity of GALNS (ratio of enzyme activity to total enzyme estimated by ELISA) by 40-60 fold over the control levels (FIG. 6). The increase in specific activity was sustained over the three time points in the study and appeared to increase over the three days of post-transfection accumulation.

I2S. A similar effect was seen with I2S, where a 6-7-fold increase in specific activity (3-5 U/mg) was observed over the control values (0.5-0.7 U/mg).

The ELISA values for both GALNS (FIG. 7) and I2S were not significantly affected by transfection of FGE. This indicates that expression of FGE does not impair translational and secretory pathways involved in sulfatase production.

In sum, all of these results for both sulfatases indicate that FGE expression dramatically increases sulfatase specific activity in cell lines that overexpress GALNS and I2S.

Co-Expression of FGE (SUMF1) and Other Sulfatase Genes

To test the effect of FGE (SUMF1) on additional sulfatase activities in normal cells we overexpressed ARSA (SEQ ID NO:14), ARSC (SEQ ID NO:18) and ARSE (SEQ ID NO:22) cDNAs in various cell lines with and without co-transfection of the FGE (SUMF1) cDNA and measured sulfatase activities. Overexpression of sulfatase cDNAs in Cos-7 cells resulted in a moderate increase of sulfatase activity, while a striking synergistic increase (20 to 50 fold) was observed when both a sulfatase gene and the FGE (SUMF1) gene were co-expressed. A similar, albeit lower, effect was observed in three additional cell lines, HepG2, LE293, and U2OS. Simultaneous overexpression of multiple sulfatase cDNAs resulted in a lower increase of each specific sulfatase activity as compared to overexpression of a single sulfatase, indicating the presence of competition of the different sulfatases for the modification machinery.

To test for functional conservation of the FGE (SUMF1) gene during evolution we overexpressed ARSA, ARSC and ARSE cDNAs in various cell lines with and without co-transfection of the MSD cDNA and measured sulfatase activities. Both the murine and the *Drosophila* FGE (SUMF1) genes were active on all three human sulfatases, with the *Drosophila* FGE (SUMF1) being less efficient. These data demonstrate a high degree of functional conservation of FGE (SUMF1) during evolution implicating significant biological importance to cellular function and survival. A similar and consistent, albeit much weaker, effect was observed by using the FGE2 (SUMF2) gene, suggesting that the protein encoded by this gene also has a sulfatase modifying activity. These data demonstrate that the amount of the FGE (SUMF1)-encoded protein is a limiting factor for sulfatase activities, a finding with important implications for the large scale production of active sulfatases to be utilized in enzyme replacement therapy.

Example 4

Identification of the Gene Mutated in MSD by Means of Functional Complementation Using Microcell Mediated Chromosome Transfer.

In a separate experiment using microcell mediated chromosome transfer by means of functional complementation we confirmed that the gene mutated in MSD is FGE. Our findings provide further insight into a novel biological mechanism affecting an entire family of proteins in distantly related organisms. In addition to identifying the molecular basis of a rare genetic disease, our data further confirms a powerful enhancing effect of the FGE gene product on the activity of sulfatases. The latter finding has direct clinical implications for the therapy of at least eight human diseases caused by sulfatase deficiencies.

The Gene for MSD Maps to Chromosome 3p26

To identify the chromosomal location of the gene mutated in MSD we attempted to rescue the deficient sulfatase enzymes by functional complementation via microcell mediated chromosome transfer. A panel of human/mouse hybrid cell lines, containing individual normal human chromosomes tagged with the dominant selectable marker HyTK, was used as the source of donor human chromosomes and fused to an immortalized cell line from a patient with MSD. All 22 human autosomes were transferred one by one to the patient cell line and hybrids were selected in hygromycin. Approximately 25 surviving colonies were picked in each of the 22 transfer experiments. These were grown separately and harvested for subsequent enzymatic testing. ArylsulfataseA (ARSA) (SEQ ID NO:15), ArylsulfataseB (ARSB) (SEQ ID NO:17), and ArylsulfataseC (ARSC) (SEQ ID NO:19) activities were tested for each of the approximately 440 clones (20×22). This analysis clearly indicated that sulfatase activities of several clones deriving from the chromosome 3 transfer was significantly higher compared to that of all the other clones. A striking variability was observed when analyzing the activities of each individual clone from the chromosome 3 transfer. To verify whether each clone had an intact human chromosome 3 from the donor cell line, we used a panel of 23 chromosome 3 polymorphic genetic markers, evenly distributed along the length of the chromosome and previously selected on the basis of having different alleles between the donor and the patient cell lines. This allowed us to examine for the presence of the donor chromosome and to identify possible loss of specific regions due to incidental chromosomal breakage. Each clone having high enzymatic activity retained the entire chromosome 3 from the donor cell line, whereas clones with low activities appeared to have lost the entire chromosome on the basis of the absence of chromosome 3 alleles from the donor cell line. The latter clones probably retained a small region of the donor chromosome containing the selectable marker gene that enabled them to survive in hygromycin containing medium. These data indicate that a normal human chromosome 3 was able to complement the defect observed in the MSD patient cell line.

To determine the specific chromosomal region containing the gene responsible for the complementing activity we used Neo-tagged chromosome 3 hybrids which were found to have lost various portions of the chromosome. In addition, we performed irradiated microcell-mediated chromosome transfer of HyTK-tagged human chromosomes 3. One hundred and fifteen chromosome 3 irradiated hybrids were tested for sulfatase activities and genotyped using a panel of 31 polymorphic microsatellite markers spanning the entire chromosome. All clones displaying high enzymatic activities appeared to have retained chromosome 3p26. A higher resolution analysis using additional markers from this region mapped the putative location for the complementing gene between markers D3S3630 and D3S2397.

Identification of the Gene Mutated in MSD

We investigated genes from the 3p26 genomic region for mutations in MSD patients. Each exon including splice junctions were PCR-amplified and analyzed by direct sequencing. Mutation analysis was performed on twelve unrelated affected individuals; five previously described MSD patients and seven unpublished cases. Several mutations were identified from our MSD cohort in the expressed sequence tag (EST) AK075459 (SEQ ID NOs:4,5), corresponding to a gene of unknown function, strongly suggesting that this was the gene involved in MSD. Each mutation was found to be absent in 100 control individuals, thus excluding the presence of a sequence polymorphism. Additional confirmatory mutation analysis was performed on reverse transcribed patients' RNAs, particularly in those cases in which genomic DNA analysis revealed the presence of a mutation in or near a splice site, possibly affecting splicing. Frameshift, nonsense, splicing, and missense mutations were also identified, suggesting that the disease is caused by a loss of function mechanism, as anticipated for a recessive disorder. This is also consistent with the observation that almost all missense mutations affect amino acids that are highly conserved throughout evolution (see below).

Fibroblasts from two patients (case 1 and 12 in Table 8) with MSD in whom we identified mutations of the FGE (SUMF1) gene (cell lines BA426 and BA920) were infected with HSV viruses containing the wild type and two mutated forms of the FGE (SUMF1) cDNA (R327X and Δex3). ARSA, ARSB, and ARSC activities were tested 72 hrs after infection. Expression of the wild type FGE (SUMF1) cDNA resulted in functional complementation of all three activities, while mutant FGE (SUMF1) cDNAs did not (Table 9). These data provide conclusive evidence for the identity of FGE (SUMF1) as the MSD gene and they prove the functional relevance of the mutations found in patients. The disease-

TABLE 8

Additional MSD Mutations identified

| Case | reference | phenotype | exon | nucleotide change | amino acid change |
|---|---|---|---|---|---|
| 1. BA426 | Conary et al, 1988 | moderate | 3 | 463T > C | S155P |
|  |  |  | 3 | 463T > C | S155P |
| 2. BA428 | Burch et al, 1986 | severe neonatal | 5 | 661delG | frameshift |
| 3. BA431 | Zenger et al, 1989 | moderate | 1 | 2T > G | M1R |
|  |  |  | 2 | 276delC | frameshift |
| 4. BA799 | Burk et al, 1981 | mild-moderate | 3 | 463T > C | S155P |
|  |  |  | 3 | 463T > C | S155P |
| 5. BA806 | unpublished | severe neonatal | 9 | 1045T > C | R349W |
| 6. BA807 | Schmidt et al, 1995 | unknown | 3 | c519 + 4delGTAA | ex 3 skipping |
|  |  |  | 9 | 1076C > A | S359X |
| 7. BA809 | Couchot et al, 1974 | mild-moderate | 1 | 1A > G | M1V |
|  |  |  | 9 | 1042G > C | A348P |
| 8. BA810 | unpublished | severe | 8 | 1006T > C | C336R |
|  |  |  | 9 | 1046G > A | R349Q |
| 9. BA811 | unpublished | severe neonatal | 3 | c519 + 4delGTAA | ex 3 skipping |
|  |  |  | 8 | 979C > T | R327X |
| 10. BA815 | unpublished | moderate | 5 | c.603-6delC | ex 6 skipping |
|  |  |  | 6 | 836C > T | A279V |
| 11. BA919 | unpublished | mild-moderate | 9 | 1033C > T | R345C |
|  |  |  | 9 | 1033C > T | R345C |
| 12. BA920 | unpublished | moderate | 5 | 653G > A | C218Y |
|  |  |  | 9 | 1033C > T | R345C |

Mutations were identified in each MSD patient tested, thus excluding locus heterogeneity. No obvious correlation was observed between the types of mutations identified and the severity of the phenotype reported in the patients, suggesting that clinical variability is not caused by by allelic heterogeneity. In three instances different patients (case 1 and 4, case 6 and 9, and case 11 and 12 in Table 6) were found to carry the same mutation. Two of these patients (case 11 and 12) originate from the same town in Sicily, suggesting the presence of a founder effect that was indeed confirmed by haplotype analysis. Surprisingly, most patients were found to be compound heterozygotes, carrying different allelic mutations, while only a few were homozygous. Albeit consistent with the absence of consanguinity reported by the parents, this was a somehow unexpected finding for a very rare recessive disorder such as MSD.

The FGE Gene and Protein

The consensus cDNA sequence of the human FGE (also used interchangeably herein as SUMF1) cDNA (SEQ ID NO:1) was assembled from several expressed sequence tag (EST) clones and partly from the corresponding genomic sequence. The gene contains nine exons and spans approximately 105 kb (see Example 1). Sequence comparison also identified the presence of a FGE gene paralog located on human chromosome 7 that we designated FGE2 (also used interchangeably herein as SUMF2) (SEQ ID NOs: 45, 46).

Functional Complementation of Sulfatase Deficiencies associated mutations result in sulfatase deficiency, thus demonstrating that FGE (SUMF1) is an essential factor for sulfatase activity.

TABLE 9

Functional complementation of sulfatase deficiencies

| Recipient MSD cell line | construct | ARSA[1] | ARSB[1] | ARSC[1] |
|---|---|---|---|---|
| BA426 | HSV amplicon | 24.0 | 22.5 | 0.15 |
|  | SUMF1-Δex3 | 42.0 | 23.8 | 0.29 |
|  | SUMF1-R327X | 33.6 | 24.2 | 0.16 |
|  | SUMF1 | 119.5 (4.9 x) | 37.8 (1.7 x) | 0.62 (4.1 x) |
| BA920 | HSV amplicon | 16.6 | 11.3 | 0.15 |
|  | SUMF1-Δex3 | 17.2 | 14.4 | 0.07 |
|  | SUMF1-R327X | 36.0 | 13.5 | 0.13 |
|  | SUMF1 | 66.5 (4.0 x) | 21.6 (1.9 x) | 0.42 (2.8 x) |
| Control range |  | 123.7-394.6 | 50.6-60.7 | 1.80-1.58 |

[1]All enzymatic activities are expressed as nmoles 4-methylumbelliferone liberated mg protein$^{-1}$ 3 hrs. MSD cell lines BA426 and BA920 were infected with the HSV amplicon alone, and with constructs carrying either mutant or wild-type SUMF1 cDNAs. The increase of single arylsulfatase activities in fibroblasts infected with the wild-type SUMF1 gene, as compared to those of cells infected with the vector alone, is indicated in parentheses. Activities measured in uninfected control fibroblasts are indicated.

Molecular Basis of MSD

Based on the hypothesis that the disease gene should be able to complement the enzymatic deficiency in a patient cell line, we performed microcell-mediated chromosome transfer to an immortalized cell line from a patient with MSD. This technique has been successfully used for the identification of genes whose predicted function could be assessed in cell lines (e.g. by measuring enzymatic activity or by detecting morphologic features). To address the problem of stochastic variability of enzyme activity we measured the activities of three different sulfatases (ARSA, ARSB and ARSC) in the complementation assay. The results of chromosome transfer clearly indicated mapping of the complementing gene to chromosome 3. Subregional mapping was achieved by generating a radiation hybrid panel for chromosome 3. Individual hybrid clones were characterized both at the genomic level, by typing 31 microsatellite markers displaying different alleles between donor and recipient cell lines, and at the functional level by testing sulfatase activities. The analysis of 130 such hybrids resulted in the mapping of the complementing region to chromosome 3p26.

Once the critical genomic region was defined, the FGE (SUMF1) gene was also identified by mutation analysis in patients' DNA. Mutations were found in all patients tested, proving that a single gene is involved in MSD. The mutations found were of different types, the majority (e.g. splice site, start site, nonsense, frameshift) putatively result in a loss function of the encoded protein, as expected for a recessive disease. Most missense mutations affect codons corresponding to amino acids that have been highly conserved during evolution, suggesting that also these mutations cause a loss of function. No correlations could be drawn between the type of mutation and the severity of the phenotype, indicating that the latter is due to unrelated factors. Unexpectedly for a rare genetic disease, many patients were found to be compound heterozygotes, carrying two different mutations. However, a founder effect was identified for one mutation originating from a small town in Sicily.

FGE (SUMF1) Gene Function

The identity of the FGE (SUMF1) gene as the "complementing factor" was demonstrated definitively by rescuing the enzymatic deficiency of four different sulfatases upon expression of exogenous FGE (SUMF1) cDNA, inserted into a viral vector, in two different patient cell lines. In each case a consistent, albeit partial, restoration of all sulfatase activities tested was observed, as compared to control patient cell lines transfected with empty vectors. On average, the increase of enzyme activities ranged between 1.7 to 4.9 fold and reached approximately half of the levels observed in normal cell lines. Enzyme activity correlates with the number of virus particles used in each experiment and with the efficiency of the infection as tested by marker protein (GFP) analysis. In the same experiments vectors containing FGE (SUMF1) cDNAs carrying two of the mutations found in the patients, R327X and Δex3, were used and no significant increase of enzyme activity was observed, thus demonstrating the functional relevance of these mutations.

As mentioned elsewhere herein, Schmidt et al. first discovered that sulfatases undergo a post-translational modification of a highly conserved cysteine, that is found at the active site of most sulfatases, to Cα-formylglycine. They also showed that this modification was defective in MSD (Schmidt, B., et al., *Cell*, 1995, 82:271-278). Our mutational and functional data provide strong evidence that FGE (SUMF1) is responsible for this modification.

The FGE (SUMF1) gene shows an extremely high degree of sequence conservation across all distantly related species analyzed, from bacteria to man. We provide evidence that that the *Drosophila* homologue of the human FGE (SUMF1) gene is able to activate overexpressed human sulfatases, proving that the observed high level of sequence similarity of the FGE (SUMF1) genes of distantly related species correlates with a striking functional conservation. A notable exception is yeast, which appears to lack the FGE (SUMF1) gene as well as any sulfatase encoding genes, indicating that sulfatase function is not required by this organism and suggesting the presence of a reciprocal influence on the evolution of FGE (SUMF1) and sulfatase genes.

Interestingly, there are two homologous genes, FGE (SUMF1) and FGE2 (SUMF2), in the genomes of all vertebrates analyzed, including humans. As evident from the phylogenetic tree, the FGE2 (SUMF2) gene appears to have evolved independently from the FGE (SUMF1) gene. In our assays the FGE2 (SUMF2) gene is also able to activate sulfatases, however it does it in a much less efficient manner compared to the FGE (SUMF1) gene. This may account for the residual sulfatase activity found in MSD patients and suggests that a complete sulfatase deficiency would be lethal. At the moment we cannot rule out the possibility that the FGE2 (SUMF2) gene has an additional, yet unknown, function.

Impact on the Therapy of Diseases Due to Sulfatase Deficiencies

A strong increase, up to 50 fold, of sulfatase activities was observed in cells overexpressing FGE (SUMF1) cDNA together with either ARSA, ARSC, or ARSE cDNAs, compared to cells overexpressing single sulfatases alone. In all cell lines a significant synergic effect was found, indicating that FGE (SUMF1) is a limiting factor for sulfatase activity. However, variability was observed among different sulfatases, possibly due to different affinity of the FGE (SUMF1)-encoded protein with the various sulfatases. Variability was also observed between different cell lines which may have different levels of endogenous formylglycine generating enzyme. Consistent with these observations, we found that the expression of the MSD gene varies among different tissues, with significantly high levels in kidney and liver. This may have important implications as tissues with low FGE (SUMF1) gene expression levels may be less capable of effectively modifying exogenously delivered sulfatase proteins (see below). Together these data suggest that the function of the FGE (SUMF1) gene has evolved to achieve a dual regulatory system, with each sulfatase being controlled by both an individual mechanism, responsible for the mRNA levels of each structural sulfatase gene, and a common mechanism shared by all sulfatases. In addition, FGE2 (SUMF2) provides partial redundancy for sulfatase modification.

These data have profound implications for the mass production of active sulfatases to be utilized in enzyme replacement therapy. Enzyme replacement studies have been reported on animal models of sulfatase deficiencies, such as a feline model of mucopolysaccharidosis VI, and proved to be effective in preventing and curing several symptoms. Therapeutic trials in humans are currently being performed for two congenital disorders due to sulfatase deficiencies, MPSII (Hunter syndrome) and MPSVI (Maroteaux-Lamy syndrome) and will soon be extended to a large number of patients.

Example 5

Enzyme Replacement Therapy with FGE-Activated GALNS for Morquio Disease MPS IVA

The primary cause of skeletal pathology in Morquio patients is keratan sulfate (KS) accumulation in epiphyseal disk (growth plate) chondrocytes due to deficiency of the lysosomal sulfatase, GALNS. The primary objective of in vivo research studies was to determine whether intravenously (IV) administered FGE-activated GALNS was able to penetrate chondrocytes of the growth plate as well as other appropriate cell types in normal mice. Notwithstanding a general lack of skeletal abnormalities, a GALNS deficient mouse model (Morquio Knock-In—MKI, S. Tomatsu, St. Louis University, Mo.) was also used to demonstrate in vivo biochemical activity of repeatedly administered FGE-activated GALNS. The lack of skeletal pathology in mouse models reflects the fact that skeletal KS is either greatly reduced or absent in rodents (Venn G, & Mason R M., *Biochem J.*, 1985, 228:443-450). These mice did, however, demonstrate detectable accumulation of GAG and other cellular abnormalities in various organs and tissues. Therefore, the overall objective of the studies was to demonstrate that FGE-activated GALNS penetrates into the growth plate (biodistribution study) and show functional GALNS enzyme activity directed towards removal of accumulated GAG in affected tissues (pharmacodynamic study).

The results of these studies demonstrated that IV injected FGE-activated GALNS was internalized by chondrocytes of the growth plate, albeit at relatively low levels compared to other tissues. In addition, FGE-activated GALNS injection over the course of 16 weeks in MKI mice effectively cleared accumulated GAG and reduced lysosomal biomarker staining in all soft tissues examined. In sum, the experiments successfully demonstrated GALNS delivery to growth plate chondrocytes and demonstrated biochemical activity in terms of GAG clearance in multiple tissues.

Biodistribution Study

Four-week-old ICR (normal) mice were given a single IV injection of 5 mg/kg FGE-activated GALNS. Liver, femur (bone), heart, kidney and spleen were collected two hours after injection and prepared for histological examination. A monoclonal anti-human GALNS antibody was used to detect the presence of injected GALNS in the various tissues. GALNS was detected in all tissues examined as compared to the vehicle controls. Moreover, GALNS was readily observed in all tissues examined using a horseradish-peroxidase reporter system, with the exception of bone. Demonstration of GALNS uptake in the growth plate required the use of a more sensitive fluorescein-isothiocyanate (FITC) reporter system and indicates that although GALNS penetrates the growth plate, it is less readily available to growth plate chondrocytes than to cells of soft tissues. Notwithstanding the requirement of a more sensitive fluorescent detection method, GALNS delivery to bone growth plate chondrocytes was observed in all growth plate sections examined as compared to the vehicle controls.

Pharmacodynamic Study in MKI Mice

Four-week-old MKI or wild-type mice were given weekly IV injections (n=8 per group) through 20 weeks of age. Each weekly injection consisted of either 2 mg/kg FGE-activated GALNS or vehicle control (no injection for wild-type mice). All mice were sacrificed for histological examination at 20 weeks of age and stained using the following methods: hematoxylin and eosin for cellular morphology, alcian blue for detection of GAGs.

Clearance of accumulated GAG was demonstrated by reduced or absent alcian blue staining in all soft tissues examined (liver, heart, kidney and spleen). This was observed only in the GALNS injected mice. Although the growth plate in the MKI mice functioned normally as evidenced by normal skeletal morphology, there were more subtle cellular abnormalities observed (including vacuolization of chondrocytes without apparent pathological effect). The vacuolized chondrocytes of the hypertrophic and proliferating zones of the growth plate were unaffected by GALNS administration. This was in contrast to the chondrocytes in the calcification zone of the growth plate where a reduction of vacuolization was observed in GALNS injected mice. The vacuolization of chondrocytes and accumulation of presumed non-KS GAG in the growth plate in MKI mice was, in general, surprising and unexpected due to the known lack of KS in the growth plate of mice. These particular observations likely reflect the fact that, in the knock-in mice, high levels of mutant GALNS are present (as opposed to knock-out mice where there is no residual mutant GALNS, no growth plate chondrocyte vacuolization and no GAG accumulation-Tomatsu S. et al., *Human Molecular Genetics*, 2003, 12:3349-3358). The vacuolization phenomenon in the growth plate may be indicative of a secondary effect on a subset of cells expressing mutant GALNS. Nonetheless, enzyme injection over the course of 16 weeks demonstrated strong evidence of multiple tissue FGE-activated GALNS delivery and in vivo enzymatic activity.

DETAILED DESCRIPTION OF THE DRAWINGS

FIG. 1: MALDI-TOF mass spectra of P23 after incubation in the absence (A) or presence (B) of a soluble extract from bovine testis microsomes. 6 pmol of P23 were incubated under standard conditions for 10 min at 37° C. in the absence or presence of 1 μl microsomal extract. The samples were prepared for MALDI-TOF mass spectrometry as described in Experimental Procedures. The monoisotopic masses MH$^+$ of P23 (2526.28) and its FGly derivative (2508.29) are indicated.

FIG. 2: Phylogenetic tree derived from an alignment of human FGE and 21 proteins of the PFAM-DUF323 seed. The numbers at the branches indicate phylogenetic distance. The proteins are designated by their TrEMBL ID number and the species name. hFGE—human FGE. Upper right: scale of the phylogenetic distances. A asterisk indicates that the gene has been further investigated. The top seven genes are part of the FGE gene family.

FIG. 3: Organisation of the human and murine FGE gene locus. Exons are shown to scale as dark boxes (human locus) and bright boxes (murine locus). The bar in the lower right corner shows the scale. The lines between the exons show the introns (not to scale). The numbers above the intron lines indicate the size of the introns in kilobases.

Figure 4:
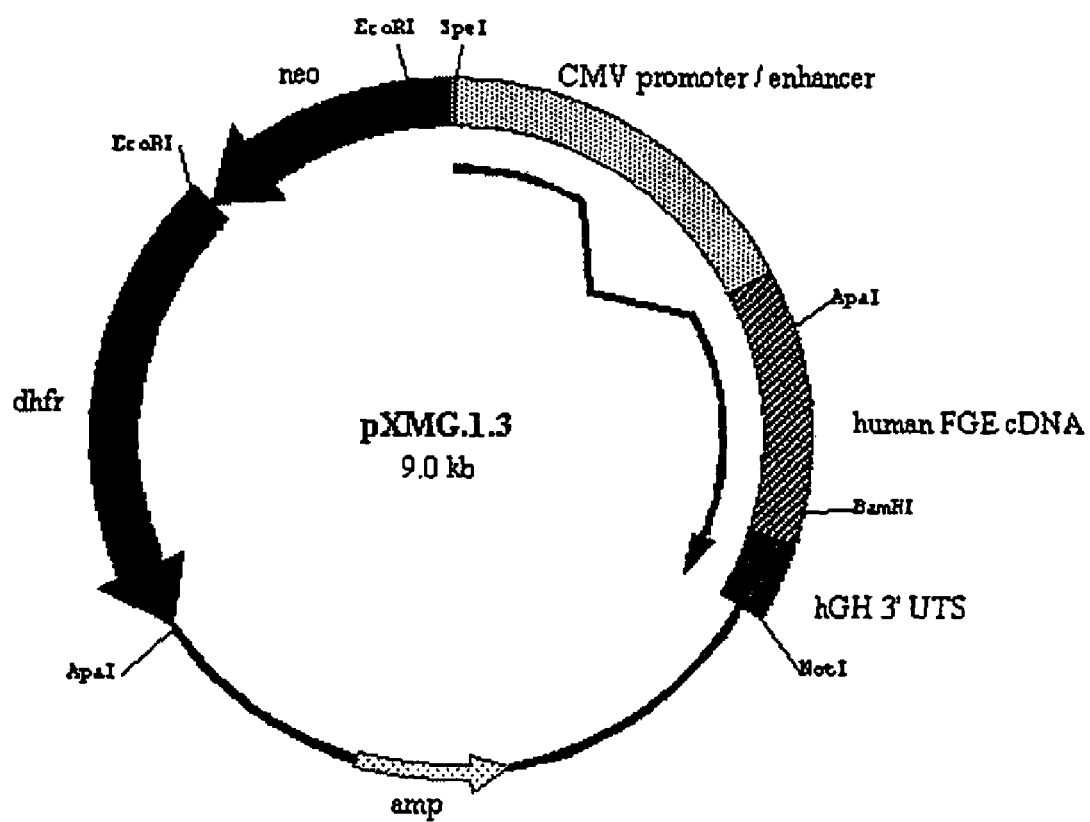
FIG. 4: Diagram showing a map of FGE Expression Plasmid pXMG.1.3

FIG. 4: Diagram showing a map of FGE Expression Plasmid pXMG.1.3

FIG. 5: Bar graph depicting N-Acetylgalactosamine 6-Sulfatase Activity in 36F Cells Transiently Transfected with FGE Expression Plasmid. Cells were transfected with either a control plasmid, pXMG.1.2, with the FGE cDNA in the reverse orientation, or a FGE expression plasmid, pXMG.1.3 in media without methotrexate (MTX). 24 hours later cells were re-fed with media containing 1.0 μM MTX. Medium was harvested and cells collected 24, 48, and 72 hours after re-feed. N-Acetylgalactosamine 6-Sulfatase activity was determined by activity assay. Each value shown is the average of two separate transfections with standard deviations indicated by error bars.

FIG. 6: Bar graph depicting N-Acetylgalactosamine 6-Sulfatase Specific Activity in 36F Cells Transiently Transfected with FGE Expression Plasmid. Cells were transfected with either a control plasmid, pXMG.1.2, with the FGE cDNA in the reverse orientation, or a FGE expression plasmid, pXMG.1.3 in media without methotrexate (MTX). 24 hours later cells were re-fed with media containing 1.0 μM MTX. Medium was harvested and cells collected 24, 48, and 72 hours after re-feed. N-Acetylgalactosamine 6-Sulfatase specific activity was determined by activity assay and ELISA and is represented as a ratio of N-Acetylgalactosamine 6-Sulfatase activity per mg of ELISA-reactive N-Acetylgalactosamine 6-Sulfatase. Each value shown is the average of two separate transfections.

Figure 7:
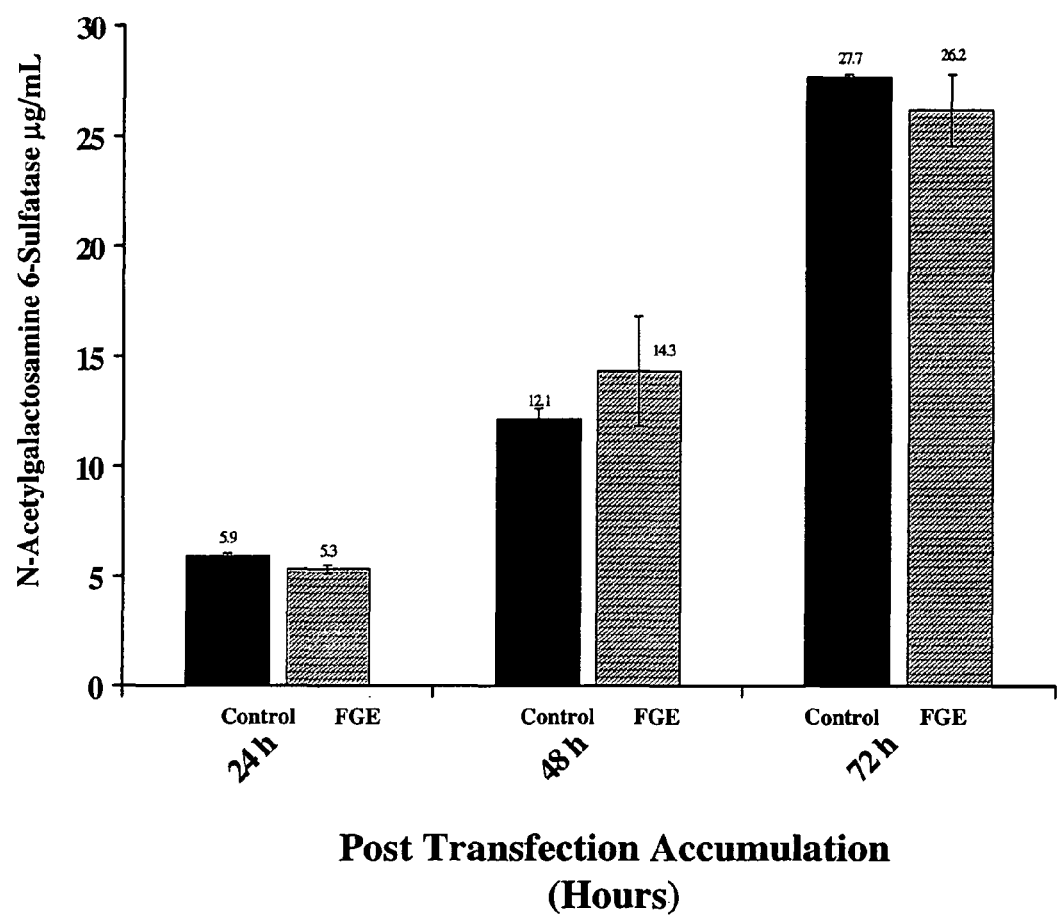
FIG. 7: Bar graph depicting N-Acetylgalactosamine 6-Sulfatase Production in 36F Cells Transiently Transfected with FGE Expression Plasmid.

FIG. 7: Bar graph depicting N-Acetylgalactosamine 6-Sulfatase Production in 36F Cells Transiently Transfected with FGE Expression Plasmid. Cells were transfected with either a control plasmid, pXMG.1.2, with the FGE cDNA in the reverse orientation, or a FGE expression plasmid, pXMG.1.3 in media without methotrexate (MTX). 24 hours later cells were re-fed with media containing 1.0 µM MTX. Medium was harvested and cells collected 24, 48, and 72 hours after re-feed. N-Acetylgalactosamine 6-Sulfatase total protein was determined by ELISA. Each value shown is the average of two separate transfections with standard deviations indicated by error bars.

Figure 8:
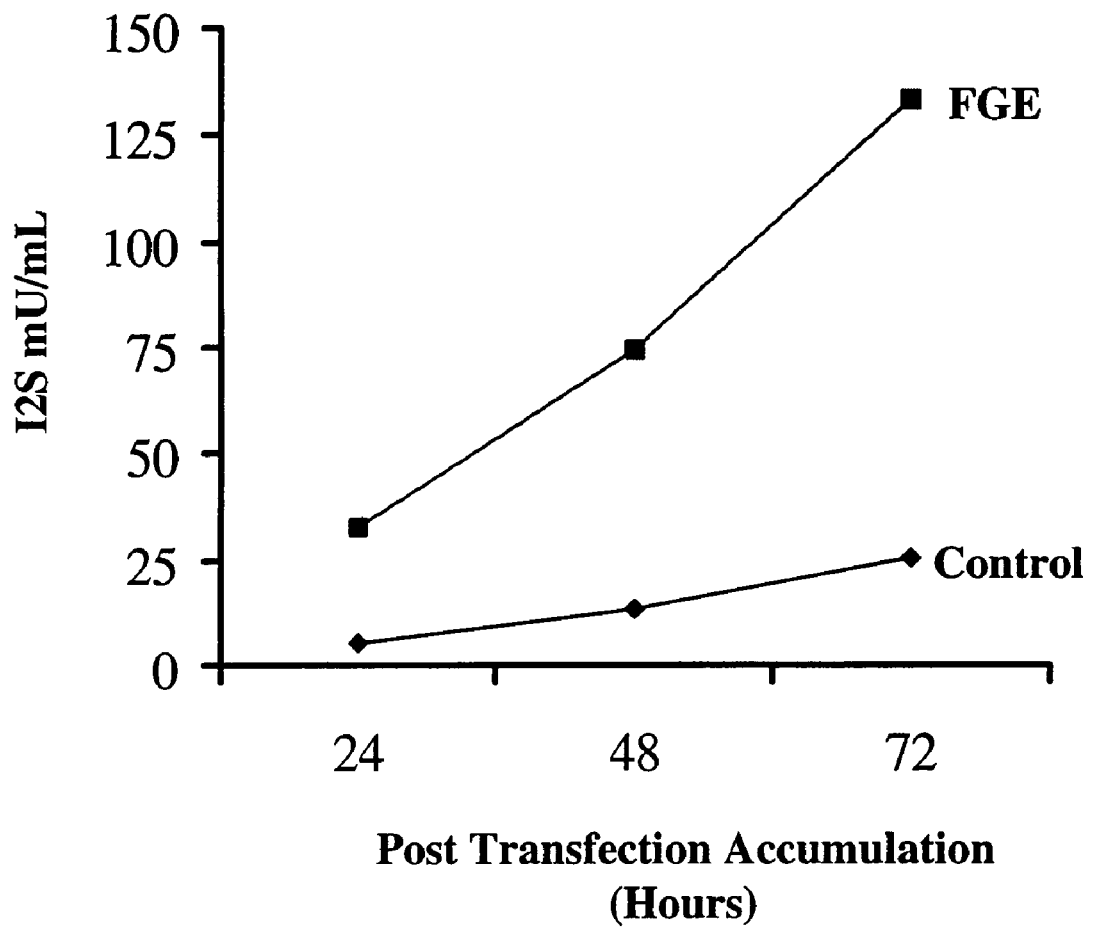
FIG. 8: Graph depicting Iduronate 2-Sulfatase Activity in 30C6 Cells Transiently Transfected with FGE Expression Plasmid.

FIG. 8: Graph depicting Iduronate 2-Sulfatase Activity in 30C6 Cells Transiently Transfected with FGE Expression Plasmid. Cells were transfected with either a control plasmid, pXMG.1.2, with the FGE cDNA in the reverse orientation, or a FGE expression plasmid, pXMG.1.3 in media without methotrexate (MTX). 24 hours later cells were re-fed with media containing 0.1 µM MTX. Medium was harvested and cells collected 24, 48, and 72 hours after re-feed. Iduronate 2-Sulfatase activity was determined by activity assay. Each value shown is the average of two separate transfections.

Figure 9:
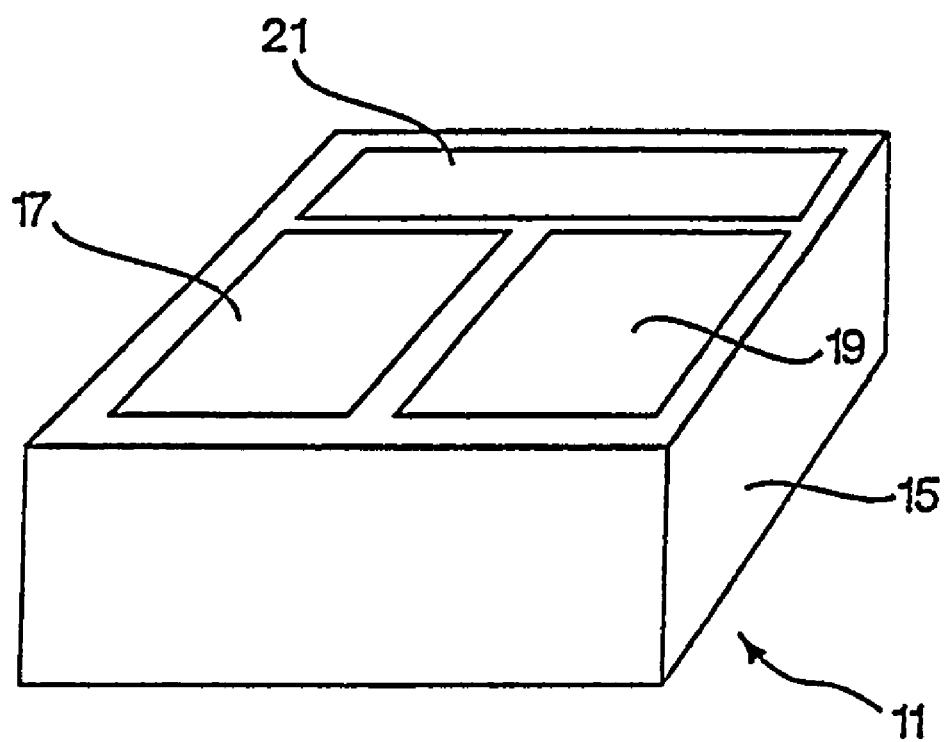
FIG. 9: Depicts a kit embodying features of the present invention.

FIG. 9: Depicts a Kit Embodying Features of the Present Invention.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety. What is claimed is presented below and is followed by a Sequence Listing.

We claim:

1. An isolated prokaryotic cell transformed with a vector comprising a heterologous polynucleotide encoding a cysteine-type sulfatase and transformed with a vector comprising a polynucleotide encoding a Formylglycine Generating Enzyme (FGE) comprising an amino acid sequence having at least 95% identity to the amino acid sequence of amino acids 34-374 of SEQ ID NO:2, wherein the FGE has $C_\alpha$-formylglycine generating activity.

2. The isolated prokaryotic cell of claim 1, wherein the Formylglycine Generating Enzyme (FGE) comprises the amino acid sequence of amino acids 34-374 of SEQ ID NO:2.

3. The isolated prokaryotic cell of claim 1, wherein the Formylglycine Generating Enzyme (FGE) comprises the amino acid sequence of SEQ ID NO:2.

4. The isolated prokaryotic cell of claim 1, wherein the cysteine-type sulfatase is selected from the group consisting of Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, and HSulf-2.

5. The isolated prokaryotic cell of claim 1, wherein the isolated prokaryotic cell is a cultured cell.

6. The isolated prokaryotic cell of claim 1, wherein the isolated prokaryotic cell is a bacterial cell.

7. The isolated prokaryotic cell of claim 6, wherein the bacterial cell is *Escherichia coli*.

8. The isolated prokaryotic cell of claim 1, wherein the vector comprising the heterologous polynucleotide encoding the cysteine-type sulfatase and the vector comprising the polynucleotide encoding the FGE are separate vectors.

9. The isolated prokaryotic cell of claim 1, wherein the vector comprising the heterologous polynucleotide encoding the cysteine-type sulfatase and the vector comprising the polynucleotide encoding the FGE is selected from the group consisting of plasmids, phagemids, and viruses.

10. The isolated prokaryotic cell of claim 1, wherein the ratio of active sulfatase to total sulfatase produced by the cell is increased by at least 5% relative to the ratio of active sulfatase to total sulfatase produced by the cell in the absence of the vector comprising the polynucleotide encoding the FGE.

11. A method of producing a cysteine-type sulfatase comprising a step of culturing the isolated prokaryotic cell of claim 1, thereby producing the cysteine-type sulfatase.

12. An isolated eukaryotic cell transfected with a vector comprising a heterologous polynucleotide encoding a cysteine-type sulfatase and further transfected with a vector comprising a heterologous polynucleotide encoding a Formylglycine Generating Enzyme (FGE) comprising an amino acid sequence having at least 95% identity to the amino acid sequence of amino acids 34-374 of SEQ ID NO:2, wherein the FGE has $C_\alpha$-formylglycine generating activity.

13. The isolated eukaryotic cell of claim 12, wherein the Formylglycine Generating Enzyme (FGE) comprises the amino acid sequence of amino acids 34-374 of SEQ ID NO:2.

14. The isolated eukaryotic cell of claim 12, wherein the Formylglycine Generating Enzyme (FGE) comprises the amino acid sequence of SEQ ID NO:2.

15. The isolated eukaryotic cell of claim 12, wherein the cysteine-type sulfatase is selected from the group consisting of Iduronate 2-Sulfatase, Sulfamidase, N-Acetylgalactosamine 6-Sulfatase, N-Acetylglucosamine 6-Sulfatase, Arylsulfatase A, Arylsulfatase B, Arylsulfatase C, Arylsulfatase D, Arylsulfatase E, Arylsulfatase F, Arylsulfatase G, HSulf-1, and HSulf-2.

16. The isolated eukaryotic cell of claim 12, wherein the isolated eukaryotic cell is a mammalian cell.

17. The isolated eukaryotic cell of claim 16, wherein the mammalian cell is a human cell.

18. The isolated eukaryotic cell of claim 12, wherein the isolated eukaryotic cell is a cultured cell.

19. The isolated eukaryotic cell of claim 12, wherein the vector comprising the heterologous polynucleotide encoding the cysteine-type sulfatase and the vector comprising the heterologous polynucleotide encoding the FGE are separate vectors.

20. The isolated eukaryotic cell of claim 12, wherein the vector comprising the heterologous polynucleotide encoding the cysteine-type sulfatase and the vector comprising the heterologous polynucleotide encoding the FGE is a plasmid or a virus vector.

21. The isolated eukaryotic cell of claim 12, wherein the ratio of active sulfatase to total sulfatase produced by the cell is increased by at least 5% relative to the ratio of active sulfatase to total sulfatase produced by the cell in the absence of the vector comprising a heterologous polynucleotide encoding a Formylglycine Generating Enzyme (FGE).

22. A method of producing a cysteine-type sulfatase comprising a step of culturing the isolated eukaryotic cell of claim 12, thereby producing the cysteine-type sulfatase.

* * * * *

UNITED STATES PATENT AND TRADEMARK OFFICE
CERTIFICATE OF CORRECTION

| | | |
|---|---|---|
| PATENT NO. | : 8,227,212 B2 | Page 1 of 1 |
| APPLICATION NO. | : 10/775678 | |
| DATED | : July 24, 2012 | |
| INVENTOR(S) | : Figura et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 616 days.

Signed and Sealed this
Twenty-third Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,227,212 B2  
APPLICATION NO. : 10/775678  
DATED : July 24, 2012  
INVENTOR(S) : von Figura et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 741 days.

Signed and Sealed this
Seventeenth Day of March, 2020

Andrei Iancu
*Director of the United States Patent and Trademark Office*

SEQUENCE LISTING

```
<160> NUMBER OF SEQ ID NOS: 96

<210> SEQ ID NO 1
<211> LENGTH: 1180
<212> TYPE: DNA
<213> ORGANISM: Homo sapiens
<220> FEATURE:
<221> NAME/KEY: CDS
<222> LOCATION: (20)..(1141)

<400> SEQUENCE: 1
acatggcccg cgggacaac atg gct gcg ccc gca cta ggg ctg gtg tgt gga        52
                    Met Ala Ala Pro Ala Leu Gly Leu Val Cys Gly
                    1               5                   10 cgt tgc cct gag ctg ggt ctc gtc ctc ttg ctg ctg ctc tcg ctg              100
Arg Cys Pro Glu Leu Gly Leu Val Leu Leu Leu Leu Leu Ser Leu
                15                  20                  25 ctg tgt gga gcg gca ggg agc cag gag gcc ggg acc ggt gcg ggc gcg         148
Leu Cys Gly Ala Ala Gly Ser Gln Glu Ala Gly Thr Gly Ala Gly Ala
            30                  35                  40 ggg tcc ctt gcg ggt tct tgc ggc tgc ggc acg ccc cag cgg cct ggc         196
Gly Ser Leu Ala Gly Ser Cys Gly Cys Gly Thr Pro Gln Arg Pro Gly
    45                  50                  55 gcc cat ggc agt tcg gca gcc gct cac cga tac tcg cgg gag gct aac         244
Ala His Gly Ser Ser Ala Ala Ala His Arg Tyr Ser Arg Glu Ala Asn
60                  65                  70                  75 gct ccg ggc ccc gta ccc gga gag cgg caa ctc gcg cac tca aag atg         292
Ala Pro Gly Pro Val Pro Gly Glu Arg Gln Leu Ala His Ser Lys Met
                80                  85                  90 gtc ccc atc cct gct gga gta ttt aca atg ggc aca gat gat cct cag         340
Val Pro Ile Pro Ala Gly Val Phe Thr Met Gly Thr Asp Asp Pro Gln
            95                  100                 105 ata aag cag gat ggg gaa gca cct gcg agg aga gtt act att gat gcc         388
Ile Lys Gln Asp Gly Glu Ala Pro Ala Arg Arg Val Thr Ile Asp Ala
        110                 115                 120 ttt tac atg gat gcc tat gaa gtc agt aat act gaa ttt gag aag ttt         436
Phe Tyr Met Asp Ala Tyr Glu Val Ser Asn Thr Glu Phe Glu Lys Phe
    125                 130                 135 gtg aac tca act ggc tat ttg aca gag gct gag aag ttt ggc gac tcc         484
Val Asn Ser Thr Gly Tyr Leu Thr Glu Ala Glu Lys Phe Gly Asp Ser
140                 145                 150                 155
```

```
ttt gtc ttt gaa ggc atg ttg agt gag caa gtg aag acc aat att caa       532
Phe Val Phe Glu Gly Met Leu Ser Glu Gln Val Lys Thr Asn Ile Gln
            160                 165                 170 cag gca gtt gca gct gct ccc tgg tgg tta cct gtg aaa ggc gct aac       580
Gln Ala Val Ala Ala Ala Pro Trp Trp Leu Pro Val Lys Gly Ala Asn
        175                 180                 185 tgg aga cac cca gaa ggg cct gac tct act att ctg cac agg ccg gat       628
Trp Arg His Pro Glu Gly Pro Asp Ser Thr Ile Leu His Arg Pro Asp
    190                 195                 200 cat cca gtt ctc cat gtg tcc tgg aat gat gcg gtt gcc tac tgc act       676
His Pro Val Leu His Val Ser Trp Asn Asp Ala Val Ala Tyr Cys Thr
205                 210                 215 tgg gca ggg aag cgg ctg ccc acg gaa gct gag tgg gaa tac agc tgt       724
Trp Ala Gly Lys Arg Leu Pro Thr Glu Ala Glu Trp Glu Tyr Ser Cys
220                 225                 230                 235 cga gga ggc ctg cat aat aga ctt ttc ccc tgg ggc aac aaa ctg cag       772
Arg Gly Gly Leu His Asn Arg Leu Phe Pro Trp Gly Asn Lys Leu Gln
                240                 245                 250 ccc aaa ggc cag cat tat gcc aac att tgg cag ggc gag ttt ccg gtg       820
Pro Lys Gly Gln His Tyr Ala Asn Ile Trp Gln Gly Glu Phe Pro Val
            255                 260                 265 acc aac act ggt gag gat ggc ttc caa gga act gcg cct gtt gat gcc       868
Thr Asn Thr Gly Glu Asp Gly Phe Gln Gly Thr Ala Pro Val Asp Ala
        270                 275                 280 ttc cct ccc aat ggt tat ggc tta tac aac ata gtg ggg aac gca tgg       916
Phe Pro Pro Asn Gly Tyr Gly Leu Tyr Asn Ile Val Gly Asn Ala Trp
    285                 290                 295 gaa tgg act tca gac tgg tgg act gtt cat cat tct gtt gaa gaa acg       964
Glu Trp Thr Ser Asp Trp Trp Thr Val His His Ser Val Glu Glu Thr
300                 305                 310                 315 ctt aac cca aaa ggt ccc cct tct ggg aaa gac cga gtg aag aaa ggt      1012
Leu Asn Pro Lys Gly Pro Pro Ser Gly Lys Asp Arg Val Lys Lys Gly
                320                 325                 330 gga tcc tac atg tgc cat agg tct tat tgt tac agg tat cgc tgt gct      1060
Gly Ser Tyr Met Cys His Arg Ser Tyr Cys Tyr Arg Tyr Arg Cys Ala
            335                 340                 345 gct cgg agc cag aac aca cct gat agc tct gct tcg aat ctg gga ttc      1108
Ala Arg Ser Gln Asn Thr Pro Asp Ser Ser Ala Ser Asn Leu Gly Phe
        350                 355                 360 cgc tgt gca gcc gac cgc ctg ccc acc atg gac tgacaaccaa gggtagtctt    1161
Arg Cys Ala Ala Asp Arg Leu Pro Thr Met Asp
    365                 370 ccccagtcca aggagcagt                                                 1180

<210> SEQ ID NO 2
<211> LENGTH: 374
<212> TYPE: PRT
<213> ORGANISM: Homo sapiens

<400> SEQUENCE: 2

Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
```

|   |   |   |   |   | 65 |   |   |   |   | 70 |   |   |   |   | 75 |   |   |   |   | 80 |
|---|---|---|---|---|---|---|---|---|---|---|---|---|---|---|---|---|---|---|---|---|

Pro Gly Glu Arg Gln Leu Ala His Ser Lys Met Val Pro Ile Pro Ala
                               85                               90                        95

Gly Val Phe Thr Met Gly Thr Asp Asp Pro Gln Ile Lys Gln Asp Gly
                 100                          105                           110

Glu Ala Pro Ala Arg Arg Val Thr Ile Asp Ala Phe Tyr Met Asp Ala
                 115                          120                           125

Tyr Glu Val Ser Asn Thr Glu Phe Glu Lys Phe Val Asn Ser Thr Gly
    130                           135                         140

Tyr Leu Thr Glu Ala Glu Lys Phe Gly Asp Ser Phe Val Phe Glu Gly
145                         150                           155                       160

Met Leu Ser Glu Gln Val Lys Thr Asn Ile Gln Gln Ala Val Ala Ala
                 165                          170                           175

Ala Pro Trp Trp Leu Pro Val Lys Gly Ala Asn Trp Arg His Pro Glu
            180                           185                         190

Gly Pro Asp Ser Thr Ile Leu His Arg Pro Asp His Pro Val Leu His
                 195                          200                        205

Val Ser Trp Asn Asp Ala Val Ala Tyr Cys Thr Trp Ala Gly Lys Arg
210                         215                           220

Leu Pro Thr Glu Ala Glu Trp Glu Tyr Ser Cys Arg Gly Gly Leu His
225                         230                           235                       240

Asn Arg Leu Phe Pro Trp Gly Asn Lys Leu Gln Pro Lys Gly Gln His
                 245                          250                           255

Tyr Ala Asn Ile Trp Gln Gly Glu Phe Pro Val Thr Asn Thr Gly Glu
            260                           265                         270

Asp Gly Phe Gln Gly Thr Ala Pro Val Asp Ala Phe Pro Pro Asn Gly
                 275                          280                        285

Tyr Gly Leu Tyr Asn Ile Val Gly Asn Ala Trp Glu Trp Thr Ser Asp
    290                           295                         300

Trp Trp Thr Val His His Ser Val Glu Glu Thr Leu Asn Pro Lys Gly
305                         310                           315                       320

Pro Pro Ser Gly Lys Asp Arg Val Lys Lys Gly Gly Ser Tyr Met Cys
                 325                          330                         335

His Arg Ser Tyr Cys Tyr Arg Tyr Arg Cys Ala Ala Arg Ser Gln Asn
            340                           345                         350

Thr Pro Asp Ser Ser Ala Ser Asn Leu Gly Phe Arg Cys Ala Ala Asp
                 355                          360                        365

Arg Leu Pro Thr Met Asp
    370

<210> SEQ ID NO 3
<211> LENGTH: 1122
<212> TYPE: DNA
<213> ORGANISM: Homo sapiens

<400> SEQUENCE: 3

```
atggctgcgc cgcactagg gctggtgtgt ggacgttgcc ctgagctggg tctcgtcctc        60
ttgctgctgc tgctctcgct gctgtgtgga gcggcaggga gccaggaggc cgggaccggt       120
gcgggcgcgg ggtcccttgc gggttcttgc ggctgcggca cgcccagcg gcctggcgcc       180
catggcagtt cggcagccgc tcaccgatac tcgcggagg ctaacgctcc gggcccgta        240
cccggagagc ggcaactcgc gcactcaaag atggtcccca tccctgctgg agtatttaca       300
atgggcacag atgatcctca gataaagcag gatggggaag cacctgcgag agagttact        360
attgatgcct tttacatgga tgcctatgaa gtcagtaata ctgaatttga aagtttgtg        420
```

| | |
|---|---:|
| aactcaactg gctatttgac agaggctgag aagtttggcg actcctttgt ctttgaaggc | 480 |
| atgttgagtg agcaagtgaa gaccaatatt caacaggcag ttgcagctgc tccctggtgg | 540 |
| ttacctgtga aaggcgctaa ctggagacac cagaagggc ctgactctac tattctgcac | 600 |
| aggccggatc atccagttct ccatgtgtcc tggaatgatg cggttgccta ctgcacttgg | 660 |
| gcagggaagc ggctgcccac ggaagctgag tgggaataca gctgtcgagg aggcctgcat | 720 |
| aatagacttt tccctgggg caacaaactg cagcccaaag ccagcatta tgccaacatt | 780 |
| tggcagggcg agtttccggt gaccaacact ggtgaggatg gcttccaagg aactgcgcct | 840 |
| gttgatgcct tccctcccaa tggttatggc ttatacaaca tagtggggaa cgcatgggaa | 900 |
| tggacttcag actggtggac tgttcatcat tctgttgaag aaacgcttaa cccaaaaggt | 960 |
| cccccttctg ggaaagaccg agtgaagaaa ggtggatcct acatgtgcca taggtcttat | 1020 |
| tgttacaggt atcgctgtgc tgctcggagc cagaacacac ctgatagctc tgcttcgaat | 1080 |
| ctgggattcc gctgtgcagc cgaccgcctg cccaccatgg ac | 1122 |

<210> SEQ ID NO 4
<211> LENGTH: 2130
<212> TYPE: DNA
<213> ORGANISM: Homo sapiens

<400> SEQUENCE: 4

| | |
|---|---:|
| acatggcccg cgggacaaca tggctgcgcc cgcactaggg ctggtgtgtg gacgttgccc | 60 |
| tgagctgggt ctcgtcctct tgctgctgct gctctcgctg ctgtgtggag cggcagggag | 120 |
| ccaggaggcc gggaccggtg cgggcgcggg gtcccttgcg ggttcttgcg gctgcggcac | 180 |
| gccccagcgg cctggcgccc atggcagttc ggcagccgct caccgatact cgcgggaggc | 240 |
| taacgctccg ggccccgtac ccggagagcg gcaactcgcg cactcaaaga tggtccccat | 300 |
| ccctgctgga gtatttacaa tgggcacaga tgatcctcag ataaagcagg atggggaagc | 360 |
| acctgcgagg agagttacta ttgatgccct ttacatggat gcctatgaag tcagtaatac | 420 |
| tgaatttgag aagtttgtga actcaactgg ctatttgaca gaggctgaga gtttggcga | 480 |
| ctcctttgtc tttgaaggca tgttgagtga gcaagtgaag accaatattc aacaggcagt | 540 |
| tgcagctgct ccctggtggt acctgtgaa aggcgctaac tggagacacc agaagggcc | 600 |
| tgactctact attctgcaca ggccggatca tccagttctc catgtgtcct ggaatgatgc | 660 |
| ggttgcctac tgcacttggg caggaagcg gctgcccacg gaagctgagt gggaatacag | 720 |
| ctgtcgagga ggcctgcata atagactttt ccctggggc aacaaactgc agcccaaagg | 780 |
| ccagcattat gccaacatt ggcagggcga ttttccggtg accaacactg gtgaggatgg | 840 |
| cttccaagga actgcgcctg ttgatgcctt ccctcccaat ggttatggct tatacaacat | 900 |
| agtggggaac gcatgggaat ggacttcaga ctggtggact gttcatcatt ctgttgaaga | 960 |
| aacgcttaac ccaaaaggtc cccttctgg gaaagaccga gtgaagaaag gtggatccta | 1020 |
| catgtgccat aggtcttatt gttacaggta tcgctgtgct gctcggagcc agaacacacc | 1080 |
| tgatagctct gcttcgaatc tgggattccg ctgtgcagcc gaccgcctgc ccaccatgga | 1140 |
| ctgacaacca agggtagtct tccccagtcc aaggagcagt cgtgtctgac ctacattggg | 1200 |
| ctttcctcag aactttgaac gatcccatgc aaagaattcc caccctgagg tgggttacat | 1260 |
| acctgcccaa tggccaaagg aacgccttg tgagaccaaa ttgctgacct gggtcagtgc | 1320 |
| atgtgcttta tggtgtggtg catctttgga gatcatcacc atattttact tttgagagtc | 1380 |
| tttaaagagg aaggggagtg gagggaaccc tgagctaggc ttcaggaggc ccgcatccta | 1440 |

-continued

```
cgcaggctct gccacagggg ttagacccca ggtccgacgc ttgaccttcc tgggcctcaa    1500
gtgccctccc ctatcaaatg aaggaatgga cagcatgacc tctgggtgtc tctccaactc    1560
accagttcta aaaagggtat cagattctat tgtgacttca tagaattat gatagattat     1620 tttttagcta ttttttccat gtgtgaacct tgagtgatac taatcatgta aagtaagagt    1680
tctcttatgt attatgttcg gaagaggggt gtggtgactc ctttatattc gtactgcact    1740
ttgtttttcc aaggaaatca gtgtctttta cgttgttatg atgaatccca catggggccg    1800
gtgatggtat gctgaagttc agccgttgaa cacataggaa tgtctgtggg gtgactctac    1860
tgtgctttat cttttaacat taagtgcctt tggttcagag gggcagtcat aagctctgtt    1920 tcccctctc cccaaagcct tcagcgaacg tgaaatgtgc gctaaacggg gaaacctgtt      1980
taattctaga tatagggaaa aaggaacgag gaccttgaat gagctatatt cagggtatcc    2040
ggtattttgt aatagggaat aggaaacctt gttggctgtg gaatatccga tgctttgaat    2100
catgcactgt gttgaataaa cgtatctgct                                     2130
```

<210> SEQ ID NO 5
<211> LENGTH: 374
<212> TYPE: PRT
<213> ORGANISM: Homo sapiens

<400> SEQUENCE: 5

```
Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Leu Tyr Met Asp Ala
        115                 120                 125

Tyr Glu Val Ser Asn Thr Glu Phe Glu Lys Phe Val Asn Ser Thr Gly
    130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255
```

```
Tyr Ala Asn Ile Trp Gln Gly Asp Phe Pro Val Thr Asn Thr Gly Glu
            260                 265                 270

Asp Gly Phe Gln Gly Thr Ala Pro Val Asp Ala Phe Pro Pro Asn Gly
        275                 280                 285

Tyr Gly Leu Tyr Asn Ile Val Gly Asn Ala Trp Glu Trp Thr Ser Asp
    290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp
    370

<210> SEQ ID NO 6
<211> LENGTH: 2297
<212> TYPE: DNA
<213> ORGANISM: Homo sapiens

<400> SEQUENCE: 6
```

| | | | | |
|---|---|---|---|---|
| cggctgtgtt gcgcagtctt catgggttcc cgacgaggag gtctctgtgg ctgcggcggc | 60 |
| tgctaactgc gccacctgct gcagcctgtc cccgccgctc tgaagcggcc gcgtcgaagc | 120 |
| cgaaatgccg ccaccccgga ccggccgagg ccttctctgg ctgggtctgg ttctgagctc | 180 |
| cgtctgcgtc gccctcggat ccgaaacgca ggccaactcg accacagatg ctctgaacgt | 240 |
| tcttctcatc atcgtggatg acctgcgccc ctccctgggc tgttatgggg ataagctggt | 300 |
| gaggtcccca aatattgacc aactggcatc ccacagcctc ctcttccaga atgcctttgc | 360 |
| gcagcaagca gtgtgcgccc cgagccgcgt ttctttcctc actggcagga gacctgacac | 420 |
| cacccgcctg tacgacttca actcctactg gagggtgcac gctggaaact ctccaccat | 480 |
| cccccagtac ttcaaggaga atggctatgt gaccatgtcg gtgggaaaag tctttcaccc | 540 |
| tgggatatct tctaaccata ccgatgattc ccgtatagc tggtcttttc caccttatca | 600 |
| tccttcctct gagaagtatg aaaacactaa gacatgtcga gggccagatg gagaactcca | 660 |
| tgccaacctg ctttgccctg tggatgtgct ggatgttccc gagggcacct tgcctgacaa | 720 |
| acagagcact gagcaagcca tacagttgtt ggaaaagatg aaaacgtcag ccagtccttt | 780 |
| cttcctggcc gttgggtatc ataagccaca catccccttc agataccca aggaatttca | 840 |
| gaagttgtat ccccttggag acatcaccct ggccccccgat cccgaggtcc ctgatggcct | 900 |
| accccctgtg gcctacaacc cctggatgga catcaggcaa cgggaagacg tccaagcctt | 960 |
| aaacatcagt gtgccgtatg gtccaattcc tgtggacttt cagcggaaaa tccgccagag | 1020 |
| ctactttgcc tctgtgtcat atttggatac acaggtcggc cgcctcttga gtgctttgga | 1080 |
| cgatcttcag ctggccaaca gcaccatcat tgcatttacc tcggatcatg gtgggctct | 1140 |
| aggtgaacat ggagaatggg ccaaatacag caattttgat gttgctaccc atgttcccct | 1200 |
| gatattctat gttcctggaa ggacggcttc acttccggag gcaggcgaga gcttttccc | 1260 |
| ttacctcgac ccttttgatt ccgcctcaca gttgatggag ccaggcaggc aatccatgga | 1320 |
| ccttgtggaa cttgtgtctc tttttcccac gctggctgga cttgcaggac tgcaggttcc | 1380 |
| acctcgctgc cccgttcctt catttcacgt tgagctgtgc agagaaggca agaaccttct | 1440 |

```
gaagcattttt cgattccgtg acttggaaga ggatccgtac ctccctggta atccccgtga    1500
actgattgcc tatagccagt atccccggcc ttcagacatc cctcagtgga attctgacaa    1560
gccgagttta aaagatataa agatcatggg ctattccata cgcaccatag actataggta    1620
tactgtgtgg gttggcttca atcctgatga atttctagct aacttttctg acatccatgc    1680 agggaactg tattttgtgg attctgaccc attgcaggat cacaatatgt ataatgattc     1740
ccaaggtgga gatctttcc agttgttgat gccttgagtt ttgccaacca tggatggcaa    1800
atgtgatgtg ctcccttcca gctggtgaga ggaggagtta gagctggtcg ttttgtgatt    1860
acccataata ttggaagcag cctgagggct agttaatcca acatgcatc aacaatttgg     1920 cctgagaata tgtaacagcc aaaccttttc gtttagtctt tattaaaatt tataattggt    1980
aattggacca gttttttttt taatttccct cttttaaaa cagttacggc ttatttactg     2040
aataaataca aagcaaacaa actcaagtta tgtcatacct ttggatacga agaccataca    2100
taataaccaa acataacatt atacacaaag aatactttca ttatttgtgg aatttagtgc    2160
atttcaaaaa gtaatcatat atcaaactag gcaccacact aagttcctga ttattttgtt    2220
tataatttaa taatatatct tatgagcct atatattcaa aatattatgt taacatgtaa     2280
tccatgtttc tttttcc                                                    2297

<210> SEQ ID NO 7
<211> LENGTH: 550
<212> TYPE: PRT
<213> ORGANISM: Homo sapiens

<400> SEQUENCE: 7

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220
```

| | | | | | | | | | | | |
|---|---|---|---|---|---|---|---|---|---|---|---|
|Tyr|His|Lys|Pro|His|Ile|Pro|Phe|Arg|Tyr|Pro|Lys|Glu|Phe|Gln|Lys|
|225| | | | |230| | | | |235| | | | |240|

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
            245                 250                 255

Asp Gly Leu Pro Pro Val Ala Tyr Asn Pro Trp Met Asp Ile Arg Gln
        260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
530                 535                 540

Phe Gln Leu Leu Met Pro
545                 550

```
<210> SEQ ID NO 8
<211> LENGTH: 2657
<212> TYPE: DNA
<213> ORGANISM: Homo sapiens

<400> SEQUENCE: 8
gaattccggg ccatgagctg ccccgtgccc gcctgctgcg cgctgctgct agtcctgggg    60
ctctgccggg cgcgtccccg gaacgcactg ctgctcctcg cggatgacgg aggctttgag   120
agtggcgcgt acaacaacag cgccatcgcc accccgcacc tggacgcctt ggcccgccgc   180
agcctcctct ttcgcaatgc cttcacctcg gtcagcagct gctctcccag ccgcgccagc   240
```

```
ctcctcactg gcctgcccca gcatcagaat gggatgtacg ggctgcacca ggacgtgcac    300
cacttcaact ccttcgacaa ggtgcggagc ctgccgctgc tgctcagcca agctggtgtg    360
cgcacaggca tcatcgggaa gaagcacgtg gggccggaga ccgtgtaccc gtttgacttt    420
gcgtacacgg aggagaatgg ctccgtcctc caggtggggc ggaacatcac tagaattaag    480
ctgctcgtcc ggaaattcct gcagactcag gatgaccggc ctttcttcct ctacgtcgcc    540
ttccacgacc cccaccgctg tgggcactcc agcccagt acggaacctt ctgtgagaag     600
tttggcaacg gagagagcgg catgggtcgt atcccagact ggaccccca ggcctacgac     660 ccactggacg tgctggtgcc ttacttcgtc cccaacaccc cggcagcccg agccgacctg    720
gccgctcagt acaccaccgt cggccgcatg gaccaaggag ttggactggt gctccaggag    780
ctgcgtgacg ccggtgtcct gaacgacaca ctggtgatct tcacgtccga caacgggatc    840
cccttcccca gcggcaggac caacctgtac tggccgggca ctgctgaacc cttactggtg    900
tcatccccgg agcacccaaa acgctggggc caagtcagcg aggcctacgt gagcctccta    960
gacctcacgc ccaccatctt ggattggttc tcgatcccgt accccagcta cgccatcttt   1020
ggctcgaaga ccatccacct cactggccgg tccctcctgc cggcgctgga ggccgagccc   1080
ctctgggcca ccgtctttgg cagccagagc caccacgagg tcaccatgtc ctaccccatg   1140
cgctccgtgc agcaccggca cttccgcctc gtgcacaacc tcaacttcaa gatgcccttt   1200
cccatcgacc aggacttcta cgtctcaccc accttccagg acctcctgaa ccgcaccaca   1260
gctggtcagc ccacgggctg gtacaaggac ctccgtcatt actactaccg ggcgcgctgg   1320
gagctctacg accggagccg ggacccccac gagacccaga acctggccac cgacccgcgc   1380
tttgctcagc ttctggagat gcttcgggac cagctggcca agtggcagtg ggagacccac   1440
gaccctgggg tgtgcgcccc cgacggcgtc ctggaggaga agctctctcc ccagtgccag   1500 ccctccaca atgagctgtg accatcccag gaggcctgtg cacacatccc aggcatgtcc   1560
cagacacatc ccacacgtgt ccgtgtggcc ggccagcctg gggagtagtg caacagccc   1620 ttccgtccac actcccatcc aaggagggtt cttccttcct gtggggtcac tcttgccatt   1680
gcctggaggg ggaccagagc atgtgaccag agcatgtgcc cagcccctcc accaccaggg   1740
gcactgccgt catggcaggg gacacagttg tccttgtgtc tgaaccatgt cccagcacgg   1800
gaattctaga catacgtggt ctgcggacag ggcagcgccc ccagcccatg acaagggagt   1860
cttgttttct ggcttggttt ggggacctgc aaatgggagg cctgaggccc tcttcaggct   1920
ttggcagcca cagatacttc tgaacccttc acagagagca ggcagggct tcggtgccgc    1980 gtggcagta cgcaggtccc accgacactc acctgggagc acggcgcctg gctcttacca    2040
gcgtctggcc tagaggaagc ctttgagcga cctttgggca ggtttctgct tcttctgttt   2100
tgcccatggt caagtccctg ttccccaggc aggtttcagc tgattggcag caggctccct   2160
gagtgatgag cttgaacctg tggtgtttct gggcagaagc ttatctttt tgagagtgtc    2220 cgaagatgaa ggcatggcga tgcccgtcct ctggcttggg ttaattcttc ggtgacactg   2280
gcattgctgg gtggtgatgc ccgtcctctg gcttgggtta attcttcggt gacactggcg   2340
ttgctgggtg gcaatgcccg tcctctggct tgggttaatt cttcggtgac actggcgttg   2400
ctgggtggcg atgcccgtcc tctggcttgg gttaattctt ggatgacgtc ggcgttgctg   2460
ggagaatgtg ccgttcctgc cctgcctcca cccacctcgg gagcagaagc ccggcctgga   2520
cacccctcgg cctggacacc cctcgaagga gagggcgctt ccttgagtag gtgggctccc   2580
cttgcccttc cctccctatc actccatact ggggtgggct ggaggaggcc acaggccagc   2640
```

```
tattgtaaaa gcttttt                                                  2657
```

<210> SEQ ID NO 9
<211> LENGTH: 502
<212> TYPE: PRT
<213> ORGANISM: Homo sapiens

<400> SEQUENCE: 9

| Met | Ser | Cys | Pro | Val | Pro | Ala | Cys | Cys | Ala | Leu | Leu | Val | Leu | Gly |
|---|---|---|---|---|---|---|---|---|---|---|---|---|---|---|
| 1 | | | | 5 | | | | | 10 | | | | | 15 |

Leu Cys Arg Ala Arg Pro Arg Asn Ala Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
 50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe

```
                       370                 375                 380
Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
                435                 440                 445

Gln Asn Leu Ala Thr Asp Pro Arg Phe Ala Gln Leu Leu Glu Met Leu
            450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 10
<211> LENGTH: 1014
<212> TYPE: DNA
<213> ORGANISM: Homo sapiens

<400> SEQUENCE: 10
cgtgcctgta atcccagcag ctactcactc aggaggctga ggcaggagaa tctcttgaac    60
ccggaaggca gaggttgcag tgagccaaga tcgcgccact gaactccagc ctgggtgaca   120
gagtgagact gtctcagaac agcaacaaca aaatgcccgc tgctgctggg tccagaagag   180
cttgaataac tgcatgttct ttttctcaat tttcatttcc cagaactggg cacctccggg   240
ctgtgaaaag ttagggaagt gtctgacacc tccagaatcc attcccaaga agtgcctctg   300
gtcccactag cacctgcgca gactcaggcc aggcctagaa tctccagttg ccctgcaag    360 tgcctggagg aaggatggct ctggcctcgg tcctccccca accctgccca agccagacag   420
acagcacctg cagacgcagg gggactgcac aattccacct gcccaggacc tgaccctggc   480
gtgtgcttgg ccctcctcct cgcccacggc gcctcagatt tcaggaccct cctcctcgcc   540
cacggcgcct cagacctcag gacctgccg tctcacgcct ttgtgaaccc caaatatctg   600
agaccagtct cagtttattt tgccaaggtt aaggatgcac ctgtgacagc ctcaggaggt   660
cctgacaaca ggtgcccgag gtggctggga atacagtttg cctttataca tcttagggag   720
acacaagatc agtatgtgta tggcgtacat tggttcagtc agccttccac tgaatacacg   780
attgagtctg gccagtgaa tccgcatttt tatgtaaaca gtaagggaac ggggcaatca   840
tataagcgtt tgtctcaggg gagccccaga gggatgactt ccagttccgt ctgtcctttg   900
tccacaagga atttccctgg gcgctaatta tgagggaggc gtgtagcttc ttatcattgt   960
agctatgtta tttagaaata aaacgggagg caggtttgcc taattcccag gttg        1014

<210> SEQ ID NO 11
<211> LENGTH: 522
<212> TYPE: PRT
<213> ORGANISM: Homo sapiens

<400> SEQUENCE: 11

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
```

-continued

```
            20                  25                  30
Ile Leu Leu Leu Leu Met Asp Asp Met Gly Trp Gly Asp Leu Gly Val
         35                  40                  45
Tyr Gly Glu Pro Ser Arg Glu Thr Pro Asn Leu Asp Arg Met Ala Ala
 50                  55                  60
Glu Gly Leu Leu Phe Pro Asn Phe Tyr Ser Ala Asn Pro Leu Cys Ser
 65                  70                  75                  80
Pro Ser Arg Ala Ala Leu Leu Thr Gly Arg Leu Pro Ile Arg Asn Gly
                 85                  90                  95
Phe Tyr Thr Thr Asn Ala His Ala Arg Asn Ala Tyr Thr Pro Gln Glu
                100                 105                 110
Ile Val Gly Gly Ile Pro Asp Ser Glu Gln Leu Leu Pro Glu Leu Leu
                115                 120                 125
Lys Lys Ala Gly Tyr Val Ser Lys Ile Val Gly Lys Trp His Leu Gly
        130                 135                 140
His Arg Pro Gln Phe His Pro Leu Lys His Gly Phe Asp Glu Trp Phe
145                 150                 155                 160
Gly Ser Pro Asn Cys His Phe Gly Pro Tyr Asp Asn Lys Ala Arg Pro
                165                 170                 175
Asn Ile Pro Val Tyr Arg Asp Trp Glu Met Val Gly Arg Tyr Tyr Glu
                180                 185                 190
Glu Phe Pro Ile Asn Leu Lys Thr Gly Glu Ala Asn Leu Thr Gln Ile
        195                 200                 205
Tyr Leu Gln Glu Ala Leu Asp Phe Ile Lys Arg Gln Ala Arg His His
        210                 215                 220
Pro Phe Phe Leu Tyr Trp Ala Val Asp Ala Thr His Ala Pro Val Tyr
225                 230                 235                 240
Ala Ser Lys Pro Phe Leu Gly Thr Ser Gln Arg Gly Arg Tyr Gly Asp
                245                 250                 255
Ala Val Arg Glu Ile Asp Asp Ser Ile Gly Lys Ile Leu Glu Leu Leu
        260                 265                 270
Gln Asp Leu His Val Ala Asp Asn Thr Phe Val Phe Thr Ser Asp
        275                 280                 285
Asn Gly Ala Ala Leu Ile Ser Ala Pro Glu Gln Gly Gly Ser Asn Gly
        290                 295                 300
Pro Phe Leu Cys Gly Lys Gln Thr Thr Phe Glu Gly Gly Met Arg Glu
305                 310                 315                 320
Pro Ala Leu Ala Trp Trp Pro Gly His Val Thr Ala Gly Gln Val Ser
                325                 330                 335
His Gln Leu Gly Ser Ile Met Asp Leu Phe Thr Thr Ser Leu Ala Leu
        340                 345                 350
Ala Gly Leu Thr Pro Pro Ser Asp Arg Ala Ile Asp Gly Leu Asn Leu
        355                 360                 365
Leu Pro Thr Leu Leu Gln Gly Arg Leu Met Asp Arg Pro Ile Phe Tyr
        370                 375                 380
Tyr Arg Gly Asp Thr Leu Met Ala Ala Thr Leu Gly Gln His Lys Ala
385                 390                 395                 400
His Phe Trp Thr Trp Thr Asn Ser Trp Glu Asn Phe Arg Gln Gly Ile
                405                 410                 415
Asp Phe Cys Pro Gly Gln Asn Val Ser Gly Val Thr Thr His Asn Leu
                420                 425                 430
Glu Asp His Thr Lys Leu Pro Leu Ile Phe His Leu Gly Arg Asp Pro
        435                 440                 445
```

```
Gly Glu Arg Phe Pro Leu Ser Phe Ala Ser Ala Glu Tyr Gln Glu Ala
    450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
                500                 505                 510

Ser Ile Pro Lys Lys Cys Leu Trp Ser His
                515                 520
```

<210> SEQ ID NO 12
<211> LENGTH: 2379
<212> TYPE: DNA
<213> ORGANISM: Homo sapiens

<400> SEQUENCE: 12

| | | | | | |
|---|---|---|---|---|---|
| ggaattccgg | tcggcctctc | gcccttcagc | tacctgtgcg | tccctccgtc | ccgtcccgtc | 60 |
| ccggggtcac | cccggagcct | gtccgctatg | cggctcctgc | ctctagcccc | aggtcggctc | 120 |
| cggcggggca | gccccgcca | cctgccctcc | tgcagcccag | cgctgctact | gctggtgctg | 180 |
| ggcggctgcc | tggggggtctt | cggggtggct | gcgggaaccc | ggaggcccaa | cgtggtgctg | 240 |
| ctcctcacgg | acgaccagga | cgaagtgctc | ggcggcatga | caccactaaa | gaaaaccaaa | 300 |
| gctctcatcg | gagagatggg | gatgactttt | tccagtgctt | atgtgccaag | tgctctctgc | 360 |
| tgccccagca | gagccagtat | cctgacagga | aagtacccac | ataatcatca | cgttgtgaac | 420 |
| aacactctgg | aggggaactg | cagtagtaag | tcctggcaga | agatccaaga | accaaatact | 480 |
| ttcccagcaa | ttctcagatc | aatgtgtggt | tatcagacct | tttttgcagg | gaaatattta | 540 |
| aatgagtacg | gagccccaga | tgcaggtgga | ctagaacacg | ttcctctggg | ttggagttac | 600 |
| tggtatgcct | tggaaaagaa | ttctaagtat | tataattaca | ccctgtctat | caatgggaag | 660 |
| gcacggaagc | atggtgaaaa | ctatagtgtg | gactacctga | cagatgtttt | ggctaatgtc | 720 |
| tccttggact | ttctggacta | caagtccaac | tttgagccct | tcttcatgat | gatcgccact | 780 |
| ccagcgcctc | attcgccttg | gacagctgca | cctcagtacc | agaaggcttt | ccagaatgtc | 840 |
| tttgcaccaa | gaaacaagaa | cttcaacatc | catggaacga | caagcactg | gttaattagg | 900 |
| caagccaaga | ctccaatgac | taattcttca | atacagtttt | tagataatgc | atttaggaaa | 960 |
| aggtggcaaa | ctctcctctc | agttgatgac | cttgtggaga | aactggtcaa | gaggctggag | 1020 |
| ttcactgggg | agctcaacaa | cacttacatc | ttctatacct | cagacaatgg | ctatcacaca | 1080 |
| ggacagtttt | ccttgccaat | agacaagaga | cagctgtatg | agtttgatat | caaagttcca | 1140 |
| ctgttggttc | gaggacctgg | gatcaaacca | aatcagacaa | gcaagatgct | ggttgccaac | 1200 |
| attgacttgg | gtcctactat | tttggacatt | gctggctacg | acctaaataa | gacacagatg | 1260 |
| gatgggatgt | ccttattgcc | cattttgaga | ggtgccagta | acttgacctg | gcgatcagat | 1320 |
| gtcctggtgg | aataccaagg | agaaggccgt | aacgtcactg | acccaacatg | cccttccctg | 1380 |
| agtcctggcg | tatctcaatg | cttcccagac | tgtgtatgtg | aagatgctta | taacaatacc | 1440 |
| tatgcctgtg | tgaggacaat | gtcagcattg | tggaatttgc | agtattgcga | gtttgatgac | 1500 |
| caggaggtgt | ttgtagaagt | ctataatctg | actgcagacc | cagaccagat | cactaacatt | 1560 |
| gctaaaacca | tagacccaga | gcttttagga | aagatgaact | atcggttaat | gatgttacag | 1620 |
| tcctgttctg | ggccaacctg | tcgcactcca | ggggttttg | accccggata | caggtttgac | 1680 |
| ccccgtctca | tgttcagcaa | tcgcggcagt | gtcaggactc | gaagattttc | caaacatctt | 1740 |

-continued

```
ctgtagcgac ctcacacagc ctctgcagat ggatccctgc acgcctcttt ctgatgaagt    1800
gattgtagta ggtgtctgta gctagtcttc aagaccacac ctggaagagt ttctgggctg    1860
gctttaagtc ctgtttgaaa aagcaaccca gtcagctgac ttcctcgtgc aatgtgttaa    1920
actgtgaact ctgcccatgt gtcaggagtg gctgtctctg gtctcttcct ttagctgaca    1980
aggacactcc tgaggtcttt gttctcactg tatttttttt atcctggggc cacagttctt    2040
gattattcct cttgtggtta aagactgaat ttgtaaaccc attcagataa atggcagtac    2100
tttaggacac acacaaacac acagatacac cttttgatat gtaagcttga cctaaagtca    2160
aaggacctgt gtagcatttc agattgagca cttcactatc aaaaatacta acatcacatg    2220
gcttgaagag taaccatcag agctgaatca tccaagtaag aacaagtacc attgttgatt    2280
gataagtaga gatacatttt ttatgatgtt catcacagtg tggtaaggtt gcaaattcaa    2340
aacatgtcac ccaagctctg ttcatgtttt tgtgaattc                            2379
```

<210> SEQ ID NO 13
<211> LENGTH: 552
<212> TYPE: PRT
<213> ORGANISM: Homo sapiens

<400> SEQUENCE: 13

Met Arg Leu Leu Pro Leu Ala Pro Gly Arg Leu Arg Arg Gly Ser Pro
1               5                   10                  15

Arg His Leu Pro Ser Cys Ser Pro Ala Leu Leu Leu Val Leu Gly
            20                  25                  30

Gly Cys Leu Gly Val Phe Gly Val Ala Ala Gly Thr Arg Arg Pro Asn
        35                  40                  45

Val Val Leu Leu Leu Thr Asp Asp Gln Asp Glu Val Leu Gly Gly Met
    50                  55                  60

Thr Pro Leu Lys Lys Thr Lys Ala Leu Ile Gly Glu Met Gly Met Thr
65                  70                  75                  80

Phe Ser Ser Ala Tyr Val Pro Ser Ala Leu Cys Cys Pro Ser Arg Ala
                85                  90                  95

Ser Ile Leu Thr Gly Lys Tyr Pro His Asn His His Val Val Asn Asn
            100                 105                 110

Thr Leu Glu Gly Asn Cys Ser Ser Lys Ser Trp Gln Lys Ile Gln Glu
        115                 120                 125

Pro Asn Thr Phe Pro Ala Ile Leu Arg Ser Met Cys Gly Tyr Gln Thr
    130                 135                 140

Phe Phe Ala Gly Lys Tyr Leu Asn Glu Tyr Gly Ala Pro Asp Ala Gly
145                 150                 155                 160

Gly Leu Glu His Val Pro Leu Gly Trp Ser Tyr Trp Tyr Ala Leu Glu
                165                 170                 175

Lys Asn Ser Lys Tyr Tyr Asn Tyr Thr Leu Ser Ile Asn Gly Lys Ala
            180                 185                 190

Arg Lys His Gly Glu Asn Tyr Ser Val Asp Tyr Leu Thr Asp Val Leu
        195                 200                 205

Ala Asn Val Ser Leu Asp Phe Leu Asp Tyr Lys Ser Asn Phe Glu Pro
    210                 215                 220

Phe Phe Met Met Ile Ala Thr Pro Ala Pro His Ser Pro Trp Thr Ala
225                 230                 235                 240

Ala Pro Gln Tyr Gln Lys Ala Phe Gln Asn Val Phe Ala Pro Arg Asn
                245                 250                 255

Lys Asn Phe Asn Ile His Gly Thr Asn Lys His Trp Leu Ile Arg Gln

```
                260              265              270
Ala Lys Thr Pro Met Thr Asn Ser Ser Ile Gln Phe Leu Asp Asn Ala
        275                  280              285
Phe Arg Lys Arg Trp Gln Thr Leu Leu Ser Val Asp Asp Leu Val Glu
    290                  295              300
Lys Leu Val Lys Arg Leu Glu Phe Thr Gly Glu Leu Asn Asn Thr Tyr
305                 310              315                  320
Ile Phe Tyr Thr Ser Asp Asn Gly Tyr His Thr Gly Gln Phe Ser Leu
                325              330                  335
Pro Ile Asp Lys Arg Gln Leu Tyr Glu Phe Asp Ile Lys Val Pro Leu
            340              345              350
Leu Val Arg Gly Pro Gly Ile Lys Pro Asn Gln Thr Ser Lys Met Leu
                355              360              365
Val Ala Asn Ile Asp Leu Gly Pro Thr Ile Leu Asp Ile Ala Gly Tyr
        370              375              380
Asp Leu Asn Lys Thr Gln Met Asp Gly Met Ser Leu Leu Pro Ile Leu
385                 390              395                  400
Arg Gly Ala Ser Asn Leu Thr Trp Arg Ser Asp Val Leu Val Glu Tyr
                405              410              415
Gln Gly Glu Gly Arg Asn Val Thr Asp Pro Thr Cys Pro Ser Leu Ser
            420              425              430
Pro Gly Val Ser Gln Cys Phe Pro Asp Cys Val Cys Glu Asp Ala Tyr
            435              440              445
Asn Asn Thr Tyr Ala Cys Val Arg Thr Met Ser Ala Leu Trp Asn Leu
        450              455              460
Gln Tyr Cys Glu Phe Asp Asp Gln Glu Val Phe Val Glu Val Tyr Asn
465                 470              475                  480
Leu Thr Ala Asp Pro Asp Gln Ile Thr Asn Ile Ala Lys Thr Ile Asp
                485              490              495
Pro Glu Leu Leu Gly Lys Met Asn Tyr Arg Leu Met Met Leu Gln Ser
            500              505              510
Cys Ser Gly Pro Thr Cys Arg Thr Pro Gly Val Phe Asp Pro Gly Tyr
            515              520              525
Arg Phe Asp Pro Arg Leu Met Phe Ser Asn Arg Gly Ser Val Arg Thr
        530              535              540
Arg Arg Phe Ser Lys His Leu Leu
545                 550

<210> SEQ ID NO 14
<211> LENGTH: 2022
<212> TYPE: DNA
<213> ORGANISM: Homo sapiens

<400> SEQUENCE: 14
ccggtaccgg ctcctcctgg gctccctcta gcgccttccc cccggcccga ctgcctggtc     60
agcgccaagt gacttacgcc cccgaccctg agcccggacc gctaggcgag gaggatcaga    120
tctccgctcg agaatctgaa ggtgccctgg tcctggagga gttccgtccc agccctgcgg    180
tctcccggta ctgctcgccc cggccctctg agcttcagg aggcggccgt cagggtcggg     240
gagtatttgg gtccggggtc tcagggaagg gcggcgcctg gtctgcggt atcggaaaga    300
gcctgctgga gccaagtagc cctcccctct tgggacaga cccctcggtc ccatgtccat    360
gggggcaccg cggtccctcc tcctggccct ggctgctggc ctggccgttg cccgtccgcc    420
caacatcgtg ctgatctttg ccgacgacct cggctatggg gacctgggct gctatgggca    480
```

```
cccagctct accactccca acctggacca gctggcggcg ggagggctgc ggttcacaga      540
cttctacgtg cctgtgtctc tgtgcacacc ctctagggcc gccctcctga ccggccggct      600
cccggttcgg atgggcatgt accctggcgt cctggtgccc agctcccggg ggggcctgcc      660
cctggaggag gtgaccgtgg ccgaagtcct ggctgcccga ggctacctca caggaatggc      720
cggcaagtgg caccttgggg tggggcctga gggggccttc ctgcccccc atcagggctt      780 ccatcgattt ctaggcatcc cgtactccca cgaccagggc ccctgccaga acctgacctg      840
cttcccgccg gccactcctt gcgacggtgg ctgtgaccag ggcctggtcc ccatcccact      900
gttggccaac ctgtccgtgg aggcgcagcc ccctggctg cccggactag aggcccgcta      960
catggctttc gcccatgacc tcatggccga cgcccagcgc caggatcgcc ccttcttcct     1020
gtactatgcc tctcaccaca cccactaccc tcagttcagt gggcagagct ttgcagagcg     1080
ttcaggccgc gggccatttg ggactccct gatggagctg gatgcagctg tggggaccct     1140
gatgacagcc ataggggacc tggggctgct tgaagagacg ctggtcatct tcactgcaga     1200
caatggacct gagaccatgc gtatgtcccg aggcggctgc tccggtctct tgcggtgtgg     1260
aaagggaacg acctacgagg gcggtgtccg agagcctgcc ttggccttct ggccaggtca     1320
tatcgctccc ggcgtgaccc acgagctggc cagctccctg acctgctgc ctaccctggc     1380 agccctggct ggggccccac tgcccaatgt caccttggat ggctttgacc tcagccccct     1440
gctgctgggc acaggcaaga gccctcggca gtctctcttc ttctacccgt cctacccaga     1500
cgaggtccgt gggttttttg ctgtgcggac tggaaagtac aaggctcact tcttcaccca     1560
gggctctgcc cacagtgata ccactgcaga ccctgcctgc cacgcctcca gctctctgac     1620
tgctcatgag cccccgctgc tctatgacct gtccaaggac cctggtgaga actacaacct     1680 gctgggggt gtggccgggg ccaccccaga ggtgctgcaa gccctgaaac agcttcagct     1740
gctcaaggcc cagttagacg cagctgtgac cttcggcccc agccaggtgg cccggggcga     1800
ggaccccgcc ctgcagatct gctgtcatcc tggctgcacc cccgcccag cttgctgcca     1860 ttgcccagat cccatgcct gagggcccct cggctggcct gggcatgtga tggctcctca     1920
ctgggagcct gtggggagg ctcaggtgtc tggagggggt ttgtgcctga taacgtaata     1980
acaccagtgg agacttgcac atctgaaaaa aaaaaaaaaa aa                        2022
```

<210> SEQ ID NO 15
<211> LENGTH: 507
<212> TYPE: PRT
<213> ORGANISM: Homo sapiens

<400> SEQUENCE: 15

```
Met Gly Ala Pro Arg Ser Leu Leu Ala Leu Ala Ala Gly Leu Ala
1               5                   10                  15

Val Ala Arg Pro Pro Asn Ile Val Leu Ile Phe Ala Asp Asp Leu Gly
            20                  25                  30

Tyr Gly Asp Leu Gly Cys Tyr Gly His Pro Ser Ser Thr Thr Pro Asn
        35                  40                  45

Leu Asp Gln Leu Ala Ala Gly Gly Leu Arg Phe Thr Asp Phe Tyr Val
    50                  55                  60

Pro Val Ser Leu Cys Thr Pro Ser Arg Ala Ala Leu Leu Thr Gly Arg
65                  70                  75                  80

Leu Pro Val Arg Met Gly Met Tyr Pro Gly Val Leu Val Pro Ser Ser
                85                  90                  95

Arg Gly Gly Leu Pro Leu Glu Glu Val Thr Val Ala Glu Val Leu Ala
            100                 105                 110
```

```
Ala Arg Gly Tyr Leu Thr Gly Met Ala Gly Lys Trp His Leu Gly Val
        115                 120                 125

Gly Pro Glu Gly Ala Phe Leu Pro Pro His Gln Gly Phe His Arg Phe
    130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Gly Cys Asp Gln Gly Leu
                165                 170                 175

Val Pro Ile Pro Leu Leu Ala Asn Leu Ser Val Glu Ala Gln Pro Pro
                180                 185                 190

Trp Leu Pro Gly Leu Glu Ala Arg Tyr Met Ala Phe Ala His Asp Leu
            195                 200                 205

Met Ala Asp Ala Gln Arg Gln Asp Arg Pro Phe Phe Leu Tyr Tyr Ala
    210                 215                 220

Ser His His Thr His Tyr Pro Gln Phe Ser Gly Gln Ser Phe Ala Glu
225                 230                 235                 240

Arg Ser Gly Arg Gly Pro Phe Gly Asp Ser Leu Met Glu Leu Asp Ala
                245                 250                 255

Ala Val Gly Thr Leu Met Thr Ala Ile Gly Asp Leu Gly Leu Leu Glu
                260                 265                 270

Glu Thr Leu Val Ile Phe Thr Ala Asp Asn Gly Pro Glu Thr Met Arg
            275                 280                 285

Met Ser Arg Gly Gly Cys Ser Gly Leu Leu Arg Cys Gly Lys Gly Thr
    290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
                325                 330                 335

Leu Pro Thr Leu Ala Ala Leu Ala Gly Ala Pro Leu Pro Asn Val Thr
                340                 345                 350

Leu Asp Gly Phe Asp Leu Ser Pro Leu Leu Leu Gly Thr Gly Lys Ser
            355                 360                 365

Pro Arg Gln Ser Leu Phe Phe Tyr Pro Ser Tyr Pro Asp Glu Val Arg
    370                 375                 380

Gly Val Phe Ala Val Arg Thr Gly Lys Tyr Lys Ala His Phe Phe Thr
385                 390                 395                 400

Gln Gly Ser Ala His Ser Asp Thr Thr Ala Asp Pro Ala Cys His Ala
                405                 410                 415

Ser Ser Ser Leu Thr Ala His Glu Pro Pro Leu Leu Tyr Asp Leu Ser
                420                 425                 430

Lys Asp Pro Gly Glu Asn Tyr Asn Leu Leu Gly Gly Val Ala Gly Ala
            435                 440                 445

Thr Pro Glu Val Leu Gln Ala Leu Lys Gln Leu Gln Leu Leu Lys Ala
    450                 455                 460

Gln Leu Asp Ala Ala Val Thr Phe Gly Pro Ser Gln Val Ala Arg Gly
465                 470                 475                 480

Glu Asp Pro Ala Leu Gln Ile Cys Cys His Pro Gly Cys Thr Pro Arg
                485                 490                 495

Pro Ala Cys Cys His Cys Pro Asp Pro His Ala
                500                 505

<210> SEQ ID NO 16
<211> LENGTH: 2228
<212> TYPE: DNA
```

<213> ORGANISM: Homo sapiens

<400> SEQUENCE: 16

| | | | | | |
|---|---|---|---|---|---|
| acaaggatgg | gtccgcgcgg | cgcggcgagc | ttgccccgag | gccccggacc | tcggcggctg | 60 |
| ctcctcccg | tcgtcctccc | gctgctgctg | ctgctgttgt | tggcgccgcc | gggctcgggc | 120 |
| gccggggcca | gccggccgcc | ccacctggtc | ttcttgctgg | cagacgacct | aggctggaac | 180 |
| gacgtcggct | tccacggctc | ccgcatccgc | acgccgcacc | tggacgcgct | ggcggccggc | 240 |
| ggggtgctcc | tggacaacta | ctacacgcag | ccgctgtgca | cgccgtcgcg | gagccagctg | 300 |
| ctcactggcc | gctaccagat | ccgtacaggt | ttacagcacc | aaataatctg | gccctgtcag | 360 |
| cccagctgtg | ttcctctgga | tgaaaaactc | ctgccccagc | tcctaaaaga | agcaggttat | 420 |
| actacccata | tggtcggaaa | atggcacctg | ggaatgtacc | ggaaagaatg | ccttccaacc | 480 |
| cgccgaggat | ttgataccta | cttttggatat | ctcctgggta | gtgaagatta | ttattcccat | 540 |
| gaacgctgta | cattaattga | cgctctgaat | gtcacacgat | gtgctcttga | ttttcgagat | 600 |
| ggcgaagaag | ttgcaacagg | atataaaaat | atgtattcaa | caaacatatt | caccaaaagg | 660 |
| gctatagccc | tcataactaa | ccatccacca | gagaagcctc | tgtttctcta | ccttgctctc | 720 |
| cagtctgtgc | atgagcccct | tcaggtccct | gaggaatact | tgaagccata | tgactttatc | 780 |
| caagacaaga | acaggcatca | ctatgcagga | atggtgtccc | ttatggatga | agcagtagga | 840 |
| aatgtcactg | cagcttttaaa | aagcagtggg | ctctggaaca | acacggtgtt | catctttct | 900 |
| acagataacg | gagggcagac | tttgcaggg | ggtaataact | ggccccttcg | aggaagaaaa | 960 |
| tggagcctgt | gggaaggagg | cgtccgaggg | gtgggctttg | tggcaagccc | cttgctgaag | 1020 |
| cagaagggcg | tgaagaaccg | ggagctcatc | cacatctctg | actggctgcc | aacactcgtg | 1080 |
| aagctggcca | ggggacacac | caatggcaca | aagcctctgg | atggcttcga | cgtgtggaaa | 1140 |
| accatcagtg | aaggaagccc | atcccccaga | attgagctgc | tgcataatat | tgacccaaac | 1200 |
| ttcgtggact | cttcaccgtg | tcccaggaac | agcatggctc | cagcaaagga | tgactcttct | 1260 |
| cttccagaat | attcagcctt | taacacatct | gtccatgctg | caattagaca | tggaaattgg | 1320 |
| aaactcctca | cgggctaccc | aggctgtggt | tactggttcc | ctccaccgtc | tcaatacaat | 1380 |
| gtttctgaga | taccctcatc | agacccacca | accaagaccc | tctggctctt | tgatattgat | 1440 |
| cgggaccctg | aagaaagaca | tgacctgtcc | agagaatatc | ctcacatcgt | cacaaagctc | 1500 |
| ctgtcccgcc | tacagttcta | ccataaacac | tcagtccccg | tgtacttccc | tgcacaggac | 1560 |
| ccccgctgtg | atcccaaggc | cactgggggtg | tggggccctt | ggatgtagga | tttcagggag | 1620 |
| gctagaaaac | ctttcaattg | gaagttggac | ctcaggcctt | ttctcacgac | tcttgtctca | 1680 |
| tttgttatcc | caacctgggt | tcacttggcc | cttctcttgc | tcttaaacca | caccgaggtg | 1740 |
| tctaatttca | acccctaatg | catttaagaa | gctgataaaa | tctgcaacac | tcctgctgtt | 1800 |
| ggctggagca | tgtgtctaga | ggtggggggtg | gctgggttta | tccccctttc | ctaagccttg | 1860 |
| ggacagctgg | gaacttaact | tgaaatagga | agttctcact | gaatcctgga | ggctggaaca | 1920 |
| gctggctctt | ttagactcac | aagtcagacg | ttcgattccc | ctctgccaat | agccagtttt | 1980 |
| attggagtga | atcacatttc | ttacgcaaat | gaagggagca | gacagtgatt | aatggttctg | 2040 |
| ttggccaagg | cttctccctg | tcggtgaagg | atcatgttca | ggcactccaa | gtgaaccacc | 2100 |
| cctcttggtt | caccccttac | tcacttatct | catcacagag | cataaggccc | attttgttgt | 2160 |
| tcaggtcaac | agcaaaatgg | cctgcaccat | gactgtggct | tttaaaataa | agaaatgtgt | 2220 |
| ttttatcg | | | | | | 2228 |

<210> SEQ ID NO 17
<211> LENGTH: 533
<212> TYPE: PRT
<213> ORGANISM: Homo sapiens

<400> SEQUENCE: 17

```
Met Gly Pro Arg Gly Ala Ala Ser Leu Pro Arg Gly Pro Gly Pro Arg
1               5                   10                  15

Arg Leu Leu Leu Pro Val Val Leu Pro Leu Leu Leu Leu Leu Leu Leu
            20                  25                  30

Ala Pro Pro Gly Ser Gly Ala Gly Ala Ser Arg Pro Pro His Leu Val
        35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
                85                  90                  95

Gln Leu Leu Thr Gly Arg Tyr Gln Ile Arg Thr Gly Leu Gln His Gln
            100                 105                 110

Ile Ile Trp Pro Cys Gln Pro Ser Cys Val Pro Leu Asp Glu Lys Leu
        115                 120                 125

Leu Pro Gln Leu Leu Lys Glu Ala Gly Tyr Thr Thr His Met Val Gly
    130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
                165                 170                 175

Ser His Glu Arg Cys Thr Leu Ile Asp Ala Leu Asn Val Thr Arg Cys
            180                 185                 190

Ala Leu Asp Phe Arg Asp Gly Glu Val Ala Thr Gly Tyr Lys Asn
        195                 200                 205

Met Tyr Ser Thr Asn Ile Phe Thr Lys Arg Ala Ile Ala Leu Ile Thr
    210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Glu Tyr Leu Lys Pro Tyr Asp
                245                 250                 255

Phe Ile Gln Asp Lys Asn Arg His His Tyr Ala Gly Met Val Ser Leu
            260                 265                 270

Met Asp Glu Ala Val Gly Asn Val Thr Ala Ala Leu Lys Ser Ser Gly
        275                 280                 285

Leu Trp Asn Asn Thr Val Phe Ile Phe Ser Thr Asp Asn Gly Gly Gln
    290                 295                 300

Thr Leu Ala Gly Gly Asn Asn Trp Pro Leu Arg Gly Arg Lys Trp Ser
305                 310                 315                 320

Leu Trp Glu Gly Gly Val Arg Gly Val Gly Phe Val Ala Ser Pro Leu
                325                 330                 335

Leu Lys Gln Lys Gly Val Lys Asn Arg Glu Leu Ile His Ile Ser Asp
            340                 345                 350

Trp Leu Pro Thr Leu Val Lys Leu Ala Arg Gly His Thr Asn Gly Thr
        355                 360                 365

Lys Pro Leu Asp Gly Phe Asp Val Trp Lys Thr Ile Ser Glu Gly Ser
    370                 375                 380
```

| Pro | Ser | Pro | Arg | Ile | Glu | Leu | Leu | His | Asn | Ile | Asp | Pro | Asn | Phe | Val |
|---|---|---|---|---|---|---|---|---|---|---|---|---|---|---|---|
| 385 | | | | 390 | | | | | 395 | | | | | 400 | |

| Asp | Ser | Ser | Pro | Cys | Pro | Arg | Asn | Ser | Met | Ala | Pro | Ala | Lys | Asp | Asp |
|---|---|---|---|---|---|---|---|---|---|---|---|---|---|---|---|
| | | | | 405 | | | | | 410 | | | | | 415 | |

| Ser | Ser | Leu | Pro | Glu | Tyr | Ser | Ala | Phe | Asn | Thr | Ser | Val | His | Ala | Ala |
|---|---|---|---|---|---|---|---|---|---|---|---|---|---|---|---|
| | | | 420 | | | | | 425 | | | | | 430 | | |

| Ile | Arg | His | Gly | Asn | Trp | Lys | Leu | Leu | Thr | Gly | Tyr | Pro | Gly | Cys | Gly |
|---|---|---|---|---|---|---|---|---|---|---|---|---|---|---|---|
| | | 435 | | | | | 440 | | | | | 445 | | | |

| Tyr | Trp | Phe | Pro | Pro | Pro | Ser | Gln | Tyr | Asn | Val | Ser | Glu | Ile | Pro | Ser |
|---|---|---|---|---|---|---|---|---|---|---|---|---|---|---|---|
| | 450 | | | | | 455 | | | | | 460 | | | | |

| Ser | Asp | Pro | Pro | Thr | Lys | Thr | Leu | Trp | Leu | Phe | Asp | Ile | Asp | Arg | Asp |
|---|---|---|---|---|---|---|---|---|---|---|---|---|---|---|---|
| 465 | | | | | 470 | | | | | 475 | | | | | 480 |

| Pro | Glu | Glu | Arg | His | Asp | Leu | Ser | Arg | Glu | Tyr | Pro | His | Ile | Val | Thr |
|---|---|---|---|---|---|---|---|---|---|---|---|---|---|---|---|
| | | | | 485 | | | | | 490 | | | | | 495 | |

| Lys | Leu | Leu | Ser | Arg | Leu | Gln | Phe | Tyr | His | Lys | His | Ser | Val | Pro | Val |
|---|---|---|---|---|---|---|---|---|---|---|---|---|---|---|---|
| | | | 500 | | | | | 505 | | | | | 510 | | |

| Tyr | Phe | Pro | Ala | Gln | Asp | Pro | Arg | Cys | Asp | Pro | Lys | Ala | Thr | Gly | Val |
|---|---|---|---|---|---|---|---|---|---|---|---|---|---|---|---|
| | | 515 | | | | | 520 | | | | | 525 | | | |

| Trp | Gly | Pro | Trp | Met |
|---|---|---|---|---|
| | 530 | | | |

<210> SEQ ID NO 18
<211> LENGTH: 2401
<212> TYPE: DNA
<213> ORGANISM: Homo sapiens

<400> SEQUENCE: 18

```
gcctccagca gctgacggga cccagctgta gtgaggttgc agtgattgag taggattggc      60
ctgcttcaaa gcagaggttt ctcatgggaa tatgcttatt aaactcccac tggtgcagaa     120
accatgaaca gaggatgaac aagtgaagtt gcaatctcct ccatcacagc tcagttcccc     180
aacaacagga tcacaagctg agatgcctt taaggaagat gaagatccct ttcctcctac     240
tgttctttct gtgggaagcc gagagccacg cagcatcaag gccgaacatc atcctggtga     300
tggctgacga cctcggcatt ggagatcctg ggtgctatgg aacaaaact atcaggactc     360
ccaatatcga ccggttggcc agtgggggag tgaaactcac tcagcacctg cagcatcac     420
cgctgtgcac accaagcagg gcagccttca tgactggccg gtaccctgtc cgatcaggaa     480
tggcatcttg gtcccgcact ggagttttcc tcttcacagc ctcttcggga ggacttccca     540
ccgatgagat tacctttgct aagcttctga aggatcaagg ttattcaaca gcactgatag     600
ggaaatggca ccttgggatg agctgtcaca gcaagactga cttctgtcac caccctttac     660
atcacggctt caattatttc tatgggatct ctttgaccaa tctgagagac tgcaagcccg     720
gagagggcag tgtcttcacc acgggcttca agaggctggt cttcctcccc ctgcagatcg     780
tcggggtcac cctccttacc cttgctgcac tcaattgtct ggggctactc cacgtgcctc     840
taggcgtttt tttcagcctt ctcttcctag cagccctaat cctgaccctt tccttgggct     900
tccttcatta cttccggccc ctgaactgct tcatgatgag gaactacgag atcattcagc     960
agcccatgtc ctatgacaat ctcacccaga ggctaacggt ggaggcggcc cagttcatac    1020
agcggaacac tgagactccg ttcctgcttg tcttgtccta cctccacgtg cacacagccc    1080
tgttctccag caaagacttt gctggcaaaa gtcaacacgg agtctacggg gatgctgttg    1140
aggaaatgga ctggagtgtg gggcagatct gaaccttct ggatgagctg agattggcta    1200
atgataccct catctacttc acatcggacc agggagcaca tgtagaggag gtgtcttcca    1260
```

```
aaggagaaat tcatggcgga agtaatggga tctataaagg aggaaaagca acaactggg    1320 aaggaggtat ccgggttcca ggcatccttc gttggcccag ggtgatacag gctggccaga    1380
agattgatga gcccactagc aacatggaca tatttcctac agtagccaag ctggctggag    1440
ctcccttgcc tgaggacagg atcattgatg acgtgatct gatgcccctg cttgaaggaa    1500
aaagccaacg ctccgatcat gagtttctct tccattactg caacgcctac ttaaatgctg    1560
tgcgctggca ccctcagaac agcacatcca tctggaaggc cttttttcttc accccccaact   1620 tcaaccccgt gggttccaac ggatgctttg ccacacacgt gtgcttctgt tcgggagtt    1680 atgtcaccca tcacgaccca cctttactct ttgatatttc caaagatccc agagagagaa    1740
acccactaac tccagcatcc gagccccggt tttatgaaat cctcaaagtc atgcaggaag    1800
ctgcggacag acacacccag accctgccag aggtgcccga tcagttttca tggaacaact    1860
ttctttggaa gccctggctt cagctgtgct gtccttccac cggcctgtct tgccagtgtg    1920
atagagaaaa acaggataag agactgagcc gctagcagcg cctggggacc agacagacgc    1980
atgtggcaaa gctcaccatc ttcactacaa acacgcctga gagtggcact ggggaaacat    2040
aactccatct acaccttgga tttggactga ttctccattt tatcacctga aggcttgggc    2100
cagagctcaa cagctactca actggagggg tgaggggat aaggtctgta gtatacagac    2160
aggaagatgg taggtttatg ccttctgtgg ccagagtctt ggactcatgg aaatagaatg    2220
aatagagggg cattcacaag gcacaccagt gcaagcagat gacaaaaagg tgcagaaggc    2280
aatcttaaaa cagaaaggtg caggaggtac cttaactcac ccctcagcaa atacctatgt    2340
caacagtata agttaccatt tactctataa tctgcagtga tgcaataacc agcataataa    2400
a                                                                   2401
```

<210> SEQ ID NO 19
<211> LENGTH: 583
<212> TYPE: PRT
<213> ORGANISM: Homo sapiens

<400> SEQUENCE: 19

```
Met Pro Leu Arg Lys Met Lys Ile Pro Phe Leu Leu Leu Phe Leu
1               5                   10                  15

Trp Glu Ala Glu Ser His Ala Ala Ser Arg Pro Asn Ile Ile Leu Val
                20                  25                  30

Met Ala Asp Asp Leu Gly Ile Gly Asp Pro Gly Cys Tyr Gly Asn Lys
            35                  40                  45

Thr Ile Arg Thr Pro Asn Ile Asp Arg Leu Ala Ser Gly Gly Val Lys
        50                  55                  60

Leu Thr Gln His Leu Ala Ala Ser Pro Leu Cys Thr Pro Ser Arg Ala
65                  70                  75                  80

Ala Phe Met Thr Gly Arg Tyr Pro Val Arg Ser Gly Met Ala Ser Trp
                85                  90                  95

Ser Arg Thr Gly Val Phe Leu Phe Thr Ala Ser Gly Gly Leu Pro
                100                 105                 110

Thr Asp Glu Ile Thr Phe Ala Lys Leu Leu Lys Asp Gln Gly Tyr Ser
            115                 120                 125

Thr Ala Leu Ile Gly Lys Trp His Leu Gly Met Ser Cys His Ser Lys
        130                 135                 140

Thr Asp Phe Cys His His Pro Leu His Gly Phe Asn Tyr Phe Tyr
145                 150                 155                 160

Gly Ile Ser Leu Thr Asn Leu Arg Asp Cys Lys Pro Gly Glu Gly Ser
                165                 170                 175
```

```
Val Phe Thr Thr Gly Phe Lys Arg Leu Val Phe Leu Pro Leu Gln Ile
            180                 185                 190

Val Gly Val Thr Leu Leu Thr Leu Ala Ala Leu Asn Cys Leu Gly Leu
        195                 200                 205

Leu His Val Pro Leu Gly Val Phe Phe Ser Leu Leu Phe Leu Ala Ala
    210                 215                 220

Leu Ile Leu Thr Leu Phe Leu Gly Phe Leu His Tyr Phe Arg Pro Leu
225                 230                 235                 240

Asn Cys Phe Met Met Arg Asn Tyr Glu Ile Ile Gln Gln Pro Met Ser
                245                 250                 255

Tyr Asp Asn Leu Thr Gln Arg Leu Thr Val Glu Ala Ala Gln Phe Ile
            260                 265                 270

Gln Arg Asn Thr Glu Thr Pro Phe Leu Val Leu Ser Tyr Leu His
        275                 280                 285

Val His Thr Ala Leu Phe Ser Ser Lys Asp Phe Ala Gly Lys Ser Gln
    290                 295                 300

His Gly Val Tyr Gly Asp Ala Val Glu Glu Met Asp Trp Ser Val Gly
305                 310                 315                 320

Gln Ile Leu Asn Leu Leu Asp Glu Leu Arg Leu Ala Asn Asp Thr Leu
                325                 330                 335

Ile Tyr Phe Thr Ser Asp Gln Gly Ala His Val Glu Glu Val Ser Ser
            340                 345                 350

Lys Gly Glu Ile His Gly Gly Ser Asn Gly Ile Tyr Lys Gly Gly Lys
        355                 360                 365

Ala Asn Asn Trp Glu Gly Gly Ile Arg Val Pro Gly Ile Leu Arg Trp
    370                 375                 380

Pro Arg Val Ile Gln Ala Gly Gln Lys Ile Asp Glu Pro Thr Ser Asn
385                 390                 395                 400

Met Asp Ile Phe Pro Thr Val Ala Lys Leu Ala Gly Ala Pro Leu Pro
                405                 410                 415

Glu Asp Arg Ile Ile Asp Gly Arg Asp Leu Met Pro Leu Leu Glu Gly
            420                 425                 430

Lys Ser Gln Arg Ser Asp His Glu Phe Leu Phe His Tyr Cys Asn Ala
        435                 440                 445

Tyr Leu Asn Ala Val Arg Trp His Pro Gln Asn Ser Thr Ser Ile Trp
    450                 455                 460

Lys Ala Phe Phe Phe Thr Pro Asn Phe Asn Pro Val Gly Ser Asn Gly
465                 470                 475                 480

Cys Phe Ala Thr His Val Cys Phe Cys Phe Gly Ser Tyr Val Thr His
                485                 490                 495

His Asp Pro Pro Leu Leu Phe Asp Ile Ser Lys Asp Pro Arg Glu Arg
            500                 505                 510

Asn Pro Leu Thr Pro Ala Ser Glu Pro Arg Phe Tyr Glu Ile Leu Lys
        515                 520                 525

Val Met Gln Glu Ala Ala Asp Arg His Thr Gln Thr Leu Pro Glu Val
    530                 535                 540

Pro Asp Gln Phe Ser Trp Asn Asn Phe Leu Trp Lys Pro Trp Leu Gln
545                 550                 555                 560

Leu Cys Cys Pro Ser Thr Gly Leu Ser Cys Gln Cys Asp Arg Glu Lys
                565                 570                 575

Gln Asp Lys Arg Leu Ser Arg
            580
```

<210> SEQ ID NO 20
<211> LENGTH: 1945
<212> TYPE: DNA
<213> ORGANISM: Homo sapiens

<400> SEQUENCE: 20

| | | | | | |
|---|---|---|---|---|---|
| ggaagccttg | gcactagcgg | cgcccgggcg | cggagtgcgc | agggcaaggt | cctgcgctct | 60 |
| gggccagcgc | tcggccatgc | gatccgccgc | gcggagggga | cgcgccgcgc | ccgccgccag | 120 |
| ggactctttg | ccggtgctac | tgttttatg | cttgcttctg | aagacgtgtg | aacctaaaac | 180 |
| tgcaaatgcc | tttaaaccaa | atatcctact | gatcatggcg | gatgatctag | cactggggga | 240 |
| tctcggttgc | tacgggaaca | atacactgag | aacgccgaat | attgaccagc | ttgcagagga | 300 |
| aggtgtgagg | ctcactcagc | acctggcggc | cgccccgctc | tgcacccaa | gccgagctgc | 360 |
| attcctcaca | gggagacatt | ccttcagatc | aggcatggac | gccagcaatg | gataccgggc | 420 |
| ccttcagtgg | aacgcaggct | caggtggact | ccctgagaac | gaaaccactt | ttgcaagaat | 480 |
| cttgcagcag | catggctatg | caaccggcct | cataggaaaa | tggcaccagg | gtgtgaattg | 540 |
| tgcatcccgc | ggggatcact | gccaccaccc | cctgaaccac | ggatttgact | atttctacgg | 600 |
| catgcccttc | acgctcacaa | acgactgtga | cccaggcagg | cccccgaag | tggacgccgc | 660 |
| cctgagggcg | cagctctggg | gttacaccca | gttcctggcg | ctggggattc | tcaccctggc | 720 |
| tgccggccag | acctgcggtt | tcttctctgt | ctccgcgaga | gcagtcaccg | gcatggccgg | 780 |
| cgtgggctgc | ctgttttca | tctcttggta | ctcctccttc | gggtttgtgc | gacgctggaa | 840 |
| ctgtatcctg | atgagaaacc | atgacgtcac | ggagcaaccc | atggtctggg | agaaaacagc | 900 |
| gagtcttatg | ctaaaggaag | ctgttctcta | tattgaaaga | cacaagcatg | gccatttct | 960 |
| cctcttcctt | tctttgctgc | atgtgcacat | tccccttgtg | accacgagtg | cattcctggg | 1020 |
| gaaaagtcag | catggcttat | atggtgataa | tgtggaggag | atggactggc | tcataggtaa | 1080 |
| ggttcttaat | gccatcgaag | acaatggttt | aaagaactca | acattcacgt | atttcacctc | 1140 |
| tgaccatgga | ggacatttag | aggcaagaga | tggacacagc | cagttagggg | gatggaacgg | 1200 |
| aatttacaaa | ggtgggaagg | gcatgggagg | atgggaaggt | gggatccgag | tgccgggat | 1260 |
| cttccactgg | ccgggggtgc | tcccggccgg | ccgagtgatt | ggagagccca | cgagcctgat | 1320 |
| ggacgtgttc | cctactgtgg | tccagctggt | gggtggcgag | gtgccccagg | acagggtgat | 1380 |
| tgatggccac | agcctggtac | ccttgctgca | gggagctgag | gcacgctcgg | cacatgagtt | 1440 |
| cctgtttcat | tactgtgggc | agcatcttca | cgcagcacgc | tggcaccaga | aggacagtgg | 1500 |
| aagcgtctgg | aaggttcatt | acacgacccc | gcagttccac | cccgaggagc | ggggcctgct | 1560 |
| aacggccgag | gcgtctgccc | atgctgaatg | gggaggcgtg | acccatcaca | gaccccttt | 1620 |
| gctctttgac | ctctccaggg | acccctccga | ggcacggccc | ctgaccccg | actccgagcc | 1680 |
| cctgtaccac | gccgtgatag | caagggtagg | tgccgcggtg | tcggagcatc | ggcagaccct | 1740 |
| gagtcctgtg | ccccagcagt | tttccatgag | caacatcctg | tggaagccgt | ggctgcagcc | 1800 |
| gtgctgcgga | catttcccgt | tctgttcatg | ccacgaggat | ggggatggca | cccctgaat | 1860 |
| gccaggactg | tgagagagga | tccaggagag | cctgactgcg | ttgcaaacaa | aattctccaa | 1920 |
| gcttggttct | atcttcagtc | cggaa | | | | 1945 |

<210> SEQ ID NO 21
<211> LENGTH: 593
<212> TYPE: PRT
<213> ORGANISM: Homo sapiens

<400> SEQUENCE: 21

```
Met Arg Ser Ala Ala Arg Arg Gly Arg Ala Ala Pro Ala Ala Arg Asp
1               5                   10                  15

Ser Leu Pro Val Leu Leu Phe Leu Cys Leu Leu Lys Thr Cys Glu
            20              25              30

Pro Lys Thr Ala Asn Ala Phe Lys Pro Asn Ile Leu Ile Met Ala
        35              40              45

Asp Asp Leu Gly Thr Gly Asp Leu Gly Cys Tyr Gly Asn Asn Thr Leu
50                  55              60

Arg Thr Pro Asn Ile Asp Gln Leu Ala Glu Glu Gly Val Arg Leu Thr
65                  70              75                  80

Gln His Leu Ala Ala Ala Pro Leu Cys Thr Pro Ser Arg Ala Ala Phe
                85              90              95

Leu Thr Gly Arg His Ser Phe Arg Ser Gly Met Asp Ala Ser Asn Gly
                100             105             110

Tyr Arg Ala Leu Gln Trp Asn Ala Gly Ser Gly Gly Leu Pro Glu Asn
            115             120             125

Glu Thr Thr Phe Ala Arg Ile Leu Gln Gln His Gly Tyr Ala Thr Gly
        130             135             140

Leu Ile Gly Lys Trp His Gln Gly Val Asn Cys Ala Ser Arg Gly Asp
145             150             155             160

His Cys His His Pro Leu Asn His Gly Phe Asp Tyr Phe Tyr Gly Met
                165             170             175

Pro Phe Thr Leu Thr Asn Asp Cys Asp Pro Gly Arg Pro Pro Glu Val
            180             185             190

Asp Ala Ala Leu Arg Ala Gln Leu Trp Gly Tyr Thr Gln Phe Leu Ala
        195             200             205

Leu Gly Ile Leu Thr Leu Ala Ala Gly Gln Thr Cys Gly Phe Phe Ser
            210             215             220

Val Ser Ala Arg Ala Val Thr Gly Met Ala Gly Val Gly Cys Leu Phe
225             230             235             240

Phe Ile Ser Trp Tyr Ser Ser Phe Gly Phe Val Arg Arg Trp Asn Cys
            245             250             255

Ile Leu Met Arg Asn His Asp Val Thr Glu Gln Pro Met Val Leu Glu
            260             265             270

Lys Thr Ala Ser Leu Met Leu Lys Glu Ala Val Ser Tyr Ile Glu Arg
        275             280             285

His Lys His Gly Pro Phe Leu Leu Phe Leu Ser Leu Leu His Val His
    290             295             300

Ile Pro Leu Val Thr Thr Ser Ala Phe Leu Gly Lys Ser Gln His Gly
305             310             315             320

Leu Tyr Gly Asp Asn Val Glu Glu Met Asp Trp Leu Ile Gly Lys Val
            325             330             335

Leu Asn Ala Ile Glu Asp Asn Gly Leu Lys Asn Ser Thr Phe Thr Tyr
        340             345             350

Phe Thr Ser Asp His Gly Gly His Leu Glu Ala Arg Asp Gly His Ser
        355             360             365

Gln Leu Gly Gly Trp Asn Gly Ile Tyr Lys Gly Gly Lys Gly Met Gly
        370             375             380

Gly Trp Glu Gly Gly Ile Arg Val Pro Gly Ile Phe Arg Trp Pro Gly
385             390             395             400

Val Leu Pro Ala Gly Arg Val Ile Gly Glu Pro Thr Ser Leu Met Asp
            405             410             415

Val Phe Pro Thr Val Val Gln Leu Val Gly Gly Glu Val Pro Gln Asp
```

```
                420             425             430
Arg Val Ile Asp Gly His Ser Leu Val Pro Leu Gln Gly Ala Glu
            435                 440                 445
Ala Arg Ser Ala His Glu Phe Leu Phe His Tyr Cys Gly Gln His Leu
            450                 455                 460
His Ala Ala Arg Trp His Gln Lys Asp Ser Gly Ser Val Trp Lys Val
465                 470                 475                 480
His Tyr Thr Thr Pro Gln Phe His Pro Glu Glu Arg Gly Leu Leu Thr
                485                 490                 495
Ala Glu Ala Ser Ala His Ala Glu Trp Gly Gly Val Thr His His Arg
                500                 505                 510
Pro Pro Leu Leu Phe Asp Leu Ser Arg Asp Pro Ser Glu Ala Arg Pro
                515                 520                 525
Leu Thr Pro Asp Ser Glu Pro Leu Tyr His Ala Val Ile Ala Arg Val
                530                 535                 540
Gly Ala Ala Val Ser Glu His Arg Gln Thr Leu Ser Pro Val Pro Gln
545                 550                 555                 560
Gln Phe Ser Met Ser Asn Ile Leu Trp Lys Pro Trp Leu Gln Pro Cys
                565                 570                 575
Cys Gly His Phe Pro Phe Cys Ser Cys His Glu Asp Gly Asp Gly Thr
                580                 585                 590
Pro

<210> SEQ ID NO 22
<211> LENGTH: 1858
<212> TYPE: DNA
<213> ORGANISM: Homo sapiens

<400> SEQUENCE: 22
ccttcctctt cttgatcggg gattcaggaa ggagcccagg agcagaggaa gtagagagag    60
agacaacatg ttacatctgc accattcttg tttgtgtttc aggagctggc tgccagcgat   120
gctcgctgta ctgctaagtt tggcaccatc agcttccagc acatttccg cctcccgacc   180
gaacatcctt cttctgatgg cggacgacct tggcattggg acattggct gctatggcaa   240
caacaccatg aggactccga atattgaccg ccttgcagag gacggcgtga agctgaccca   300
acacatctct gccgcatctt tgtgcacccc aagcagagcc gccttcctca cgggcagata   360
ccctgtgcga tcagggatgg tttccagcat tggttaccgt gttcttcagt ggaccggagc   420
atctggaggt cttccaacaa atgagacaac ttttgcaaaa atactgaaag agaaaggcta   480
tgccactgga ctcattggaa atggcatctg ggtctcaac tgtgagtcag ccagtgatca   540
ttgccaccac cctctccatc atggctttga gcatttctac ggaatgcctt ctctccttga t   600
gggtgattgc gcccgctggg aactctcaga gaagcgtgtc aacctggaac aaaaactcaa   660
cttcctcttc caagtcctgg ccttggttgc cctcacactg gtagcaggga agctcacaca   720
cctgatacc gtctcgtgga tgccggtcat ctggtcagcc ctttcggccg tcctcctcct   780
cgcaagctcc tattttgtgg gtgctctgat tgtccatgcc gattgctttc tgatgagaaa   840
ccacaccatc acggagcagc ccatgtgctt ccaaagaacg acacccctta ttctgcagga   900
ggttgcgtcc tttctcaaaa ggaataagca tgggcctttc ctcctctttg tttcctttct   960
acacgttcac atccctctta tcactatgga gaacttcctc gggaagagtc tccacgggct  1020
gtatggggac aacgtagagg agatggactg gatggtagga cggatccttg acactttgga  1080
cgtggagggt ttgagcaaca gcaccctcat ttattttacg tcggatcacg gcggttccct  1140
```

-continued

```
agagaatcaa cttggaaaca cccagtatgg tggctggaat ggaatttata aaggtgggaa    1200
gggcatggga ggatgggaag gtgggatccg cgtgcccggg atcttccgct ggcccggggt    1260
gctcccggcc ggccgagtga ttggcgagcc cacgagtctg atggacgtgt tccccaccgt    1320
ggtccggctg gcgggcggcg aggtgcccca ggacagagtg attgacgcc aagaccttct     1380 gcccttgctc ctggggacag cccaacactc agaccacgag ttcctgatgc attattgtga    1440
gaggtttctg cacgcagcca ggtggcatca acgggacaga ggaacaatgt ggaaagtcca    1500
ctttgtgacg cctgtgttcc agccagaggg agccggtgcc tgctatggaa gaaaggtctg    1560
cccgtgcttt ggggaaaaag tagtccacca cgatccacct ttgctctttg acctctcaag    1620
agacccttct gagacccaca tcctcacacc agcctcagag cccgtgttct atcaggtgat    1680
ggaacgagtc cagcaggcgg tgtgggaaca ccagcggaca ctcagcccag ttcctctgca    1740
gctggacagg ctgggcaaca tctggagacc gtggctgcag ccctgctgtg gcccgttccc    1800
cctctgctgg tgccttaggg aagatgaccc acaataaatg tctgcagtga aaagctgg     1858
```

<210> SEQ ID NO 23
<211> LENGTH: 589
<212> TYPE: PRT
<213> ORGANISM: Homo sapiens

<400> SEQUENCE: 23

```
Met Leu His Leu His His Ser Cys Leu Cys Phe Arg Ser Trp Leu Pro
1               5                   10                  15

Ala Met Leu Ala Val Leu Leu Ser Leu Ala Pro Ser Ala Ser Ser Asp
            20                  25                  30

Ile Ser Ala Ser Arg Pro Asn Ile Leu Leu Met Ala Asp Asp Leu
        35                  40                  45

Gly Ile Gly Asp Ile Gly Cys Tyr Gly Asn Asn Thr Met Arg Thr Pro
    50                  55                  60

Asn Ile Asp Arg Leu Ala Glu Asp Gly Val Lys Leu Thr Gln His Ile
65                  70                  75                  80

Ser Ala Ala Ser Leu Cys Thr Pro Ser Arg Ala Ala Phe Leu Thr Gly
                85                  90                  95

Arg Tyr Pro Val Arg Ser Gly Met Val Ser Ser Ile Gly Tyr Arg Val
            100                 105                 110

Leu Gln Trp Thr Gly Ala Ser Gly Gly Leu Pro Thr Asn Glu Thr Thr
        115                 120                 125

Phe Ala Lys Ile Leu Lys Glu Lys Gly Tyr Ala Thr Gly Leu Ile Gly
    130                 135                 140

Lys Trp His Leu Gly Leu Asn Cys Glu Ser Ala Ser Asp His Cys His
145                 150                 155                 160

His Pro Leu His His Gly Phe Glu His Phe Tyr Gly Met Pro Phe Ser
                165                 170                 175

Leu Met Gly Asp Cys Ala Arg Trp Glu Leu Ser Glu Lys Arg Val Asn
            180                 185                 190

Leu Glu Gln Lys Leu Asn Phe Leu Phe Gln Val Leu Ala Leu Val Ala
        195                 200                 205

Leu Thr Leu Val Ala Gly Lys Leu Thr His Leu Ile Pro Val Ser Trp
    210                 215                 220

Met Pro Val Ile Trp Ser Ala Leu Ser Ala Val Leu Leu Leu Ala Ser
225                 230                 235                 240

Ser Tyr Phe Val Gly Ala Leu Ile Val His Ala Asp Cys Phe Leu Met
                245                 250                 255
```

Arg Asn His Thr Ile Thr Glu Gln Pro Met Cys Phe Gln Arg Thr Thr
            260                 265                 270

Pro Leu Ile Leu Gln Glu Val Ala Ser Phe Leu Lys Arg Asn Lys His
        275                 280                 285

Gly Pro Phe Leu Leu Phe Val Ser Phe Leu His Val His Ile Pro Leu
    290                 295                 300

Ile Thr Met Glu Asn Phe Leu Gly Lys Ser Leu His Gly Leu Tyr Gly
305                 310                 315                 320

Asp Asn Val Glu Glu Met Asp Trp Met Val Gly Arg Ile Leu Asp Thr
                325                 330                 335

Leu Asp Val Glu Gly Leu Ser Asn Ser Thr Leu Ile Tyr Phe Thr Ser
            340                 345                 350

Asp His Gly Gly Ser Leu Glu Asn Gln Leu Gly Asn Thr Gln Tyr Gly
        355                 360                 365

Gly Trp Asn Gly Ile Tyr Lys Gly Gly Lys Gly Met Gly Gly Trp Glu
    370                 375                 380

Gly Gly Ile Arg Val Pro Gly Ile Phe Arg Trp Pro Gly Val Leu Pro
385                 390                 395                 400

Ala Gly Arg Val Ile Gly Glu Pro Thr Ser Leu Met Asp Val Phe Pro
                405                 410                 415

Thr Val Val Arg Leu Ala Gly Gly Glu Val Pro Gln Asp Arg Val Ile
            420                 425                 430

Asp Gly Gln Asp Leu Leu Pro Leu Leu Leu Gly Thr Ala Gln His Ser
        435                 440                 445

Asp His Glu Phe Leu Met His Tyr Cys Glu Arg Phe Leu His Ala Ala
    450                 455                 460

Arg Trp His Gln Arg Asp Arg Gly Thr Met Trp Lys Val His Phe Val
465                 470                 475                 480

Thr Pro Val Phe Gln Pro Glu Gly Ala Gly Ala Cys Tyr Gly Arg Lys
                485                 490                 495

Val Cys Pro Cys Phe Gly Glu Lys Val Val His His Asp Pro Pro Leu
            500                 505                 510

Leu Phe Asp Leu Ser Arg Asp Pro Ser Glu Thr His Ile Leu Thr Pro
        515                 520                 525

Ala Ser Glu Pro Val Phe Tyr Gln Val Met Glu Arg Val Gln Gln Ala
    530                 535                 540

Val Trp Glu His Gln Arg Thr Leu Ser Pro Val Pro Leu Gln Leu Asp
545                 550                 555                 560

Arg Leu Gly Asn Ile Trp Arg Pro Trp Leu Gln Pro Cys Cys Gly Pro
                565                 570                 575

Phe Pro Leu Cys Trp Cys Leu Arg Glu Asp Asp Pro Gln
            580                 585

<210> SEQ ID NO 24
<211> LENGTH: 1996
<212> TYPE: DNA
<213> ORGANISM: Homo sapiens

<400> SEQUENCE: 24
gggttctgct cctagacatt agagagataa tacggctgat agacaacaag aaggtattcc     60
aagctgcaca atgaggccca ggagaccgtt ggtcttcatg tctttggtgt gtgcactctt    120
gaacacatgg ccagggcaca cagggtgcat gacgacaagg cctaatattg tcctaatcat    180
ggttgatgac ctgggtattg gagatctggg ctgctacggc aatgacacca tgaggacgcc    240
tcacatcgac cgccttgcca gggaaggcgt gcgactgact cagcacatct ctgccgcctc    300

```
cctctgcagc caagccggt ccgcgttctt gacgggaaga tacccatcc gatcaggtat      360 ggtttctagt ggtaatagac gtgtcatcca aaatcttgca gtccccgcag gcctccctct      420
taatgagaca acacttgcag ccttgctaaa gaagcaagga tacagcacgg ggcttatagg      480
caaatggcac caaggcttga actgcgactc ccgaagtgac cagtgccacc atccatataa      540
ttatgggttt gactactact atggcatgcc gttcactctc gttgacagct gctggccgga      600
cccctctcgt aacacggaat tagcctttga gagtcagctc tggctctgtg tgcagctagt      660
tgccattgcc atcctcaccc taaccttggg gaagctgagc ggctgggtct ctgttccctg      720
gctcctgatc ttctccatga ttctgtttat tttcctcttg ggctatgctt ggttctccag      780
ccacacgtcc cctttatact gggactgcct cctcatgcgg gggcacgaga tcacggagca      840
gcccatgaag gctgaacgag ctggatccat tatggtgaag gaagcgattt cctttttaga      900
aaggcacagt aaggaaactt tccttctctt tttctccttt cttcacgtgc acacacctct      960
ccccaccacg gacgatttca ctggcaccag caagcatggc ttgtatgggg ataatgtgga     1020
agagatggac tccatggtgg gcaagattct tgatgctatc gatgattttg gcctaaggaa     1080
caacaccctt gtctacttta catcagatca cggagggcat ttggaagcta ggcgagggca     1140
tgcccaactt ggtggatgga atggaatata caaggtgga aaaggcatgg ggggctggga      1200
aggtggaatc cgcgtcccag gaattgtccg atggcctgga aagtaccag ctggacggtt      1260 gattaaggaa cctacaagtt taatggatat tttaccaact gtcgcatcag tgtcaggagg     1320
aagtctccct caggacaggg tcattgacgg ccgagacctc atgcccttgc tgcagggcaa     1380
cgtcaggcac tcggagcatg aatttctttt ccactactgt ggctcctacc tgcacgccgt     1440
gcggtggatc cccaaggacg acagtgggtc agtttggaag gctcactatg tgaccccggt     1500
attccagcca ccagcttctg gtggctgcta tgtcacctca ttatgcagat gtttcggaga     1560
acaggttacc taccacaacc cccctctgct cttcgatctc tccagggacc cctcagagtc     1620
cacacccctg acacctgcca cagagcccct ctatgatttt gtgattaaaa aggtggccaa     1680
cgccctgaag gaacaccagg aaaccatcgt gcctgtgacc taccaactct cagaactgaa     1740
tcagggcagg acgtggctga agccttgctg tggggtgttc ccattttgtc tgtgtgacaa     1800
ggaagaggaa gtctctcagc ctcggggtcc taacgagaag agataattac aatcaggcta     1860
ccagaggaag cctttggtcc taacgagaag agataattac aatcaggcta ccaaaggaag     1920
cactaacttt ggtgctttca gttggcaag gagtgcattt aatagtcaat aaattcatct     1980
accattccag attatt                                                     1996

<210> SEQ ID NO 25
<211> LENGTH: 591
<212> TYPE: PRT
<213> ORGANISM: Homo sapiens

<400> SEQUENCE: 25

Met Arg Pro Arg Arg Pro Leu Val Phe Met Ser Leu Val Cys Ala Leu
1               5                   10                  15

Leu Asn Thr Trp Pro Gly His Thr Gly Cys Met Thr Thr Arg Pro Asn
            20                  25                  30

Ile Val Leu Ile Met Val Asp Asp Leu Gly Ile Gly Asp Leu Gly Cys
        35                  40                  45

Tyr Gly Asn Asp Thr Met Arg Thr Pro His Ile Asp Arg Leu Ala Arg
    50                  55                  60

Glu Gly Val Arg Leu Thr Gln His Ile Ser Ala Ala Ser Leu Cys Ser
```

```
                65                  70                  75                  80
Pro Ser Arg Ser Ala Phe Leu Thr Gly Arg Tyr Pro Ile Arg Ser Gly
                    85                  90                  95

Met Val Ser Ser Gly Asn Arg Val Ile Gln Asn Leu Ala Val Pro
                100                 105                 110

Ala Gly Leu Pro Leu Asn Glu Thr Leu Ala Ala Leu Leu Lys Lys
                115                 120                 125

Gln Gly Tyr Ser Thr Gly Leu Ile Gly Lys Trp His Gln Gly Leu Asn
            130                 135                 140

Cys Asp Ser Arg Ser Asp Gln Cys His His Pro Tyr Asn Tyr Gly Phe
145                 150                 155                 160

Asp Tyr Tyr Tyr Gly Met Pro Phe Thr Leu Val Asp Ser Cys Trp Pro
                    165                 170                 175

Asp Pro Ser Arg Asn Thr Glu Leu Ala Phe Glu Ser Gln Leu Trp Leu
                180                 185                 190

Cys Val Gln Leu Val Ala Ile Ala Ile Leu Thr Leu Thr Phe Gly Lys
                195                 200                 205

Leu Ser Gly Trp Val Ser Val Pro Trp Leu Leu Ile Phe Ser Met Ile
    210                 215                 220

Leu Phe Ile Phe Leu Leu Gly Tyr Ala Trp Phe Ser Ser His Thr Ser
225                 230                 235                 240

Pro Leu Tyr Trp Asp Cys Leu Leu Met Arg Gly His Glu Ile Thr Glu
                    245                 250                 255

Gln Pro Met Lys Ala Glu Arg Ala Gly Ser Ile Met Val Lys Glu Ala
                260                 265                 270

Ile Ser Phe Leu Glu Arg His Ser Lys Glu Thr Phe Leu Leu Phe Phe
            275                 280                 285

Ser Phe Leu His Val His Thr Pro Leu Pro Thr Thr Asp Phe Thr
290                 295                 300

Gly Thr Ser Lys His Gly Leu Tyr Gly Asp Asn Val Glu Glu Met Asp
305                 310                 315                 320

Ser Met Val Gly Lys Ile Leu Asp Ala Ile Asp Asp Phe Gly Leu Arg
                325                 330                 335

Asn Asn Thr Leu Val Tyr Phe Thr Ser Asp His Gly Gly His Leu Glu
                340                 345                 350

Ala Arg Arg Gly His Ala Gln Leu Gly Gly Trp Asn Gly Ile Tyr Lys
            355                 360                 365

Gly Gly Lys Gly Met Gly Gly Trp Glu Gly Gly Ile Arg Val Pro Gly
        370                 375                 380

Ile Val Arg Trp Pro Gly Lys Val Pro Ala Gly Arg Leu Ile Lys Glu
385                 390                 395                 400

Pro Thr Ser Leu Met Asp Ile Leu Pro Thr Val Ala Ser Val Ser Gly
                405                 410                 415

Gly Ser Leu Pro Gln Asp Arg Val Ile Asp Gly Arg Asp Leu Met Pro
                420                 425                 430

Leu Leu Gln Gly Asn Val Arg His Ser Glu His Glu Phe Leu Phe His
            435                 440                 445

Tyr Cys Gly Ser Tyr Leu His Ala Val Arg Trp Ile Pro Lys Asp Asp
        450                 455                 460

Ser Gly Ser Val Trp Lys Ala His Tyr Val Thr Pro Val Phe Gln Pro
465                 470                 475                 480

Pro Ala Ser Gly Gly Cys Tyr Val Thr Ser Leu Cys Arg Cys Phe Gly
                485                 490                 495
```

```
Glu Gln Val Thr Tyr His Asn Pro Pro Leu Leu Phe Asp Leu Ser Arg
            500                 505                 510

Asp Pro Ser Glu Ser Thr Pro Leu Thr Pro Ala Thr Glu Pro Leu Tyr
        515                 520                 525

Asp Phe Val Ile Lys Lys Val Ala Asn Ala Leu Lys Glu His Gln Glu
    530                 535                 540

Thr Ile Val Pro Val Thr Tyr Gln Leu Ser Glu Leu Asn Gln Gly Arg
545                 550                 555                 560

Thr Trp Leu Lys Pro Cys Cys Gly Val Phe Pro Cys Leu Cys Asp
                565                 570                 575

Lys Glu Glu Glu Val Ser Gln Pro Arg Gly Pro Asn Glu Lys Arg
            580                 585                 590

<210> SEQ ID NO 26
<211> LENGTH: 1578
<212> TYPE: DNA
<213> ORGANISM: Homo sapiens

<400> SEQUENCE: 26
atgggctggc tttttctaaa ggttttgttg gcgggagtga gtttctcagg atttctttat      60
cctcttgtgg attttttgcat cagtgggaaa acaagaggac agaagccaaa ctttgtgatt     120
attttggccg atgacatggg gtggggtgac ctgggagcaa actgggcaga aacaaaggac     180
actgccaacc ttgataagat ggcttcggag ggaatgaggt ttgtggattt ccatgcagct     240
gcctccacct gctcaccctc ccgggcttcc ttgctcaccg gccggcttgg ccttcgcaat     300
ggagtcacac gcaactttgc agtcacttct gtgggaggcc ttccgctcaa cgagaccacc     360
ttggcagagg tgctgcagca ggcgggttac gtcactggga taataggcaa atggcatctt     420
ggacaccacg gctcttatca ccccaacttc cgtggttttg attactactt tggaatccca     480
tatagccatg atatgggctg tactgatact ccaggctaca accaccctcc ttgtccagcg     540
tgtccacagg gtgatggacc atcaaggaac cttcaaagag actgttacac tgacgtggcc     600
ctccctcttt atgaaaacct caacattgtg gagcagccgg tgaacttgag cagccttgcc     660
cagaagtatg ctgagaaagc aacccagttc atccagcgtg caagcaccag cgggaggccc     720
ttcctgctct atgtggctct ggcccacatg cacgtgccct acctgtgac tcagctacca     780 gcagcgccac ggggcagaag cctgtatggt gcagggctct gggagatgga cagtctggtg     840
ggccagatca aggacaaagt tgaccacaca gtgaaggaaa acacattcct ctggtttaca     900
ggagacaatg gcccgtgggc tcagaagtgt gagctagcgg gcagtgtggg tcccttcact     960
ggattttggc aaactcgtca aggggaagt ccagccaagc agacgacctg gaaggaggg      1020 caccgggtcc cagcactggc ttactggcct ggcagagttc agttaatgt caccagcact     1080 gccttgttaa gcgtgctgga cattttttcca actgtggtag ccctggccca ggccagctta     1140
cctcaaggac ggcgctttga tggtgtggac gtctccgagg tgctcttttgg ccggtcacag     1200 cctgggcaca gggtgctgtt ccaccccaac agcggggcag ctggagagtt tggagccctg     1260
cagactgtcc gcctggagcg ttacaaggcc ttctacatta ccggtggagc cagggcgtgt     1320
gatgggagca cggggcctga gctgcagcat aagtttcctc tgattttcaa cctggaagac     1380
gataccgcag aagctgtgcc cctagaaaga ggtggtgcgg agtaccaggc tgtgctgccc     1440
gaggtcagaa aggttcttgc agacgtcctc caagacattg ccaacgacaa catctccagc     1500
gcagattaca ctcaggaccc ttcagtaact ccctgctgta atccctacca aattgcctgc     1560
cgctgtcaag ccgcataa                                                   1578
```

-continued

<210> SEQ ID NO 27
<211> LENGTH: 525
<212> TYPE: PRT
<213> ORGANISM: Homo sapiens

<400> SEQUENCE: 27

| | | | | | | | | | | | | | | | |
|---|---|---|---|---|---|---|---|---|---|---|---|---|---|---|---|
| Met | Gly | Trp | Leu | Phe | Leu | Lys | Val | Leu | Leu | Ala | Gly | Val | Ser | Phe | Ser |
| 1 | | | | 5 | | | | | 10 | | | | | 15 | |
| Gly | Phe | Leu | Tyr | Pro | Leu | Val | Asp | Phe | Cys | Ile | Ser | Gly | Lys | Thr | Arg |
| | | | 20 | | | | | 25 | | | | | 30 | | |
| Gly | Gln | Lys | Pro | Asn | Phe | Val | Ile | Ile | Leu | Ala | Asp | Asp | Met | Gly | Trp |
| | | 35 | | | | | 40 | | | | | 45 | | | |
| Gly | Asp | Leu | Gly | Ala | Asn | Trp | Ala | Glu | Thr | Lys | Asp | Thr | Ala | Asn | Leu |
| | 50 | | | | | 55 | | | | | 60 | | | | |
| Asp | Lys | Met | Ala | Ser | Glu | Gly | Met | Arg | Phe | Val | Asp | Phe | His | Ala | Ala |
| 65 | | | | | 70 | | | | | 75 | | | | | 80 |
| Ala | Ser | Thr | Cys | Ser | Pro | Ser | Arg | Ala | Ser | Leu | Leu | Thr | Gly | Arg | Leu |
| | | | | 85 | | | | | 90 | | | | | 95 | |
| Gly | Leu | Arg | Asn | Gly | Val | Thr | Arg | Asn | Phe | Ala | Val | Thr | Ser | Val | Gly |
| | | | 100 | | | | | 105 | | | | | 110 | | |
| Gly | Leu | Pro | Leu | Asn | Glu | Thr | Thr | Leu | Ala | Glu | Val | Leu | Gln | Gln | Ala |
| | | 115 | | | | | 120 | | | | | 125 | | | |
| Gly | Tyr | Val | Thr | Gly | Ile | Ile | Gly | Lys | Trp | His | Leu | Gly | His | His | Gly |
| | 130 | | | | | 135 | | | | | 140 | | | | |
| Ser | Tyr | His | Pro | Asn | Phe | Arg | Gly | Phe | Asp | Tyr | Tyr | Phe | Gly | Ile | Pro |
| 145 | | | | | 150 | | | | | 155 | | | | | 160 |
| Tyr | Ser | His | Asp | Met | Gly | Cys | Thr | Asp | Thr | Pro | Gly | Tyr | Asn | His | Pro |
| | | | | 165 | | | | | 170 | | | | | 175 | |
| Pro | Cys | Pro | Ala | Cys | Pro | Gln | Gly | Asp | Gly | Pro | Ser | Arg | Asn | Leu | Gln |
| | | | 180 | | | | | 185 | | | | | 190 | | |
| Arg | Asp | Cys | Tyr | Thr | Asp | Val | Ala | Leu | Pro | Leu | Tyr | Glu | Asn | Leu | Asn |
| | | 195 | | | | | 200 | | | | | 205 | | | |
| Ile | Val | Glu | Gln | Pro | Val | Asn | Leu | Ser | Ser | Leu | Ala | Gln | Lys | Tyr | Ala |
| | 210 | | | | | 215 | | | | | 220 | | | | |
| Glu | Lys | Ala | Thr | Gln | Phe | Ile | Gln | Arg | Ala | Ser | Thr | Ser | Gly | Arg | Pro |
| 225 | | | | | 230 | | | | | 235 | | | | | 240 |
| Phe | Leu | Leu | Tyr | Val | Ala | Leu | Ala | His | Met | His | Val | Pro | Leu | Pro | Val |
| | | | | 245 | | | | | 250 | | | | | 255 | |
| Thr | Gln | Leu | Pro | Ala | Ala | Pro | Arg | Gly | Arg | Ser | Leu | Tyr | Gly | Ala | Gly |
| | | | 260 | | | | | 265 | | | | | 270 | | |
| Leu | Trp | Glu | Met | Asp | Ser | Leu | Val | Gly | Gln | Ile | Lys | Asp | Lys | Val | Asp |
| | | 275 | | | | | 280 | | | | | 285 | | | |
| His | Thr | Val | Lys | Glu | Asn | Thr | Phe | Leu | Trp | Phe | Thr | Gly | Asp | Asn | Gly |
| | 290 | | | | | 295 | | | | | 300 | | | | |
| Pro | Trp | Ala | Gln | Lys | Cys | Glu | Leu | Ala | Gly | Ser | Val | Gly | Pro | Phe | Thr |
| 305 | | | | | 310 | | | | | 315 | | | | | 320 |
| Gly | Phe | Trp | Gln | Thr | Arg | Gln | Gly | Gly | Ser | Pro | Ala | Lys | Gln | Thr | Thr |
| | | | | 325 | | | | | 330 | | | | | 335 | |
| Trp | Glu | Gly | Gly | His | Arg | Val | Pro | Ala | Leu | Ala | Tyr | Trp | Pro | Gly | Arg |
| | | | 340 | | | | | 345 | | | | | 350 | | |
| Val | Pro | Val | Asn | Val | Thr | Ser | Thr | Ala | Leu | Leu | Ser | Val | Leu | Asp | Ile |
| | | 355 | | | | | 360 | | | | | 365 | | | |
| Phe | Pro | Thr | Val | Val | Ala | Leu | Ala | Gln | Ala | Ser | Leu | Pro | Gln | Gly | Arg |
| | 370 | | | | | 375 | | | | | 380 | | | | |

```
Arg Phe Asp Gly Val Asp Val Ser Glu Val Leu Phe Gly Arg Ser Gln
385                 390                 395                 400

Pro Gly His Arg Val Leu Phe His Pro Asn Ser Gly Ala Ala Gly Glu
            405                 410                 415

Phe Gly Ala Leu Gln Thr Val Arg Leu Glu Arg Tyr Lys Ala Phe Tyr
            420                 425                 430

Ile Thr Gly Gly Ala Arg Ala Cys Asp Gly Ser Thr Gly Pro Glu Leu
            435                 440                 445

Gln His Lys Phe Pro Leu Ile Phe Asn Leu Glu Asp Asp Thr Ala Glu
            450                 455                 460

Ala Val Pro Leu Glu Arg Gly Gly Ala Glu Tyr Gln Ala Val Leu Pro
465                 470                 475                 480

Glu Val Arg Lys Val Leu Ala Asp Val Leu Gln Asp Ile Ala Asn Asp
            485                 490                 495

Asn Ile Ser Ser Ala Asp Tyr Thr Gln Asp Pro Ser Val Thr Pro Cys
            500                 505                 510

Cys Asn Pro Tyr Gln Ile Ala Cys Arg Cys Gln Ala Ala
            515                 520                 525

<210> SEQ ID NO 28
<211> LENGTH: 4669
<212> TYPE: DNA
<213> ORGANISM: Homo sapiens

<400> SEQUENCE: 28
cgcagaccgt cgctaatgaa tcttggggcc ggtgtcgggc ggggcggct  tgatcggcaa      60
ctaggaaacc ccaggcgcag aggccaggag cgagggcagc gaggatcaga ggccaggcct     120
tcccggctgc cggcgctcct cggaggtcag ggcagatgag gaacatgact ctccccttc      180
ggaggaggaa ggaagtcccg ctgccacctt atctctgctc ctctgcctcc tcctgttcc      240
cagagctttt tctctagaga agattttgaa ggcggctttt gtgctgacgg ccacccacca     300
tcatctaaag aagataaact tggcaaatga catgcaggtt cttcaaggca gaataattgc     360
agaaaatctt caaggacccc tatctgcaga tgttctgaat acctctgaga atagagattg     420
attattcaac caggatacct aattcaagaa ctccagaaat caggagacgg agacattttg     480
tcagttttgc aacattggac caaatacaat gaagtattct tgctgtgctc tggttttggc     540
tgtcctgggc acagaattgc tgggaagcct ctgttcgact gtcagatccc cgaggttcag     600
aggacggata cagcaggaac gaaaaaacat ccgacccaac attattcttg tgcttaccga     660
tgatcaagat gtggagctgg gtccctgca  agtcatgaac aaaacgagaa agattatgga     720
acatgggggg gccaccttca tcaatgcctt tgtgactaca cccatgtgct gcccgtcacg     780
gtcctccatg ctcaccggga gtatgtgca  caatcacaat gtctacacca caacgagaa      840
ctgctcttcc ccctcgtggc aggccatgca tgagcctcgg acttttgctg tatatcttaa     900
caacactggc tacagaacag ccttttttgg aaaatacctc aatgaatata atggcagcta     960
catccccccct gggtggcgag aatggcttgg attaatcaag aattctcgct tctataatta    1020
cactgttttgt cgcaatggca tcaaagaaaa gcatggattt gattatgcaa aggactactt    1080
cacagactta atcactaacg agagcattaa ttacttcaaa atgtctaaga gaatgtatcc    1140
ccataggccc gttatgatgg tgatcagcca cgctgcgccc acggccccg aggactcagc     1200
cccacagttt tctaaactgt accccaatgc ttcccaacac ataactccta gttataacta    1260
tgcaccaaat atggataaac actggattat gcagtacaca ggaccaatgc tgcccatcca    1320
catggaattt acaaacattc tacagcgcaa aaggctccag actttgatgt cagtggatga    1380
```

```
ttctgtggag aggctgtata acatgctcgt ggagacgggg gagctggaga atacttacat    1440
catttacacc gccgaccatg gttaccatat tgggcagttt ggactggtca aggggaaatc    1500
catgccatat gactttgata ttcgtgtgcc tttttttatt cgtggtccaa gtgtagaacc    1560
aggatcaata gtcccacaga tcgttctcaa cattgacttg gcccccacga tcctggatat    1620
tgctgggctc gacacacctc ctgatgtgga cggcaagtct gtcctcaaac ttctggaccc    1680
agaaaagcca ggtaacaggt ttcgaacaaa caagaaggcc aaaatttggc gtgatacatt    1740
cctagtggaa agaggcaaat ttctacgtaa aaggaagaa tccagcaaga atatccaaca    1800
gtcaaatcac ttgcccaaat atgaacgggt caaagaacta tgccagcagg ccaggtacca    1860
gacagcctgt gaacaaccgg ggcagaagtg gcaatgcatt gaggatacat ctggcaagct    1920
tcgaattcac aagtgtaaag gacccagtga cctgctcaca gtccggcaga gcacgcggaa    1980
cctctacgct cgcggcttcc atgacaaaga caaagagtgc agttgtaggg agtctggtta    2040
ccgtgccagc agaagccaaa gaaagagtca acggcaattc ttgagaaacc aggggactcc    2100
aaagtacaag cccagatttg tccatactcg gcagacacgt tccttgtccg tcgaatttga    2160
aggtgaaata tatgacataa atctggaaga agaagaagaa ttgcaagtgt tgcaaccaag    2220
aaacattgct aagcgtcatg atgaaggcca aaggggcca agagatctcc aggcttccag    2280
tggtggcaac aggggcagga tgctggcaga tagcagcaac gccgtgggcc cacctaccac    2340
tgtccgagtg acacacaagt gttttattct tcccaatgac tctatccatt gtgagagaga    2400
actgtaccaa tcggccagag cgtggaagga ccataaggca tacattgaca aagagattga    2460
agctctgcaa gataaaatta agaatttaag agaagtgaga ggacatctga agagaaggaa    2520
gcctgaggaa tgtagctgca gtaaacaaag ctattacaat aaagagaaag gtgtaaaaaa    2580
gcaagagaaa ttaaagagcc atcttcaccc attcaaggag gctgctcagg aagtagatag    2640
caaactgcaa cttttcaagg agaacaaccg taggaggaag aaggagagga aggagaagag    2700
acggcagagg aaggggaag agtgcagcct gcctggcctc acttgcttca cgcatgacaa    2760
caaccactgg cagacagccc cgttctggaa cctgggatct ttctgtgctt gcacgagttc    2820
taacaataac acctactggt gtttgcgtac agttaatgag acgcataatt ttcttttctg    2880
tgagtttgct actggctttt tggagtattt tgatatgaat acagatcctt atcagctcac    2940
aaatacagtg cacacggtag aacgaggcat tttgaatcag ctacacgtac aactaatgga    3000
gctcagaagc tgtcaaggat ataagcagtg caacccaaga cctaagaatc ttgatgttgg    3060
aaataaagat ggaggaagct atgacctaca cagaggacag ttatgggatg gatgggaagg    3120
ttaatcagcc ccgtctcact gcagacatca actggcaagg cctagaggag ctacacagtg    3180
tgaatgaaaa catctatgag tacagacaaa actacagact tagtctggtg gactggacta    3240
attacttgaa ggatttagat agagtatttg cactgctgaa gagtcactat gagcaaaata    3300
aaacaaataa gactcaaact gctcaaagtg acgggttctt ggttgtctct gctgagcacg    3360
ctgtgtcaat ggagatggcc tctgctgact cagatgaaga cccaaggcat aaggttggga    3420
aaacacctca tttgaccttg ccagctgacc ttcaaaccct gcatttgaac cgaccaacat    3480
taagtccaga gagtaaactt gaatggaata acgacattcc agaagttaat catttgaatt    3540
ctgaacactg gagaaaaacc gaaaaatgga cgggcatga agagactaat catctggaaa    3600
ccgatttcag tggcgatggc atgacagagc tagagctcgg gcccagcccc aggctgcagc    3660
ccattcacag gcacccgaaa gaacttcccc agtatggtgg tcctggaaag gacatttttg    3720
aagatcaact atatcttcct gtgcattccg atggaatttc agttcatcag atgttcacca    3780
```

-continued

```
tggccaccgc agaacaccga agtaattcca gcatagcggg gaagatgttg accaaggtgg    3840
agaagaatca cgaaaaggag aagtcacagc acctagaagg cagcacctcc tcttcactct    3900
cctctgatta gatgaaactg ttaccttacc ctaaacacag tatttctttt taacttttt     3960 atttgtaaac taataaaggt aatcacagcc accaacattc caagctaccc tgggtacctt    4020
tgtgcagtag aagctagtga gcatgtgagc aagcggtgtg cacacggaga ctcatcgtta    4080
taatttacta tctgccaaga gtagaaagaa aggctgggga tatttgggtt ggcttggttt    4140 tgatttttg cttgtttgtt tgttttgtac taaaacagta ttatcttttg aatatcgtag     4200
ggacataagt atatacatgt tatccaatca agatggctag aatggtgcct ttctgagtgt    4260
ctaaaacttg acacccctgg taaatctttc aacacacttc cactgcctgc gtaatgaagt    4320
tttgattcat ttttaaccac tggaattttt caatgccgtc attttcagtt agatgatttt    4380
gcactttgag attaaaatgc catgtctatt tgattagtct tatttttta ttttacagg      4440 cttatcagtc tcactgttgg ctgtcattgt gacaaagtca aataaccccc caaggacgac    4500
acacagtatg gatcacatat tgtttgacat taagcttttg ccagaaaatg ttgcatgtgt    4560
tttacctcga cttgctaaaa tcgattagca gaaaggcatg gctaataatg ttggtggtga    4620
aaataaataa ataagtaaat gaaaaaaaaa aaaaaaaaa aaaaaaaa                  4669
```

<210> SEQ ID NO 29
<211> LENGTH: 871
<212> TYPE: PRT
<213> ORGANISM: Homo sapiens

<400> SEQUENCE: 29

```
Met Lys Tyr Ser Cys Cys Ala Leu Val Leu Ala Val Leu Gly Thr Glu
1               5                   10                  15

Leu Leu Gly Ser Leu Cys Ser Thr Val Arg Ser Pro Arg Phe Arg Gly
                20                  25                  30

Arg Ile Gln Gln Glu Arg Lys Asn Ile Arg Pro Asn Ile Ile Leu Val
            35                  40                  45

Leu Thr Asp Asp Gln Asp Val Glu Leu Gly Ser Leu Gln Val Met Asn
        50                  55                  60

Lys Thr Arg Lys Ile Met Glu His Gly Gly Ala Thr Phe Ile Asn Ala
65                  70                  75                  80

Phe Val Thr Thr Pro Met Cys Cys Pro Ser Arg Ser Ser Met Leu Thr
                85                  90                  95

Gly Lys Tyr Val His Asn His Asn Val Tyr Thr Asn Asn Glu Asn Cys
            100                 105                 110

Ser Ser Pro Ser Trp Gln Ala Met His Glu Pro Arg Thr Phe Ala Val
        115                 120                 125

Tyr Leu Asn Asn Thr Gly Tyr Arg Thr Ala Phe Phe Gly Lys Tyr Leu
    130                 135                 140

Asn Glu Tyr Asn Gly Ser Tyr Ile Pro Pro Gly Trp Arg Glu Trp Leu
145                 150                 155                 160

Gly Leu Ile Lys Asn Ser Arg Phe Tyr Asn Tyr Thr Val Cys Arg Asn
                165                 170                 175

Gly Ile Lys Glu Lys His Gly Phe Asp Tyr Ala Lys Asp Tyr Phe Thr
            180                 185                 190

Asp Leu Ile Thr Asn Glu Ser Ile Asn Tyr Phe Lys Met Ser Lys Arg
        195                 200                 205

Met Tyr Pro His Arg Pro Val Met Met Val Ile Ser His Ala Ala Pro
    210                 215                 220
```

```
His Gly Pro Glu Asp Ser Ala Pro Gln Phe Ser Lys Leu Tyr Pro Asn
225                 230                 235                 240

Ala Ser Gln His Ile Thr Pro Ser Tyr Asn Tyr Ala Pro Asn Met Asp
            245                 250                 255

Lys His Trp Ile Met Gln Tyr Thr Gly Pro Met Leu Pro Ile His Met
                260                 265                 270

Glu Phe Thr Asn Ile Leu Gln Arg Lys Arg Leu Gln Thr Leu Met Ser
            275                 280                 285

Val Asp Asp Ser Val Glu Arg Leu Tyr Asn Met Leu Val Glu Thr Gly
290                 295                 300

Glu Leu Glu Asn Thr Tyr Ile Ile Tyr Thr Ala Asp His Gly Tyr His
305                 310                 315                 320

Ile Gly Gln Phe Gly Leu Val Lys Gly Lys Ser Met Pro Tyr Asp Phe
                325                 330                 335

Asp Ile Arg Val Pro Phe Phe Ile Arg Gly Pro Ser Val Glu Pro Gly
            340                 345                 350

Ser Ile Val Pro Gln Ile Val Leu Asn Ile Asp Leu Ala Pro Thr Ile
            355                 360                 365

Leu Asp Ile Ala Gly Leu Asp Thr Pro Pro Asp Val Asp Gly Lys Ser
370                 375                 380

Val Leu Lys Leu Leu Asp Pro Glu Lys Pro Gly Asn Arg Phe Arg Thr
385                 390                 395                 400

Asn Lys Lys Ala Lys Ile Trp Arg Asp Thr Phe Leu Val Glu Arg Gly
                405                 410                 415

Lys Phe Leu Arg Lys Lys Glu Glu Ser Ser Lys Asn Ile Gln Gln Ser
                420                 425                 430

Asn His Leu Pro Lys Tyr Glu Arg Val Lys Glu Leu Cys Gln Gln Ala
            435                 440                 445

Arg Tyr Gln Thr Ala Cys Glu Gln Pro Gly Gln Lys Trp Gln Cys Ile
450                 455                 460

Glu Asp Thr Ser Gly Lys Leu Arg Ile His Lys Cys Lys Gly Pro Ser
465                 470                 475                 480

Asp Leu Leu Thr Val Arg Gln Ser Thr Arg Asn Leu Tyr Ala Arg Gly
                485                 490                 495

Phe His Asp Lys Asp Lys Glu Cys Ser Cys Arg Glu Ser Gly Tyr Arg
                500                 505                 510

Ala Ser Arg Ser Gln Arg Lys Ser Gln Arg Gln Phe Leu Arg Asn Gln
            515                 520                 525

Gly Thr Pro Lys Tyr Lys Pro Arg Phe Val His Thr Arg Gln Thr Arg
530                 535                 540

Ser Leu Ser Val Glu Phe Glu Gly Glu Ile Tyr Asp Ile Asn Leu Glu
545                 550                 555                 560

Glu Glu Glu Glu Leu Gln Val Leu Gln Pro Arg Asn Ile Ala Lys Arg
                565                 570                 575

His Asp Glu Gly His Lys Gly Pro Arg Asp Leu Gln Ala Ser Ser Gly
            580                 585                 590

Gly Asn Arg Gly Arg Met Leu Ala Asp Ser Ser Asn Ala Val Gly Pro
            595                 600                 605

Pro Thr Thr Val Arg Val Thr His Lys Cys Phe Ile Leu Pro Asn Asp
            610                 615                 620

Ser Ile His Cys Glu Arg Glu Leu Tyr Gln Ser Ala Arg Ala Trp Lys
625                 630                 635                 640

Asp His Lys Ala Tyr Ile Asp Lys Glu Ile Glu Ala Leu Gln Asp Lys
```

```
                    645                 650                 655
Ile Lys Asn Leu Arg Glu Val Arg Gly His Leu Lys Arg Arg Lys Pro
            660                 665                 670

Glu Glu Cys Ser Cys Ser Lys Gln Ser Tyr Tyr Asn Lys Glu Lys Gly
        675                 680                 685

Val Lys Lys Gln Glu Lys Leu Lys Ser His Leu His Pro Phe Lys Glu
    690                 695                 700

Ala Ala Gln Glu Val Asp Ser Lys Leu Gln Leu Phe Lys Glu Asn Asn
705                 710                 715                 720

Arg Arg Arg Lys Lys Glu Arg Lys Glu Lys Arg Gln Arg Lys Gly
                725                 730                 735

Glu Glu Cys Ser Leu Pro Gly Leu Thr Cys Phe Thr His Asp Asn Asn
            740                 745                 750

His Trp Gln Thr Ala Pro Phe Trp Asn Leu Gly Ser Phe Cys Ala Cys
        755                 760                 765

Thr Ser Ser Asn Asn Thr Tyr Trp Cys Leu Arg Thr Val Asn Glu
    770                 775                 780

Thr His Asn Phe Leu Phe Cys Glu Phe Ala Thr Gly Phe Leu Glu Tyr
785                 790                 795                 800

Phe Asp Met Asn Thr Asp Pro Tyr Gln Leu Thr Asn Thr Val His Thr
                805                 810                 815

Val Glu Arg Gly Ile Leu Asn Gln Leu His Val Gln Leu Met Glu Leu
            820                 825                 830

Arg Ser Cys Gln Gly Tyr Lys Gln Cys Asn Pro Arg Pro Lys Asn Leu
        835                 840                 845

Asp Val Gly Asn Lys Asp Gly Gly Ser Tyr Asp Leu His Arg Gly Gln
    850                 855                 860

Leu Trp Asp Gly Trp Glu Gly
865                 870

<210> SEQ ID NO 30
<211> LENGTH: 4279
<212> TYPE: DNA
<213> ORGANISM: Homo sapiens

<400> SEQUENCE: 30
gggccatttc tggacaacag ctgctatttt cacttgagcc caagttaatt tctcggggag     60
ttctcgggcg cgcacaggca gctcggtttg ccctgcgatt gagctgcggg tcgcggccgg    120
cgccggcctc tccaatggca aatgtgtgtg gctggaggcg agcgcgaggc tttcggcaaa    180
ggcagtcgag tgtttgcaga ccggggcgag tcctgtgaaa gcagataaaa gaaacatttt    240
attaacgtgt cattacgagg ggagcgcccg gccggggctg tcgcactccc cgcggaacat    300
ttggctccct ccagctccta gagaggagaa gaagaaagcg gaaagaggc  agattcacgt    360 cgtttccagc caagtggacc tgatcgatgg ccctcctgaa tttatcacga tatttgattt    420
attagcgatg cccctggtt tgtgtgttac gcacacacac gtgcacacaa ggctctggct    480
cgcttccctc cctcgtttcc agctcctggg cgaatcccac atctgtttca actctccgcc    540
gagggcgagc aggagcgaga gtgtgtcgaa tctgcgagtg aagagggacg agggaaaaga    600
aacaaagcca cagacgcaac ttgagactcc cgcatcccaa aagaagcacc agatcagcaa    660
aaaaagaaga tgggcccccc gagcctcgtg ctgtgcttgc tgtccgcaac tgtgttctcc    720
ctgctgggtg gaagctcggc cttcctgtcg caccaccgcc tgaaaggcag gtttcagagg    780
gaccgcagga acatccgccc caacatcatc ctggtgctga cggacgacca ggatgtggag    840
```

```
ctgggttcca tgcaggtgat gaacaagacc cggcgcatca tggagcaggg cggggcgcac    900
ttcatcaacg ccttcgtgac cacacccatg tgctgcccct cacgctcctc catcctcacc    960
ggcaagtacg tccacaacca caacacctac accaacaatg agaactgctc ctcgccctcc   1020
tggcaggcac agcacgagag ccgcaccttt gccgtgtacc tcaatagcac tggctaccgg   1080
acagctttct tcgggaagta tcttaatgaa tacaacggct cctacgtgcc acccggctgg   1140
aaggagtggg tcggactcct taaaaactcc cgcttttata actacacgct gtgtcggaac   1200
ggggtgaaag agaagcacgg ctccgactac tccaaggatt acctcacaga cctcatcacc   1260
aatgacagcg tgagcttctt ccgcacgtcc aagaagatgt acccgcacag gccagtcctc   1320
atggtcatca gccatgcagc cccccacggc cctgaggatt cagccccaca atattcacgc   1380
ctcttcccaa acgcatctca gcacatcacg ccgagctaca actacgcgcc caacccggac   1440
aaacactgga tcatgcgcta cacggggccc atgaagccca tccacatgga attcaccaac   1500
atgctccagc ggaagcgctt gcagaccctc atgtcggtgg acgactccat ggagacgatt   1560
tacaacatgc tggttgagac gggcgagctg acaacacgt acatcgtata caccgccgac    1620
cacggttacc acatcggcca gtttggcctg gtgaaaggga atccatgcc atatgagttt    1680
gacatcaggg tcccgttcta cgtgaggggc cccaacgtgg aagccggctg tctgaatccc   1740
cacatcgtcc tcaacattga cctggccccc accatcctgg acattgcagg cctggacata   1800
cctgcggata tggacgggaa atccatcctc aagctgctgg acacggagcg gccggtgaat   1860
cggtttcact tgaaaagaa gatgagggtc tggcgggact ccttcttggt ggagagaggc    1920
aagctgctac acaagagaga caatgacaag gtggacgccc aggaggagaa ctttctgccc   1980
aagtaccagc gtgtgaagga cctgtgtcag cgtgctgagt accagacggc gtgtgagcag   2040
ctgggacaga agtggcagtg tgtggaggac gccacgggga gctgaagct gcataagtgc     2100
aagggcccca tgcggctggg cggcagcaga gccctctcca acctcgtgcc caagtactac   2160
gggcagggca gcgaggcctg cacctgtgac agcggggact acaagctcag cctgccggga   2220
cgccggaaaa aactcttcaa gaagaagtac aaggccagct atgtccgcag tcgctccatc   2280
cgctcagtgg ccatcgaggt ggacggcagg gtgtaccacg taggcctggg tgatgccgcc   2340
cagccccgaa acctcaccaa gcggcactgg ccaggggccc ctgaggacca agatgacaag   2400
gatggtgggg acttcagtgg cactggaggc cttcccgact actcagccgc caaccccatt   2460
aaagtgacac atcggtgcta catcctagag aacgacacag tccagtgtga cctggacctg   2520
tacaagtccc tgcaggcctg gaaagaccac aagctgcaca tcgaccacga gattgaaacc   2580
ctgcagaaca aaattaagaa cctgagggaa gtccgaggtc acctgaagaa aaagcggcca   2640
gaagaatgtg actgtcacaa aatcagctac acacccagc acaaaggccg cctcaagcac   2700
agaggctcca gtctgcatcc tttcaggaag ggcctgcaag agaaggacaa ggtgtggctg   2760
ttgcgggagc agaagcgcaa gaagaaactc cgcaagctgc tcaagcgcct gcagaacaac   2820
gacacgtgca gcatgccagg cctcacgtgc ttcacccacg acaaccagca ctggcagacg   2880
gcgcctttct ggacactggg gcctttctgt gcctgcacca gcgccaacaa taacacgtac   2940
tggtgcatga ggaccatcaa tgagactcac aatttcctct tctgtgaatt tgcaactggc   3000
ttcctagagt actttgatct caacacagac ccctaccagc tgatgaatgc agtgaacaca   3060
ctggacaggg atgtcctcaa ccagctacac gtacagctca tggagctgag gagctgcaag   3120
ggttacaagc agtgtaaccc ccggactcga aacatggacc tgggacttaa agatggagga   3180
agctatgagc aatacaggca gtttcagcgt cgaaagtggc cagaaatgaa gagaccttct   3240
```

```
tccaaatcac tgggacaact gtgggaaggc tgggaaggtt aagaaacaac agaggtggac    3300
ctccaaaaac atagaggcat cacctgactg cacaggcaat gaaaaaccat gtgggtgatt    3360
tccagcagac ctgtgctatt ggccaggagg cctgagaaag caagcacgca ctctcagtca    3420
acatgacaga ttctggagga taaccagcag gagcagagat aacttcagga agtccatttt    3480
tgcccctgct tttgctttgg attatacctc accagctgca caaaatgcat tttttcgtat    3540
caaaaagtca ccactaaccc tcccccagaa gctcacaaag gaaaacggag agagcgagcg    3600
agagagattt ccttggaaat ttctcccaag ggcgaaagtc attggaattt ttaaatcata    3660
ggggaaaagc agtcctgttc taaatcctct tattcttttg gtttgtcaca agaaggaac    3720 taagaagcag gacagaggca acgtggagag gctgaaaaca gtgcagagac gtttgacaat    3780
gagtcagtag cacaaaagag atgacattta cctagcatat aaaccctggt tgcctctgaa    3840
gaaactgcct tcattgtata tatgtgacta tttacatgta atcaacatgg gaactttag    3900 gggaacctaa taagaaatcc caattttcag gagtggtggt gtcaataaac gctctgtggc    3960
cagtgtaaaa gaaaaaaaaa aaaaattgtg gacatttctg ttcctgtcca gataccattt    4020
ctcctagtat ttctttgtta tgtcccagaa ctgatgtttt ttttttaagg tactgaaaag    4080
aaatgaagtt gatgtatgtc ccaagttttg atgaaactgt atttgtaaaa aaaattttgt    4140
agtttaagta ttgtcataca gtgttcaaaa ccccagccaa tgaccagcag ttggtatgaa    4200
gaacctttga cattttgtaa aaggccattt cttggggaaa aaaaaaaaa aaaaaaaaa    4260 aaaaaaaaaa aaaaaaaa                                                  4279

<210> SEQ ID NO 31
<211> LENGTH: 870
<212> TYPE: PRT
<213> ORGANISM: Homo sapiens

<400> SEQUENCE: 31

Met Gly Pro Pro Ser Leu Val Leu Cys Leu Leu Ser Ala Thr Val Phe
1               5                   10                  15

Ser Leu Leu Gly Gly Ser Ser Ala Phe Leu Ser His His Arg Leu Lys
            20                  25                  30

Gly Arg Phe Gln Arg Asp Arg Arg Asn Ile Arg Pro Asn Ile Ile Leu
        35                  40                  45

Val Leu Thr Asp Asp Gln Asp Val Glu Leu Gly Ser Met Gln Val Met
    50                  55                  60

Asn Lys Thr Arg Arg Ile Met Glu Gln Gly Gly Ala His Phe Ile Asn
65                  70                  75                  80

Ala Phe Val Thr Thr Pro Met Cys Cys Pro Ser Arg Ser Ser Ile Leu
                85                  90                  95

Thr Gly Lys Tyr Val His Asn His Asn Thr Tyr Thr Asn Asn Glu Asn
            100                 105                 110

Cys Ser Ser Pro Ser Trp Gln Ala Gln His Glu Ser Arg Thr Phe Ala
        115                 120                 125

Val Tyr Leu Asn Ser Thr Gly Tyr Arg Thr Ala Phe Phe Gly Lys Tyr
    130                 135                 140

Leu Asn Glu Tyr Asn Gly Ser Tyr Val Pro Pro Gly Trp Lys Glu Trp
145                 150                 155                 160

Val Gly Leu Leu Lys Asn Ser Arg Phe Tyr Asn Tyr Thr Leu Cys Arg
                165                 170                 175

Asn Gly Val Lys Glu Lys His Gly Ser Asp Tyr Ser Lys Asp Tyr Leu
            180                 185                 190
```

-continued

```
Thr Asp Leu Ile Thr Asn Asp Ser Val Ser Phe Phe Arg Thr Ser Lys
        195                 200                 205
Lys Met Tyr Pro His Arg Pro Val Leu Met Val Ile Ser His Ala Ala
    210                 215                 220
Pro His Gly Pro Glu Asp Ser Ala Pro Gln Tyr Ser Arg Leu Phe Pro
225                 230                 235                 240
Asn Ala Ser Gln His Ile Thr Pro Ser Tyr Asn Tyr Ala Pro Asn Pro
                245                 250                 255
Asp Lys His Trp Ile Met Arg Tyr Thr Gly Pro Met Lys Pro Ile His
            260                 265                 270
Met Glu Phe Thr Asn Met Leu Gln Arg Lys Arg Leu Gln Thr Leu Met
        275                 280                 285
Ser Val Asp Asp Ser Met Glu Thr Ile Tyr Asn Met Leu Val Glu Thr
    290                 295                 300
Gly Glu Leu Asp Asn Thr Tyr Ile Val Tyr Thr Ala Asp His Gly Tyr
305                 310                 315                 320
His Ile Gly Gln Phe Gly Leu Val Lys Gly Lys Ser Met Pro Tyr Glu
                325                 330                 335
Phe Asp Ile Arg Val Pro Phe Tyr Val Arg Gly Pro Asn Val Glu Ala
            340                 345                 350
Gly Cys Leu Asn Pro His Ile Val Leu Asn Ile Asp Leu Ala Pro Thr
        355                 360                 365
Ile Leu Asp Ile Ala Gly Leu Asp Ile Pro Ala Asp Met Asp Gly Lys
    370                 375                 380
Ser Ile Leu Lys Leu Leu Asp Thr Glu Arg Pro Val Asn Arg Phe His
385                 390                 395                 400
Leu Lys Lys Lys Met Arg Val Trp Arg Asp Ser Phe Leu Val Glu Arg
                405                 410                 415
Gly Lys Leu Leu His Lys Arg Asp Asn Asp Lys Val Asp Ala Gln Glu
            420                 425                 430
Glu Asn Phe Leu Pro Lys Tyr Gln Arg Val Lys Asp Leu Cys Gln Arg
        435                 440                 445
Ala Glu Tyr Gln Thr Ala Cys Glu Gln Leu Gly Gln Lys Trp Gln Cys
    450                 455                 460
Val Glu Asp Ala Thr Gly Lys Leu Lys Leu His Lys Cys Lys Gly Pro
465                 470                 475                 480
Met Arg Leu Gly Gly Ser Arg Ala Leu Ser Asn Leu Val Pro Lys Tyr
                485                 490                 495
Tyr Gly Gln Gly Ser Glu Ala Cys Thr Cys Asp Ser Gly Asp Tyr Lys
            500                 505                 510
Leu Ser Leu Ala Gly Arg Arg Lys Lys Leu Phe Lys Lys Lys Tyr Lys
        515                 520                 525
Ala Ser Tyr Val Arg Ser Arg Ser Ile Arg Ser Val Ala Ile Glu Val
    530                 535                 540
Asp Gly Arg Val Tyr His Val Gly Leu Gly Asp Ala Ala Gln Pro Arg
545                 550                 555                 560
Asn Leu Thr Lys Arg His Trp Pro Gly Ala Pro Glu Asp Gln Asp Asp
                565                 570                 575
Lys Asp Gly Gly Asp Phe Ser Gly Thr Gly Gly Leu Pro Asp Tyr Ser
            580                 585                 590
Ala Ala Asn Pro Ile Lys Val Thr His Arg Cys Tyr Ile Leu Glu Asn
        595                 600                 605
Asp Thr Val Gln Cys Asp Leu Asp Leu Tyr Lys Ser Leu Gln Ala Trp
    610                 615                 620
```

```
Lys Asp His Lys Leu His Ile Asp His Glu Ile Glu Thr Leu Gln Asn
625                 630                 635                 640

Lys Ile Lys Asn Leu Arg Glu Val Arg Gly His Leu Lys Lys Arg
            645                 650                 655

Pro Glu Glu Cys Asp Cys His Lys Ile Ser Tyr His Thr Gln His Lys
                660                 665                 670

Gly Arg Leu Lys His Arg Gly Ser Ser Leu His Pro Phe Arg Lys Gly
            675                 680                 685

Leu Gln Glu Lys Asp Lys Val Trp Leu Leu Arg Glu Gln Lys Arg Lys
690                 695                 700

Lys Lys Leu Arg Lys Leu Leu Lys Arg Leu Gln Asn Asn Asp Thr Cys
705                 710                 715                 720

Ser Met Pro Gly Leu Thr Cys Phe Thr His Asp Asn Gln His Trp Gln
                725                 730                 735

Thr Ala Pro Phe Trp Thr Leu Gly Pro Phe Cys Ala Cys Thr Ser Ala
                740                 745                 750

Asn Asn Asn Thr Tyr Trp Cys Met Arg Thr Ile Asn Glu Thr His Asn
            755                 760                 765

Phe Leu Phe Cys Glu Phe Ala Thr Gly Phe Leu Glu Tyr Phe Asp Leu
770                 775                 780

Asn Thr Asp Pro Tyr Gln Leu Met Asn Ala Val Asn Thr Leu Asp Arg
785                 790                 795                 800

Asp Val Leu Asn Gln Leu His Val Gln Leu Met Glu Leu Arg Ser Cys
                805                 810                 815

Lys Gly Tyr Lys Gln Cys Asn Pro Arg Thr Arg Asn Met Asp Leu Gly
            820                 825                 830

Leu Lys Asp Gly Gly Ser Tyr Glu Gln Tyr Arg Gln Phe Gln Arg Arg
            835                 840                 845

Lys Trp Pro Glu Met Lys Arg Pro Ser Ser Lys Ser Leu Gly Gln Leu
            850                 855                 860

Trp Glu Gly Trp Glu Gly
865                 870

<210> SEQ ID NO 32
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Leu or Val
<220> FEATURE:
<221> NAME/KEY: VARIANT
<222> LOCATION: 2
<223> OTHER INFORMATION: Cys or Ser
<220> FEATURE:
<221> NAME/KEY: misc_feature
<222> LOCATION: 3
<223> OTHER INFORMATION: Xaa can be any naturally occurring amino acid

<400> SEQUENCE: 32

Xaa Xaa Xaa Pro Ser Arg
1               5

<210> SEQ ID NO 33
<211> LENGTH: 23
<212> TYPE: PRT
<213> ORGANISM: Artificial Sequence
<220> FEATURE:
```

-continued

<223> OTHER INFORMATION: Sequence derived from human Arylsulfatase A

<400> SEQUENCE: 33

Met Thr Asp Phe Tyr Val Pro Val Ser Leu Cys Thr Pro Ser Arg Ala
1               5                   10                  15
Ala Leu Leu Thr Gly Arg Ser
            20

<210> SEQ ID NO 34
<211> LENGTH: 16
<212> TYPE: PRT
<213> ORGANISM: Artificial Sequence
<220> FEATURE:
<223> OTHER INFORMATION: a variant of the ASA65-80 peptide, in which
      residues Cys69, Pro71 and Arg73, critical for FGly formation, were
      scrambled

<400> SEQUENCE: 34

Pro Val Ser Leu Pro Thr Arg Ser Cys Ala Ala Leu Leu Thr Gly Arg
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: a variant of the ASA65-80 peptide, in which the
      Cys69 was replaced by a Serine

<400> SEQUENCE: 35

Pro Val Ser Leu Ser Thr Pro Ser Arg Ala Ala Leu Leu Thr Gly Arg
1               5                   10                  15

<210> SEQ ID NO 36
<211> LENGTH: 19
<212> TYPE: DNA
<213> ORGANISM: Artificial Sequence
<220> FEATURE:
<223> OTHER INFORMATION: human FGE-specific PCR primer

<400> SEQUENCE: 36
ccaatgtagg tcagacacg                                                    19

<210> SEQ ID NO 37
<211> LENGTH: 16
<212> TYPE: DNA
<213> ORGANISM: Artificial Sequence
<220> FEATURE:
<223> OTHER INFORMATION: human FGE-specific PCR primer

<400> SEQUENCE: 37
acatggcccg cgggac                                                       16

<210> SEQ ID NO 38
<211> LENGTH: 19
<212> TYPE: DNA
<213> ORGANISM: Artificial Sequence
<220> FEATURE:
<223> OTHER INFORMATION: human FGE-specific PCR primer

<400> SEQUENCE: 38
cgactgctcc ttggactgg                                                    19

<210> SEQ ID NO 39
<211> LENGTH: 24
<212> TYPE: DNA
<213> ORGANISM: Artificial Sequence

```
<220> FEATURE:
<223> OTHER INFORMATION: human FGE-specific PCR primer

<400> SEQUENCE: 39
ggaattcggg acaacatggc tgcg                                          24

<210> SEQ ID NO 40
<211> LENGTH: 54
<212> TYPE: DNA
<213> ORGANISM: Artificial Sequence
<220> FEATURE:
<223> OTHER INFORMATION: HA-specific primer

<400> SEQUENCE: 40
cccaagctta tgcgtagtca ggcacatcat acggatagtc catggtgggc aggc         54

<210> SEQ ID NO 41
<211> LENGTH: 57
<212> TYPE: DNA
<213> ORGANISM: Artificial Sequence
<220> FEATURE:
<223> OTHER INFORMATION: c-myc -specific primer

<400> SEQUENCE: 41
cccaagctta caggtcttct tcagaaatca gcttttgttc gtccatggtg ggcaggc      57

<210> SEQ ID NO 42
<211> LENGTH: 54
<212> TYPE: DNA
<213> ORGANISM: Artificial Sequence
<220> FEATURE:
<223> OTHER INFORMATION: RGS-His6 - specific primer

<400> SEQUENCE: 42
cccaagctta gtgatggtga tggtgatgcg atcctctgtc catggtgggc aggc         54

<210> SEQ ID NO 43
<211> LENGTH: 15
<212> TYPE: PRT
<213> ORGANISM: Artificial Sequence
<220> FEATURE:
<223> OTHER INFORMATION: tryptic oligopeptide from a human FGE
      preparation

<400> SEQUENCE: 43

Ser Gln Asn Thr Pro Asp Ser Ser Ala Ser Asn Leu Gly Phe Arg
1               5                   10                  15

<210> SEQ ID NO 44
<211> LENGTH: 19
<212> TYPE: PRT
<213> ORGANISM: Artificial Sequence
<220> FEATURE:
<223> OTHER INFORMATION: tryptic oligopeptide from a human FGE
      preparation
<220> FEATURE:
<221> NAME/KEY: MISC_FEATURE
<222> LOCATION: (1)..(19)
<223> OTHER INFORMATION: tryptic oligopeptide from a human FGE
      preparation

<400> SEQUENCE: 44

Met Val Pro Ile Pro Ala Gly Val Phe Thr Met Gly Thr Asp Asp Pro
1               5                   10                  15

Gln Ile Lys

<210> SEQ ID NO 45
```

```
<211> LENGTH: 906
<212> TYPE: DNA
<213> ORGANISM: Homo sapiens

<400> SEQUENCE: 45
atggcccggc atgggttacc gctgctgccc ctgctgtcgc tcctggtcgg cgcgtggctc      60
aagctaggaa atggacaggc tactagcatg gtccaactgc agggtgggag attcctgatg     120
ggaacaaatt ctccagacag cagagatggt gaagggcctg tgcggaggc gacagtgaaa      180 ccctttgcca tcgacatatt tcctgtcacc aacaaagatt tcagggattt tgtcagggag     240
aaaaagtatc ggacagaagc tgagatgttt ggatggagct ttgtctttga ggactttgtc     300
tctgatgagc tgagaaacaa agccacccag ccaatgaagt ctgtactctg gtggcttcca     360
gtggaaaagg cattttggag gcagcctgca ggtcctggct ctggcatccg agagagactg     420
gagcacccag tgttacacgt gagctggaat gacgcccgtg cctactgtgc ttggcgggga     480
aaacgactgc ccacggagga gagtgggag tttgccgccc gagggggctt gaagggtcaa      540
gtttacccat gggggaactg gttccagcca aaccgcacca acctgtggca gggaaagttc     600
cccaagggag acaaagctga ggatggcttc catggagtct ccccagtgaa tgctttcccc     660
gcccagaaca actacgggct ctatgacctc ctggggaacg tgtgggagtg gacagcatca     720
ccgtaccagg ctgctgagca ggacatgcgc gtcctccggg gggcatcctg gatcgacaca     780
gctgatggct ctgccaatca ccgggcccgg gtcaccacca ggatgggcaa cactccagat     840
tcagcctcag acaacctcgg tttccgctgt gctgcagacg caggccggcc gccaggggag     900
ctgtaa                                                              906

<210> SEQ ID NO 46
<211> LENGTH: 301
<212> TYPE: PRT
<213> ORGANISM: Homo sapiens

<400> SEQUENCE: 46

Met Ala Arg His Gly Leu Pro Leu Leu Pro Leu Leu Ser Leu Leu Val
1               5                   10                  15

Gly Ala Trp Leu Lys Leu Gly Asn Gly Gln Ala Thr Ser Met Val Gln
                20                  25                  30

Leu Gln Gly Gly Arg Phe Leu Met Gly Thr Asn Ser Pro Asp Ser Arg
            35                  40                  45

Asp Gly Glu Gly Pro Val Arg Glu Ala Thr Val Lys Pro Phe Ala Ile
        50                  55                  60

Asp Ile Phe Pro Val Thr Asn Lys Asp Phe Arg Asp Phe Val Arg Glu
65                  70                  75                  80

Lys Lys Tyr Arg Thr Glu Ala Glu Met Phe Gly Trp Ser Phe Val Phe
                85                  90                  95

Glu Asp Phe Val Ser Asp Glu Leu Arg Asn Lys Ala Thr Gln Pro Met
                100                 105                 110

Lys Ser Val Leu Trp Trp Leu Pro Val Glu Lys Ala Phe Trp Arg Gln
            115                 120                 125

Pro Ala Gly Pro Gly Ser Gly Ile Arg Glu Arg Leu Glu His Pro Val
        130                 135                 140

Leu His Val Ser Trp Asn Asp Ala Arg Ala Tyr Cys Ala Trp Arg Gly
145                 150                 155                 160

Lys Arg Leu Pro Thr Glu Glu Glu Trp Glu Phe Ala Ala Arg Gly Gly
                165                 170                 175

Leu Lys Gly Gln Val Tyr Pro Trp Gly Asn Trp Phe Gln Pro Asn Arg
```

```
            180                 185                 190
Thr Asn Leu Trp Gln Gly Lys Phe Pro Lys Gly Asp Lys Ala Glu Asp
        195                 200                 205

Gly Phe His Gly Val Ser Pro Val Asn Ala Phe Pro Ala Gln Asn Asn
    210                 215                 220

Tyr Gly Leu Tyr Asp Leu Leu Gly Asn Val Trp Glu Trp Thr Ala Ser
225                 230                 235                 240

Pro Tyr Gln Ala Ala Glu Gln Asp Met Arg Val Leu Arg Gly Ala Ser
                245                 250                 255

Trp Ile Asp Thr Ala Asp Gly Ser Ala Asn His Arg Ala Arg Val Thr
            260                 265                 270

Thr Arg Met Gly Asn Thr Pro Asp Ser Ala Ser Asp Asn Leu Gly Phe
        275                 280                 285

Arg Cys Ala Ala Asp Ala Gly Arg Pro Pro Gly Glu Leu
    290                 295                 300

<210> SEQ ID NO 47
<211> LENGTH: 927
<212> TYPE: DNA
<213> ORGANISM: Mus musculus

<400> SEQUENCE: 47
atgcgctctg agttctggtt ccccagcatg ggttccttgc tccctccggt gttgctgctg      60
aggctcctgt cctgccccag gcttcagcta ggacatgccc aggatcctgc catggtgcat     120
ctgccaggtg gccggtttct gatggggaca gacgctccag atggcagaga cggtgaaggg     180
cctgcccggg aagtgacagt aaaacccttt gccatcgaca tatttccagt caccaataaa     240
gacttcaggg agtttgtcag ggagaagaag taccagactg aagccgaggc attcgggtgg     300
agcttcgtct ttgaggattt tgtctcccct gagctcagaa agcaagaaaa tctgatgccg     360
gctgttcact ggtggcagcc agtgccaaag gcattttgga ggcagcctgc aggtcccggc     420
tctggcatcc gagagaaact ggagcttccc gtggtacacg tgagctggaa cgacgctggt     480
gcttactgcg catggcgggg gagacgcttg cccacagaag aggagtggga gtttgcagcc     540
cgagggggct tgaagggtca ggtttatcca tgggggaacc ggttccagcc aaaccgcacc     600
aacttatggc agggaaagtt ccccaaaggt gacaaagctg aagatggttt tcatggactg     660
tcaccagtga acgctttccc cccacagaac aactacggac tgtatgacct catgggcaat     720
gtgtgggagt ggacagcgtc cacataccaa cctgctggcc aggacatgcg tgtcctccgg     780
ggggcatcat ggatcgacac cgcagacggc tctgctaatc acagggctcg ggtcaccacc     840
aggatgggaa acactccaga ctcagcctca gacaacctgg gcttccgctg cgcctccagt     900
gcaggccgac cgaaggagga cctgtga                                         927

<210> SEQ ID NO 48
<211> LENGTH: 308
<212> TYPE: PRT
<213> ORGANISM: Mus musculus

<400> SEQUENCE: 48

Met Arg Ser Glu Phe Trp Phe Pro Ser Met Gly Ser Leu Leu Pro Pro
1               5                   10                  15

Val Leu Leu Leu Arg Leu Leu Ser Cys Pro Arg Leu Gln Leu Gly His
            20                  25                  30

Ala Gln Asp Pro Ala Met Val His Leu Pro Gly Gly Arg Phe Leu Met
        35                  40                  45
```

```
Gly Thr Asp Ala Pro Asp Gly Arg Asp Gly Glu Gly Pro Ala Arg Glu
            50                  55                  60

Val Thr Val Lys Pro Phe Ala Ile Asp Ile Phe Pro Val Thr Asn Lys
 65                  70                  75                  80

Asp Phe Arg Glu Phe Val Arg Glu Lys Lys Tyr Gln Thr Glu Ala Glu
                 85                  90                  95

Ala Phe Gly Trp Ser Phe Val Phe Glu Asp Phe Val Ser Pro Glu Leu
            100                 105                 110

Arg Lys Gln Glu Asn Leu Met Pro Ala Val His Trp Trp Gln Pro Val
            115                 120                 125

Pro Lys Ala Phe Trp Arg Gln Pro Ala Gly Pro Ser Gly Ile Arg
            130                 135                 140

Glu Lys Leu Glu Leu Pro Val Val His Val Ser Trp Asn Asp Ala Gly
145                 150                 155                 160

Ala Tyr Cys Ala Trp Arg Gly Arg Arg Leu Pro Thr Glu Glu Trp
                165                 170                 175

Glu Phe Ala Ala Arg Gly Gly Leu Lys Gly Gln Val Tyr Pro Trp Gly
            180                 185                 190

Asn Arg Phe Gln Pro Asn Arg Thr Asn Leu Trp Gln Gly Lys Phe Pro
            195                 200                 205

Lys Gly Asp Lys Ala Glu Asp Gly Phe His Gly Leu Ser Pro Val Asn
210                 215                 220

Ala Phe Pro Pro Gln Asn Asn Tyr Gly Leu Tyr Asp Leu Met Gly Asn
225                 230                 235                 240

Val Trp Glu Trp Thr Ala Ser Thr Tyr Gln Pro Ala Gly Gln Asp Met
                245                 250                 255

Arg Val Leu Arg Gly Ala Ser Trp Ile Asp Thr Ala Asp Gly Ser Ala
            260                 265                 270

Asn His Arg Ala Arg Val Thr Thr Arg Met Gly Asn Thr Pro Asp Ser
            275                 280                 285

Ala Ser Asp Asn Leu Gly Phe Arg Cys Ala Ser Ser Ala Gly Arg Pro
            290                 295                 300

Lys Glu Asp Leu
305

<210> SEQ ID NO 49
<211> LENGTH: 855
<212> TYPE: DNA
<213> ORGANISM: Mus musculus

<400> SEQUENCE: 49
atggtcccca ttcctgctgg agtattcaca atgggcactg atgatcctca gatcaggcag    60
gatggagaag cccctgccag agagtcact gttgatggct ttacatgga cgcctatgaa    120 gtcagcaatg cggattttga aagtttgtg aactcgactg ctatttgac agaggctgag    180 aagtttggag actctttcgt ctttgaaggc atgttgagcg agcaagtgaa aacgcatatc    240
caccaggcag ttgcagctgc tccatggtgg ttgcctgtca agggagctaa ttggagacac    300
ccagagggtc cggactccag tattctgcac aggtcaaatc atccggttct ccatgtttcc    360
tggaacgatg ctgttgccta ctgcacatgg gcgggcaaga ggttgcctac tgaggcagag    420
tgggaataca gctgtagagg aggcctgcag aacaggcttt tcccctgggg caacaaactg    480
cagcccaaag acagcatta tgccaacatc tggcagggca gtttcctgt gagcaacact    540 ggcgaggatg gcttccaagg aactgccccc gttgatgcct ttcctcccaa tggctatggc    600
ttatacaaca tagtggggaa tgtgtgggag tggacctcag actggtggac tgttcaccat    660
```

```
tctgttgagg aaacgttcaa cccaaagggt cccacttctg ggaaagaccg agtgaagaag      720
ggtggatcct acatgtgcca taagtcctat tgctataggt accgctgtgc agctcgaagc      780
cagaacacac cagatagctc tgcatccaac ctgggattcc gatgtgcagc cgaccacctg      840
cccaccgcag actga                                                      855

<210> SEQ ID NO 50
<211> LENGTH: 284
<212> TYPE: PRT
<213> ORGANISM: Mus musculus

<400> SEQUENCE: 50

Met Val Pro Ile Pro Ala Gly Val Phe Thr Met Gly Thr Asp Asp Pro
1               5                   10                  15

Gln Ile Arg Gln Asp Gly Glu Ala Pro Ala Arg Arg Val Thr Val Asp
            20                  25                  30

Gly Phe Tyr Met Asp Ala Tyr Glu Val Ser Asn Ala Asp Phe Glu Lys
        35                  40                  45

Phe Val Asn Ser Thr Gly Tyr Leu Thr Glu Ala Glu Lys Phe Gly Asp
    50                  55                  60

Ser Phe Val Phe Glu Gly Met Leu Ser Glu Gln Val Lys Thr His Ile
65                  70                  75                  80

His Gln Ala Val Ala Ala Pro Trp Trp Leu Pro Val Lys Gly Ala
                85                  90                  95

Asn Trp Arg His Pro Glu Gly Pro Asp Ser Ser Ile Leu His Arg Ser
            100                 105                 110

Asn His Pro Val Leu His Val Ser Trp Asn Asp Ala Val Ala Tyr Cys
        115                 120                 125

Thr Trp Ala Gly Lys Arg Leu Pro Thr Glu Ala Glu Trp Glu Tyr Ser
    130                 135                 140

Cys Arg Gly Gly Leu Gln Asn Arg Leu Phe Pro Trp Gly Asn Lys Leu
145                 150                 155                 160

Gln Pro Lys Gly Gln His Tyr Ala Asn Ile Trp Gln Gly Lys Phe Pro
                165                 170                 175

Val Ser Asn Thr Gly Glu Asp Gly Phe Gln Gly Thr Ala Pro Val Asp
            180                 185                 190

Ala Phe Pro Pro Asn Gly Tyr Gly Leu Tyr Asn Ile Val Gly Asn Val
        195                 200                 205

Trp Glu Trp Thr Ser Asp Trp Trp Thr Val His His Ser Val Glu Glu
    210                 215                 220

Thr Phe Asn Pro Lys Gly Pro Thr Ser Gly Lys Asp Arg Val Lys Lys
225                 230                 235                 240

Gly Gly Ser Tyr Met Cys His Lys Ser Tyr Cys Tyr Arg Tyr Arg Cys
                245                 250                 255

Ala Ala Arg Ser Gln Asn Thr Pro Asp Ser Ser Ala Ser Asn Leu Gly
            260                 265                 270

Phe Arg Cys Ala Ala Asp His Leu Pro Thr Ala Asp
        275                 280

<210> SEQ ID NO 51
<211> LENGTH: 1011
<212> TYPE: DNA
<213> ORGANISM: Drosophila melanogaster

<400> SEQUENCE: 51
atgacaacaa ttatattagt cctctttatt tggatagttt tattcaatga cgtatccagc      60
```

```
gactgtggct gccaaaagct cgaccggaag gccccggata tgccgtccat ttccggacaa    120
gtgtgccagc aacgagcaca gggtgcacac agccactacc gggattacta tggcgaactg    180
gagccaaata ttgcggacat gtcactgctt ccgggaggca cggtttacat gggtactgac    240
aaaccgcact ttccggccga ccgcgaggct ccggaacggc aggtgaagct gaatgacttc    300
tacatcgaca agtatgaggt ttccaacgaa gcctttgcga agtttgttct gcacactaac    360
tacaccacgg aggctgagcg atatggcgac agttttctgt ttaagagcct tttgagccca    420
ttggagcaga agaacctaga ggacttccga gtggcgagcg ctgtctggtg gtacaaagtg    480
gccggcgtga actggcgaca tccaaatggc gtggacagca atatagacca cttaggccga    540
cacccggtag tgcacgtatc gtggcgcgac gctgtggagt actgtaagtg ggccggcaag    600
cggttgccca gcgaggcgga gtgggaggcg gcttgcaggg gcggcaagga gcgcaaactg    660
tttccctggg gcaacaagct gatgccaagg aatgaacatt ggctgaacat ctggcaggga    720
gactttcccg atggcaacct ggctgaagat gggtttgagt acaccagccc cgtggatgcc    780
ttccgacaga atatttacga cctgcacaac atggtgggca cgtctggga gtggacggca    840 gatctgtggg acgtaaatga cgttagcgat aatccaaatc gggtcaagaa gggcggttct    900
tatctgtgtc acaagtccta ctgctacagg tacaggtgcg cggcacgctc gcagaacaca    960
gaagacagtt cagccggtaa cctgggtttt cggtgcgcca agaatgcgtg a            1011
```

<210> SEQ ID NO 52
<211> LENGTH: 336
<212> TYPE: PRT
<213> ORGANISM: Drosophila melanogaster

<400> SEQUENCE: 52

```
Met Thr Thr Ile Ile Leu Val Leu Phe Ile Trp Ile Val Leu Phe Asn
1               5                   10                  15

Asp Val Ser Ser Asp Cys Gly Cys Gln Lys Leu Asp Arg Lys Ala Pro
            20                  25                  30

Asp Met Pro Ser Ile Ser Gly Gln Val Cys Gln Gln Arg Ala Gln Gly
        35                  40                  45

Ala His Ser His Tyr Arg Asp Tyr Tyr Gly Glu Leu Glu Pro Asn Ile
    50                  55                  60

Ala Asp Met Ser Leu Leu Pro Gly Gly Thr Val Tyr Met Gly Thr Asp
65                  70                  75                  80

Lys Pro His Phe Pro Ala Asp Arg Glu Ala Pro Glu Arg Gln Val Lys
                85                  90                  95

Leu Asn Asp Phe Tyr Ile Asp Lys Tyr Glu Val Ser Asn Glu Ala Phe
            100                 105                 110

Ala Lys Phe Val Leu His Thr Asn Tyr Thr Thr Glu Ala Glu Arg Tyr
        115                 120                 125

Gly Asp Ser Phe Leu Phe Lys Ser Leu Leu Ser Pro Leu Glu Gln Lys
    130                 135                 140

Asn Leu Glu Asp Phe Arg Val Ala Ser Ala Val Trp Trp Tyr Lys Val
145                 150                 155                 160

Ala Gly Val Asn Trp Arg His Pro Asn Gly Val Asp Ser Asp Ile Asp
                165                 170                 175

His Leu Gly Arg His Pro Val Val His Val Ser Trp Arg Asp Ala Val
            180                 185                 190

Glu Tyr Cys Lys Trp Ala Gly Lys Arg Leu Pro Ser Glu Ala Glu Trp
        195                 200                 205
```

```
Glu Ala Ala Cys Arg Gly Gly Lys Glu Arg Lys Leu Phe Pro Trp Gly
            210                 215                 220

Asn Lys Leu Met Pro Arg Asn Glu His Trp Leu Asn Ile Trp Gln Gly
225                 230                 235                 240

Asp Phe Pro Asp Gly Asn Leu Ala Glu Asp Gly Phe Glu Tyr Thr Ser
                245                 250                 255

Pro Val Asp Ala Phe Arg Gln Asn Ile Tyr Asp Leu His Asn Met Val
            260                 265                 270

Gly Asn Val Trp Glu Trp Thr Ala Asp Leu Trp Asp Val Asn Asp Val
                275                 280                 285

Ser Asp Asn Pro Asn Arg Val Lys Lys Gly Gly Ser Tyr Leu Cys His
            290                 295                 300

Lys Ser Tyr Cys Tyr Arg Tyr Arg Cys Ala Ala Arg Ser Gln Asn Thr
305                 310                 315                 320

Glu Asp Ser Ser Ala Gly Asn Leu Gly Phe Arg Cys Ala Lys Asn Ala
                325                 330                 335
```

<210> SEQ ID NO 53
<211> LENGTH: 870
<212> TYPE: DNA
<213> ORGANISM: Anopheles gambiae

<400> SEQUENCE: 53

```
ccggagagct tgctcgatct ggtggaacat tccaagcggt tcgaagacat gagccttatc      60
ccaggaggtg aatatgtaat cggcacaaat gaacctatct tcgtcaagga tcgcgaatca     120
ccggcccggc ccgcgacgat ccgcgacttt tacctcgacc agtacgaagt ctccaacgca     180
cagttcaagg cattcgtcga ccagacgggc tacgtcacgg aggcgaaaaa gtttggcgac     240
agcttcgtct tccagcagct gctcagcgaa ccggtgcgcc agcagtacga agatttccgc     300
gtggcggcgg cgccctggtg gtacaaggta cgtggagcct cctggcagca tccggaaggt     360
gatgtgtcac gtgatataag cgaccgattg gaccatccgg tggtgcacgt gtcctggaac     420
gatgcggtcg cgtactgcgc ctggaaaggg aagcgcctgc cgacggaagc ggaatgggaa     480
gcggcctgcc ggggcggtcg caagcagaag ctgttcccct ggggtaacaa gctgatgccg     540
aaggagcagc acatgatgaa catatggcag ggcgagttcc cggacagcaa tctgaaggag     600
gatggctacg agaccacctg cccggtgacg tccttccgcc agaacccgtt cgagctgtac     660
aacatcgttg caacgtgtg ggagtggacg gcggatcttt gggacgcgaa ggatgcggcc     720
atcgagcgca agccgggcag cgatccaccg aatcgggtga aaaagggtgg ctcatacctg     780
tgtcacgaat cgtactgcta tcgctatcgc tgtgcggctc gatcgcagaa caccgaggac     840
agttcggcgg gcaatctggg cttccggtgc                                      870
```

<210> SEQ ID NO 54
<211> LENGTH: 290
<212> TYPE: PRT
<213> ORGANISM: Anopheles gambiae

<400> SEQUENCE: 54

```
Pro Glu Ser Leu Leu Asp Leu Val Glu His Ser Lys Arg Phe Glu Asp
1               5                   10                  15

Met Ser Leu Ile Pro Gly Gly Glu Tyr Val Ile Gly Thr Asn Glu Pro
                20                  25                  30

Ile Phe Val Lys Asp Arg Glu Ser Pro Ala Arg Pro Ala Thr Ile Arg
            35                  40                  45

Asp Phe Tyr Leu Asp Gln Tyr Glu Val Ser Asn Ala Gln Phe Lys Ala
```

```
                50                  55                  60
Phe Val Asp Gln Thr Gly Tyr Val Thr Glu Ala Glu Lys Phe Gly Asp
 65                  70                  75                  80

Ser Phe Val Phe Gln Gln Leu Leu Ser Glu Pro Val Arg Gln Tyr
                 85                  90                  95

Glu Asp Phe Arg Val Ala Ala Ala Pro Trp Trp Tyr Lys Val Arg Gly
                100                 105                 110

Ala Ser Trp Gln His Pro Glu Gly Asp Val Ser Arg Asp Ile Ser Asp
                115                 120                 125

Arg Leu Asp His Pro Val Val His Val Ser Trp Asn Asp Ala Val Ala
                130                 135                 140

Tyr Cys Ala Trp Lys Gly Lys Arg Leu Pro Thr Glu Ala Glu Trp Glu
145                 150                 155                 160

Ala Ala Cys Arg Gly Gly Arg Lys Gln Lys Leu Phe Pro Trp Gly Asn
                165                 170                 175

Lys Leu Met Pro Lys Glu Gln His Met Met Asn Ile Trp Gln Gly Glu
                180                 185                 190

Phe Pro Asp Ser Asn Leu Lys Glu Asp Gly Tyr Glu Thr Thr Cys Pro
                195                 200                 205

Val Thr Ser Phe Arg Gln Asn Pro Phe Glu Leu Tyr Asn Ile Val Gly
                210                 215                 220

Asn Val Trp Glu Trp Thr Ala Asp Leu Trp Asp Ala Lys Asp Ala Ala
225                 230                 235                 240

Ile Glu Arg Lys Pro Gly Ser Asp Pro Pro Asn Arg Val Lys Lys Gly
                245                 250                 255

Gly Ser Tyr Leu Cys His Glu Ser Tyr Cys Tyr Arg Tyr Arg Cys Ala
                260                 265                 270

Ala Arg Ser Gln Asn Thr Glu Asp Ser Ser Ala Gly Asn Leu Gly Phe
                275                 280                 285

Arg Cys
    290

<210> SEQ ID NO 55
<211> LENGTH: 945
<212> TYPE: DNA
<213> ORGANISM: Streptomyces coelicolor

<400> SEQUENCE: 55
gtggccgtgg ccgccccgtc ccccgcggcc gccgcggagc cggggcccgc cgcccgtccg      60
cgctcgaccc gcggacaggt gcgcctgccg ggcggtgagt tcgcgatggg ggacgccttc     120
ggggagggat atccggccga cggcgagaca cccgtgcaca cggtgcgcct gcggcccttc     180
cacatcgacg agaccgccgt caccaacgcc cggttcgccg ccttcgtcaa ggcgaccggc     240
catgtgaccg acgccgaacg cttcggctcc tcggccgtct tccacctggt cgtcgccgcc     300
ccggacgccg acgtcctcgg cagcgccgcc ggcgcccccg gtggatcaa cgtgcggggc      360 gcccactggc gccgcccga gggcgcccgc tccgacatca ccggccggcc gaaccatccg     420
gtcgtccacg tctcctggaa cgatgccacc gcctacgcgc ggtgggccgg caagcgcctg     480
cccaccgagg ccgaatggga gtacgccgcc cgcgggggac tggccggccg ccgctacgcc     540
tggggcgacg agctgacccc gggcggccgg tggcgctgca acatctggca gggccgcttc     600
ccgcacgtca acacggccga ggacgggcac ctgagcaccg caccggtcaa gtcctaccgg     660
cccaacggcc acggcctgtg aacaccgcg ggcaacgtgt gggaatggtg ctccgactgg     720
ttctcgccca cctactacgc cgaatcaccc accgtcgacc cgcacggccc cgggaccggg     780
```

```
gcggcacggg tgctgcgcgg cggctcctac ctgtgccacg actcctactg caaccgctac    840
cgggtcgccg cccgctcctc caacaccccg gactcctcgt ccggcaacct cggattccgc    900
tgcgccaacg acgcggacct cacgtccgga tcagccgctg agtga                     945
```

```
<210> SEQ ID NO 56
<211> LENGTH: 314
<212> TYPE: PRT
<213> ORGANISM: Streptomyces coelicolor

<400> SEQUENCE: 56

Met Ala Val Ala Ala Pro Ser Pro Ala Ala Ala Glu Pro Gly Pro
1               5                   10                  15

Ala Ala Arg Pro Arg Ser Thr Arg Gly Gln Val Arg Leu Pro Gly Gly
        20                  25                  30

Glu Phe Ala Met Gly Asp Ala Phe Gly Glu Gly Tyr Pro Ala Asp Gly
            35                  40                  45

Glu Thr Pro Val His Thr Val Arg Leu Arg Pro Phe His Ile Asp Glu
        50                  55                  60

Thr Ala Val Thr Asn Ala Arg Phe Ala Ala Phe Val Lys Ala Thr Gly
65                  70                  75                  80

His Val Thr Asp Ala Glu Arg Phe Gly Ser Ser Ala Val Phe His Leu
                85                  90                  95

Val Val Ala Ala Pro Asp Ala Asp Val Leu Gly Ser Ala Ala Gly Ala
            100                 105                 110

Pro Trp Trp Ile Asn Val Arg Gly Ala His Trp Arg Arg Pro Glu Gly
        115                 120                 125

Ala Arg Ser Asp Ile Thr Gly Arg Pro Asn His Pro Val Val His Val
    130                 135                 140

Ser Trp Asn Asp Ala Thr Ala Tyr Ala Arg Trp Ala Gly Lys Arg Leu
145                 150                 155                 160

Pro Thr Glu Ala Glu Trp Glu Tyr Ala Ala Arg Gly Gly Leu Ala Gly
                165                 170                 175

Arg Arg Tyr Ala Trp Gly Asp Glu Leu Thr Pro Gly Gly Arg Trp Arg
            180                 185                 190

Cys Asn Ile Trp Gln Gly Arg Phe Pro His Val Asn Thr Ala Glu Asp
        195                 200                 205

Gly His Leu Ser Thr Ala Pro Val Lys Ser Tyr Arg Pro Asn Gly His
    210                 215                 220

Gly Leu Trp Asn Thr Ala Gly Asn Val Trp Glu Trp Cys Ser Asp Trp
225                 230                 235                 240

Phe Ser Pro Thr Tyr Tyr Ala Glu Ser Pro Thr Val Asp Pro His Gly
                245                 250                 255

Pro Gly Thr Gly Ala Ala Arg Val Leu Arg Gly Gly Ser Tyr Leu Cys
            260                 265                 270

His Asp Ser Tyr Cys Asn Arg Tyr Arg Val Ala Ala Arg Ser Ser Asn
        275                 280                 285

Thr Pro Asp Ser Ser Gly Asn Leu Gly Phe Arg Cys Ala Asn Asp
    290                 295                 300

Ala Asp Leu Thr Ser Gly Ser Ala Ala Glu
305                 310

<210> SEQ ID NO 57
<211> LENGTH: 1005
<212> TYPE: DNA
<213> ORGANISM: Corynebacterium efficiens
```

<400> SEQUENCE: 57

```
gtggttcgcc atcgactggg ccaccggccc tgcacactga ggattacgtc catgagtaac       60
tgctgctccc cgtcaagcgc acaatggcgt accactaccc gggatttatc agatcctgtc      120
aatcccacca ctccatgcaa cccggaacaa tcccgcgatg ctgtgacact gccgggtgga      180
gctttccaca tgggcgatca tcacggggag gggtacccgg cggacgggga ggggccagta      240
catgaggttc acctcgcccc cttcggcatt aatgtcacca cggtcacgaa tgccgagttc      300
ggacgattta ttgaagccac agggtatacg acgacagcgg aacgctacgg tgtctcggct      360
gtattctacg cagcgttcca agggcaacgc gctgacattc ttcgccaggt tcccggcgtg      420
ccctggtggc tggcggtcaa gggtgcgaac tggcagcgtc ccaacggccc cggatccacc      480
ctggacgggc ttgaggacca ccccgtcgtt cacgtttcct gggatgatgc cgttgcctac      540
tgcacctggg ctggcggtcg tctgcccacc gaagccgagt gggaatacgc cgcccggggt      600
ggactgcagg gcgcacgata tgcctggggg gataacctcg ccctagacgg gaggtggaac      660
tgcaatatct ggcagggggg cttccccatg gagaacaccg ccgcggatgg ttacctcacc      720
actgcaccgg tgaagaccta cacgcccaat ggatacggtc tgtggcagat ggcagggaat      780
gtatgggaat ggtgccagga ctggtttgat gcggagtact actcccgtgc ttcctccatc      840
aacccgcggg gaccggatac cggtgcgcgc cgggtgatgc gcggaggctc gtatctctgc      900
catgattcct actgcaacag ataccgggtg gccgcccgca attcgaacac cccggattcc      960
acctcgggga ataccggttt ccggtgcgtt ttcgatagtc cttga                    1005
```

<210> SEQ ID NO 58
<211> LENGTH: 334
<212> TYPE: PRT
<213> ORGANISM: Corynebacterium efficiens

<400> SEQUENCE: 58

```
Met Val Arg His Arg Leu Gly His Arg Pro Cys Thr Leu Arg Ile Thr
 1               5                  10                  15

Ser Met Ser Asn Cys Cys Ser Pro Ser Ser Ala Gln Trp Arg Thr Thr
            20                  25                  30

Thr Arg Asp Leu Ser Asp Pro Val Asn Pro Thr Thr Pro Cys Asn Pro
        35                  40                  45

Glu Gln Ser Arg Asp Ala Val Thr Leu Pro Gly Gly Ala Phe His Met
    50                  55                  60

Gly Asp His His Gly Glu Gly Tyr Pro Ala Asp Gly Glu Gly Pro Val
65                  70                  75                  80

His Glu Val His Leu Ala Pro Phe Gly Ile Asn Val Thr Thr Val Thr
                85                  90                  95

Asn Ala Glu Phe Gly Arg Phe Ile Glu Ala Thr Gly Tyr Thr Thr Thr
            100                 105                 110

Ala Glu Arg Tyr Gly Val Ser Ala Val Phe Tyr Ala Ala Phe Gln Gly
        115                 120                 125

Gln Arg Ala Asp Ile Leu Arg Gln Val Pro Gly Val Pro Trp Trp Leu
    130                 135                 140

Ala Val Lys Gly Ala Asn Trp Gln Arg Pro Asn Gly Pro Gly Ser Thr
145                 150                 155                 160

Leu Asp Gly Leu Glu Asp His Pro Val His Val Ser Trp Asp Asp
                165                 170                 175

Ala Val Ala Tyr Cys Thr Trp Ala Gly Gly Arg Leu Pro Thr Glu Ala
            180                 185                 190
```

Glu Trp Glu Tyr Ala Ala Arg Gly Gly Leu Gln Gly Ala Arg Tyr Ala
              195                 200                 205

Trp Gly Asp Asn Leu Ala Leu Asp Gly Arg Trp Asn Cys Asn Ile Trp
        210                 215                 220

Gln Gly Gly Phe Pro Met Glu Asn Thr Ala Ala Asp Gly Tyr Leu Thr
225                 230                 235                 240

Thr Ala Pro Val Lys Thr Tyr Thr Pro Asn Gly Tyr Gly Leu Trp Gln
                245                 250                 255

Met Ala Gly Asn Val Trp Glu Trp Cys Gln Asp Trp Phe Asp Ala Glu
            260                 265                 270

Tyr Tyr Ser Arg Ala Ser Ser Ile Asn Pro Arg Gly Pro Asp Thr Gly
        275                 280                 285

Ala Arg Arg Val Met Arg Gly Gly Ser Tyr Leu Cys His Asp Ser Tyr
    290                 295                 300

Cys Asn Arg Tyr Arg Val Ala Ala Arg Asn Ser Asn Thr Pro Asp Ser
305                 310                 315                 320

Thr Ser Gly Asn Thr Gly Phe Arg Cys Val Phe Asp Ser Pro
                325                 330

<210> SEQ ID NO 59
<211> LENGTH: 1017
<212> TYPE: DNA
<213> ORGANISM: Novosphingobium aromaticivorans

<400> SEQUENCE: 59
atggcgcaac cattccgatc gacggcggcc agtcgtacaa gtattgaacg ccatctcgaa      60
cccaattgca ggagcacgtc gcgaatggtc gaacgccccg gcatgcgcct gatcgaaggc     120
ggcactttca ccatgggctc ggaagccttc tacccggagg aagcgccgct tcgccgggtg     180
aaggtagaca gcttctggat cgatgaagcg ccggtgacga acgcacagtt cgccgcattc     240
gtggaggcca cgggatacgt cactgtggcc gagatcgagc cggatcccaa ggactacccc     300
ggcatgctcc cgggcatgga ccgcgcggga tcgctggtgt tccagaaaac agcagggccg     360
gtcgacatgg cggatgcgtc caactggtgg cactttacct ttggcgcctg ctggaagcat     420
ccacttggac cgggcagttc catcgatggg atcgaggacc atcccgtcgt tcacgtcgcc     480
tatgccgatg ccgaggccta tgccaaatgg cgggcaaggg atctgccgac cgaagccgag     540
ttcgaatatg ctgcgcgcgg cgggttggac ggttccgaat tttcctgggg agacgaactc     600
gcacctgaag gccggatgat ggccaactac tggcaaggcc tgtttccctt cgccaaccag     660
tgcctcgatg gctgggaacg gacatcgccc gtccgcaact tcccgcccaa cggctatggt     720
ctttacgaca tgatcgggaa cacgtgggag tggacctgcg attggtgggc gacaagccg     780 ctgactccgc aaaggaaatc ggcatgctgc gcgatcagca atccgcgcgg cggcaagctc     840
aaggacagct tcgacccgtc gcaacccgca atgcgcatcg gccggaaggt cataaagggc     900
ggttcgcacc tgtgtgcggc caattactgc cagcgctatc gccccgcagc acgccatcct     960
gaaatggttg ataccgcgac gacgcacatc ggcttcaggt gtgtggtgcg gccctga     1017

<210> SEQ ID NO 60
<211> LENGTH: 338
<212> TYPE: PRT
<213> ORGANISM: Novosphingobium aromaticivorans

<400> SEQUENCE: 60

Met Ala Gln Pro Phe Arg Ser Thr Ala Ala Ser Arg Thr Ser Ile Glu
1               5                   10                  15

Arg His Leu Glu Pro Asn Cys Arg Ser Thr Ser Arg Met Val Glu Arg
            20                  25                  30

Pro Gly Met Arg Leu Ile Glu Gly Gly Thr Phe Thr Met Gly Ser Glu
        35                  40                  45

Ala Phe Tyr Pro Glu Glu Ala Pro Leu Arg Arg Val Lys Val Asp Ser
 50                  55                  60

Phe Trp Ile Asp Glu Ala Pro Val Thr Asn Ala Gln Phe Ala Ala Phe
65                  70                  75                  80

Val Glu Ala Thr Gly Tyr Val Thr Val Ala Glu Ile Glu Pro Asp Pro
                85                  90                  95

Lys Asp Tyr Pro Gly Met Leu Pro Gly Met Asp Arg Ala Gly Ser Leu
            100                 105                 110

Val Phe Gln Lys Thr Ala Gly Pro Val Asp Met Ala Asp Ala Ser Asn
        115                 120                 125

Trp Trp His Phe Thr Phe Gly Ala Cys Trp Lys His Pro Leu Gly Pro
130                 135                 140

Gly Ser Ser Ile Asp Gly Ile Glu Asp His Pro Val His Val Ala
145                 150                 155                 160

Tyr Ala Asp Ala Glu Ala Tyr Ala Lys Trp Ala Gly Lys Asp Leu Pro
                165                 170                 175

Thr Glu Ala Glu Phe Glu Tyr Ala Ala Arg Gly Gly Leu Asp Gly Ser
            180                 185                 190

Glu Phe Ser Trp Gly Asp Glu Leu Ala Pro Glu Gly Arg Met Met Ala
        195                 200                 205

Asn Tyr Trp Gln Gly Leu Phe Pro Phe Ala Asn Gln Cys Leu Asp Gly
210                 215                 220

Trp Glu Arg Thr Ser Pro Val Arg Asn Phe Pro Pro Asn Gly Tyr Gly
225                 230                 235                 240

Leu Tyr Asp Met Ile Gly Asn Thr Trp Glu Trp Thr Cys Asp Trp Trp
                245                 250                 255

Ala Asp Lys Pro Leu Thr Pro Gln Arg Lys Ser Ala Cys Cys Ala Ile
            260                 265                 270

Ser Asn Pro Arg Gly Gly Lys Leu Lys Asp Ser Phe Asp Pro Ser Gln
        275                 280                 285

Pro Ala Met Arg Ile Gly Arg Lys Val Ile Lys Gly Gly Ser His Leu
290                 295                 300

Cys Ala Ala Asn Tyr Cys Gln Arg Tyr Arg Pro Ala Ala Arg His Pro
305                 310                 315                 320

Glu Met Val Asp Thr Ala Thr Thr His Ile Gly Phe Arg Cys Val Val
                325                 330                 335

Arg Pro

<210> SEQ ID NO 61
<211> LENGTH: 1119
<212> TYPE: DNA
<213> ORGANISM: Mesorhizobium loti

<400> SEQUENCE: 61
atgggcccac gaggtcgagg tcaaaaaccg catgaaaggc gacgcggtca tgttcgacat     60
tgccgggaag ttctagccga tagcgggtgg gcggctgatg gagatgagca cgccgtgtca    120
tttcgggatc tttcgatgaa cgcccctgcc gaagtcttcg agcgcgctgc agccgaacgg    180
tcgtaccccg gaatggtctg gatccccggc ggtaccttcc tgatgggctc agacaaccac    240
tatccggagg aggcaccggc ccaccgggtc agggtcgacg gcttctggat ggacaaattc    300

```
accgtctcca accgcgactt cgaacgcttc gttgcggcga caggacatgt cactcttgcc    360
gagaaacccg ccaatcccga cgactatccc ggtgccttac ccgatctgct ggctccgtcc    420
tcgatgatgt tcaggaagcc ggccggccct gtcgaccttg caatcacta caattggtgg     480 gtctatgtcc gcggcgccaa ctggcgccat ccacgcgggc cggcaagtac aatcaagaag    540
gttgcagatc atccggtcgt gcatgtggcc tacgaggatg tcgtggccta tgccaactgg    600
gcaggcaagg aacttcccac cgaggccgag tgggaattcg cggcgcgagg cggcctcgat    660
gccgccgaat acgtctgggg caacgagctt acgccggccg ggaagcacat ggccaacatc    720
tggcaaggag actttcccta ccggaatact gtcgacgacg ttacgaata tacggcccca    780 gtaggctcgt tcccggccaa cgactacggt ctctacgaca tggccggcaa tgtctggcaa    840
tggacgaccg actggtacca ggaccacaag gcgatcgaca gcccgtgctg caccgctgtc    900
aatccgcgtg gcggccatcg cgaagcgagc tatgacaccc ggctacctga cgttaagatc    960
cctcgcaagg tcaccaaggg tggctcccat ctgtgcgcgc cgaactactg tcggcgctac   1020
cggcccgcgg cgcgaatggc gcaacccgtc gacactgcaa tctcccatct cggctttcgc   1080
tgcatcgtgc gaaggaaaat ggaattgaac gcgcagtaa                          1119
```

<210> SEQ ID NO 62
<211> LENGTH: 372
<212> TYPE: PRT
<213> ORGANISM: Mesorhizobium loti

<400> SEQUENCE: 62

```
Met Gly Pro Arg Gly Arg Gly Gln Lys Pro His Glu Arg Arg Gly
1               5                   10                  15

His Val Arg His Cys Arg Glu Val Leu Ala Asp Ser Gly Trp Ala Ala
            20                  25                  30

Asp Gly Asp Glu His Ala Val Ser Phe Arg Asp Leu Ser Met Asn Ala
        35                  40                  45

Pro Ala Glu Val Phe Glu Arg Ala Ala Glu Arg Ser Tyr Pro Gly
    50                  55                  60

Met Val Trp Ile Pro Gly Gly Thr Phe Leu Met Gly Ser Asp Asn His
65              70                  75                  80

Tyr Pro Glu Glu Ala Pro Ala His Arg Val Arg Val Asp Gly Phe Trp
                85                  90                  95

Met Asp Lys Phe Thr Val Ser Asn Arg Asp Phe Glu Arg Phe Val Ala
            100                 105                 110

Ala Thr Gly His Val Thr Leu Ala Glu Lys Pro Ala Asn Pro Asp Asp
        115                 120                 125

Tyr Pro Gly Ala Leu Pro Asp Leu Leu Ala Pro Ser Ser Met Met Phe
    130                 135                 140

Arg Lys Pro Ala Gly Pro Val Asp Leu Gly Asn His Tyr Asn Trp Trp
145             150                 155                 160

Val Tyr Val Arg Gly Ala Asn Trp Arg His Pro Arg Gly Pro Ala Ser
                165                 170                 175

Thr Ile Lys Lys Val Ala Asp His Pro Val His Val Ala Tyr Glu
            180                 185                 190

Asp Val Val Ala Tyr Ala Asn Trp Ala Gly Lys Glu Leu Pro Thr Glu
        195                 200                 205

Ala Glu Trp Glu Phe Ala Ala Arg Gly Gly Leu Asp Ala Ala Glu Tyr
    210                 215                 220

Val Trp Gly Asn Glu Leu Thr Pro Ala Gly Lys His Met Ala Asn Ile
```

```
225                 230                 235                 240

Trp Gln Gly Asp Phe Pro Tyr Arg Asn Thr Val Asp Asp Gly Tyr Glu
                245                 250                 255

Tyr Thr Ala Pro Val Gly Ser Phe Pro Ala Asn Asp Tyr Gly Leu Tyr
            260                 265                 270

Asp Met Ala Gly Asn Val Trp Gln Trp Thr Thr Asp Trp Tyr Gln Asp
        275                 280                 285

His Lys Ala Ile Asp Ser Pro Cys Cys Thr Ala Val Asn Pro Arg Gly
    290                 295                 300

Gly His Arg Glu Ala Ser Tyr Asp Thr Arg Leu Pro Asp Val Lys Ile
305                 310                 315                 320

Pro Arg Lys Val Thr Lys Gly Gly Ser His Leu Cys Ala Pro Asn Tyr
                325                 330                 335

Cys Arg Arg Tyr Arg Pro Ala Ala Arg Met Ala Gln Pro Val Asp Thr
            340                 345                 350

Ala Ile Ser His Leu Gly Phe Arg Cys Ile Val Arg Arg Lys Met Glu
        355                 360                 365

Leu Asn Ala Gln
    370
```

<210> SEQ ID NO 63
<211> LENGTH: 1251
<212> TYPE: DNA
<213> ORGANISM: Burkholderia fungorum

<400> SEQUENCE: 63

```
atgaagagtg aaagagatcg agagcccgca aagtcgtccc gctcgaacgg gtcggtcgca     60
gcaacccaaa cgcgcgccgg tcgcgtgcgc aaactaatgt tgtggggcgc cctgctcgtc    120
atactgcccg cctgtgtcgg cgccgcggtc agttgggcct tcacgccgca cgcacccgct    180
cacccgcaaa tcgttttcgg cgacggcacg catggtccgc tcggcatggc gtgggtgccc    240
ggcggccagt tcctcatggg cagcgacgcc aaacaggcgc aaccgaacga acgccccgcg    300
cacaaggtca aggtgcacgg cttctggatg gaccgccatc acgtgaccaa cgccgaattc    360
cgccgcttcg tcgaagcgac cggctacgtc accacggccg agaagaaacc cgactgggag    420
accctgaaag tccagttgcc gcccggcacg ccgcgcccgc ccgagagcgc gatggtggcg    480
ggtgcaatgg tgttcgtcgg caccagccgt cccgtgccgc tagacgacta ttcgcagtgg    540
tggcgctatg tgcctggcgc taactggcgt catccagccg ggcctgagag caacatcatc    600
ggtaaagatg atcaccccgt ggttcaagtg tcctacgaag atgcgcaggc ttatgcgaaa    660
tgggccggca agcgtctgcc gaccgaagcc gaatgggaat tcgccgcgcg cggcggcctc    720
gaacaggcca cgtatgcgtg ggcgatcag ttctctccca acggcaaaca gatggccaac     780
gtctggcagg gccagcagcc gcagtctttc cccgttgtca acccgaaagc gggtggcgcg    840
ctcggtacaa gtccggtggg tactttcccg gccaacggct acggcctttc cgacatgacc    900
ggcaacgcct ggcagtgggt tgccgactgg tatcgcgcgg atcagttcag gcgtgaggcg    960
gtaagcacca gcgcgatcga caatccggtg ggcccgagcg agtcgtggga ccccgcagac   1020
cagggcgtgc ccgtcaacgc gcccaagcgt gtcacacgcg gcggttcgtt cctctgcaac   1080
gaaatctatt gcctgagcta ccggcccagc gcgagacgcg gcaccgatcc ctacaacagc   1140
atgtcgcatc tgggcttccg gctggtgatg gacgaagaca cctggaaaga agccggtgct   1200
cgccaggctt cggcgaaagc tgccggcgcg cctggaaccc ctggcggcta g            1251
```

-continued

```
<210> SEQ ID NO 64
<211> LENGTH: 416
<212> TYPE: PRT
<213> ORGANISM: Burkholderia fungorum

<400> SEQUENCE: 64

Met Lys Ser Glu Arg Asp Arg Glu Pro Ala Lys Ser Ser Arg Ser Asn
1               5                   10                  15

Gly Ser Val Ala Ala Thr Gln Thr Arg Ala Gly Arg Val Arg Lys Leu
            20                  25                  30

Met Leu Trp Gly Ala Leu Leu Val Ile Leu Pro Ala Cys Val Gly Ala
        35                  40                  45

Ala Val Ser Trp Ala Phe Thr Pro His Ala Pro Ala His Pro Gln Ile
    50                  55                  60

Val Phe Gly Asp Gly Thr His Gly Pro Leu Gly Met Ala Trp Val Pro
65                  70                  75                  80

Gly Gly Gln Phe Leu Met Gly Ser Asp Ala Lys Gln Ala Gln Pro Asn
                85                  90                  95

Glu Arg Pro Ala His Lys Val Lys Val His Gly Phe Trp Met Asp Arg
            100                 105                 110

His His Val Thr Asn Ala Glu Phe Arg Arg Phe Val Glu Ala Thr Gly
        115                 120                 125

Tyr Val Thr Thr Ala Glu Lys Lys Pro Asp Trp Glu Thr Leu Lys Val
    130                 135                 140

Gln Leu Pro Pro Gly Thr Pro Arg Pro Pro Glu Ser Ala Met Val Ala
145                 150                 155                 160

Gly Ala Met Val Phe Val Gly Thr Ser Arg Pro Val Pro Leu Asp Asp
                165                 170                 175

Tyr Ser Gln Trp Trp Arg Tyr Val Pro Gly Ala Asn Trp Arg His Pro
            180                 185                 190

Ala Gly Pro Glu Ser Asn Ile Ile Gly Lys Asp Asp His Pro Val Val
        195                 200                 205

Gln Val Ser Tyr Glu Asp Ala Gln Ala Tyr Ala Lys Trp Ala Gly Lys
    210                 215                 220

Arg Leu Pro Thr Glu Ala Glu Trp Glu Phe Ala Ala Arg Gly Gly Leu
225                 230                 235                 240

Glu Gln Ala Thr Tyr Ala Trp Gly Asp Gln Phe Ser Pro Asn Gly Lys
                245                 250                 255

Gln Met Ala Asn Val Trp Gln Gly Gln Gln Pro Gln Ser Phe Pro Val
            260                 265                 270

Val Asn Pro Lys Ala Gly Gly Ala Leu Gly Thr Ser Pro Val Gly Thr
        275                 280                 285

Phe Pro Ala Asn Gly Tyr Gly Leu Ser Asp Met Thr Gly Asn Ala Trp
    290                 295                 300

Gln Trp Val Ala Asp Trp Tyr Arg Ala Asp Gln Phe Arg Arg Glu Ala
305                 310                 315                 320

Val Ser Thr Ser Ala Ile Asp Asn Pro Val Gly Pro Ser Glu Ser Trp
                325                 330                 335

Asp Pro Ala Asp Gln Gly Val Pro Val Asn Ala Pro Lys Arg Val Thr
            340                 345                 350

Arg Gly Gly Ser Phe Leu Cys Asn Glu Ile Tyr Cys Leu Ser Tyr Arg
        355                 360                 365

Pro Ser Ala Arg Arg Gly Thr Asp Pro Tyr Asn Ser Met Ser His Leu
    370                 375                 380

Gly Phe Arg Leu Val Met Asp Glu Asp Thr Trp Lys Glu Ala Gly Ala
```

```
385                 390                 395                 400
Arg Gln Ala Ser Ala Lys Ala Ala Gly Ala Pro Gly Thr Pro Gly Gly
                405                 410                 415

<210> SEQ ID NO 65
<211> LENGTH: 912
<212> TYPE: DNA
<213> ORGANISM: Sinorhizobium meliloti

<400> SEQUENCE: 65
atggtctggg ttcccggagc gaccttcatg atggggtcga acgaccatta cccggaggaa      60
gcgcccgtgc atccggtaac cgtcgacgga ttctggatcg atgtgacacc ggtaacgaac     120
cgccagtttc tcgaattcgt aaatgcgacg gggcatgtga ccttcgcgga agaaagccg      180 cgcgccgaag actatccggg cgctccgcca tccaatctaa gggccggttc gctcgtcttc     240 acaccccga agcgaccgct gcagggaacg gatatatcgc agtggtggat attcacgctg      300
ggtgccaact ggcggcaccc gctcgggcgc aagagcagca tcggagcgat tctggatcat     360
ccggtcgtcc atgtcgctta cagcgacgca aaggcctatg ccgaatgggc cggcaaggac     420
ctcccgaccg agaccgagtg ggagctggcg gcccgcggcg gcctcgatgg ggctgaattt     480
tcctggggcg gcgagcttgc gccgggcgga atcacatgg ccaatacttg cagggaagt      540 tttccggtcg agaattctat ggacgatggt ttcgcgcgaa catcgccggt cagattttac     600
ccgccgaacg gctacggcct ctacgacatg atcggcaatg tgtgggagtg gaccacggat     660
tactggtccg tgcgccaccc ggaagcggcc gccaagcctt gctgcattcc gagcaatccc     720
cgcaatgccg atgccgatgc gagtatcgat ccggcggcga gcgtgaaagt tccgcgccgg     780
gtgctcaagg tggatcgca tctctgcgcg ccgaactact gccggcggta ccgccctgcg     840
gcgaggcacg cccaggaaat cgacgacgac accagccatg tcggtttccg atgtgtcagg     900
cgcgttcgat aa                                                        912

<210> SEQ ID NO 66
<211> LENGTH: 303
<212> TYPE: PRT
<213> ORGANISM: Sinorhizobium meliloti

<400> SEQUENCE: 66

Met Val Trp Val Pro Gly Ala Thr Phe Met Met Gly Ser Asn Asp His
1               5                   10                  15

Tyr Pro Glu Glu Ala Pro Val His Pro Val Thr Val Asp Gly Phe Trp
            20                  25                  30

Ile Asp Val Thr Pro Val Thr Asn Arg Gln Phe Leu Glu Phe Val Asn
        35                  40                  45

Ala Thr Gly His Val Thr Phe Ala Glu Arg Lys Pro Arg Ala Glu Asp
    50                  55                  60

Tyr Pro Gly Ala Pro Pro Ser Asn Leu Arg Ala Gly Ser Leu Val Phe
65                  70                  75                  80

Thr Pro Pro Lys Arg Pro Leu Gln Gly Thr Asp Ile Ser Gln Trp Trp
                85                  90                  95

Ile Phe Thr Leu Gly Ala Asn Trp Arg His Pro Leu Gly Arg Lys Ser
            100                 105                 110

Ser Ile Gly Ala Ile Leu Asp His Pro Val Val His Val Ala Tyr Ser
        115                 120                 125

Asp Ala Lys Ala Tyr Ala Glu Trp Ala Gly Lys Asp Leu Pro Thr Glu
    130                 135                 140
```

-continued

```
Thr Glu Trp Glu Leu Ala Ala Arg Gly Gly Leu Asp Gly Ala Glu Phe
145                 150                 155                 160

Ser Trp Gly Gly Glu Leu Ala Pro Gly Gly Asn His Met Ala Asn Thr
                165                 170                 175

Trp Gln Gly Ser Phe Pro Val Glu Asn Ser Met Asp Asp Gly Phe Ala
            180                 185                 190

Arg Thr Ser Pro Val Arg Phe Tyr Pro Pro Asn Gly Tyr Gly Leu Tyr
        195                 200                 205

Asp Met Ile Gly Asn Val Trp Glu Trp Thr Thr Asp Tyr Trp Ser Val
    210                 215                 220

Arg His Pro Glu Ala Ala Lys Pro Cys Cys Ile Pro Ser Asn Pro
225                 230                 235                 240

Arg Asn Ala Asp Ala Asp Ala Ser Ile Asp Pro Ala Ala Ser Val Lys
                245                 250                 255

Val Pro Arg Arg Val Leu Lys Gly Gly Ser His Leu Cys Ala Pro Asn
            260                 265                 270

Tyr Cys Arg Arg Tyr Arg Pro Ala Ala Arg His Ala Gln Glu Ile Asp
        275                 280                 285

Thr Thr Thr Ser His Val Gly Phe Arg Cys Val Arg Arg Val Arg
    290                 295                 300
```

<210> SEQ ID NO 67
<211> LENGTH: 1065
<212> TYPE: DNA
<213> ORGANISM: Microscilla sp.

<400> SEQUENCE: 67

| | | | | | | |
|---|---|---|---|---|---|---|
| atgaaataca | ttttttagt | tctttttctta | tgggccttga | cccgatgtac | cggaaagtat | 60 |
| gaggacaaga | gagtggaaac | tgatacttcc | agaccaaaag | ccgaagcgtc | agatataaaa | 120 |
| gttcccgaag | gaatggctta | tattcccgcg | ggccagtaca | tgatgggagg | taaatcagac | 180 |
| caggcttata | aggatgaata | tccccgccat | aacgtgaagg | tttcggcttt | ttatatggac | 240 |
| cttacagaag | tgaccaatgc | ggagtttaag | cggtttgtag | acgaaacggg | ctacgtgacc | 300 |
| attgctgaga | agatattga | ctgggaagag | ttaaagtctc | aggtgccaca | gggtaccccg | 360 |
| aagcctcctg | attctgtgct | tcaggcaggt | tcactggttt | tcaagcagac | agatgaaccc | 420 |
| gtttctctcc | aggattattc | acagtggtgg | aatggactca | tcgagccaa | ctggcgaaat | 480 |
| ccggagggtc | caggtagtac | gattgaggat | cgtatggatc | atccggtggt | acacgtttcc | 540 |
| tttgaagatg | tccaagcgta | tgcggattgg | gccggtaagc | gcctgcctac | tgaggcagaa | 600 |
| tgggaatggg | ccgccatggg | aggccaaaat | gacgtgaaat | atccatgggg | aaatgaatcg | 660 |
| gtcgaacaag | catccgataa | agcaaacttt | tggcagggga | attttccaca | tcaaaactat | 720 |
| gccctcgatg | gattcgaacg | caccgcccct | gtacgctcct | tcccagcgaa | tgggtacggc | 780 |
| ctatatgata | tggctggcaa | tgtgtgggaa | tggtgccagg | ataagtatga | tgtcaatgct | 840 |
| tatgaaagct | ataagcaaaa | aggactgaca | gaagacccca | cgggttctga | gcactacaac | 900 |
| gaccctaggg | aaccgtatac | tcctaagcat | gtgatcagag | ggggttcttt | cctatgcaat | 960 |
| gacagctact | gtagtgggta | tcgtgtttca | cgtcgtatga | gttccagtag | agattcaggt | 1020 |
| tttaatcata | cgggattcag | gtgtgtgaaa | gatgtaaatg | gatag | | 1065 |

<210> SEQ ID NO 68
<211> LENGTH: 354
<212> TYPE: PRT
<213> ORGANISM: Microscilla sp.

<400> SEQUENCE: 68

| | | | | | | | | | | | | | | |
|---|---|---|---|---|---|---|---|---|---|---|---|---|---|---|
| Met | Lys | Tyr | Ile | Phe | Leu | Val | Leu | Phe | Leu | Trp | Ala | Leu | Thr | Arg | Cys |
| 1 | | | | 5 | | | | | 10 | | | | | 15 | |
| Thr | Gly | Lys | Tyr | Glu | Asp | Lys | Arg | Val | Glu | Thr | Asp | Thr | Ser | Arg | Pro |
| | | | 20 | | | | | 25 | | | | | 30 | | |
| Lys | Ala | Glu | Ala | Ser | Asp | Ile | Lys | Val | Pro | Glu | Gly | Met | Ala | Tyr | Ile |
| | | | 35 | | | | | 40 | | | | | 45 | | |
| Pro | Ala | Gly | Gln | Tyr | Met | Met | Gly | Gly | Lys | Ser | Asp | Gln | Ala | Tyr | Lys |
| | 50 | | | | | 55 | | | | | 60 | | | | |
| Asp | Glu | Tyr | Pro | Arg | His | Asn | Val | Lys | Val | Ser | Ala | Phe | Tyr | Met | Asp |
| 65 | | | | | 70 | | | | | 75 | | | | | 80 |
| Leu | Thr | Glu | Val | Thr | Asn | Ala | Glu | Phe | Lys | Arg | Phe | Val | Asp | Glu | Thr |
| | | | | 85 | | | | | 90 | | | | | 95 | |
| Gly | Tyr | Val | Thr | Ile | Ala | Glu | Lys | Asp | Ile | Asp | Trp | Glu | Glu | Leu | Lys |
| | | | 100 | | | | | 105 | | | | | 110 | | |
| Ser | Gln | Val | Pro | Gln | Gly | Thr | Pro | Lys | Pro | Pro | Asp | Ser | Val | Leu | Gln |
| | | | 115 | | | | | 120 | | | | | 125 | | |
| Ala | Gly | Ser | Leu | Val | Phe | Lys | Gln | Thr | Asp | Glu | Pro | Val | Ser | Leu | Gln |
| | 130 | | | | | 135 | | | | | 140 | | | | |
| Asp | Tyr | Ser | Gln | Trp | Trp | Glu | Trp | Thr | Ile | Gly | Ala | Asn | Trp | Arg | Asn |
| 145 | | | | | 150 | | | | | 155 | | | | | 160 |
| Pro | Glu | Gly | Pro | Gly | Ser | Thr | Ile | Glu | Asp | Arg | Met | Asp | His | Pro | Val |
| | | | | 165 | | | | | 170 | | | | | 175 | |
| Val | His | Val | Ser | Phe | Glu | Asp | Val | Gln | Ala | Tyr | Ala | Asp | Trp | Ala | Gly |
| | | | 180 | | | | | 185 | | | | | 190 | | |
| Lys | Arg | Leu | Pro | Thr | Glu | Ala | Glu | Trp | Glu | Trp | Ala | Ala | Met | Gly | Gly |
| | | | 195 | | | | | 200 | | | | | 205 | | |
| Gln | Asn | Asp | Val | Lys | Tyr | Pro | Trp | Gly | Asn | Glu | Ser | Val | Glu | Gln | Ala |
| | 210 | | | | | 215 | | | | | 220 | | | | |
| Ser | Asp | Lys | Ala | Asn | Phe | Trp | Gln | Gly | Asn | Phe | Pro | His | Gln | Asn | Tyr |
| 225 | | | | | 230 | | | | | 235 | | | | | 240 |
| Ala | Leu | Asp | Gly | Phe | Glu | Arg | Thr | Ala | Pro | Val | Arg | Ser | Phe | Pro | Ala |
| | | | | 245 | | | | | 250 | | | | | 255 | |
| Asn | Gly | Tyr | Gly | Leu | Tyr | Asp | Met | Ala | Gly | Asn | Val | Trp | Glu | Trp | Cys |
| | | | 260 | | | | | 265 | | | | | 270 | | |
| Gln | Asp | Lys | Tyr | Asp | Val | Asn | Ala | Tyr | Glu | Ser | Tyr | Lys | Gln | Lys | Gly |
| | | | 275 | | | | | 280 | | | | | 285 | | |
| Leu | Thr | Glu | Asp | Pro | Thr | Gly | Ser | Glu | His | Tyr | Asn | Asp | Pro | Arg | Glu |
| | 290 | | | | | 295 | | | | | 300 | | | | |
| Pro | Tyr | Thr | Pro | Lys | His | Val | Ile | Arg | Gly | Gly | Ser | Phe | Leu | Cys | Asn |
| 305 | | | | | 310 | | | | | 315 | | | | | 320 |
| Asp | Ser | Tyr | Cys | Ser | Gly | Tyr | Arg | Val | Ser | Arg | Met | Ser | Ser | Ser |
| | | | | 325 | | | | | 330 | | | | | 335 |
| Arg | Asp | Ser | Gly | Phe | Asn | His | Thr | Gly | Phe | Arg | Cys | Val | Lys | Asp | Val |
| | | | 340 | | | | | 345 | | | | | 350 | | |
| Asn | Gly | | | | | | | | | | | | | | |

<210> SEQ ID NO 69
<211> LENGTH: 876
<212> TYPE: DNA
<213> ORGANISM: Pseudomonas putida KT2440

<400> SEQUENCE: 69
atggtgcacg tgccgggcgg cgagttcagc tttggttcaa gccgctttta cgacgaagaa    60

-continued

```
ggcccgcctc acccgccaa ggtgtccggc ttctggattg acgtgcatcc ggtcaccaac    120
gcccagttcg cgcgcttcgt caaggccacg gggtatgtca cccatgccga gcgcggtacc    180
cgtgtcgagg acgaccctgc cctgcccgac gcgctgcgga taccgggtgc gatggtgttt    240
catcagggtg cggacgtgct cggccccggc tggcagttcg tgcccggcgc caactggcga    300
cacccgcaag ggccgggcag cagcctggcc gggctggaca accatccggt ggtgcagatc    360
gccctggaag atgcccaggc ctatgcccgc tgggcaggcc gcgaactgcc cagcgaggcg    420
cagctggaat acgccatgcg cggcggcctg accgatgccg acttcagctg ggtaccacc     480 gagcagccca aggcaagct catggccaat acctggcagg gtcagttccc ttatcgcaat     540
gcggcgaagg atggttttac cggtacatcg cccgtgggtt gcttcccggc caacggcttt    600
ggcctgttcg atgccggcgg caatgtctgg gagctgactc gcacgggcta tcggccaggc    660
catgacgcac agcgcgacgc caagctcgac ccctcaggcc cggccctgag tgacagcttc    720
gacccggcag accccggcgt gccggtggcg gtaatcaaag gcggctcgca cctgtgttcg    780
gcggaccgct gcatgcgcta ccgcccctcg gcacgccagc cgcagccggt gttcatgacg    840
acctcgcacg tgggttcag aacgattcgg caatga                             876
```

<210> SEQ ID NO 70
<211> LENGTH: 291
<212> TYPE: PRT
<213> ORGANISM: Pseudomonas putida KT2440

<400> SEQUENCE: 70

```
Met Val His Val Pro Gly Gly Glu Phe Ser Phe Gly Ser Ser Arg Phe
1               5                   10                  15

Tyr Asp Glu Glu Gly Pro Pro His Pro Ala Lys Val Ser Gly Phe Trp
            20                  25                  30

Ile Asp Val His Pro Val Thr Asn Ala Gln Phe Ala Arg Phe Val Lys
        35                  40                  45

Ala Thr Gly Tyr Val Thr His Ala Glu Arg Gly Thr Arg Val Glu Asp
    50                  55                  60

Asp Pro Ala Leu Pro Asp Ala Leu Arg Ile Pro Gly Ala Met Val Phe
65                  70                  75                  80

His Gln Gly Ala Asp Val Leu Gly Pro Gly Trp Gln Phe Val Pro Gly
                85                  90                  95

Ala Asn Trp Arg His Pro Gln Gly Pro Gly Ser Ser Leu Ala Gly Leu
            100                 105                 110

Asp Asn His Pro Val Val Gln Ile Ala Leu Glu Asp Ala Gln Ala Tyr
        115                 120                 125

Ala Arg Trp Ala Gly Arg Glu Leu Pro Ser Glu Ala Gln Leu Glu Tyr
    130                 135                 140

Ala Met Arg Gly Gly Leu Thr Asp Ala Asp Phe Ser Trp Gly Thr Thr
145                 150                 155                 160

Glu Gln Pro Lys Gly Lys Leu Met Ala Asn Thr Trp Gln Gly Gln Phe
                165                 170                 175

Pro Tyr Arg Asn Ala Ala Lys Asp Gly Phe Thr Gly Thr Ser Pro Val
            180                 185                 190

Gly Cys Phe Pro Ala Asn Gly Phe Gly Leu Phe Asp Ala Gly Gly Asn
        195                 200                 205

Val Trp Glu Leu Thr Arg Thr Gly Tyr Arg Pro Gly His Asp Ala Gln
    210                 215                 220

Arg Asp Ala Lys Leu Asp Pro Ser Gly Pro Ala Leu Ser Asp Ser Phe
225                 230                 235                 240
```

Asp Pro Ala Asp Pro Gly Val Pro Val Ala Val Ile Lys Gly Gly Ser
            245                 250                 255

His Leu Cys Ser Ala Asp Arg Cys Met Arg Tyr Arg Pro Ser Ala Arg
        260                 265                 270

Gln Pro Gln Pro Val Phe Met Thr Thr Ser His Val Gly Phe Arg Thr
    275                 280                 285

Ile Arg Gln
    290

<210> SEQ ID NO 71
<211> LENGTH: 780
<212> TYPE: DNA
<213> ORGANISM: Ralstonia metallidurans

<400> SEQUENCE: 71

```
atggtcgcgg gcgggatggt gttcgtcggc accaacagcc cggtgccgct gcgcgaatac      60
tggcgctggt ggcgcttcgt acctggcgcg gactggcgtc acccgaccgg cccgggcagt     120
tccatcgaag caaggacaa tcatcccgtc gtgcaggtct cgtatgaaga cgcgcaggcg     180
tacgccaagt gggccggcaa gcgtctgccc accgaggccg agtgggagtt tgccgcccgt     240
ggcggcctgg agcaggccac ctacgcctgg ggtgacaagt tcgcgccgga tggccggcag     300
atggcgaatg tctggcaggg ccagcaggtg cagccgttcc cggtggtcag cgccaaggcg     360
ggcggcgcgg ctggcaccag tgctgtcggc acgttcccgg caatggcta tgggctctat     420
gacatgaccg gcaacgcctg gcagtgggtg gccgactggt atcgcgcgga ccagttccgc     480
cgcgaagcca cggtggcggc agtgctgcag aatccgaccg gcccggccga ttcgtgggac     540
ccgaccgaac ctggcgtgcc ggtgtcggcg cccaagcggg tcacgcgcgg tggctcgttc     600
ctctgcaacg aggacttctg cctcagctac cgcccgagtg cccggcgcgg taccgacccg     660
tacaccagca tgtcgcacct aggcttccgg ctcgtgatgg atgacgcccg ttgggcagaa     720
gttcgcaagc agccagccgt ggcaatggcc gcgggcgggc agcagaacgt gcagaaataa     780
```

<210> SEQ ID NO 72
<211> LENGTH: 259
<212> TYPE: PRT
<213> ORGANISM: Ralstonia metallidurans

<400> SEQUENCE: 72

Met Val Ala Gly Gly Met Val Phe Val Gly Thr Asn Ser Pro Val Pro
1               5                   10                  15

Leu Arg Glu Tyr Trp Arg Trp Trp Arg Phe Val Pro Gly Ala Asp Trp
            20                  25                  30

Arg His Pro Thr Gly Pro Gly Ser Ser Ile Glu Gly Lys Asp Asn His
        35                  40                  45

Pro Val Val Gln Val Ser Tyr Glu Asp Ala Gln Ala Tyr Ala Lys Trp
    50                  55                  60

Ala Gly Lys Arg Leu Pro Thr Glu Ala Glu Trp Glu Phe Ala Ala Arg
65                  70                  75                  80

Gly Gly Leu Glu Gln Ala Thr Tyr Ala Trp Gly Asp Lys Phe Ala Pro
                85                  90                  95

Asp Gly Arg Gln Met Ala Asn Val Trp Gln Gly Gln Gln Val Gln Pro
            100                 105                 110

Phe Pro Val Val Ser Ala Lys Ala Gly Gly Ala Ala Gly Thr Ser Ala
        115                 120                 125

Val Gly Thr Phe Pro Gly Asn Gly Tyr Gly Leu Tyr Asp Met Thr Gly

```
                130             135             140
Asn Ala Trp Gln Trp Val Ala Asp Trp Tyr Arg Ala Asp Gln Phe Arg
145                 150                 155                 160

Arg Glu Ala Thr Val Ala Ala Val Leu Gln Asn Pro Thr Gly Pro Ala
                165                 170                 175

Asp Ser Trp Asp Pro Thr Glu Pro Gly Val Pro Val Ser Ala Pro Lys
            180                 185                 190

Arg Val Thr Arg Gly Gly Ser Phe Leu Cys Asn Glu Asp Phe Cys Leu
        195                 200                 205

Ser Tyr Arg Pro Ser Ala Arg Arg Gly Thr Asp Pro Tyr Thr Ser Met
    210                 215                 220

Ser His Leu Gly Phe Arg Leu Val Met Asp Asp Ala Arg Trp Ala Glu
225                 230                 235                 240

Val Arg Lys Gln Pro Ala Val Ala Met Ala Ala Gly Gly Gln Gln Asn
                245                 250                 255

Val Gln Lys

<210> SEQ ID NO 73
<211> LENGTH: 876
<212> TYPE: DNA
<213> ORGANISM: Prochlorococcus marinus

<400> SEQUENCE: 73
gtgaccacat ctttgccagt agagatggta accatccccg cagggctcta tcgagttggc      60
tgtgatcgct gctatccgga tggttcagtt cgctgctatc cggaggaaac acccgcgcga     120
gaagtgcagc ttgactcatt ccagatcgac gtagggccag tcaccaatgc cagttccga     180
gctttcgtta cgccacgca gcatctcaca gtctcggagc taccacctga tccaacgctc     240
tatcccgatc tagcgcccga ggaacgcatc cctgaatcag ttgtctttca accgcctcca     300
gcaacggtgg atcgcagcaa acccttgagc tggtggaccc tcatggctgg ggctgattgg     360
cgtcatcccc aaggacccga agcacgatc gatggccttg atgatcaccc tgtcgtgcat     420
gtcgcctatg ccgacgccat cgcctatgcc cattgggctg caagcgtct ccctctgct     480
gaagagtggg aagtagccgc ccgcggggt cttgtcgatg cccaatacgc tgggggaat     540
gaactcactc ccaataaccg ctggatggcg aacatctggc aaggtccttt cccttggcac     600
aacgaggagc tagacggctg gttctggacc tcgcccgttg gcagctttcc tgccaacggc     660
tatggactct ggatgtttg cggcaatgtg tgggaatgga ccaactctgt ttatcccgtg     720
gcgtcaggcc accaggaacg gcgaactatc aaaggcggat cgtttctctg cgcagataat     780
tactgcgtac gttatcgacc ctctgcacta caaggccaga cagtagacac tgccacctgt     840
cacatgggct ttcgctgtgc aaaaggaggg ccttga                               876

<210> SEQ ID NO 74
<211> LENGTH: 291
<212> TYPE: PRT
<213> ORGANISM: Prochlorococcus marinus

<400> SEQUENCE: 74

Met Thr Thr Ser Leu Pro Val Glu Met Val Thr Ile Pro Ala Gly Leu
1               5                   10                  15

Tyr Arg Val Gly Cys Asp Arg Cys Tyr Pro Asp Gly Ser Val Arg Cys
            20                  25                  30

Tyr Pro Glu Glu Thr Pro Ala Arg Glu Val Gln Leu Asp Ser Phe Gln
        35                  40                  45
```

| | | | | | | | | | | | | |
|---|---|---|---|---|---|---|---|---|---|---|---|---|
|Ile|Asp|Val|Gly|Pro|Val|Thr|Asn|Ala|Gln|Phe|Arg|Ala|Phe|Val|Ser|
| |50| | | | |55| | | | |60| | | | |

Ala Thr Gln His Leu Thr Val Ser Glu Leu Pro Asp Pro Thr Leu
65                  70                  75                  80

Tyr Pro Asp Leu Ala Pro Glu Glu Arg Ile Pro Glu Ser Val Val Phe
                85                  90                  95

Gln Pro Pro Pro Ala Thr Val Asp Arg Ser Lys Pro Leu Ser Trp Trp
            100                 105                 110

Thr Leu Met Ala Gly Ala Asp Trp Arg His Pro Gln Gly Pro Glu Ser
            115                 120                 125

Thr Ile Asp Gly Leu Asp Asp His Pro Val Val His Val Ala Tyr Ala
            130                 135                 140

Asp Ala Ile Ala Tyr Ala His Trp Ala Gly Lys Arg Leu Pro Ser Ala
145                 150                 155                 160

Glu Glu Trp Glu Val Ala Ala Arg Gly Gly Leu Val Asp Ala Gln Tyr
                165                 170                 175

Ala Trp Gly Asn Glu Leu Thr Pro Asn Asn Arg Trp Met Ala Asn Ile
            180                 185                 190

Trp Gln Gly Pro Phe Pro Trp His Asn Glu Glu Leu Asp Gly Trp Phe
            195                 200                 205

Trp Thr Ser Pro Val Gly Ser Phe Pro Ala Asn Gly Tyr Gly Leu Leu
            210                 215                 220

Asp Val Cys Gly Asn Val Trp Glu Trp Thr Asn Ser Val Tyr Pro Val
225                 230                 235                 240

Ala Ser Gly His Gln Glu Arg Arg Thr Ile Lys Gly Ser Phe Leu
                245                 250                 255

Cys Ala Asp Asn Tyr Cys Val Arg Tyr Arg Pro Ser Ala Leu Gln Gly
            260                 265                 270

Gln Thr Val Asp Thr Ala Thr Cys His Met Gly Phe Arg Cys Ala Lys
            275                 280                 285

Gly Gly Pro
    290

<210> SEQ ID NO 75
<211> LENGTH: 1017
<212> TYPE: DNA
<213> ORGANISM: Caulobacter crescentus CB15

<400> SEQUENCE: 75

```
ttgggaaaac tgacggcgct tcccgtcctg atgcttctgg cgctggccgg ctgcggccag     60
ccggcgccca aggcttgcct ggcggacctg ccggttccag atccccagaa ccgcacggcg    120
ggtatggttc ggctggcggg cggcgacttc cagatgggcg ctgcgccgct cgtccggag    180 gagggaccgc cccagacggt cacggtcccg ccgttctgga tcgatcagac agaggtcacc    240
aacgccgcct tcgcgcggtt cgtcgaggcc acgggttatc gcaccgtggc cgagcgaccg    300
ctcgaccccg cgcgctacgc ccacgtaccg gcggcgcagc ggcgtccggc ctcgctcgtc    360
ttcgtggggg cgaaggggc gaggtcggac gatccttccc aatggtggca ggtgatcccc    420
ggcgccgact ggcggcatcc cgaaggtccc ggctcgaaca tccggggcag ggacgcctgg    480
ccggtggtgc atatcgcgtg ggaggacgcc atggcctacg cccgctggct gggccgtgac    540
ctgcccacag aggccgaatg ggagtacgcc gcgcgcggcg ggctggttgg caagcgctac    600
acctggggcg accaggctca ggatcctgca aagccgcgcg ccaatacttg caaggcgtg    660 ttcccggccc aggaccttgg caatgacggc ttcaaggcca agcccgcgcc ggtcggctgc    720
```

-continued

```
ttcccgccca acggctatgg cctgcgcgac atggccggca atgtctggga gtggacccgc    780
gactggttca agccgggcct ggatccggtc agcgtcctcg aaaccggcgg ccgcccgag     840 gcccgcgcgc tggatcccga ggacccgaac acgcccaagc acgtcgtgaa gggcggttcg    900
ttcctgtgcg ccgacgacta ctgcttccgc tatcgacctg cggcgcgaac gccggggccg    960
ccggacagcg gcgcatcgca tgtcggtttc cgcaccgtgc tccgcgccga gcgctga     1017
```

<210> SEQ ID NO 76
<211> LENGTH: 338
<212> TYPE: PRT
<213> ORGANISM: Caulobacter crescentus CB15

<400> SEQUENCE: 76

```
Met Gly Lys Leu Thr Ala Leu Pro Val Leu Met Leu Ala Leu Ala
1               5                   10                  15

Gly Cys Gly Gln Pro Ala Pro Lys Ala Cys Leu Ala Asp Leu Pro Val
                20                  25                  30

Pro Asp Pro Gln Asn Arg Thr Ala Gly Met Val Arg Leu Ala Gly Gly
            35                  40                  45

Asp Phe Gln Met Gly Ala Ala Pro Leu Arg Pro Glu Glu Gly Pro Pro
        50                  55                  60

Gln Thr Val Thr Val Pro Pro Phe Trp Ile Asp Gln Thr Glu Val Thr
65                  70                  75                  80

Asn Ala Ala Phe Ala Arg Phe Val Glu Ala Thr Gly Tyr Arg Thr Val
                85                  90                  95

Ala Glu Arg Pro Leu Asp Pro Ala Arg Tyr Ala His Val Pro Ala Ala
            100                 105                 110

Gln Arg Arg Pro Ala Ser Leu Val Phe Val Gly Ala Lys Gly Ala Arg
        115                 120                 125

Ser Asp Asp Pro Ser Gln Trp Trp Gln Val Ile Pro Gly Ala Asp Trp
    130                 135                 140

Arg His Pro Glu Gly Pro Gly Ser Asn Ile Arg Gly Arg Asp Ala Trp
145                 150                 155                 160

Pro Val Val His Ile Ala Trp Glu Asp Ala Met Ala Tyr Ala Arg Trp
                165                 170                 175

Leu Gly Arg Asp Leu Pro Thr Glu Ala Glu Trp Glu Tyr Ala Ala Arg
            180                 185                 190

Gly Gly Leu Val Gly Lys Arg Tyr Thr Trp Gly Asp Gln Ala Gln Asp
        195                 200                 205

Pro Ala Lys Pro Arg Ala Asn Thr Trp Gln Gly Val Phe Pro Ala Gln
    210                 215                 220

Asp Leu Gly Asn Asp Gly Phe Lys Ala Lys Pro Ala Pro Val Gly Cys
225                 230                 235                 240

Phe Pro Pro Asn Gly Tyr Gly Leu Arg Asp Met Ala Gly Asn Val Trp
                245                 250                 255

Glu Trp Thr Arg Asp Trp Phe Lys Pro Gly Leu Asp Pro Val Ser Val
            260                 265                 270

Leu Glu Thr Gly Gly Pro Pro Glu Ala Arg Ala Leu Asp Pro Glu Asp
        275                 280                 285

Pro Asn Thr Pro Lys His Val Val Lys Gly Gly Ser Phe Leu Cys Ala
    290                 295                 300

Asp Asp Tyr Cys Phe Arg Tyr Arg Pro Ala Ala Arg Thr Pro Gly Pro
305                 310                 315                 320

Pro Asp Ser Gly Ala Ser His Val Gly Phe Arg Thr Val Leu Arg Ala
                325                 330                 335
```

Glu Arg

<210> SEQ ID NO 77
<211> LENGTH: 900
<212> TYPE: DNA
<213> ORGANISM: Mycobacterium tuberculosis H37Rv

<400> SEQUENCE: 77

```
gtgctgaccg agttggttga cctgcccggc ggatcgttcc gcatgggctc gacgcgcttc      60
taccccgaag aagcgccgat tcataccgtg accgtgcgcg cctttgcggt agagcgacac     120
ccggtgacca acgcgcaatt tgccgaattc gtctccgcga caggctatgt gacggttgca     180
gaacaacccc ttgaccccgg gctctaccca ggagtggacg cagcagacct gtgtcccggt     240
gcgatggtgt tttgtccgac ggccgggccg gtcgacctgc gtgactggcg caatggtgg      300
gactgggtac ctggcgcctg ctggcgccat ccgtttggcc gggacagcga tatcgccgac     360
cgagccggcc acccggtcgt acaggtggcc tatccggacg ccgtggccta cgcacgatgg     420
gctggtcgac gcctaccgac cgaggccgag tgggagtacg cggcccgtgg cggaaccacg     480
gcaacctatg cgtggggcga ccaggagaag ccggggggca tgctcatggc gaacacctgg     540
cagggccggt ttccttaccg caacgacggt gcattgggct gggtgggaac ctccccggtg     600
ggcaggtttc cggccaacgg gtttggcttg ctcgacatga tcggaaacgt ttgggagtgg     660
accaccaccg agttctatcc acaccatcgc atcgatccac cctcgacggc tgctgcgca      720
ccggtcaagc tcgctacagc cgccgacccg acgatcagcc agaccctcaa gggcggctcg     780
cacctgtgcg cgccggagta ctgccaccgc taccgcccgg cggcgcgctc gccgcagtcg     840
caggacaccg cgaccaccca tatcgggttc cggtgcgtgg ccgacccggt gtccgggtag     900
```

<210> SEQ ID NO 78
<211> LENGTH: 299
<212> TYPE: PRT
<213> ORGANISM: Mycobacterium tuberculosis H37Rv

<400> SEQUENCE: 78

```
Met Leu Thr Glu Leu Val Asp Leu Pro Gly Gly Ser Phe Arg Met Gly
1               5                   10                  15

Ser Thr Arg Phe Tyr Pro Glu Glu Ala Pro Ile His Thr Val Thr Val
            20                  25                  30

Arg Ala Phe Ala Val Glu Arg His Pro Val Thr Asn Ala Gln Phe Ala
        35                  40                  45

Glu Phe Val Ser Ala Thr Gly Tyr Val Thr Val Ala Glu Gln Pro Leu
    50                  55                  60

Asp Pro Gly Leu Tyr Pro Gly Val Asp Ala Ala Asp Leu Cys Pro Gly
65                  70                  75                  80

Ala Met Val Phe Cys Pro Thr Ala Gly Pro Val Asp Leu Arg Asp Trp
                85                  90                  95

Arg Gln Trp Trp Asp Trp Val Pro Gly Ala Cys Trp Arg His Pro Phe
            100                 105                 110

Gly Arg Asp Ser Asp Ile Ala Asp Arg Ala Gly His Pro Val Val Gln
        115                 120                 125

Val Ala Tyr Pro Asp Ala Val Ala Tyr Ala Arg Trp Ala Gly Arg Arg
    130                 135                 140

Leu Pro Thr Glu Ala Glu Trp Glu Tyr Ala Ala Arg Gly Gly Thr Thr
145                 150                 155                 160

Ala Thr Tyr Ala Trp Gly Asp Gln Glu Lys Pro Gly Gly Met Leu Met
```

```
                    165                 170                 175
Ala Asn Thr Trp Gln Gly Arg Phe Pro Tyr Arg Asn Asp Gly Ala Leu
            180                 185                 190

Gly Trp Val Gly Thr Ser Pro Val Gly Arg Phe Pro Ala Asn Gly Phe
        195                 200                 205

Gly Leu Leu Asp Met Ile Gly Asn Val Trp Glu Trp Thr Thr Thr Glu
        210                 215                 220

Phe Tyr Pro His His Arg Ile Asp Pro Pro Ser Thr Ala Cys Cys Ala
225                 230                 235                 240

Pro Val Lys Leu Ala Thr Ala Ala Asp Pro Thr Ile Ser Gln Thr Leu
                245                 250                 255

Lys Gly Gly Ser His Leu Cys Ala Pro Glu Tyr Cys His Arg Tyr Arg
            260                 265                 270

Pro Ala Ala Arg Ser Pro Gln Ser Gln Asp Thr Ala Thr Thr His Ile
        275                 280                 285

Gly Phe Arg Cys Val Ala Asp Pro Val Ser Gly
        290                 295

<210> SEQ ID NO 79
<211> LENGTH: 7
<212> TYPE: PRT
<213> ORGANISM: Artificial Sequence
<220> FEATURE:
<223> OTHER INFORMATION: conserved domain in prokaryotes and prokaryotes
<220> FEATURE:
<221> NAME/KEY: MISC_FEATURE
<222> LOCATION: 3, 4
<223> OTHER INFORMATION: Any amino acid
<220> FEATURE:
<221> NAME/KEY: MISC_FEATURE
<222> LOCATION: 6
<223> OTHER INFORMATION: Gly or Ala

<400> SEQUENCE: 79

Arg Val Xaa Xaa Gly Xaa Ser
1               5

<210> SEQ ID NO 80
<211> LENGTH: 630
<212> TYPE: DNA
<213> ORGANISM: Oncorhynchus mykiss

<400> SEQUENCE: 80
tcaggtggct gctgcccct  ggtggttgcc tgtcagagga gcagactgga ggcaccctga      60 gggcccccgac tccagcatca cagacaggct ggaccaccct gtgctgcatg tgtcatggca   120
ggacgctgtg gcctactgct cctgggccta caagagacta cccacagagg ctgagtggga   180
gtacgcctgc agagggggcc tacaggagag actttacccg tggggaaca  aactgaaacc   240 taaaggacag cactacgcca acctctggca gggaaagttc cccacacaca actcagaaga   300
ggacgggtac actaaaacct caccagtgaa gtcatttcct gcaaatggct atggcctgta   360
caacatggta gggaatgcat gggagtggac atctgactgg tggactgtac accacaccac   420
agatgaacag cacaacccgg caggtccacc atcaggcaca gaccgagtga agaaaggagg   480
ctcctacatg tgccataagt catactgtta caggtacagg tgtgcagcac ggagtcagaa   540
cacccctgac agctctgcct ctaacctagg gttccgctgt gtctcccagg agcagccgta   600
acctttcacc ctcgaccctg acatgggtag                                     630

<210> SEQ ID NO 81
<211> LENGTH: 655
```

<212> TYPE: DNA
<213> ORGANISM: Danio rerio
<220> FEATURE:
<221> NAME/KEY: misc_feature
<222> LOCATION: 590
<223> OTHER INFORMATION: n is a, c, g, or t
<220> FEATURE:
<221> NAME/KEY: misc_feature
<222> LOCATION: 626
<223> OTHER INFORMATION: n is a, c, g, or t

<400> SEQUENCE: 81

```
caaatggttt tatttacata aaaaaatcct cttagtttga agtgtaagac agtgagatta      60
gtgatgtttg aggttatgga tcaacatcag aggcgcagcg aagcccaag ttcgaggctg     120
aactgtccgg tgtgttctga ctgcgagcgg cacacctgta tctgtagcag taagacttgt    180
ggcacatgta ggatcctcct ttcttgactc tgtctgtccc tgattctggt ccctttgggt    240
taaacttgtc ttctgcagtg tgatgcacag tccaccagtc tgccgtccac tcccacgcat    300
ttcccaccat gtcatacagg ccaaagccat gggaggaaa agacatcacc ggggatgtgt     360
tggcatagcc gtcctctgca gtgttgtgat tagggaaatc tccctgccac aggttagcat    420
agtgctgccc tcttggcatt aatttatttc cccatgggta catcctgtcc tgtagtcctc    480
ctctacaggc caactcccat tcagcttctg taggaagtct gcgtttggcc cattgacagt    540
acgcccgtgc atcatcccat gaaacatgca gagcagggtg attcattctn gtgtgtatgg    600
ttgaatctgg tcctttctgg tgtctncagt ctgcacccttt cactggtgac cacca        655
```

<210> SEQ ID NO 82
<211> LENGTH: 773
<212> TYPE: DNA
<213> ORGANISM: Oryzias latipes
<220> FEATURE:
<221> NAME/KEY: misc_feature
<222> LOCATION: 690
<223> OTHER INFORMATION: n is a, c, g, or t
<220> FEATURE:
<221> NAME/KEY: misc_feature
<222> LOCATION: 755
<223> OTHER INFORMATION: n is a, c, g, or t

<400> SEQUENCE: 82

```
tctcctttt tccataaata acattagagt ccttacattc tgcctttaca tacattgtca      60
gagacagtac aaaaaatctg cctttgtaaa attagagtta caaaaatata ttttagattt    120
gacttcttca gaattgtcgg tggcagcaaa agaatcggat tgatctcatg acaagagcgt    180
gagccagaag ttcttggatc aaactgattt ggttctgtca tcgtttctgt tcagcagcac    240
agcgaaaacc aagattggaa gcggagctgt ctggagtgtt ttggcttcga gcagcacatc    300
tgtacctgta acaataagac ttgtggcaca tgtacgagcc tcctttcttc accttatctg    360
tgcctgacgg aggacccgtt gggttgtgct gatggtctgt tgtgtggtgc acgctccacc    420
agtctgaggt ccactcccat gcgttcccca ccatgtcata cagaccaaaa gcattgcctg    480
ggaaggacat caccggggag gttttagtgt agccatcctc tgcagagttg tgtgctggga    540
attcccctg ccagaggttg gcgtaatgct gtcccttgg gtttagcttg tttccccagg      600
ggtagagtct gtccttcagg ccgcccctgc aggcaacctc ccactctgcc tcagtgggaa    660
gtctcttgtt gacccaggag cagtaagccn aggcatcatt cccagaaacc tgaacgacgg    720
atgatccatc ctgtctgtga tgttggagtc tggancttca gggtgcttcc agt           773
```

<210> SEQ ID NO 83
<211> LENGTH: 566

<212> TYPE: DNA
<213> ORGANISM: Xenopus laevis
<220> FEATURE:
<221> NAME/KEY: misc_feature
<222> LOCATION: 6
<223> OTHER INFORMATION: n is a, c, g, or t
<220> FEATURE:
<221> NAME/KEY: misc_feature
<222> LOCATION: 47
<223> OTHER INFORMATION: n is a, c, g, or t
<220> FEATURE:
<221> NAME/KEY: misc_feature
<222> LOCATION: 81
<223> OTHER INFORMATION: n is a, c, g, or t

<400> SEQUENCE: 83

| | | | | | |
|---|---|---|---|---|---|
| atatgnaact | aaaggtaatg | taattggaat | gatggatttc | acaaggnctg | agagttccct | 60
| attgctcctg | cttgtcgtgt | nacaggtcac | ggagccggcg | ccacacagcg | aaatcccagg | 120
| ttggaggccg | agctgtcggg | tgtattctga | cttcgagcag | cacagcgata | cctgtagcaa | 180
| taggactcat | ggcacatgta | ggagcctcct | ttcttcactc | tatcatttcc | cgtagaaggt | 240
| cctttcgggt | tgtgaacctc | atctgctgta | tgatgagtgt | cccaccaatc | agatgtccac | 300
| tcccaagcat | ttcccaccat | gttatataga | ccataaccat | tggctgggaa | agcagttaca | 360
| ggtgaagtct | gcacataacc | atcctctcca | gtgttttggg | ttggaaaatc | ccctgccag | 420
| acattcgcat | aatgttgtcc | ctttggttcc | agcttgttcc | cccatggaaa | aatcctgttc | 480
| tcaagtcccc | cgcggcaggc | gtattcccac | tcagcttcag | ttggaaggcg | tttacctgcc | 540
| caggtgcaga | aagcagaagc | atcatt | | | | 566

<210> SEQ ID NO 84
<211> LENGTH: 647
<212> TYPE: DNA
<213> ORGANISM: Silurana tropicalis

<400> SEQUENCE: 84

| | | | | | |
|---|---|---|---|---|---|
| gccgcttttt | tttttttttt | tttttttttt | catcacaaaa | ataatttat | taataaaata | 60
| ggattttgtg | ttcattctta | ttatgaagga | caaggaatgt | cattgaaatt | tttgttttca | 120
| caaggtcttg | ggagttcctt | cctgctcagg | tcattttgca | gtggtcacgg | agccgacgcc | 180
| acgcagcgga | atcccaggtt | agaggccgag | ctgtcaggtg | tattctgact | tcgagcagca | 240
| cagcgatacc | tgtagcagta | ggactcatgg | cacatgtatg | agcctccttt | tttcaccttg | 300
| tcttttcccg | taaaaggacc | tttcggggttg | taagtctcat | ctgctgtatg | atgagtgtcc | 360
| caccaatcgg | atgtccactc | ccaagcattt | cccaccatgt | tatataggct | ataaccattg | 420
| gctgggaaag | cggttacagg | tgaagtctgc | acatagccgt | cctctccagt | gttttgggtt | 480
| ggaaattccc | cctgccagac | attcgcataa | tgttctccct | ttggttccag | cttgttcccc | 540
| cacggaaaaa | gcctgttctc | aagtccccca | cgggaggcat | attcccactc | agcttctgtc | 600
| ggaaggcgct | tacccgccca | ggtgcagaag | gcagaagcat | cgttcca | | 647

<210> SEQ ID NO 85
<211> LENGTH: 636
<212> TYPE: DNA
<213> ORGANISM: Salmo salar

<400> SEQUENCE: 85

| | | | | | |
|---|---|---|---|---|---|
| atagacattt | tttaaatatt | ttacaacaaa | atatattcca | taaatatcca | catgtcatgc | 60
| ggtaatcctg | catttcatga | agaacactga | catcactggc | tgtatgaaga | ggtgcacttg | 120
| atttgtttcg | cctggcgggc | aagataggca | gagttagcac | cctagactag | agccaatggc | 180

```
gaatggtaca aaaagggaaa agtcagacta cccatgtcag ggtcaagggt aaaaggttac    240
ggctgctcct gggagacaca gcggaaccct aggttagagg cagagctgtc aggggtgttc    300
tgactccgtg ctgcacacct gtacctgtaa cagtatgact tatggcacat gtaggagcct    360
cctttcttca ctcggtctgt gcctgatggt ggacctgccg ggttgtgccg ttcatctgtg    420
gtgtggtgta cagtccacca gtcagatgtc cactcccatg cattccctac catgttgtac    480
aggccatagc catttgcagg aaatgacttc actggtgagg ttttggtgta cccgtcctct    540
tctgagttgt gtgtggggaa ctttccctgc cagaggttgg cgtagtgctg tcctttaggt    600
ttcagtttgt tcccccacgg gtaaagtctg tcctgt                              636

<210> SEQ ID NO 86
<211> LENGTH: 415
<212> TYPE: DNA
<213> ORGANISM: Sus scrofa

<400> SEQUENCE: 86
agtttcctgt gaccaacacc ggagaggatg gcttccgagg aactgcgcct gttgatgcct    60
ttcctcccaa tggttatggc ctttacaata tagtagggaa cgcctgggaa tggacctcag   120
actggtggac cattcaccat gctgctgaag aaacaattaa cccatcaagt tcttcctgct   180
gcaccgaata cagagccgc cactacgtga tgaaagcaga gaaggcccc ccttctggga    240 aagaccgggt gaagaaaggg ggatcctata tgtgccataa gtcctactgc tacaggtacc   300
gctgtgctgc tcgaagccag aacacgccgg cagctcggc ttcaaatctg ggttccgct    360 gtgcagctga ccaccagccc accacaggct gagtcaggaa gagtcttccc gaatc         415

<210> SEQ ID NO 87
<211> LENGTH: 595
<212> TYPE: DNA
<213> ORGANISM: Bos taurus

<400> SEQUENCE: 87
ccacgcgtcc gggggcaaca aactgcagcc gaaaggccag cattatagcc aacatcttgg    60
caaggcgagt ttcctgtgac caacaccggg gaggacggct tccgagggac cgcgcctgtt   120
gacgcctttc ctcccaatgg ttattggctt atacaatata gtagggaacg cctgggagtg   180
gacttcagac tggtggactg ttcaccattc tgctgaagaa acgattaacc caaaaggccc    240
cccttctggg aaagaccggg tgaagaaagg tggatcctac atgtgccata atcctattg    300 ctacaggtat cgctgtgctg ctcgaagcca gaacacaccc gacagctctg cttcgaatct   360
gggattccgt tgtgcagctg accacctgcc caccacaggc taagagccaa aaagagcctt   420
cccgaacccg agaagtcgtg tctactctgc acgcggcttc cctcagaagg ctgaacaacc   480
tgctgtgaag aattcccacc ccaaggtggg ttacatacct tgcccagtgg ccaaaggacc   540
tatggcaaga ccaaattgct gagctgatca gcatgtgcgc tttattgggg gatgg          595

<210> SEQ ID NO 88
<211> LENGTH: 1611
<212> TYPE: DNA
<213> ORGANISM: Homo sapiens
<220> FEATURE:
<221> NAME/KEY: CDS
<222> LOCATION: (1)..(1608)

<400> SEQUENCE: 88 atg cta ctg ctg tgg gtg tcg gtg gtc gca gcc ttg gcg ctg gcg gta    48
Met Leu Leu Leu Trp Val Ser Val Val Ala Ala Leu Ala Leu Ala Val
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |

```
ctg gcc ccc gga gca ggg gag cag agg cgg aga gca gcc aaa gcg ccc      96
Leu Ala Pro Gly Ala Gly Glu Gln Arg Arg Arg Ala Ala Lys Ala Pro
             20                  25                  30 aat gtg gtg ctg gtc gtg agc gac tcc ttc gat gga agg tta aca ttt     144
Asn Val Val Leu Val Val Ser Asp Ser Phe Asp Gly Arg Leu Thr Phe
         35                  40                  45 cat cca gga agt cag gta gtg aaa ctt cct ttt atc aac ttt atg aag     192
His Pro Gly Ser Gln Val Val Lys Leu Pro Phe Ile Asn Phe Met Lys
     50                  55                  60 aca cgt ggg act tcc ttt ctg aat gcc tac aca aac tct cca att tgt     240
Thr Arg Gly Thr Ser Phe Leu Asn Ala Tyr Thr Asn Ser Pro Ile Cys
 65                  70                  75                  80 tgc cca tca cgc gca gca atg tgg agt ggc ctc ttc act cac tta aca     288
Cys Pro Ser Arg Ala Ala Met Trp Ser Gly Leu Phe Thr His Leu Thr
                 85                  90                  95 gaa tct tgg aat aat ttt aag ggt cta gat cca aat tat aca aca tgg     336
Glu Ser Trp Asn Asn Phe Lys Gly Leu Asp Pro Asn Tyr Thr Thr Trp
             100                 105                 110 atg gat gtc atg gag agg cat ggc tac cga aca cag aaa ttt ggg aaa     384
Met Asp Val Met Glu Arg His Gly Tyr Arg Thr Gln Lys Phe Gly Lys
         115                 120                 125 ctg gac tat act tca gga cat cac tcc att agt aat cgt gtg gaa gcg     432
Leu Asp Tyr Thr Ser Gly His His Ser Ile Ser Asn Arg Val Glu Ala
     130                 135                 140 tgg aca aga gat gtt gct ttc tta ctc aga caa gaa ggc agg ccc atg     480
Trp Thr Arg Asp Val Ala Phe Leu Leu Arg Gln Glu Gly Arg Pro Met
145                 150                 155                 160 gtt aat ctt atc cgt aac agg act aaa gtc aga gtg atg gaa agg gat     528
Val Asn Leu Ile Arg Asn Arg Thr Lys Val Arg Val Met Glu Arg Asp
                 165                 170                 175 tgg cag aat aca gac aaa gca gta aac tgg tta aga aag gaa gca att     576
Trp Gln Asn Thr Asp Lys Ala Val Asn Trp Leu Arg Lys Glu Ala Ile
             180                 185                 190 aat tac act gaa cca ttt gtt att tac ttg gga tta aat tta cca cac     624
Asn Tyr Thr Glu Pro Phe Val Ile Tyr Leu Gly Leu Asn Leu Pro His
         195                 200                 205 cct tac cct tca cca tct tct gga gaa aat ttt gga tct tca aca ttt     672
Pro Tyr Pro Ser Pro Ser Ser Gly Glu Asn Phe Gly Ser Ser Thr Phe
     210                 215                 220 cac aca tct ctt tat tgg ctt gaa aaa gtg tct cat gat gcc atc aaa     720
His Thr Ser Leu Tyr Trp Leu Glu Lys Val Ser His Asp Ala Ile Lys
225                 230                 235                 240 atc cca aag tgg tca cct ttg tca gaa atg cac cct gta gat tat tac     768
Ile Pro Lys Trp Ser Pro Leu Ser Glu Met His Pro Val Asp Tyr Tyr
                 245                 250                 255 tct tct tat aca aaa aac tgc act gga aga ttt aca aaa aaa gaa att     816
Ser Ser Tyr Thr Lys Asn Cys Thr Gly Arg Phe Thr Lys Lys Glu Ile
             260                 265                 270 aag aat att aga gca ttt tat tat gct atg tgt gct gag aca gat gcc     864
Lys Asn Ile Arg Ala Phe Tyr Tyr Ala Met Cys Ala Glu Thr Asp Ala
         275                 280                 285 atg ctt ggt gaa att att ttg gcc ctt cat caa tta gat ctt ctt cag     912
Met Leu Gly Glu Ile Ile Leu Ala Leu His Gln Leu Asp Leu Leu Gln
     290                 295                 300 aaa act att gtc ata tac tcc tca gac cat gga gag ctg gcc atg gaa     960
Lys Thr Ile Val Ile Tyr Ser Ser Asp His Gly Glu Leu Ala Met Glu
305                 310                 315                 320 cat cga cag ttt tat aaa atg agc atg tac gag gct agt gca cat gtt    1008
His Arg Gln Phe Tyr Lys Met Ser Met Tyr Glu Ala Ser Ala His Val
```

```
                    325                 330                 335
ccg ctt ttg atg atg gga cca gga att aaa gcc ggc cta caa gta tca      1056
Pro Leu Leu Met Met Gly Pro Gly Ile Lys Ala Gly Leu Gln Val Ser
            340                 345                 350 aat gtg gtt tct ctt gtg gat att tac cct acc atg ctt gat att gct      1104
Asn Val Val Ser Leu Val Asp Ile Tyr Pro Thr Met Leu Asp Ile Ala
                355                 360                 365 gga att cct ctg cct cag aac ctg agt gga tac tct ttg ttg ccg tta      1152
Gly Ile Pro Leu Pro Gln Asn Leu Ser Gly Tyr Ser Leu Leu Pro Leu
        370                 375                 380 tca tca gaa aca ttt aag aat gaa cat aaa gtc aaa aac ctg cat cca      1200
Ser Ser Glu Thr Phe Lys Asn Glu His Lys Val Lys Asn Leu His Pro
385                 390                 395                 400 ccc tgg att ctg agt gaa ttc cat gga tgt aat gtg aat gcc tcc acc      1248
Pro Trp Ile Leu Ser Glu Phe His Gly Cys Asn Val Asn Ala Ser Thr
                405                 410                 415 tac atg ctt cga act aac cac tgg aaa tat ata gcc tat tcg gat ggt      1296
Tyr Met Leu Arg Thr Asn His Trp Lys Tyr Ile Ala Tyr Ser Asp Gly
        420                 425                 430 gca tca ata ttg cct caa ctc ttt gat ctt tcc tcg gat cca gat gaa      1344
Ala Ser Ile Leu Pro Gln Leu Phe Asp Leu Ser Ser Asp Pro Asp Glu
            435                 440                 445 tta aca aat gtt gct gta aaa ttt cca gaa att act tat tct ttg gat      1392
Leu Thr Asn Val Ala Val Lys Phe Pro Glu Ile Thr Tyr Ser Leu Asp
450                 455                 460 cag aag ctt cat tcc att ata aac tac cct aaa gtt tct gct tct gtc      1440
Gln Lys Leu His Ser Ile Ile Asn Tyr Pro Lys Val Ser Ala Ser Val
465                 470                 475                 480 cac cag tat aat aaa gag cag ttt atc aag tgg aaa caa agt ata gga      1488
His Gln Tyr Asn Lys Glu Gln Phe Ile Lys Trp Lys Gln Ser Ile Gly
                485                 490                 495 cag aat tat tca aac gtt ata gca aat ctt agg tgg cac caa gac tgg      1536
Gln Asn Tyr Ser Asn Val Ile Ala Asn Leu Arg Trp His Gln Asp Trp
        500                 505                 510 cag aag gaa cca agg aag tat gaa aat gca att gat cag tgg ctt aaa      1584
Gln Lys Glu Pro Arg Lys Tyr Glu Asn Ala Ile Asp Gln Trp Leu Lys
            515                 520                 525 acc cat atg aat cca aga gca gtt tga                                  1611
Thr His Met Asn Pro Arg Ala Val
        530                 535

<210> SEQ ID NO 89
<211> LENGTH: 536
<212> TYPE: PRT
<213> ORGANISM: Homo sapiens

<400> SEQUENCE: 89

Met Leu Leu Leu Trp Val Ser Val Val Ala Ala Leu Ala Leu Ala Val
1               5                   10                  15

Leu Ala Pro Gly Ala Gly Glu Gln Arg Arg Ala Ala Lys Ala Pro
            20                  25                  30

Asn Val Val Leu Val Val Ser Asp Ser Phe Asp Gly Arg Leu Thr Phe
                35                  40                  45

His Pro Gly Ser Gln Val Val Lys Leu Pro Phe Ile Asn Phe Met Lys
        50                  55                  60

Thr Arg Gly Thr Ser Phe Leu Asn Ala Tyr Thr Asn Ser Pro Ile Cys
65                  70                  75                  80

Cys Pro Ser Arg Ala Ala Met Trp Ser Gly Leu Phe Thr His Leu Thr
                85                  90                  95
```

```
Glu Ser Trp Asn Asn Phe Lys Gly Leu Asp Pro Asn Tyr Thr Thr Trp
                100                 105                 110

Met Asp Val Met Glu Arg His Gly Tyr Arg Thr Gln Lys Phe Gly Lys
            115                 120                 125

Leu Asp Tyr Thr Ser Gly His His Ser Ile Ser Asn Arg Val Glu Ala
        130                 135                 140

Trp Thr Arg Asp Val Ala Phe Leu Leu Arg Gln Glu Gly Arg Pro Met
145                 150                 155                 160

Val Asn Leu Ile Arg Asn Arg Thr Lys Val Arg Val Met Glu Arg Asp
                165                 170                 175

Trp Gln Asn Thr Asp Lys Ala Val Asn Trp Leu Arg Lys Glu Ala Ile
            180                 185                 190

Asn Tyr Thr Glu Pro Phe Val Ile Tyr Leu Gly Leu Asn Leu Pro His
        195                 200                 205

Pro Tyr Pro Ser Pro Ser Ser Gly Glu Asn Phe Gly Ser Ser Thr Phe
    210                 215                 220

His Thr Ser Leu Tyr Trp Leu Glu Lys Val Ser His Asp Ala Ile Lys
225                 230                 235                 240

Ile Pro Lys Trp Ser Pro Leu Ser Glu Met His Pro Val Asp Tyr Tyr
                245                 250                 255

Ser Ser Tyr Thr Lys Asn Cys Thr Gly Arg Phe Thr Lys Lys Glu Ile
            260                 265                 270

Lys Asn Ile Arg Ala Phe Tyr Tyr Ala Met Cys Ala Glu Thr Asp Ala
        275                 280                 285

Met Leu Gly Glu Ile Ile Leu Ala Leu His Gln Leu Asp Leu Leu Gln
    290                 295                 300

Lys Thr Ile Val Ile Tyr Ser Ser Asp His Gly Glu Leu Ala Met Glu
305                 310                 315                 320

His Arg Gln Phe Tyr Lys Met Ser Met Tyr Glu Ala Ser Ala His Val
                325                 330                 335

Pro Leu Leu Met Met Gly Pro Gly Ile Lys Ala Gly Leu Gln Val Ser
            340                 345                 350

Asn Val Val Ser Leu Val Asp Ile Tyr Pro Thr Met Leu Asp Ile Ala
        355                 360                 365

Gly Ile Pro Leu Pro Gln Asn Leu Ser Gly Tyr Ser Leu Leu Pro Leu
    370                 375                 380

Ser Ser Glu Thr Phe Lys Asn Glu His Lys Val Lys Asn Leu His Pro
385                 390                 395                 400

Pro Trp Ile Leu Ser Glu Phe His Gly Cys Asn Val Asn Ala Ser Thr
                405                 410                 415

Tyr Met Leu Arg Thr Asn His Trp Lys Tyr Ile Ala Tyr Ser Asp Gly
            420                 425                 430

Ala Ser Ile Leu Pro Gln Leu Phe Asp Leu Ser Ser Asp Pro Asp Glu
        435                 440                 445

Leu Thr Asn Val Ala Val Lys Phe Pro Glu Ile Thr Tyr Ser Leu Asp
    450                 455                 460

Gln Lys Leu His Ser Ile Ile Asn Tyr Pro Lys Val Ser Ala Ser Val
465                 470                 475                 480

His Gln Tyr Asn Lys Glu Gln Phe Ile Lys Trp Lys Gln Ser Ile Gly
                485                 490                 495

Gln Asn Tyr Ser Asn Val Ile Ala Asn Leu Arg Trp His Gln Asp Trp
            500                 505                 510

Gln Lys Glu Pro Arg Lys Tyr Glu Asn Ala Ile Asp Gln Trp Leu Lys
        515                 520                 525
```

```
Thr His Met Asn Pro Arg Ala Val
    530             535
```

<210> SEQ ID NO 90
<211> LENGTH: 1722
<212> TYPE: DNA
<213> ORGANISM: Homo sapiens
<220> FEATURE:
<221> NAME/KEY: CDS
<222> LOCATION: (1)..(1719)

<400> SEQUENCE: 90

```
atg ggg gcg ctg gca gga ttc tgg atc ctc tgc ctc ctc act tat ggt         48
Met Gly Ala Leu Ala Gly Phe Trp Ile Leu Cys Leu Leu Thr Tyr Gly
1               5                   10                  15 tac ctg tcc tgg ggc cag gcc tta gaa gag gag gaa gaa ggg gcc tta         96
Tyr Leu Ser Trp Gly Gln Ala Leu Glu Glu Glu Glu Glu Gly Ala Leu
            20                  25                  30 cta gct caa gct gga gag aaa cta gag ccc agc aca act tcc acc tcc        144
Leu Ala Gln Ala Gly Glu Lys Leu Glu Pro Ser Thr Thr Ser Thr Ser
        35                  40                  45 cag ccc cat ctc att ttc atc cta gcg gat gat cag gga ttt aga gat        192
Gln Pro His Leu Ile Phe Ile Leu Ala Asp Asp Gln Gly Phe Arg Asp
    50                  55                  60 gtg ggt tac cac gga tct gag att aaa aca cct act ctt gac aag ctc        240
Val Gly Tyr His Gly Ser Glu Ile Lys Thr Pro Thr Leu Asp Lys Leu
65                  70                  75                  80 gct gcc gaa gga gtt aaa ctg gag aac tac tat gtc cag cct att tgc        288
Ala Ala Glu Gly Val Lys Leu Glu Asn Tyr Tyr Val Gln Pro Ile Cys
                85                  90                  95 aca cca tcc agg agt cag ttt att act gga aag tat cag ata cac acc        336
Thr Pro Ser Arg Ser Gln Phe Ile Thr Gly Lys Tyr Gln Ile His Thr
            100                 105                 110 gga ctt caa cat tct atc ata aga cct acc caa ccc aac tgt tta cct        384
Gly Leu Gln His Ser Ile Ile Arg Pro Thr Gln Pro Asn Cys Leu Pro
        115                 120                 125 ctg gac aat gcc acc cta cct cag aaa ctg aag gag gtt gga tat tca        432
Leu Asp Asn Ala Thr Leu Pro Gln Lys Leu Lys Glu Val Gly Tyr Ser
    130                 135                 140 acg cat atg gtc gga aaa tgg cac ttg ggt ttt tac aga aaa gaa tgc        480
Thr His Met Val Gly Lys Trp His Leu Gly Phe Tyr Arg Lys Glu Cys
145                 150                 155                 160 atg ccc acc aga aga gga ttt gat acc ttt ttt ggt tcc ctt ttg gga        528
Met Pro Thr Arg Arg Gly Phe Asp Thr Phe Phe Gly Ser Leu Leu Gly
                165                 170                 175 agt ggg gat tac tat aca cac tac aaa tgt gac agt cct ggg atg tgt        576
Ser Gly Asp Tyr Tyr Thr His Tyr Lys Cys Asp Ser Pro Gly Met Cys
            180                 185                 190 ggc tat gac ttg tat gaa aac gac aat gct gcc tgg gac tat gac aat        624
Gly Tyr Asp Leu Tyr Glu Asn Asp Asn Ala Ala Trp Asp Tyr Asp Asn
        195                 200                 205 ggc ata tac tcc aca cag atg tac act cag aga gta cag caa atc tta        672
Gly Ile Tyr Ser Thr Gln Met Tyr Thr Gln Arg Val Gln Gln Ile Leu
    210                 215                 220 gct tcc cat aac ccc aca aag cct ata ttt tta tat att gcc tat caa        720
Ala Ser His Asn Pro Thr Lys Pro Ile Phe Leu Tyr Ile Ala Tyr Gln
225                 230                 235                 240 gct gtt cat tca cca ctg caa gct cct ggc agg tat ttc gaa cac tac        768
Ala Val His Ser Pro Leu Gln Ala Pro Gly Arg Tyr Phe Glu His Tyr
                245                 250                 255 cga tcc att atc aac ata aac agg agg aga tat gct gcc atg ctt tcc        816
```

-continued

```
Arg Ser Ile Ile Asn Ile Asn Arg Arg Arg Tyr Ala Ala Met Leu Ser
            260                 265                 270 tgc tta gat gaa gca atc aac aac gtg aca ttg gct cta aag act tat      864
Cys Leu Asp Glu Ala Ile Asn Asn Val Thr Leu Ala Leu Lys Thr Tyr
        275                 280                 285 ggt ttc tat aac aac agc att atc att tac tct tca gat aat ggt ggc      912
Gly Phe Tyr Asn Asn Ser Ile Ile Tyr Ser Ser Asp Asn Gly Gly
    290                 295                 300 cag cct acg gca gga ggg agt aac tgg cct ctc aga ggt agc aaa gga      960
Gln Pro Thr Ala Gly Gly Ser Asn Trp Pro Leu Arg Gly Ser Lys Gly
305                 310                 315                 320 aca tat tgg gaa gga ggg atc cgg gct gta ggc ttt gtg cat agc cca     1008
Thr Tyr Trp Glu Gly Gly Ile Arg Ala Val Gly Phe Val His Ser Pro
                325                 330                 335 ctt ctg aaa aac aag gga aca gtg tgt aag gaa ctt gtg cac atc act     1056
Leu Leu Lys Asn Lys Gly Thr Val Cys Lys Glu Leu Val His Ile Thr
            340                 345                 350 gac tgg tac ccc act ctc att tca ctg gct gaa gga cag att gat gag     1104
Asp Trp Tyr Pro Thr Leu Ile Ser Leu Ala Glu Gly Gln Ile Asp Glu
        355                 360                 365 gac att caa cta gat ggc tat gat atc tgg gag acc ata agt gag ggt     1152
Asp Ile Gln Leu Asp Gly Tyr Asp Ile Trp Glu Thr Ile Ser Glu Gly
370                 375                 380 ctt cgc tca ccc cga gta gat att ttg cat aac att gac ccc ata tac     1200
Leu Arg Ser Pro Arg Val Asp Ile Leu His Asn Ile Asp Pro Ile Tyr
385                 390                 395                 400 acc aag gca aaa aat ggc tcc tgg gca gca ggc tat ggg atc tgg aac     1248
Thr Lys Ala Lys Asn Gly Ser Trp Ala Ala Gly Tyr Gly Ile Trp Asn
                405                 410                 415 act gca atc cag tca gcc atc aga gtg cag cac tgg aaa ttg ctt aca     1296
Thr Ala Ile Gln Ser Ala Ile Arg Val Gln His Trp Lys Leu Leu Thr
            420                 425                 430 gga aat cct ggc tac agc gac tgg gtc ccc cct cag tct ttc agc aac     1344
Gly Asn Pro Gly Tyr Ser Asp Trp Val Pro Pro Gln Ser Phe Ser Asn
        435                 440                 445 ctg gga ccg aac cgg tgg cac aat gaa cgg atc acc ttg tca act ggc     1392
Leu Gly Pro Asn Arg Trp His Asn Glu Arg Ile Thr Leu Ser Thr Gly
450                 455                 460 aaa agt gta tgg ctt ttc aac atc aca gcc gac cca tat gag agg gtg     1440
Lys Ser Val Trp Leu Phe Asn Ile Thr Ala Asp Pro Tyr Glu Arg Val
465                 470                 475                 480 gac cta tct aac agg tat cca gga atc gtg aag aag ctc cta cgg agg     1488
Asp Leu Ser Asn Arg Tyr Pro Gly Ile Val Lys Lys Leu Leu Arg Arg
                485                 490                 495 ctc tca cag ttc aac aaa act gca gtg ccg gtc agg tat ccc ccc aaa     1536
Leu Ser Gln Phe Asn Lys Thr Ala Val Pro Val Arg Tyr Pro Pro Lys
            500                 505                 510 gac ccc aga agt aac cct agg ctc aat gga ggg gtc tgg gga cca tgg     1584
Asp Pro Arg Ser Asn Pro Arg Leu Asn Gly Gly Val Trp Gly Pro Trp
        515                 520                 525 tat aaa gag gaa acc aag aaa aag aag cca agc aaa aat cag gct gag     1632
Tyr Lys Glu Glu Thr Lys Lys Lys Lys Pro Ser Lys Asn Gln Ala Glu
530                 535                 540 aaa aag caa aag aaa agc aaa aaa aag aag aaa cag cag aaa gca         1680
Lys Lys Gln Lys Lys Ser Lys Lys Lys Lys Lys Gln Gln Lys Ala
545                 550                 555                 560 gtc tca ggt tca act tgc cat tca ggt gtt act tgt gga taa             1722
Val Ser Gly Ser Thr Cys His Ser Gly Val Thr Cys Gly
                565                 570
```

<210> SEQ ID NO 91
<211> LENGTH: 573
<212> TYPE: PRT
<213> ORGANISM: Homo sapiens

<400> SEQUENCE: 91

Met Gly Ala Leu Ala Gly Phe Trp Ile Leu Cys Leu Leu Thr Tyr Gly
1               5                   10                  15

Tyr Leu Ser Trp Gly Gln Ala Leu Glu Glu Glu Glu Gly Ala Leu
        20                  25                  30

Leu Ala Gln Ala Gly Glu Lys Leu Glu Pro Ser Thr Thr Ser Thr Ser
        35                  40                  45

Gln Pro His Leu Ile Phe Ile Leu Ala Asp Asp Gln Gly Phe Arg Asp
    50                  55                  60

Val Gly Tyr His Gly Ser Glu Ile Lys Thr Pro Thr Leu Asp Lys Leu
65                  70                  75                  80

Ala Ala Glu Gly Val Lys Leu Glu Asn Tyr Tyr Val Gln Pro Ile Cys
                85                  90                  95

Thr Pro Ser Arg Ser Gln Phe Ile Thr Gly Lys Tyr Gln Ile His Thr
            100                 105                 110

Gly Leu Gln His Ser Ile Ile Arg Pro Thr Gln Pro Asn Cys Leu Pro
        115                 120                 125

Leu Asp Asn Ala Thr Leu Pro Gln Lys Leu Lys Glu Val Gly Tyr Ser
    130                 135                 140

Thr His Met Val Gly Lys Trp His Leu Gly Phe Tyr Arg Lys Glu Cys
145                 150                 155                 160

Met Pro Thr Arg Arg Gly Phe Asp Thr Phe Phe Gly Ser Leu Leu Gly
                165                 170                 175

Ser Gly Asp Tyr Tyr Thr His Tyr Lys Cys Asp Ser Pro Gly Met Cys
            180                 185                 190

Gly Tyr Asp Leu Tyr Glu Asn Asp Asn Ala Ala Trp Asp Tyr Asp Asn
        195                 200                 205

Gly Ile Tyr Ser Thr Gln Met Tyr Thr Gln Arg Val Gln Gln Ile Leu
    210                 215                 220

Ala Ser His Asn Pro Thr Lys Pro Ile Phe Leu Tyr Ile Ala Tyr Gln
225                 230                 235                 240

Ala Val His Ser Pro Leu Gln Ala Pro Gly Arg Tyr Phe Glu His Tyr
                245                 250                 255

Arg Ser Ile Ile Asn Ile Asn Arg Arg Tyr Ala Ala Met Leu Ser
            260                 265                 270

Cys Leu Asp Glu Ala Ile Asn Asn Val Thr Leu Ala Leu Lys Thr Tyr
        275                 280                 285

Gly Phe Tyr Asn Asn Ser Ile Ile Tyr Ser Ser Asp Asn Gly Gly
    290                 295                 300

Gln Pro Thr Ala Gly Gly Ser Asn Trp Pro Leu Arg Gly Ser Lys Gly
305                 310                 315                 320

Thr Tyr Trp Glu Gly Gly Ile Arg Ala Val Gly Phe Val His Ser Pro
                325                 330                 335

Leu Leu Lys Asn Lys Gly Thr Val Cys Lys Glu Leu Val His Ile Thr
            340                 345                 350

Asp Trp Tyr Pro Thr Leu Ile Ser Leu Ala Glu Gly Gln Ile Asp Glu
        355                 360                 365

Asp Ile Gln Leu Asp Gly Tyr Asp Ile Trp Glu Thr Ile Ser Glu Gly
    370                 375                 380

Leu Arg Ser Pro Arg Val Asp Ile Leu His Asn Ile Asp Pro Ile Tyr

```
385                 390                 395                 400
Thr Lys Ala Lys Asn Gly Ser Trp Ala Ala Gly Tyr Gly Ile Trp Asn
                405                 410                 415
Thr Ala Ile Gln Ser Ala Ile Arg Val Gln His Trp Lys Leu Leu Thr
                420                 425                 430
Gly Asn Pro Gly Tyr Ser Asp Trp Val Pro Pro Gln Ser Phe Ser Asn
                435                 440                 445
Leu Gly Pro Asn Arg Trp His Asn Glu Arg Ile Thr Leu Ser Thr Gly
                450                 455                 460
Lys Ser Val Trp Leu Phe Asn Ile Thr Ala Asp Pro Tyr Glu Arg Val
465                 470                 475                 480
Asp Leu Ser Asn Arg Tyr Pro Gly Ile Val Lys Lys Leu Leu Arg Arg
                485                 490                 495
Leu Ser Gln Phe Asn Lys Thr Ala Val Pro Val Arg Tyr Pro Pro Lys
                500                 505                 510
Asp Pro Arg Ser Asn Pro Arg Leu Asn Gly Gly Val Trp Gly Pro Trp
                515                 520                 525
Tyr Lys Glu Glu Thr Lys Lys Lys Pro Ser Lys Asn Gln Ala Glu
                530                 535                 540
Lys Lys Gln Lys Lys Ser Lys Lys Lys Lys Gln Gln Lys Ala
545                 550                 555                 560
Val Ser Gly Ser Thr Cys His Ser Gly Val Thr Cys Gly
                565                 570

<210> SEQ ID NO 92
<211> LENGTH: 1710
<212> TYPE: DNA
<213> ORGANISM: Homo sapiens
<220> FEATURE:
<221> NAME/KEY: CDS
<222> LOCATION: (1)..(1707)

<400> SEQUENCE: 92 atg cac acc ctc act ggc ttc tcc ctg gtc agc ctg ctc agc ttc ggc      48
Met His Thr Leu Thr Gly Phe Ser Leu Val Ser Leu Leu Ser Phe Gly
1               5                   10                  15 tac ctg tcc tgg gac tgg gcc aag ccg agc ttc gtg gcc gac ggg ccc      96
Tyr Leu Ser Trp Asp Trp Ala Lys Pro Ser Phe Val Ala Asp Gly Pro
                20                  25                  30 ggg gag gct ggc gag cag ccc tcg gcc gct ccg ccc cag cct ccc cac     144
Gly Glu Ala Gly Glu Gln Pro Ser Ala Ala Pro Pro Gln Pro Pro His
            35                  40                  45 atc atc ttc atc ctc acg gac gac caa ggc tac cac gac gtg ggc tac     192
Ile Ile Phe Ile Leu Thr Asp Asp Gln Gly Tyr His Asp Val Gly Tyr
        50                  55                  60 cat ggt tca gat atc gag acc cct acg ctg gac agg ctg gcg gcc aag     240
His Gly Ser Asp Ile Glu Thr Pro Thr Leu Asp Arg Leu Ala Ala Lys
65                  70                  75                  80 ggg gtc aag ttg gag aat tat tac atc cag ccc atc tgc acg cct tcg     288
Gly Val Lys Leu Glu Asn Tyr Tyr Ile Gln Pro Ile Cys Thr Pro Ser
                85                  90                  95 cgg agc cag ctc ctc act ggc agg tac cag atc cac aca gga ctc cag     336
Arg Ser Gln Leu Leu Thr Gly Arg Tyr Gln Ile His Thr Gly Leu Gln
                100                 105                 110 cat tcc atc atc cgc cca cag cag ccc aac tgc ctg ccc ctg gac cag     384
His Ser Ile Ile Arg Pro Gln Gln Pro Asn Cys Leu Pro Leu Asp Gln
            115                 120                 125 gtg aca ctg cca cag aag ctg cag gag gca ggt tat tcc acc cat atg     432
Val Thr Leu Pro Gln Lys Leu Gln Glu Ala Gly Tyr Ser Thr His Met
```

```
                130                 135                 140
gtg ggc aag tgg cac ctg ggc ttc tac cgg aag gag tgt ctg ccc acc        480
Val Gly Lys Trp His Leu Gly Phe Tyr Arg Lys Glu Cys Leu Pro Thr
145                 150                 155                 160 cgt cgg ggc ttc gac acc ttc ctg ggc tcg ctc acg ggc aat gtg gac        528
Arg Arg Gly Phe Asp Thr Phe Leu Gly Ser Leu Thr Gly Asn Val Asp
                    165                 170                 175 tat tac acc tat gac aac tgt gat ggc cca ggc gtg tgc ggc ttc gac        576
Tyr Tyr Thr Tyr Asp Asn Cys Asp Gly Pro Gly Val Cys Gly Phe Asp
                180                 185                 190 ctg cac gag ggt gag aat gtg gcc tgg ggc ctc agc ggc cag tac tcc        624
Leu His Glu Gly Glu Asn Val Ala Trp Gly Leu Ser Gly Gln Tyr Ser
            195                 200                 205 act atg ctt tac gcc cag cgc gcc agc cat atc ctg gcc agc cac agc        672
Thr Met Leu Tyr Ala Gln Arg Ala Ser His Ile Leu Ala Ser His Ser
        210                 215                 220 cct cag cgt ccc ctc ttc ctc tat gtg gcc ttc cag gca gta cac aca        720
Pro Gln Arg Pro Leu Phe Leu Tyr Val Ala Phe Gln Ala Val His Thr
225                 230                 235                 240 ccc ctg cag tcc cct cgt gag tac ctg tac cgc tac cgc acc atg ggc        768
Pro Leu Gln Ser Pro Arg Glu Tyr Leu Tyr Arg Tyr Arg Thr Met Gly
                    245                 250                 255 aat gtg gcc cgg cgg aag tac gcg gcc atg gtg acc tgc atg gat gag        816
Asn Val Ala Arg Arg Lys Tyr Ala Ala Met Val Thr Cys Met Asp Glu
                260                 265                 270 gct gtg cgc aac atc acc tgg gcc ctc aag cgc tac ggt ttc tac aac        864
Ala Val Arg Asn Ile Thr Trp Ala Leu Lys Arg Tyr Gly Phe Tyr Asn
            275                 280                 285 aac agt gtc atc atc ttc tcc agt gac aat ggt ggc cag act ttc tcg        912
Asn Ser Val Ile Ile Phe Ser Ser Asp Asn Gly Gly Gln Thr Phe Ser
        290                 295                 300 ggg ggc agc aac tgg ccg ctc cga gga cgc aag ggc act tat tgg gaa        960
Gly Gly Ser Asn Trp Pro Leu Arg Gly Arg Lys Gly Thr Tyr Trp Glu
305                 310                 315                 320 ggt ggc gtg cgg ggc cta ggc ttt gtc cac agt ccc ctg ctc aag cga       1008
Gly Gly Val Arg Gly Leu Gly Phe Val His Ser Pro Leu Leu Lys Arg
                    325                 330                 335 aag caa cgg aca agc cgg gca ctg atg cac atc act gac tgg tac ccg       1056
Lys Gln Arg Thr Ser Arg Ala Leu Met His Ile Thr Asp Trp Tyr Pro
                340                 345                 350 acc ctg gtg ggt ctg gca ggt ggt acc acc tca gca gcc gat ggg cta       1104
Thr Leu Val Gly Leu Ala Gly Gly Thr Thr Ser Ala Ala Asp Gly Leu
            355                 360                 365 gat ggc tac gac gtg tgg ccg gcc atc agc gag ggc cgg gcc tca cca       1152
Asp Gly Tyr Asp Val Trp Pro Ala Ile Ser Glu Gly Arg Ala Ser Pro
        370                 375                 380 cgc acg gag atc ctg cac aac att gac cca ctc tac aac cat gcc cag       1200
Arg Thr Glu Ile Leu His Asn Ile Asp Pro Leu Tyr Asn His Ala Gln
385                 390                 395                 400 cat ggc tcc ctg gag ggc ggc ttt ggc atc tgg aac acc gcc gtg cag       1248
His Gly Ser Leu Glu Gly Gly Phe Gly Ile Trp Asn Thr Ala Val Gln
                    405                 410                 415 gct gcc atc cgc gtg ggt gag tgg aag ctg ctg aca gga gac ccc ggc       1296
Ala Ala Ile Arg Val Gly Glu Trp Lys Leu Leu Thr Gly Asp Pro Gly
                420                 425                 430 tat ggc gat tgg atc cca ccg cag aca ctg gcc acc ttc ccg ggt agc       1344
Tyr Gly Asp Trp Ile Pro Pro Gln Thr Leu Ala Thr Phe Pro Gly Ser
            435                 440                 445 tgg tgg aac ctg gaa cga atg gcc agt gtc cgc cag gcc gtg tgg ctc       1392
Trp Trp Asn Leu Glu Arg Met Ala Ser Val Arg Gln Ala Val Trp Leu
```

```
                450                 455                 460
ttc aac atc agt gct gac cct tat gaa cgg gag gac ctg gct ggc cag      1440
Phe Asn Ile Ser Ala Asp Pro Tyr Glu Arg Glu Asp Leu Ala Gly Gln
465                 470                 475                 480 cgg cct gat gtg gtc cgc acc ctg ctg gct cgc ctg gcc gaa tat aac      1488
Arg Pro Asp Val Val Arg Thr Leu Leu Ala Arg Leu Ala Glu Tyr Asn
                485                 490                 495 cgc aca gcc atc ccg gta cgc tac cca gct gag aac ccc cgg gct cat      1536
Arg Thr Ala Ile Pro Val Arg Tyr Pro Ala Glu Asn Pro Arg Ala His
            500                 505                 510 cct gac ttt aat ggg ggt gct tgg ggg ccc tgg gcc agt gat gag gaa      1584
Pro Asp Phe Asn Gly Gly Ala Trp Gly Pro Trp Ala Ser Asp Glu Glu
        515                 520                 525 gag gag gaa gag gaa ggg agg gct cga agc ttc tcc cgg ggt cgt cgc      1632
Glu Glu Glu Glu Glu Gly Arg Ala Arg Ser Phe Ser Arg Gly Arg Arg
    530                 535                 540 aag aaa aaa tgc aag att tgc aag ctt cga tcc ttt ttc cgt aaa ctc      1680
Lys Lys Lys Cys Lys Ile Cys Lys Leu Arg Ser Phe Phe Arg Lys Leu
545                 550                 555                 560 aac acc agg cta atg tcc caa cgg atc tga                              1710
Asn Thr Arg Leu Met Ser Gln Arg Ile
                565

<210> SEQ ID NO 93
<211> LENGTH: 569
<212> TYPE: PRT
<213> ORGANISM: Homo sapiens

<400> SEQUENCE: 93

Met His Thr Leu Thr Gly Phe Ser Leu Val Ser Leu Leu Ser Phe Gly
1               5                   10                  15

Tyr Leu Ser Trp Asp Trp Ala Lys Pro Ser Phe Val Ala Asp Gly Pro
            20                  25                  30

Gly Glu Ala Gly Glu Gln Pro Ser Ala Ala Pro Gln Pro Pro His
        35                  40                  45

Ile Ile Phe Ile Leu Thr Asp Asp Gln Gly Tyr His Asp Val Gly Tyr
    50                  55                  60

His Gly Ser Asp Ile Glu Thr Pro Thr Leu Asp Arg Leu Ala Ala Lys
65                  70                  75                  80

Gly Val Lys Leu Glu Asn Tyr Tyr Ile Gln Pro Ile Cys Thr Pro Ser
                85                  90                  95

Arg Ser Gln Leu Leu Thr Gly Arg Tyr Gln Ile His Thr Gly Leu Gln
            100                 105                 110

His Ser Ile Ile Arg Pro Gln Gln Pro Asn Cys Leu Pro Leu Asp Gln
        115                 120                 125

Val Thr Leu Pro Gln Lys Leu Gln Glu Ala Gly Tyr Ser Thr His Met
    130                 135                 140

Val Gly Lys Trp His Leu Gly Phe Tyr Arg Lys Glu Cys Leu Pro Thr
145                 150                 155                 160

Arg Arg Gly Phe Asp Thr Phe Leu Gly Ser Leu Thr Gly Asn Val Asp
                165                 170                 175

Tyr Tyr Thr Tyr Asp Asn Cys Asp Gly Pro Gly Val Cys Gly Phe Asp
            180                 185                 190

Leu His Glu Gly Glu Asn Val Ala Trp Gly Leu Ser Gly Gln Tyr Ser
        195                 200                 205

Thr Met Leu Tyr Ala Gln Arg Ala Ser His Ile Leu Ala Ser His Ser
    210                 215                 220
```

```
Pro Gln Arg Pro Leu Phe Leu Tyr Val Ala Phe Gln Ala Val His Thr
225                 230                 235                 240

Pro Leu Gln Ser Pro Arg Glu Tyr Leu Tyr Arg Tyr Arg Thr Met Gly
            245                 250                 255

Asn Val Ala Arg Arg Lys Tyr Ala Ala Met Val Thr Cys Met Asp Glu
        260                 265                 270

Ala Val Arg Asn Ile Thr Trp Ala Leu Lys Arg Tyr Gly Phe Tyr Asn
    275                 280                 285

Asn Ser Val Ile Ile Phe Ser Ser Asp Asn Gly Gln Thr Phe Ser
290                 295                 300

Gly Gly Ser Asn Trp Pro Leu Arg Gly Arg Lys Gly Tyr Trp Glu
305                 310                 315                 320

Gly Gly Val Arg Gly Leu Gly Phe Val His Ser Pro Leu Leu Lys Arg
            325                 330                 335

Lys Gln Arg Thr Ser Arg Ala Leu Met His Ile Thr Asp Trp Tyr Pro
        340                 345                 350

Thr Leu Val Gly Leu Ala Gly Thr Thr Ser Ala Ala Asp Gly Leu
    355                 360                 365

Asp Gly Tyr Asp Val Trp Pro Ala Ile Ser Glu Gly Arg Ala Ser Pro
370                 375                 380

Arg Thr Glu Ile Leu His Asn Ile Asp Pro Leu Tyr Asn His Ala Gln
385                 390                 395                 400

His Gly Ser Leu Glu Gly Gly Phe Gly Ile Trp Asn Thr Ala Val Gln
            405                 410                 415

Ala Ala Ile Arg Val Gly Glu Trp Lys Leu Leu Thr Gly Asp Pro Gly
        420                 425                 430

Tyr Gly Asp Trp Ile Pro Pro Gln Thr Leu Ala Thr Phe Pro Gly Ser
    435                 440                 445

Trp Trp Asn Leu Glu Arg Met Ala Ser Val Arg Gln Ala Val Trp Leu
450                 455                 460

Phe Asn Ile Ser Ala Asp Pro Tyr Glu Arg Glu Asp Leu Ala Gly Gln
465                 470                 475                 480

Arg Pro Asp Val Val Arg Thr Leu Leu Ala Arg Leu Ala Glu Tyr Asn
            485                 490                 495

Arg Thr Ala Ile Pro Val Arg Tyr Pro Ala Glu Asn Pro Arg Ala His
        500                 505                 510

Pro Asp Phe Asn Gly Gly Ala Trp Gly Pro Trp Ala Ser Asp Glu Glu
    515                 520                 525

Glu Glu Glu Glu Glu Gly Arg Ala Arg Ser Phe Ser Arg Gly Arg Arg
530                 535                 540

Lys Lys Lys Cys Lys Ile Cys Lys Leu Arg Ser Phe Phe Arg Lys Leu
545                 550                 555                 560

Asn Thr Arg Leu Met Ser Gln Arg Ile
            565

<210> SEQ ID NO 94
<211> LENGTH: 2067
<212> TYPE: DNA
<213> ORGANISM: Homo sapiens
<220> FEATURE:
<221> NAME/KEY: CDS
<222> LOCATION: (1)..(2064)

<400> SEQUENCE: 94 atg cta att tca gga aga gaa gag aac caa ata gac ata tcc aag acc    48
Met Leu Ile Ser Gly Arg Glu Glu Asn Gln Ile Asp Ile Ser Lys Thr
1               5                   10                  15
```

```
aca gag gta gat tgt ttt gtg gtt gaa tta gga agt cta cac aat cct       96
Thr Glu Val Asp Cys Phe Val Val Glu Leu Gly Ser Leu His Asn Pro
         20                  25                  30 aca cgg aac cca cag cga att ttc acc aag cac gtg gcc acc aag tca      144
Thr Arg Asn Pro Gln Arg Ile Phe Thr Lys His Val Ala Thr Lys Ser
             35                  40                  45 tcc agc tcc aaa tgt cag ctg gac caa ggt gga aaa agc ctg gtc cag      192
Ser Ser Ser Lys Cys Gln Leu Asp Gln Gly Gly Lys Ser Leu Val Gln
 50                  55                  60 tgc att tta ccc aga tct tca aag ctc ctc tca ccc ttg tgt ctc ccc      240
Cys Ile Leu Pro Arg Ser Ser Lys Leu Leu Ser Pro Leu Cys Leu Pro
 65                  70                  75                  80 cat ccg tgt gga gct tta ctt ctg tat aga tcc tca gga atc gcc tct      288
His Pro Cys Gly Ala Leu Leu Leu Tyr Arg Ser Ser Gly Ile Ala Ser
                 85                  90                  95 gct ctt gct gcc ttt aca gac tcc ctc tct agg agc tgc tgg ctg tca      336
Ala Leu Ala Ala Phe Thr Asp Ser Leu Ser Arg Ser Cys Trp Leu Ser
                100                 105                 110 gtg tcc ctg tgc tgt ttg ttt tgc ggt gtt gat ggc aca ttt atg aca      384
Val Ser Leu Cys Cys Leu Phe Cys Gly Val Asp Gly Thr Phe Met Thr
            115                 120                 125 aga aac gcc aga ccc aac att gtc ctg ctg atg gca gat gac ctt gga      432
Arg Asn Ala Arg Pro Asn Ile Val Leu Leu Met Ala Asp Asp Leu Gly
130                 135                 140 gtg ggg gat ttg tgc tgc tac ggt aat aac tca gtg agc aca cct aat      480
Val Gly Asp Leu Cys Cys Tyr Gly Asn Asn Ser Val Ser Thr Pro Asn
145                 150                 155                 160 att gac cgc ctg gca agt gaa gga gtg agg ctt acc cag cat ctc gca      528
Ile Asp Arg Leu Ala Ser Glu Gly Val Arg Leu Thr Gln His Leu Ala
                165                 170                 175 gct gct tcc atg tgc acc cca agt cgg gct gcc ttc ctg acc ggc cgg      576
Ala Ala Ser Met Cys Thr Pro Ser Arg Ala Ala Phe Leu Thr Gly Arg
                180                 185                 190 tac ccc atc aga tca ggg atg gtg tct gcc tac aac ctg aac cgt gcc      624
Tyr Pro Ile Arg Ser Gly Met Val Ser Ala Tyr Asn Leu Asn Arg Ala
            195                 200                 205 ttc acg tgg ctt ggt ggg tca ggt ggt ctt ccc acc aat gaa acg act      672
Phe Thr Trp Leu Gly Gly Ser Gly Gly Leu Pro Thr Asn Glu Thr Thr
210                 215                 220 ttt gcc aag ctg ctg cag cac cgt ggc tac cgc acg gga ctc ata ggc      720
Phe Ala Lys Leu Leu Gln His Arg Gly Tyr Arg Thr Gly Leu Ile Gly
225                 230                 235                 240 aaa tgg cac ctg ggt ttg agc tgc gcc tct cgg aat gat cac tgt tac      768
Lys Trp His Leu Gly Leu Ser Cys Ala Ser Arg Asn Asp His Cys Tyr
                245                 250                 255 cac ccg ctc aac cat ggt ttt cac tac ttt tac ggg gtg cct ttt gga      816
His Pro Leu Asn His Gly Phe His Tyr Phe Tyr Gly Val Pro Phe Gly
                260                 265                 270 ctt tta agc gac tgc cag gca tcc aag aca cca gaa ctg cac cgc tgg      864
Leu Leu Ser Asp Cys Gln Ala Ser Lys Thr Pro Glu Leu His Arg Trp
            275                 280                 285 ctc agg atc aaa ctg tgg atc tcc acg gta gcc ctt gcc ctg gtt cct      912
Leu Arg Ile Lys Leu Trp Ile Ser Thr Val Ala Leu Ala Leu Val Pro
290                 295                 300 ttt ctg ctt ctc att ccc aag ttc gcc cgc tgg ttc tca gtg cca tgg      960
Phe Leu Leu Leu Ile Pro Lys Phe Ala Arg Trp Phe Ser Val Pro Trp
305                 310                 315                 320 aag gtc atc ttt gtc ttt gct ctc ctc gcc ttt ctg ttt ttc act tcc     1008
Lys Val Ile Phe Val Phe Ala Leu Leu Ala Phe Leu Phe Phe Thr Ser
                325                 330                 335
```

| | |
|---|---|
| tgg tac tct agt tat gga ttt act cga cgt tgg aat tgc atc ctt atg<br>Trp Tyr Ser Ser Tyr Gly Phe Thr Arg Arg Trp Asn Cys Ile Leu Met<br>340                         345                           350 | 1056 |
| agg aac cat gaa att atc cag cag cca atg aaa gag gag aaa gta gct<br>Arg Asn His Glu Ile Ile Gln Gln Pro Met Lys Glu Glu Lys Val Ala<br>355                         360                          365 | 1104 |
| tcc ctc atg ctg aag gag gca ctt gct ttc att gaa agg tac aaa agg<br>Ser Leu Met Leu Lys Glu Ala Leu Ala Phe Ile Glu Arg Tyr Lys Arg<br>370                         375                          380 | 1152 |
| gaa cct ttt ctc ctc ttt ttt tcc ttc ctg cac gta cat act cca ctc<br>Glu Pro Phe Leu Leu Phe Phe Ser Phe Leu His Val His Thr Pro Leu<br>385                         390                          395                          400 | 1200 |
| atc tcc aaa aag aag ttt gtt ggg cgc agt aaa tat ggc agg tat ggg<br>Ile Ser Lys Lys Lys Phe Val Gly Arg Ser Lys Tyr Gly Arg Tyr Gly<br>                         405                          410                          415 | 1248 |
| gac aat gta gaa gaa atg gat tgg atg gtg ggt aaa atc ctg gat gcc<br>Asp Asn Val Glu Glu Met Asp Trp Met Val Gly Lys Ile Leu Asp Ala<br>                         420                          425                          430 | 1296 |
| ctg gac cag gag cgc ctg gcc aac cac acc ttg gtg tac ttc acc tct<br>Leu Asp Gln Glu Arg Leu Ala Asn His Thr Leu Val Tyr Phe Thr Ser<br>                         435                          440                          445 | 1344 |
| gac aac ggg ggc cac ctg gag ccc ctg gac ggg gct gtt cag ctg ggt<br>Asp Asn Gly Gly His Leu Glu Pro Leu Asp Gly Ala Val Gln Leu Gly<br>450                         455                          460 | 1392 |
| ggc tgg aac ggg atc tac aaa ggt ggc aaa gga atg gga gga tgg gaa<br>Gly Trp Asn Gly Ile Tyr Lys Gly Gly Lys Gly Met Gly Gly Trp Glu<br>465                         470                          475                          480 | 1440 |
| gga ggt atc cgt gtg cca ggg ata ttc cgg tgg ccg tca gtc ttg gag<br>Gly Gly Ile Arg Val Pro Gly Ile Phe Arg Trp Pro Ser Val Leu Glu<br>                         485                          490                          495 | 1488 |
| gct ggg aga gtg atc aat gag ccc acc agc tta atg gac atc tat ccg<br>Ala Gly Arg Val Ile Asn Glu Pro Thr Ser Leu Met Asp Ile Tyr Pro<br>                         500                          505                          510 | 1536 |
| acg ctg tct tat ata ggc gga ggg atc ttg tcc cag gac aga gtg att<br>Thr Leu Ser Tyr Ile Gly Gly Gly Ile Leu Ser Gln Asp Arg Val Ile<br>                         515                          520                          525 | 1584 |
| gac ggc cag aac cta atg ccc ctg ctg gaa gga agg gcg tcc cac tcc<br>Asp Gly Gln Asn Leu Met Pro Leu Leu Glu Gly Arg Ala Ser His Ser<br>530                         535                          540 | 1632 |
| gac cac gag ttc ctc ttc cac tac tgt ggg gtc tat ctg cac acg gtc<br>Asp His Glu Phe Leu Phe His Tyr Cys Gly Val Tyr Leu His Thr Val<br>545                         550                          555                          560 | 1680 |
| agg tgg cat cag aag gac tgt gca act gtg tgg aaa gct cat tat gtg<br>Arg Trp His Gln Lys Asp Cys Ala Thr Val Trp Lys Ala His Tyr Val<br>                         565                          570                          575 | 1728 |
| act cct aaa ttc tac cct gaa gga aca ggt gcc tgc tat ggg agt gga<br>Thr Pro Lys Phe Tyr Pro Glu Gly Thr Gly Ala Cys Tyr Gly Ser Gly<br>                         580                          585                          590 | 1776 |
| ata tgt tca tgt tcg ggg gat gta acc tac cac gac cca cca ctc ctc<br>Ile Cys Ser Cys Ser Gly Asp Val Thr Tyr His Asp Pro Pro Leu Leu<br>                         595                          600                          605 | 1824 |
| ttt gac atc tca aga gac cct tca gaa gcc ctt cca ctg aac cct gac<br>Phe Asp Ile Ser Arg Asp Pro Ser Glu Ala Leu Pro Leu Asn Pro Asp<br>610                         615                          620 | 1872 |
| aat gag cca tta ttt gac tcc gtg atc aaa aag atg gag gca gcc ata<br>Asn Glu Pro Leu Phe Asp Ser Val Ile Lys Lys Met Glu Ala Ala Ile<br>625                         630                          635                          640 | 1920 |
| aga gag cat cgt agg aca cta aca cct gtc cca cag cag ttc tct gtg<br>Arg Glu His Arg Arg Thr Leu Thr Pro Val Pro Gln Gln Phe Ser Val<br>                         645                          650                          655 | 1968 |

```
ttc aac aca att tgg aaa cca tgg ctg cag cct tgc tgt ggg acc ttc   2016
Phe Asn Thr Ile Trp Lys Pro Trp Leu Gln Pro Cys Cys Gly Thr Phe
            660                 665                 670 ccc ttc tgt ggg tgt gac aag gaa gat gac atc ctt ccc atg gct ccc   2064
Pro Phe Cys Gly Cys Asp Lys Glu Asp Asp Ile Leu Pro Met Ala Pro
            675                 680                 685 tga                                                               2067
```

<210> SEQ ID NO 95
<211> LENGTH: 688
<212> TYPE: PRT
<213> ORGANISM: Homo sapiens

<400> SEQUENCE: 95

```
Met Leu Ile Ser Gly Arg Glu Glu Asn Gln Ile Asp Ile Ser Lys Thr
1               5                   10                  15

Thr Glu Val Asp Cys Phe Val Val Glu Leu Gly Ser Leu His Asn Pro
            20                  25                  30

Thr Arg Asn Pro Gln Arg Ile Phe Thr Lys His Val Ala Thr Lys Ser
        35                  40                  45

Ser Ser Ser Lys Cys Gln Leu Asp Gln Gly Gly Lys Ser Leu Val Gln
    50                  55                  60

Cys Ile Leu Pro Arg Ser Ser Lys Leu Leu Ser Pro Leu Cys Leu Pro
65                  70                  75                  80

His Pro Cys Gly Ala Leu Leu Leu Tyr Arg Ser Ser Gly Ile Ala Ser
                85                  90                  95

Ala Leu Ala Ala Phe Thr Asp Ser Leu Ser Arg Ser Cys Trp Leu Ser
            100                 105                 110

Val Ser Leu Cys Cys Leu Phe Cys Gly Val Asp Gly Thr Phe Met Thr
        115                 120                 125

Arg Asn Ala Arg Pro Asn Ile Val Leu Leu Met Ala Asp Asp Leu Gly
    130                 135                 140

Val Gly Asp Leu Cys Cys Tyr Gly Asn Asn Ser Val Ser Thr Pro Asn
145                 150                 155                 160

Ile Asp Arg Leu Ala Ser Glu Gly Val Arg Leu Thr Gln His Leu Ala
                165                 170                 175

Ala Ala Ser Met Cys Thr Pro Ser Arg Ala Ala Phe Leu Thr Gly Arg
            180                 185                 190

Tyr Pro Ile Arg Ser Gly Met Val Ser Ala Tyr Asn Leu Asn Arg Ala
        195                 200                 205

Phe Thr Trp Leu Gly Gly Ser Gly Gly Leu Pro Thr Asn Glu Thr Thr
    210                 215                 220

Phe Ala Lys Leu Leu Gln His Arg Gly Tyr Arg Thr Gly Leu Ile Gly
225                 230                 235                 240

Lys Trp His Leu Gly Leu Ser Cys Ala Ser Arg Asn Asp His Cys Tyr
                245                 250                 255

His Pro Leu Asn His Gly Phe His Tyr Phe Tyr Gly Val Pro Phe Gly
            260                 265                 270

Leu Leu Ser Asp Cys Gln Ala Ser Lys Thr Pro Glu Leu His Arg Trp
        275                 280                 285

Leu Arg Ile Lys Leu Trp Ile Ser Thr Val Ala Leu Ala Leu Val Pro
    290                 295                 300

Phe Leu Leu Leu Ile Pro Lys Phe Ala Arg Trp Phe Ser Val Pro Trp
305                 310                 315                 320

Lys Val Ile Phe Val Phe Ala Leu Leu Ala Phe Leu Phe Phe Thr Ser
```

```
                325                 330                 335
Trp Tyr Ser Ser Tyr Gly Phe Thr Arg Arg Trp Asn Cys Ile Leu Met
                340                 345                 350

Arg Asn His Glu Ile Ile Gln Gln Pro Met Lys Glu Glu Lys Val Ala
                355                 360                 365

Ser Leu Met Leu Lys Glu Ala Leu Ala Phe Ile Glu Arg Tyr Lys Arg
                370                 375                 380

Glu Pro Phe Leu Leu Phe Phe Ser Phe Leu His Val His Thr Pro Leu
385                 390                 395                 400

Ile Ser Lys Lys Lys Phe Val Gly Arg Ser Lys Tyr Gly Arg Tyr Gly
                405                 410                 415

Asp Asn Val Glu Glu Met Asp Trp Met Val Gly Lys Ile Leu Asp Ala
                420                 425                 430

Leu Asp Gln Glu Arg Leu Ala Asn His Thr Leu Val Tyr Phe Thr Ser
                435                 440                 445

Asp Asn Gly Gly His Leu Glu Pro Leu Asp Gly Ala Val Gln Leu Gly
                450                 455                 460

Gly Trp Asn Gly Ile Tyr Lys Gly Gly Lys Gly Met Gly Gly Trp Glu
465                 470                 475                 480

Gly Gly Ile Arg Val Pro Gly Ile Phe Arg Trp Pro Ser Val Leu Glu
                485                 490                 495

Ala Gly Arg Val Ile Asn Glu Pro Thr Ser Leu Met Asp Ile Tyr Pro
                500                 505                 510

Thr Leu Ser Tyr Ile Gly Gly Ile Leu Ser Gln Asp Arg Val Ile
                515                 520                 525

Asp Gly Gln Asn Leu Met Pro Leu Leu Glu Gly Arg Ala Ser His Ser
530                 535                 540

Asp His Glu Phe Leu Phe His Tyr Cys Gly Val Tyr Leu His Thr Val
545                 550                 555                 560

Arg Trp His Gln Lys Asp Cys Ala Thr Val Trp Lys Ala His Tyr Val
                565                 570                 575

Thr Pro Lys Phe Tyr Pro Glu Gly Thr Gly Ala Cys Tyr Gly Ser Gly
                580                 585                 590

Ile Cys Ser Cys Ser Gly Asp Val Thr Tyr His Asp Pro Pro Leu Leu
                595                 600                 605

Phe Asp Ile Ser Arg Asp Pro Ser Glu Ala Leu Pro Leu Asn Pro Asp
                610                 615                 620

Asn Glu Pro Leu Phe Asp Ser Val Ile Lys Met Glu Ala Ala Ile
625                 630                 635                 640

Arg Glu His Arg Arg Thr Leu Thr Pro Val Pro Gln Gln Phe Ser Val
                645                 650                 655

Phe Asn Thr Ile Trp Lys Pro Trp Leu Gln Pro Cys Cys Gly Thr Phe
                660                 665                 670

Pro Phe Cys Gly Cys Asp Lys Glu Asp Asp Ile Leu Pro Met Ala Pro
                675                 680                 685

<210> SEQ ID NO 96
<211> LENGTH: 4
<212> TYPE: PRT
<213> ORGANISM: Homo sapiens

<400> SEQUENCE: 96

Lys Asp Glu Leu
1
```